(12) United States Patent
Bachmann et al.

(10) Patent No.: US 7,279,165 B2
(45) Date of Patent: Oct. 9, 2007

(54) AMYLOID β1-6 ANTIGEN ARRAYS

(75) Inventors: Martin F. Bachmann, Seuzach (CH); Alain Tissot, Zürich (CH); Rainer Ortmann, Saint Louis (FR); Rainer Lüönd, Therwil (CH); Matthias Staufenbiel, Lorrach (DE); Peter Frey, Bern (CH)

(73) Assignee: Cytos Biotechnology AG, Zurich-Schlieren (CH)

( * ) Notice: Subject to any disclaimer, the term of this patent is extended or adjusted under 35 U.S.C. 154(b) by 590 days.

(21) Appl. No.: 10/622,087

(22) Filed: Jul. 18, 2003

(65) Prior Publication Data
US 2004/0141984 A1 Jul. 22, 2004

Related U.S. Application Data

(60) Provisional application No. 60/470,432, filed on May 15, 2003, provisional application No. 60/396,639, filed on Jul. 19, 2002.

(51) Int. Cl.
*A61K 39/385* (2006.01)
*C07K 17/06* (2006.01)

(52) U.S. Cl. ............... 424/193.1; 424/194.1; 424/184.1; 424/400; 530/403; 530/404; 530/405; 530/406; 435/235.1

(58) Field of Classification Search ............. None
See application file for complete search history.

(56) References Cited

U.S. PATENT DOCUMENTS

| | | | |
|---|---|---|---|
| 4,722,840 A | 2/1988 | Valenzuela et al. | |
| 4,959,314 A | 9/1990 | Mark et al. | |
| 5,071,651 A | 12/1991 | Sabara et al. | |
| 5,143,726 A | 9/1992 | Thornton et al. | |
| 5,334,394 A | 8/1994 | Kossovsky et al. | |
| 5,374,426 A | 12/1994 | Sabara et al. | |
| 5,565,548 A | 10/1996 | Neurath et al. | |
| 5,580,859 A | 12/1996 | Felgner et al. | |
| 5,698,424 A | 12/1997 | Mastico et al. | |
| 5,739,026 A | 4/1998 | Garoff et al. | |
| 5,766,602 A | 6/1998 | Xiong et al. | |
| 5,770,380 A | 6/1998 | Hamilton et al. | |
| 5,789,245 A | 8/1998 | Dubensky, Jr. et al. | |
| 5,792,462 A | 8/1998 | Johnston et al. | |
| 5,814,482 A | 9/1998 | Dubensky, Jr. et al. | |
| 5,871,747 A | 2/1999 | Gengoux-Sedlik et al. | |
| 5,916,818 A | 6/1999 | Irsch et al. | |
| 5,928,647 A | 7/1999 | Rock | |
| 5,935,821 A | 8/1999 | Chatterjee et al. | |
| 6,004,763 A | 12/1999 | Gengoux et al. | |
| 6,054,312 A | 4/2000 | Larocca et al. | |
| 6,180,771 B1 | 1/2001 | Thomas et al. | |
| 6,231,864 B1 | 5/2001 | Birkett | |
| 6,380,364 B1 | 4/2002 | Mueller et al. | |
| 6,827,937 B2 | 12/2004 | Murray | |
| 6,932,971 B2 | 8/2005 | Bachmann et al. | |
| 6,964,769 B2 * | 11/2005 | Sebbel et al. | ............ 424/189.1 |
| 7,115,266 B2 | 10/2006 | Bachmann | |
| 7,128,911 B2 | 10/2006 | Bachmann et al. | |
| 2002/0052311 A1 | 5/2002 | Solomon et al. | |
| 2002/0064533 A1 | 5/2002 | Murray | |
| 2002/0081295 A1 | 6/2002 | Schiller et al. | |
| 2003/0157479 A1 | 8/2003 | Bachmann et al. | |
| 2003/0175290 A1 | 9/2003 | Renner et al. | |
| 2003/0175711 A1 | 9/2003 | Renner et al. | |
| 2003/0219459 A1 | 11/2003 | Bachmann et al. | |
| 2004/0076611 A1 | 4/2004 | Bachmann et al. | |
| 2004/0076645 A1 | 4/2004 | Bachmann et al. | |

FOREIGN PATENT DOCUMENTS

| | | |
|---|---|---|
| EP | 0 038 154 A1 | 10/1981 |
| EP | 0 259 149 B1 | 12/1993 |
| EP | 0 578 293 A1 | 1/1994 |
| EP | 0 385 610 B1 | 3/1994 |
| EP | WO 94/06472 A1 | 3/1994 |

(Continued)

OTHER PUBLICATIONS

Holtzman et al (2002) Advanced Drug Delivery Reviews 54: 1603-1613.*

(Continued)

*Primary Examiner*—Bruce R. Campell
*Assistant Examiner*—Michelle Horning
(74) *Attorney, Agent, or Firm*—Sterne, Kessler, Goldstein & Fox P.L.L.C.

(57) ABSTRACT

The present invention is related to the fields of molecular biology, virology, immunology and medicine. The invention provides a composition comprising an ordered and repetitive antigen or antigenic determinant array, and in particular an Aβ1-6 peptide-VLP-composition. More specifically, the invention provides a composition comprising a virus-like particle and at least one Aβ1-6 peptide bound thereto. The invention also provides a process for producing the conjugates and the ordered and repetitive arrays, respectively. The compositions of the invention are useful in the production of vaccines for the treatment of Alzheimer's disease and as a pharmaccine to prevent or cure Alzheimer's disease and to efficiently induce immune responses, in particular antibody responses. Furthermore, the compositions of the invention are particularly useful to efficiently induce self-specific immune responses within the indicated context.

30 Claims, 23 Drawing Sheets

FOREIGN PATENT DOCUMENTS

| | | |
|---|---|---|
| EP | 0 465 081 B1 | 4/1994 |
| EP | 0 283 505 B1 | 7/1994 |
| EP | 0 425 082 B1 | 4/1995 |
| JP | 09202735 A | 8/1997 |
| WO | WO 90/15878 A1 | 12/1990 |
| WO | WO 92/11291 A1 | 7/1992 |
| WO | WO 94/15585 A1 | 7/1994 |
| WO | WO 96/05293 A1 | 2/1996 |
| WO | WO 96/30523 A2 | 10/1996 |
| WO | WO 97/31948 A1 | 9/1997 |
| WO | WO 98/15631 A1 | 4/1998 |
| WO | WO 96/28624 A1 | 7/1998 |
| WO | WO 98/40100 A1 | 9/1998 |
| WO | WO 99/07839 A2 | 2/1999 |
| WO | WO 99/07839 A3 | 2/1999 |
| WO | WO 99/28478 A1 | 6/1999 |
| WO | WO 99/40934 A1 | 8/1999 |
| WO | WO 99/57289 A2 | 11/1999 |
| WO | WO 99/57289 A3 | 11/1999 |
| WO | WO 99/67293 A1 | 12/1999 |
| WO | WO 00/23955 A1 | 4/2000 |
| WO | WO 00/32227 A2 | 6/2000 |
| WO | WO 00/50461 A1 | 8/2000 |
| WO | WO 00/59928 A1 | 10/2000 |
| WO | WO 01/53457 A2 | 7/2001 |
| WO | WO 01/62284 A2 | 8/2001 |
| WO | WO 01/85208 A2 | 11/2001 |
| WO | WO 01/53457 A3 | 4/2002 |
| WO | WO 02/056905 A2 | 7/2002 |
| WO | WO 02/056907 A2 | 7/2002 |
| WO | WO 03/024480 A2 | 3/2003 |

OTHER PUBLICATIONS

Bowie et al (1990) Science, 247 (4948): 1306-1310.*
Frenkel et al (2000) PNAS, 97 (21): 11455-11459.*
Vasiljeva et al (1998) FEBS Letters 431: 7-11.*
Robinson and Sauer (1998) PNAS, 95: 5929-5934.*
Golmohammadi et al (1996) Structure, 4: 543-554.*
Adhin, M.R., et al., "Nucleotide Sequence from the ssRNA Bacteriophage JP34 Resolves the Discrepancy between Serological and Biophysical Classification," *Virology* 170(1):238-242, Academic Press, Inc. (1989).
Ansel, K.M., et al., "A chemokine-driven positive feedback loop organizes lymphoid follicles," *Nature* 406(6793):309-314, Nature Publishing Group (2000).
Ansel, K.M., et al., "In Vivo-activated CD4 T Cells Upregulate CXC Cheomkine Receptor 5 and Reprogram Their Response to Lymphoid Chemokines," *J. Exp. Med.* 190(8):1123-1134, The Rockefeller University Press (1999).
Bachmann, M.F., and Zinkernagel, R.M., "The influence of virus structure on antibody responses and virus serotype formation," *Immunology Today* 17(12):553-558, Elsevier Science Ltd. (1996).
Bachmann, M.F., and Zinkernagel, R.M., "Neutralizing Antiviral B Cell Responses," *Annu. Rev. Immunol.* 15:235-270, Annual Reviews, Inc. (1997).
Bachmann, M.F., et al., "Dendritic cells process exogenous viral proteins and virus-like particles for class I presentation to CD8+ cytotoxic T lymphocytes," *Eur. J. Immunol.* 26(11):2595-2600, VCH Verlagsgesellschaft mbH (1996).
Bachmann, M.F., et al., "TRANCE, a Tumor Necrosis Factor Family Member Critical for CD40 Ligand-independent T Helper Cell Activation," *J. Exp. Med.* 189(7):1025-1031, The Rockefeller University Press (1999).
Bard, F. et al., "Peripherally administered antibodies against amyloid β-peptide enter the central nervous system and reduce pathology in a mouse model of Alzheimer disease," *Nat. Med.* 6(8):916-919, Nature Publishing Company (2000).

Bass, S., and Yang, M., "Expressing cloned genes in *Escherichia coli*," in *Protein Function: A Practical Approach*, 2nd ed., Creighton, T.E., ed., IRL Press, Oxford, Great Britain, 175:29-55, (1997).
Bowie, J.U., et al., "Deciphering the message in protein sequences: tolerance to amino acid substitutions.," *Science* 247(4948):1306-1310, (1990).
Brown, W.L., et al., "RNA bacteriophage capsid-mediated drug delivery and epitope presentation.," *Intervirology* 45(4-6):371-380, S. Karger AG Basel (2002).
Cesareni, G., "Peptide display on filamentous phage capsids: A new powerful tool to study protein-ligand interaction," *FEBS Lett.* 307(1):66-70, Elsevier Science Publishers B.V. (1992).
Chackerian, B., et al., "Induction of autoantibodies to mouse CCR5 with recombinant papillomavirus particles," *Proc Natl. Acad. Sci USA* 96(5):2373-2378, (1999).
Crameri, R. and Suter, M., "Display of biologically active proteins on the surface of filamentous phages: a cDNA cloning system for selection of functional gene products linked to the genetic information responsible for their production," *Gene* 137(1):69-75, Elsevier Science Publishers B.V. (1993).
de la Cruz, V.F., et al., "Immunogenicity and Epitope Mapping of Foreign Sequences via Genetically Engineered Filamentous Phage," *J. Biol. Chem.* 263:4318-4322, The American Society for Biochemistry and Molecular Biology, Inc. (1988).
Dodart, J.-C., et al., "Immunotherapy for Alzheimer's disease: will vaccination work?," *TRENDS in Molecular Medicine* 9(3):85-87, (2003).
Donnelly, J.J., et al., "DNA Vaccines," *Annu. Rev. Immunol.* 15:617-648, Annual Reviews, Inc. (1997).
Fehr, T., et al., "T cell-Independent type I antibody response against B cell epitopes expressed repetitively on recombinant virus particles," *Proc. Natl. Acad. Sci* 95(16):9477-9481, (1998).
Fehr, T., et al., "Role of Repetitive Antigen Patterns for Induction of Antibodies Against Antibodies," *J Exp Med.* 185(10):1785-1792, The Rockefeller University Press (1997).
Frenkel, D., et al., "Generation of auto-antibodies towards Alzheimer's disease vaccination," *Vaccine* 19(17-19):2615-2619, Elsevier Science, Ltd. (2001).
Frenkel, D., et al., "Immunization against Alzheimer's beta - amyloid plaques via EFRH phage administration," *PNAS* 97(21):11455-11459, (2000).
Frolov, I., et al., "Alphavirus-based expression vectors: strategies and applications," *Proc. Natl. Acad. Sci* 93(21):11371-11377, (1996).
Gilman, S., et al., "Clinical effects of Abeta immunization (AN1792) in patients with AD in an interrupted trial," *Neurology* 64(9):1553-1562, (2005).
Golmohammadi, R., et al., "The crystal structure of bacteriophage Qβ at 3.5Å resolution," *Structure* 4(5):543-554, Current Biology, Ltd. (1996).
Harris, S.J., et al., "Prediction of murine MHC class I epitopes in a major house dust mite allergen and induction of T1-type CD8+ T cell responses," *International Immunology* 9(2):273-280, (1997).
Hedrick, J.A., and Zlotnik, A., "Identification and Characterization of a Novel β Chemokine Containing Six Conserved Cysteines," *J. Immunol.* 159(4):1589-1593, The American Association of Immunologists (1997).
Hilleman, M.R., "Six decades of vaccine development—a personal history," *Nat. Med. Vaccine Suppl.* 4(5 Suppl):507-514, (1998).
Holtzman, D.M., et al., "Abeta immunization and anti-Abeta antibodies: potential therapies for the prevention and treatment of Alzheimer's disease," *Advanced Durg Delivery Reviews* 54(12):1603-1613, Elsevier Science (2002).
Iannolo, G., et al., "Construction Exploitation and Evolution of a New Peptide Library Displayed at High Density by Fusion to the Major Coat Protein of Filamentous Phage," *Biol. Chem.* 378(6):517-521, Walter de Gruyter & Co. (1997).
Iannolo, G., et al., "Modifying Filamentous Phage Capsid: Limits in the Size of the Major Capsid Protein," *J. Mol. Biol.* 248(4):835-844, Academic Press, Ltd. (1995).
Janus, C., "Vaccines for Alzheimer's disease: how close are we?," *CNS Drugs* 17(7):457-474, Adis Data Information (2003).

Jegerlehner, A., et al., "A molecular assembly system that renders antigens of choise highly repetitive for induction of protective B cell responses," *Vaccine* 20(25-26):3104-3112, Elsevier Science, Ltd. (2002).

Kastelein, R.A. et al., "Effect of the sequence upstream from the ribosome-binding site on the yield of protein from the cloned gene for phage MS2 coat protein," *Gene* 23(3):245-254, Elsevier (1983).

Klovins, J., et al., "Nucleotide sequence of a ssRNA phage from Acinetobacter: kinship to coliphages," *Journal of general Virology* 83(Pt 6):1523-1533, SGM (2002).

Kovacsovics-Bankowski, M., et al., "Efficient major histocompatibility complex class I presentation of exogenous antigen upon phagocytosis by macrophages," *Proc. Natl. Acad. Sci. USA* 90:4942-4946, National Academy Press (1993).

Kozlovska, T.M., et al., "Recombinant RNA phage Qβ capsid particles synthesized and self-assembled in *Escherichia coli*," *Gene* 137(1):133-137, Elsevier Science Publishers B.V. (1993).

Kozlovska, T.M., et al., "RNA Phage Qβ Coat Protein as a Carrier for Foreign Epitopes," *Intervirology* 39(1-2):9-15, S. Karger AG (1996).

Kozlovskaya, T.M., et al., "Formation of capsid-like structures as a result of the expression of a cloned envelope protein gene from RNA-containing bacteriophage," *Dokl. Akad. Nauk. SSSR* 287:452-455, Erivan Akademiia Nauk Armianskol Ssr (1986).

Kratz, P.A., et al., "Native display of complete foreign protein domains on the surface of hepatitis B virus capsids," *Proc. Natl. Acad. Sci* 96(5):1915-1920, (1999).

Lechner, F., et al. "Virus-like particles as a modular system for novel vaccines," *Intervirology* 45(4-6):212-217, S. Karger AG Basel (2002).

Lim, F., et al., "The RNA-binding Site of Bacteriophage Qβ Coat Protein," *J. Biol. Chem.* 271(50):31839-31845, The American Society for Biochemistry and Molecular Biology, Inc. (1996).

Loktev, V.B., et al., "Design of Immunogens as components of a new generation of molecular vaccines," *J. Biotechnol.* 44(1-3):129-37, Elsevier Science (1996).

Lo-Man, R., et al., "A recombinant virus-like particle system derived from parvovirus as an efficient antigen carrier to elicit a polarized Th1 immune response without adjuvant," *Eur. J. Immunol.* 28(4):1401-1407, Wiley-VCH Verlag GmbH (1998).

McGeer, P.L., McGeer, E., "Is there a future for vaccination as a treatment for Alzheimer's disease?," *Neurobiology of Aging* 24(3):391-395, (2003).

Minenkova, O.O., et al., "Design of specific immunogens using filamentous phage as the carrier," *Gene* 128(1):85-88, Elsevier Science Publishers B.V. (1993).

NCBI Entrez, GenBank Report, Accession No. AAA16663, from Kozlovska, T.M., et al. (Mar. 1994).

NCBI Entrez, GenBank Report, Accession No. AAC14699, from Beekwilder, M.J., et al. (Apr. 1998).

NCBI Entrez, GenBank Report, Accession No. AAC14704, from Beekwilder, M.J., et al. (Apr. 1998).

NCBI Entrez, GenBank Report, Accession No. CAA30374, from Inokuchi, Y., et al. (Feb. 1999).

NCBI Entrez, GenBank Report, Accession No. NP_040754, from Inokuchi, Y., et al. (Jun. 2003).

NCBI Entrez, GenBank Report, Accession No. P03611, from Weber, K., et al. (Nov. 1997).

NCBI Entrez, GenBank Report, Accession No. VCBPM2, from Min Jou, W., et al. (Jan. 2001).

NCBI Entrez, GenBank Report, Accession No. VCBPQB, from Maita, T., and Konigsberg, W. (Dec. 1993).

Neurath, A.R., et al., "Hepatitis B Virus surface antigen (HBsAg) as carrier for synthetic peptides having an attached hydrophobic tail," *Mol. Immunol.* 26:53-62, Pergamon Press (1989).

Ni, C.-Z., et al., "Crystal structure of the coat protein from the GA bacteriophage: Model of the unassembled dimer," *Protein Sci.* 5:2485-2493, Cambridge University Press (1996).

Nieland, J.D., et al., "Chimeric papillomavirus virus-like particles induce a murine self-antigen-specific protective and therapeutic antitumor immune response," *Journal of Cellular Biochemistry* 73(2):145-152, Wiley-Liss Inc. (1999).

Ormstad, H., et al., "Airborne house dust particles and diesel exhaust particles as allergen carriers.," *Clinical and Experimental Allergy* 28(6):702-708, Blackwell Science Ltd. (1998).

O'Shea, E.K., et al., "Evidence That the Leucine Zipper is a Coiled Coil," *Science* 243(4890):538-542, American Association for the Advancement of Science (1989).

O'Shea, E.K., et al., "Mechanism of Specificity in the Fos-Jun Oncoprotein Heterodimer," *Cell* 68(4):699-708, Cell Press (1992).

Pasek, M., et al., "Hepatitis B virus genes and their expression in *E. coli*," *Nature* 282(5739):575-578, Macmillan Journals Ltd. (1979).

Perham, R.N., et al., "Engineering a peptide epitope display system on filamentous bacteriophage," *FEMS Microbiol. Rev.* 17(1-2):25-31, Elsevier Science Publishers on behalf of the Federation of European Microbiological Societies (1995).

Petrenko, V.A., et al., "A library of organic landscapes on filamentous phage," *Protein Engin.* 9(9):797-801, Oxford University Press (1996).

Priano, C., et al., "A Complete Plasmid-based Complemenation System for RNA Coliphage Qβ: Three Proteins of Bacteriophages Qβ (Group III) and SP (Group IV) can be Interchanged," *J. Mol. Biol.* 249(2):283-297, Academic Press, Ltd. (1995).

Raychaudhuri, S., and Rock, K.L., "Fully mobilizing host defense: Building better vaccines," *Nat. Biotechnol.* 16(11):1025-1031, Nature America, Inc. (1998).

Robinson, C.R., and Sauer, R.T., "Optimizing the stability of single-chain proteins by linker length and composition mutagenesis," *PNAS* 95(11):5929-5934, National Academy of Science (1998).

Roesch, P.L., and Blomfield, I.C., "Leucine alters the interaction of the leucine-responsive regulatory protein (Lrp) with the *fim* switch to stimulate site-specific recombination in *Escherichia coli*," *Mol. Microbiol.* 27(4):751-761, Blackwell Science, Ltd. (1998).

Roher, A.E., et al., "Isolation and Chemical Characterization of Alzeheimer's Disease Paired Helical Filament Cytoskeletons: Differentiation from Amyloid Plaque Core Protein," *J. Cell Biol.* 107(6 Pt 2):2703-2716, The Rockefeller University Press (1988).

Roher, A.E., et al., "Morphological and Biochemical Analyses of Amyloid Plaque Core Proteins Purified from Alzheimer Disease Brain Tissue," *J. Neurochem.* 61(5):1916-1926, Raven Press, Ltd. (1993).

Romagnani, S., "The Th1/Th2 paradigm," *Immunol. Today* 18(6):263-266, Elsevier Science Ltd. (1997).

Schenk, D., et al., "Immunization with amyloid-β attenuates Alzheimer-disease-like pathology in the PDAPP mouse," *Nature* 400(6740):173-177, Nature Publishing Group (1999).

Selkoe, D.J., "Translating cell biology into therapeutic advances in Alzheimer's disease," *Nature* 399(6738 Suppl):A23-A31, Nature Publishing Group (1999).

Sturchler-Pierrat, C., et al., "Two amyloid precursor protein transgenic mouse models with Alzheimer disease-like pathology," *Proc. Natl. Acad. Sci. USA* 94(24):13287-13292, National Academy Press (1997).

Townsend, A., and Bodmer, H., "Antigen recognition by class I-restricted T lymphocytes," *Ann. Rev. Immunol.* 7:601-624, Annual Reviews, Inc. (1989).

Ulrich, R., et al., "Core particles of hepatitis B virus as carrier for foreign epitopes," *Adv. Virus Res.* 50:141-182, Academic Press (1998).

Vasiljeva, I., et al., "Mosaic Qβ coats as a new presentation model," *FEBS Lett.* 431(1):7-11, Federation of European Biochemical Societies (1998).

Willis, A.E., et al., "Immunological properties of foreign peptides in multiple display on a filamentous bacteriophage," *Gene* 128(1):79-83, Elsevier Science Publishers B.V. (1993).

Witherell, G.W., and Uhlenbeck, O.C., "Specific RNA Binding by Qβ Coat Protein," *Biochemistry* 28(1):71-76, American Chemical Society (1989).

Witte, L., et al., "Monoclonal antibodies targeting the VEGF receptor-2 (Flk1/KDR) as an anti-angiogenic therapeutic strategy," *Cancer and Metastasis Reviews* 17(2):155-161, Kluwer Academic Publishers (1998).

Wynne, S.A., et al., "The Crystal Structure of the Human Hepatitis B Virus Capsid," *Mol. Cell* 3(6):771-780, Cell Press (1999).

Zhou, S., and Standring, D.N., "Cys Residues of the Hepatitis B Virus Capsid Protein Are Not Essential for the Assembly of Viral Core Particles but Can Influence Their Stability," *J. Virol.* 66(9):5393-5398, American Society for Microbiology (1992).

Abraham, J.M., et al., "An invertible element of DNA controls phase variation of type 1 fimbriae of *Escherichia coli*," *Proc. Natl. Acad. Sci. USA* 82:5724-5727, National Academy Press (1985).

Abraham, S.N., et al., "Glycerol-Induced Unraveling of the Tight Helical Conformation of *Escherichia coli* Type 1 Fimbriae," *J. Bacteriol.* 174:5145-5148, American Society for Microbiology (1992).

Adhin, M.R., et al., "Nucleotide Sequence from the ssRNA Bacteriophage JP34 Resolves the Discrepancy between Serological and Biophysical Classification," *Virology* 170:238-242, Academic Press, Inc. (1989).

Aguzzi, A., "Prion diseases, blood and the immune system: concerns and reality," *Haematologica* 85:3-10, Il Pensiero Scientifico Editore (Jan. 2000).

Ansel, K.M., et al., "In Vivo-activated CD4 T Cells Upregulate CXC Cheomkine Receptor 5 and Reprogram Their Response to Lymphoid Chemokines," *J. Exp. Med.* 190:1123-1134, The Rockefeller University Press (1999).

Ansel, K.M., et al., "A chemokine-driven positive feedback loop organizes lymphoid follicles," *Nature* 406:309-314, Nature Publishing Group (Jul. 2000).

Antonysamy, M.A., et al., "Evidence for a Role of IL-17 in Organ Allograft Rejection: IL-17 Promotes the Functional Differentiation of Dendritic Cell Progenitors," *J. Immunol.* 162:577-584, The American Association of Immunologists (1999).

Arenberg, D.A., et al., "The murine CC chemokine, 6C-kine, inhibits tumor growth and angiogenesis in a human lung cancer SCID mouse model," *Cancer Immunol. Immunother.* 49:587-592, Springer-Verlag (Jan. 2001).

Arnon, R., et al., "A mimotope peptide-based vaccine against *Schistosoma mansoni*: synthesis and characterization," *Immunology* 101:555-562, Blackwell Science, Ltd. (Dec. 2000).

Bachmann, M.F., and Zinkernagel, R.M., "The influence of virus structure on antibody responses and virus serotype formation," *Immunol. Today* 17:553-558, Elsevier Science, Ltd. (1996).

Bachmann, M.F., and Zinkernagel, R.M., "Neutralizing Antiviral B Cell Responses," *Annu. Rev. Immunol.* 15:235-270, Annual Reviews, Inc. (1997).

Bachmann, M.F., et al., "TRANCE, a Tumor Necrosis Factor Family Member Critical for CD40 Ligand-independent T Helper Cell Activation," *J. Exp. Med.* 189:1025-1031, The Rockefeller University Press (1999).

Banerjee, R.R., and Lazar, M.A., "Dimerization of Resistin and Resistin-like Molecules Is Determined by a Single Cysteine," *J. Biol. Chem.* 276:25970-25973, The American Society for Biochemistry and Molecular Biology, Inc. (Jul. 2001).

Bard, F. et al., "Peripherally administered antibodies against amyloid β-peptide enter the central nervous system and reduce pathology in a mouse model of Alzheimer disease," *Nat. Med.* 6:916-919, Nature Publishing Company (Aug. 2000).

Bass, S., and Yang, M., "Expressing cloned genes in *Escherichia coli*," in *Protein Function: A Practical Approach*, 2nd ed., Creighton, T.E., ed., IRL Press, Oxford, Great Britain, pp. 29-55 (1997).

Bernhagen, J., et al., "Purification, Bioactivity, and Secondary Structure Analysis of Mouse and Human Macrophage Migration Inhibitory Factor (MIF)," *Biochemistry* 33:14144-14155, American Chemical Society (1994).

Biaselle, C.J., and Millar, D.B., "Studies on Triton X-100 detergent micelles," *Biophys. Chem.* 3:355-361, North-Holland Publushing Company (1975).

Bleul, C.C., et al., "The lymphocyte chemoattractant SDF-1 is a ligand for LESTR/fusin and blocks HIV-1 entry," *Nature* 382:829-833, Nature Publishing Group (1996).

Blomfield, I.C., et al., "Type 1 Fimbriation and *fimE* Mutants of *Escherichia coli* K-12," *J. Bacteriol.* 173:5298-5307, American Society for Microbiology (1991).

Blomfield, I.C., et al., "Integration host factor stimulates both FimB- and FimE-mediated site-specific DNA inversion that controls phase variation of type 1 fimbriae expression in *Escherichia coli*" *Mol. Microbiol.* 23:705-717, Blackwell Science, Ltd. (1997).

Boder, E.T., and Wittrup, K.D., "Yeast Surface Display for Directed Evolution of Protein Expression, Affinity, and Stability," *Methods Enzymol.* 328:430-444, Academic Press (Oct. 2000).

Bonci, A., et al., "Relatedness and Phylogeny Within the Family of Periplasmic Chaperones Involved in the Assembly of Pili or Capsule-Like Structures of Gram-Negative Bacteria," *J. Mol. Evol.* 44:299-309, Springer-Verlag (1997).

Brandner, S., et al., "A crucial role for B cells in neuroinvasive scrapie," *Transfus. Clin. Biol.* 6:17-23, Elsevier, Paris (1999).

Brinton, Jr., C.C., "The structure, function, synthesis and genetic control of bacterial pili and a molecular model for DNA and RNA transport in gram negative bacteria," *Trans. N.Y. Acad. Sci.* 27:1003-1054, New York Academy of Sciences (1965).

Brown, K.D., et al., "A family of small inducible proteins secreted by leukocytes are members of a new superfamily that includes leukocyte and fibroblast-derived inflammatory agents, growth factors, and indicators of various activation processes," *J. Immunol.* 142:679-687, The American Association of Immunologists (1989).

Brown, P.M., et al., "A Single-Step Purification of Biologically Active Recombinant Human Interleukin-5 from a Baculovirus Expression System," *Protein Expr. Purif.* 6:63-71, Academic Press, Inc. (1995).

Brown, K.L., et al., "Scrapie replication in lymphoid tissues depends on prion protein-expressing follicular dendritic cells," *Nat. Med.* 11:1308-1312, Nature Publishing Company (1999).

Bullitt, E., et al., "Development of pilus organelle subassemblies in vitro depends on chaperone uncapping of a beta zipper," *Proc. Natl. Acad. Sci. USA* 93:12890-12895, National Academy Press (1996).

Bullitt, E., and Makowski, L., "Bacterial Adhesion Pili Are Heterologous Assemblies of Similar Subunits," *Biophys. J.* 74:623-632, Biophysical Society (1998).

Burger, J.A., et al., "Blood-derived nurse-like cells protect chronic lymphocytic leukemia B cells from spontaneous apoptosis through stromal cell-derived factor-1," *Blood* 96:2655-2663, The American Society of Hematology (Oct. 2000).

Burghoff, R.L., et al., "Utilization of the Mouse Large Intestine To Select an *Escherichia coli* F-18 DNA Sequence That Enhances Colonizing Ability and Stimulates Synthesis of Type 1 Fimbriae," *Infect. Immun.* 61:1293-1300, American Society for Microbiology (1993).

Cannon-Carlson S., et al., "Expression, Purification, and Characterization of Recombinant Human Interleukin-13 from NS-O Cells," *Protein Expr. Purif.*12:239-248, Academic Press (1998).

Chabaud, M., et al., "Enhancing Effect of IL-17 on IL-1-Induced IL-6 and Leukemia Inhibitory Factor Production by Rheumatoid Arthritis Synoviocytes and Its Regulation by Th2 Cytokines," *J. Immunol.* 161: 409-414, The American Association of Immunologists (1998).

Chabaud, M., et al., "Human Interleukin-17. A T Cell-Derived Proinflammatory Cytokine Produced by the Rheumatoid Synovium," *Arthritis Rheum.* 42:963-970, Wiley-Liss, Inc. (1999).

Chabaud, M., et al., "Contribution of Interleukin 17 to synovium matrix destruction in rheumatoid arthritis," *Cytokine* 12:1092-1099, Cell Press (Jul. 2000).

Clark, H.F, et al., "Comparative Characterization of a C-Type Virus-Producing Cell Line (VSW) and a Virus-Free Cell Line (VH2) From *Vipera russelli*," *J. Natl. Cancer Inst.* 51:645-657, Oxford University Press (1973).

Clark-Lewis, I., et al., "Chemical Synthesis, Purification, and Characterization of Two Inflammatory Proteins, Neutrophil Activating Peptide 1 (Interleukin-8) and Neutrophil Activating Peptide 2," *Biochemistry* 30:3128-3135, American Chemical Society (1991).

Coffman, R.L., et al., "Antibody to Interleukin-5 Inhibits Helminth-Induced Eosinophilia in Mice," *Science* 245:308-310, American Association for the Advancement of Science (1989).

Cohen, C., and Parry D.A.D, "α-Helical coiled coils-a widespread motif in proteins," *Trends Biochem. Sci.* 11:245-248, Elsevier Science Publishers B.V. (1986).

Corti, M., et al., "GM1-ganglioside-Triton X-100 mixed micelles: changes of micellar properties studie by laser-light scattering and enzymatic methods," *Chem. Phys. Lipids* 28:197-214, Elsevier/North-Holland Scientific Publishers, Ltd. (1981).

Coutelier, J.-P., et al., "IgG2a Restriction of murine antibodies elicited by viral infections," *J. Exp. Med.* 165:64-69, The Rockefeller University Press (1987).

Crump, M.P., et al., "Solution Structure of Eotaxin, a Chemokine That Selectively Recruits Eosinophils in Allergic Inflammation," *J. Biol. Chem.* 273:22471-22479, The American Society for Biochemistry and Molecular Biology, Inc. (1998).

Davis, N.L., et al., "In Vitro Synthesis of Infectious Venezuelan Equine Encephalitis Virus RNA from a cDNA Clone: Analysis of a Viable Deletion Mutant," *Virology* 171:189-204, Academic Press (1989).

Daugherty, P.S., et al., "Development of an optimized expression system for the screening of antibody libraries displayed on the *Escherichia coli* surface," *Protein Eng.* 12:613-621, Oxford University Press (1999).

Dealwis, C., et al., "Crystal structure of chemically synthesized [N33A] stromal cell-derived factor 1α, a potent ligand for the HIV-1 "fusin" coreceptor," *Proc. Natl. Acad. Sci. USA* 95:6941-6946, National Academy Science (Jun. 2001).

Dodson, K.W., et al., "Outer-membrane PapC molecular usher discriminately recognizes periplasmic chaperone-pilus subunit complexes," *Proc. Natl. Acad. Sci. USA* 90:3670-3674, National Academy Press (1993).

Dudler, J., et al., "Effect of interleukin 17 on proteoglycan degradation in murine knee joints," *Ann. Rheum. Dis.* 59:529-532, Bmj Publishing Group (Jul. 2000).

Eckhardt, S.G., et al., "Hepatitis B Virus Core Antigen Has Two Nuclear Localization Sequences in the Arginine-Rich Carboxyl Terminus," *J. Virol.* 65:575-582, American Society for Microbiology (1991).

Eisenmesser, E.Z., et al., "Expression, Purification, Refolding, and Characterization of Recombinant Human Interleukin-13: Utilization of Intracellular Processing," *Protein Expr. Purif.* 20:186-195, Academic Press (Nov. 2000).

Eisenmesser, E.Z., et al., "Solution Structure of Interleukin-13 and Insights into Receptor Engagement," *J. Mol. Biol.* 310:231-241, Academic Press (Jun. 2001).

Eisenstein, B.I., "Phase Variation of Type 1 Fimbriae in *Escherichia coli* Is Under Transcriptional Control," *Science* 214:337-339, American Association for the Advancement of Science (1981).

Elisseeva, E.L., et al., "NMR Studies of Active N-terminal Peptides of Stromal Cell-derived Factor-1," *J. Biol. Chem.* 275:26799-26805, The American Society for Biochemistry and Molecular Biology, Inc. (Sep. 2000).

Eshdat, Y., et al., "Dissociation and Reassembly of *Escherichia coli* Type 1 Pili," *J. Bacteriol.* 148:308-314, American Society for Microbiology (1981).

Ettinger, R., et al., "A Critical Role for Lymphotoxin-β Receptor in the Development of Diabetes in Nonobese Diabetic Mice," *J. Exp. Med.* 193:1333-1339, The Rockefeller University Press (Jun. 2001).

Fehr, T., et al., "Role of Repetitive Antigen Patterns for Induction of Antibodies Against Antibodies," *J Exp. Med.* 185:1785-1792, The Rockefeller University Press (1997).

Folkman, J., and Klagsbrun, M., "Angiogenic Factors," *Science* 235:442-447, American Association for the Advancement of Science (1987).

Folkman, J., "Angiogenesis in cancer, vascular, rheumatoid and other disease," *Nat. Med.* 1:27-31, Nature Publishing Company (1995).

Forssmann, U., et al., "Eotaxin-2, a Novel CC Chemokine that Is Selective for the Chemokine Receptor CCR3, and Acts Like Eotaxin on Human Eosinophil and Basophil Leukocytes," *J. Exp. Med.* 185:2171-2176, The Rockefeller University Press (1997).

Fossiez, F., et al., "T Cell Interleukin-17 Induces Stromal Cells to Produce Proinflammatory and Hematopoietic Cytokines," *J. Exp. Med.* 183:2593-2603, The Rockefeller University Press (1996).

Fossiez, F., et al., "Interleukin-17," *Intern. Rev. Immunol.* 16:541-551, Harwood Academic Publishers (1998).

Fujiwara, K., et al., "Novel preparation method of immunogen for hydrophobic hapten, enzyme immunoassay for daunomycin and adriamycin," *J. Immunol. Methods* 45:195-203, Elsevier/North-Holland Biomedical Press (1981).

Gally, D.L., et al., "Environmental Regulation of the *fim* Switch Controlling Type 1 Fimbrial Phase Variation in *Escherichia coli* K-12: Effects of Temperature and Media," *J. Bacteriol.* 175:6186-6193, American Society for Microbiology (1993).

Gally, D. L., et al., "Interaction of FimB and FimE with the *fim* switch that controls the phase variation of type 1 fimbriate in *Escherichia coli* K-12," *Mol. Microbiol.* 21:725-738, Blackwell Science, Ltd. (1996).

Gherardi, E. et al., "A single-step procedure for cloning and selection of antibody-secreting hybridomas," *J. Immunol. Methods* 126: 61-68, Elsevier (1990).

Golmohammadi, R., et al., "The crystal structure of bacteriophage Qβ at 3.5Å resolution," *Structure* 4:543-554, Current Biology, Ltd. (1996).

Gunn, M.D., et al., "A B-cell-homing chemokine made in lymphoid follicles activates Burkitt's lymphoma receptor-1," *Nature* 391:799-803, Nature Publishing Group (1998).

Hanes, J., et al., "Picomolar affinity antibodies from a fully synthetic naive library selected and evolved by ribosome display," *Nat. Biotechnol.* 18:1287-1292, Nature Publishing Company (Dec. 2000).

Hanson, M.S., et al., "Purification of the *Escherichia coli* Type 1 Pilin and Minor Pilus Proteins and Partial Characterization of the Adhesin Protein," *J. Bacteriol.* 170:3350-3358, American Society for Microbiology (1988).

Hanson, M.S., and Brinton, Jr., C.C., "Identification and characterization of *E. coli* type-1 pilus tip adhesion protein," *Nature* 332:265-268, Nature Publishing Group (1988).

Harrison, J.L., et al., "Screening of Phage Antibody Libraries," *Methods Enzymol.* 267:83-109, Macmillan Publishers, Ltd. (1996).

Haslam, D.B., et al., "The amino-terminal domain of the P-pilus adhesin determines receptor specificity," *Mol. Microbiol.* 14:399-409, Blackwell Scientific Publications (1994).

Hedrick, J.A., and Zlotnik, A., "Identification and Characterization of a Novel β Chemokine Containing Six Conserved Cysteines," *J. Immunol.* 159: 1589-1593, The American Association of Immunologists (1997).

Heveker, N., et al., "Dissociation of the signalling and antiviral properties of SDF-1-derived small peptides," *Curr. Biol.* 8:369-376, Current Biology, Ltd. (1998).

Hirel, P.-H., et al., "Extent of N-terminal methionine excision from *Escherichia coli* proteins is governed by the side-chain length of the penultimate amino acid," *Proc. Natl. Acad. Sci. USA* 86:8247-8251, National Academy Press (1989).

Holmes, W.D., et al., "Solution Studies of Recombinant Human Stromal-Cell-Derived Factor-1," *Prot. Expr. Purif.* 21:367-377, Academic Press (Apr. 2001).

Holmgren, A., et al., "Conserved immunoglobulin-like features in a family of periplasmic pilus chaperones in bacteria," *EMBO J.* 11:1617-1622, Oxford University Press (1992).

Holmgren, A., and Bränden, C.-I., "Crystal structure of chaperon protein PapD reveals as immunoglobulin fold," *Nature* 342:248-251, Nature Publishing Group (1989).

Hultgren, S.J., et al., "The PapG adhesin of uropathogenic *Escherichia coli* contains separate regions for receptor binding and for the incorporation into the pilus," *Proc. Nat. Acad. Sci. USA* 86:4357-4361, National Academy Press (1989).

Hultgren, S.J., et al., "PapD and superfamily of periplasmic immunoglobulin-like pilus chaperones," *Adv. Prot. Chem.* 44:99-123, Academic Press, Inc. (1993).

Hultgren, S.J., et al., "Pilus and Nonpilus Bacterial Adhesins: Assembly and Function in Cell Recognition," *Cell* 73:887-901, Cell Press (1993).

Hultgren, S.J., et al., "Bacterial Adhesins and Their Assembly," in *Escherichia coli and Salmonella*, Neidhardt, F.C., et al., eds., ASM Press, Washington, D.C. pp. 2730-2756 (1996).

Humbles, A.A., et al., "Kinetics of Eotaxin Generation and Its Relationship to Eosinophil Accumulation in Allergic Airways Disease: Analysis in a Guinea Pig Model In Vivo," *J. Exp. Med.* 186:601-612, The Rockefeller University Press (1997).

Hung, D.L., et al., "Molecular basis of two subfamilies of immunoglobulin-like chaperones," *EMBO J.* 15:3792-3805, Oxford University Press (1996).

Hung, D.L. and Hultgren, S.J., "Pilus Biogenesis via the Chaperone/Usher Pathway: An Integration of Structure and Function," *J. Struct. Biol.* 124:201-220, Academic Press (1998).

Ikeda, T., et al., "Determination of Three Isoforms of the Receptor Activator of Nuclear Factor-κB Ligand and Their Differential Expression in Bone and Thymus," *Endocrinology* 142:1419-1426, The Endocrine Society (Apr. 2001).

Ingley, E., et al., "Production and purification of recombinant human interleukin-5 from yeast and baculovirus expression systems," *Eur. J. Biochem.* 196:623-629, Blackwell Science, Ltd. (1991).

Jacob-Dubuisson, F., et al., "PapD chaperone function in pilus biogenesis depends on oxidant and chaperone-like activities of DsbA," *Proc. Natl. Acad. Sci. USA* 91:11552-11556, National Academy Press (1994).

Jacob-Dubuisson, F., et al., "Initiation of assembly and association of the structural elements of a bacterial pilus depend on two specialized tip proteins," *EMBO J.* 12:837-847, Oxford University Press (1993).

Jacob-Dubuisson, F., et al., "Chaperone-assisted Self-assembly of Pili Independent of Cellular Energy," *J. Biol. Chem.* 269:12447-12455, The American Society for Biochemistry and Molecular Biology, Inc. (1994).

Jiang, X., et al., "Norwalk Virus Genome Cloning and Characterization," *Science* 250:1580-1583, American Association for the Advancement of Science (1990).

Jones, C.H., et al., "FimC is a periplasmic PapD-like chaperone that directs assembly of type 1 pili in bacteria," *Proc. Natl. Acad. Sci. USA* 90:8397-8401, National Academy Press (1993).

Jones, C.H., et al., "FimH adhesin of type 1 pili is assembled into a fibrillar tip structure in the Enterobacteriaceae," *Proc. Natl. Acad. Sci. USA* 92:2081-2085, National Academy Press (1995).

Josien, R., et al., "TRANCE, a Tumor Necrosis Factor Family Member, Enhances the Longevity and Adjuvant Properties of Dendritic Cells In Vivo," *J. Exp. Med.* 191: 495-501, The Rockefeller University Press (Feb. 2000).

Jovanovic, D.V., et al., "IL-17 Stimulates the Production and Expression of Proinflammatory Cytokines, IL-β and TNFα, by Human Macrophages," *J. Immunol.* 160:3513-3521, The American Association of Immunologists (1998).

Kapp, U., et al., "Interleukin 13 Is Secreted by and Stimulates the Growth of Hodgkin and Reed-Sternberg Cells," *J. Exp. Med.* 189:1939-1945, The Rockefeller University Press (1999).

Kastelein, R.A. et al., "Effect of the sequence upstream from the ribosome-binding site on the yield of protein from the cloned gene for phage MS2 coat protein," *Gene* 23:245-254, Elsevier (1983).

Kim, K.J., et al., "Inhibition of vascular endothelial growth factor-induced angiogenesis suppresses tumour growth in vivo," *Nature* 362:841-844, Nature Publishing Group (1993).

Kim, K.-H., et al., "A Cysteine-rich Adipose Tissue-specific Secretory Factor Inhibits Adipocyte Differentiation," *J. Biol. Chem.* 276:11252-11256, The American Society for Biochemistry and Molecular Biology, Inc. (Apr. 2001).

Klemm, P., "The *fimA* gene encoding the type-1 fimbrial subunit of *Escherichia coli*. Nucleotide sequence and primary structure of the protein," *Euro. J. Biochem.* 143:395-399, Blackwell Science, Ltd. (1984).

Klemm, P., and Christiansen, G., "Three *fim* genes required for the regulation of length and mediation of adhesion of *Escherichia coli* type 1 fimbriae," Mol. Gen. Genet. 208:439-445, Springer-Verlag (1987).

Klemm, P., et al., "The major subunit of *Escherichia coli* type 1 fimbriate is not required for D-mannose-specific adhesion," *Mol. Microbiol.* 4:553-559, Blackwell Scientific Publications (1990).

Klemm, P., and Christiansen, G., "The *fimD* gene required for cell surface localization of *Escherichia coli* type 1 fimbriae," *Mol. Gen. Genet.* 220:334-338, Springer-Verlag (1990).

Klemm, P., "FimC, a chaperone-like periplasmic protein of *Escherichia coli* involved in biogenesis of type 1 fimbriae," *Res. Microbiol.* 143:831-838, Institut Pasteur/Elsevier (1992).

Klemm, P., and Krogfelt, K.A., "Type 1 Fimbriae of *Escherichia coli*," in *Fimbriae*, Klemm, P., ed., CRC Press, Inc., Boca Raton, FL., pp. 9-26 (1994).

Kodama, S., et al., "Characterization of recombinant murine interleukin 5 expressed in Chinese hamster ovary cells," *Glycobiology* 2:419-427, Oxford University Press (1992).

Kodama, S., et al., "Carbohydrate Structures of Human Interleukin 5 Expressed in Chinese Hamster Ovary Cells," *J. Biochem.* (Tokyo) 110:693-701, Japanese Biochemical Society (1991).

Kopf, M., et al., "IL-5-Deficient Mice Have a Developmental Defect in CD5' B-1 Cells and Lack Eosinophilia but have Normal Antibody and Cytotoxic T Cell Responses," *Immunity* 4:15-24, Cell Press (1996).

Koschel, M., et al., "Extensive Mutagenesis of the Hepatitis B Virus Core Gene and Mapping of Mutations That Allow Capsid Formation" *J. Virol* 73:2153-2160, American Society for Microbiology (1999).

Koths, K., "Structure-Function Studies on Human Macrophage Colony-Stimulating Factor (M-CSF)," *Mol. Reprod. Dev.* 46:31-38, Wiley-Liss, Inc. (1997).

Kozlovska, T.M., et al., "Recombinant RNA phage Qβ capsid particles synthesized and self-assembled in *Escherichia coli*," *Gene* 137:133-137, Elsevier Science Publishers B.V. (1993).

Kozlovskaya, T.M., et al., "Formation of capsid-like structures as a result of the expression of a cloned envelope protein gene from RNA-containing bacteriophage fr," *Dokl. Akad. Nauk. SSSR* 287: 452-455, Erivan Akademiia Nauk Armianskoi Ssr (1986).

Kozlovskaya, T.M., et al., "Formation of capsid-like structures as a result of the expression of a cloned envelope protein gene from RNA-containing bacteriophage fr," STNEasy, Accession No. 1986:219892, CAplus English abstract (1986) (Document AT37).

Krogfelt, K.A., et al., "Direct Evidence that the FimH Protein Is the Mannose-Specific Adhesin of *Escherichia coli* Type 1 Fimbriae," *Infect. Immun.* 58:1995-1998, American Society for Microbiology (1990).

Kuehn, M.J., et al., "Structural Basis of Pilus Subunit Recognition by the PapD Chaperone," *Science* 262:1234-1241, American Association for the Advancement of Science (1993).

Kunimoto, D.Y, et al., "High-level production of murine interleukin-5 (IL-5) utilizing recombinant baculovirus expression. Purification of the rIL-5 and its use in assessing the biologic role of IL-5 glycosylation," *Cytokine* 3:224-230, W.B. Saunders Company (1991).

Landschulz, W.H., et al., "The Leucine Zipper: A Hypothetical Structure Common to a New Class of DNA Binding Proteins," *Science* 240:1759-1764, American Association for the Advancement of Science (1988).

Leake, C.J., et al., "Cytopathic Effect and Plaque Formation by Arboviruses in a Continuous Cell Line (XTC-2) from the Toad *Xenopus laevis*," *J. gen. Virol.* 35:335-339, Cambridge University Press (1977).

Lee, K.H., et al., "Two-Dimensional Electrophoresis of Proteins as a Tool in the Metabolic Engineering of Cell Cycle Regulation," *Biotech. Bioeng.* 50:336-340, John Wiley & Sons, Inc. (1996).

Leech, M., et al., "Involvement of macrophage migration inhibitory factor in the evolution of rat adjuvant arthritis," *Arthritis Rheum.* 41:910-917, Arthritis Foundation (1998).

Leech, M., et al. "Regulation of macrophage migration inhibitory factor by endogenous glucocorticoid in rat adjuvant-induced arthritis," *Arthritis Rheum.* 43:827-833, Arthritis Foundation (Apr. 2000).

Liljeström, P., and Garoff, H., "A new generation of animal cell expression vectors based on the semliki forest virus replicon," *Bio/technology* 9:1356-1361, Nature Publishing Company (1991).

Liljeström, P., "Alphavirus expression systems," *Curr. Opin. Biotechnol.* 5:495-500, Current Biology, Ltd. (1994).

Lim, F., et al., "The RNA-binding Site of Bacteriophage Qβ Coat Protein," *J. Biol. Chem.* 271:31839-31845, The American Society for Biochemistry and Molecular Biology, Inc. (1996).

Lin, E.Y., et al., "Colony-stimulating Factor 1 Promotes Progression of Mammary Tumors to Malignancy," *J. Exp. Med.* 193:727-739, The Rockefeller University Press (Mar. 2001).

Lindberg, F., et al., "PapD, a Periplasmic Transport Protein in P-Pilus Biogenesis," *J. Bacteriol. 171*:6052-6058, American Society for Microbiology (1989).

Lo-Man, R., et al., "A recombinant virus-like particle system derived from parvovirus as an efficient antigen carrier to elicit a polarized Th1 immune response without adjuvant," *Eur. J. Immunol. 28*:1401-1407, Wiley-VCH Verlag GmbH (1998).

López, O., et al., "Direct formation of mixed micelles in the solubilization of phospholipid liposomes by Triton X-100," *FEBS Lett. 426*:314-318, Elsevier (1998).

Lowe, M.A., et al., "Immunoelectron Microscopic Analysis of Elongation of Type 1 Fimbriae in *Escherichia coli*," *J. Bacteriol. 169*:157-163, American Society for Microbiology (1987).

Lu, D., et al., "Identification of the Residues in the Extracellular Region of KDR Important for Interaction with Vascular Endothelial Growth Factor and Neutralizing Anti-KDR Antibodies," *J. Biol. Chem. 275*:14321-14330, The American Society for Biochemistry and Molecular Biology, Inc. (May 2000).

Lum, L., et al., "Evidence for a Role of a Tumor Necrosis Factorα(TNF-α)-converting Enzyme-like Protease in Shedding of TRANCE, a TNF Family Member Involved in Osteoclastogenesis and Dendritic Cell Survival," *J. Biol. Chem. 274*:13613-13618, The American Society for Biochemistry and Molecular Biology, Inc. (1999).

Lundstrom, K., "Alphaviruses as expression vectors," *Curr. Opin. Biotechnol. 8*:578-582, Current Biology, Ltd. (1997).

Luther, S.A., et al., "BLC Expression in Pancreatic Islets Causes B Cell Recruitment and Lymphotoxin-Dependent Lymhoid Neogenesis" *Immunity 12*:471-481, Cell Press (May 2000).

Mackay, J.L., and Browning, J.L., "Turning off follicular dendritic cells," *Nature 395*:26-27, Macmillan Magazines, Ltd. (1998).

Martiny-Baron, G., and Marmé, D., "VEGF-mediated tumour angiogenesis: a new target for cancer therapy," *Curr. Opin. Biotechnol. 6*:675-680, Current Biology, Ltd. (1995).

Matsui, S.M., et al., " The Isolation and Characterization of a Norwalk Virus-Specific cDNA," *J. Clin. Invest. 87*:1456-1461, The American Society for Clinical Investigation, Inc. (1991).

Matsumoto, M., et al., "Role of Lymphotoxin and the Type 1 TNF Receptor in the Formation of Germinal Centers," *Science 271*:1289-1291, American Association for the Advancement of Science (1996).

Matthews, W., et al., "A receptor tyrosine kinase cDNA isolated from a population of enriched primitive hematopoietic cells and exhibiting close genetic linkage to *c-kit*," *Proc. Natl. Acad. Sci. USA 88*:9026-9030, National Academy Press (1991).

Matusevicius, D., et al., "Interleukin-17 mRNA expression in blood and CSF mononuclear cells is augmented in multiple sclerosis," *Mult. Scler. 5*:101-104, Stockton Press (1999).

Mayer, K.L., and Stone, M.J., "NMR Solution Structure and Receptor Peptide Binding of the CC Chemokine Eotaxin-2," *Biochemistry 39*:8382-8395, American Chemical Society (Jul. 2000).

McClain, M.S., et al., "Roles of *fimB* and *fimE* in Site-Specific DNA Inversion Associated with Phase Variation of Type 1 Fimbriae in *Escherichia coli*," *J. Bacteriol. 173*:5308-5314, American Society for Microbiology (1991).

McPherson, P.S., "Regulatory Role of SH3 Domain-mediated Protein-Protein Interactions in Synaptic Vesicle Endocytosis," *Cell Signal 11*:229-238, Elsevier Science, Inc. (1999).

Mikulowska, A., et al., "Macrophage Migration Inhibitory Factor Is Involved in the Pathogenesis of Collagen Type II-Induced Arthritis in Mice," *J. Immunol. 158*:5514-5517, The American Association of Immunologists (1997).

Millauer, B., et al., "Glioblastoma growth inhibited in vivo by a dominant-negative Flk-1 mutant," *Nature 367*:576-579, Nature Publishing Group (1994).

Min, H., et al., "Osteoprotegerin Reverses Osteoporosis by Inhibiting Endosteal Osteoclasts and Prevents Vascular Calcification by Blocking a Process Resembling Osteoclastogenesis," *J. Exp. Med. 192*:463-474, The Rockefeller University Press (Aug. 2000).

Mitchell, D.L., et al., "Purification and characterization of recombinant murine interleukin-5 glycoprotein, from a Baculovirus expression system," *Biochem. Soc. Trans. 21*:332S, Portland Press (1993).

Montrasio, F. et al., "Impaired Prion Replication in Spleens of Mice Lacking Functional Follicular Dendritic Cells," *Science 288*:1257-1259, American Association for the Advancement of Science (May 2000).

Morein, B., et al., "Iscom, a novel structure for antigenic presentation of membrane proteins from enveloped viruses," *Nature 308*:457-460, Nature Publishing Group (1984).

Moriya, C., et al., "Large quantity production with extreme convenience of human SDF-1α and SDF-1β by a Sendai virus vector," *FEBS Lett. 425*:105-111, Amsterdam Elsevier Science B.V. (1998).

Müller, A., et al., "Involvement of chemokine receptors in breast cancer metastasis," *Nature 410*:50-56, Nature Publishing Group (Mar. 2001).

Murphy, Jr., K.P., et al., "Expression of Human Interleukin-17 in *Pichia pastoris*: Purification and Characterization," *Protein Expr. Purif. 12*:208-214, Academic Press (1998).

Nagira, M., et al., "Molecular Cloning of a Novel Human CC Chemokine Secondary Lymphoid-Tissue Chemokine That Is a Potent Chemoattractant for Lymphocytes and Mapped to Chromosome 9p13," *J. Biol. Chem. 272*:19518-19524, The American Society for Biochemistry and Molecular Biology, Inc. (1997).

Nanki, T., et al., "Stromal Cell-Derived Factor-1-CXC Chemokine Receptor 4 Interactions Play a Central Role in CD4+ T Cell Accumulation in Rheumatoid Arthritis Synovium," *J. Immunol. 165*:6590-6598, The American Association of Immunologists (Dec. 2000).

Naureckiene, S., and Uhlin., B.E., "In vitro analysis of mRNA processing by Rnase E in the pap operon of *Esherichia coli*," *Mol. Microbiol. 21*:55-68, Blackwell Science, Ltd. (1996).

Neirynck, S., et al., "A universal influenza A vaccine based on the extracellular domain of the M2 protein," *Nat. Med. 5*:1157-1163, Nature Publishing Company (1999).

Newman, J.V., et al., "Stimulation of *Escherichia coli* F-18Col Type-1 fimbriae synthesis by *leuX*," *FEMS Microbiol. Lett. 122*:281-287, Elsevier (1994).

Ni, C.-Z., et al., "Crystal structure of the coat protein from the GA bacteriophage: Model of the unassembled dimer," *Protein Sci. 5*:2485-2493, Cambridge University Press (1996).

Nilsson, P., et al., "Mutations Affecting mRNA Processing and Fimbrial Biogenesis in the *Escherichia coli pap* Operon," *J. Bacteriol. 178*:683-690, American Society for Microbiology (1996).

Oberlin, E., et al., "The CXC chemokine SDF-1 is the ligand for LESTR/fusin and prevents infection by T-cell-line-adapted HIV-1," *Nature 382*:833-835, Nature Publishing Group (1996).

Ohnishi, Y., et al., "Crystal Structure of Recombinant Native SDF-1α with Additional Mutagenesis Studies: An Attempt at a More Comprehensive Interpretation of Accumulated Structure-Activity Relationship Data," *J. Interferon Cytokine Res. 20*:691-700, Mary Ann Liebert, Inc. (Aug. 2000).

Olszewska, W., et al., "Protection against Measles Virus-Induced Encephalitis by Anti-mimotope Antibodies: The Role of Antibody Affinity," *Virology 272*:98-105, Academic Press (Jun. 2000).

Orndorff, P.E., and Falkow, S., "Identification and Characterization of a Gene Product That Regulates Type 1 Piliation in *Escherichia coli*," *J. Bacteriol. 160*:61-66, American Society for Microbiology (1984).

Orndorff, P.E., and Falkow, S., "Nucleotide Sequence of *PilA*, the Gene Encoding the Structural Component of Type 1 Pili in *Escherichia coli*," *J. Bacteriol. 162*:454-457, American Society for Microbiology (1985).

O'Shea, E.K., et al., "Evidence That the Leucine Zipper Is a Coiled Coil," *Science 243*:538-542, American Association for the Advancement of Science (1989).

O'Shea, E.K., et al., "Mechanism of Specificity in the Fos-Jun Oncoprotein Heterodimer," *Cell 68*:699-708, Cell Press (1992).

Pandit, J., et al., "Three-dimensional Structure of Dimeric Human Recombinant Macrophage Colony-Stimulating Factor," *Science 258*:1358-1362, American Association for the Advancement of Science (1992).

Pierrot, C., et al., "Expression of Rat Interleukin-5 and Generation of Neutralizing Antiserum: a Comparative Study of Rat IL-5 Produced in *Escherichia coli* and Insect Cells," *Biochem. Biophys. Res. Commun. 253*:756-760, Academic Press (1998).

Pierson-Mullany, L.K., et al. "Characterization of polyclonal allergen-specific IgE responses by affinity distributions," *Mol. Immunol.* 37:613-620, Elsevier Science, Ltd. (Aug. 2000).

Piossek, C., et al., "Vascular Endothelial Growth Factor (VEGF) Receptor II-derived Peptides Inhibit VEGF," *J. Biol. Chem.* 274:5612-5619, The American Society for Biochemistry and Molecular Biology, Inc. (1999).

Presta, L.G., et al., "Humanization of an Anti-Vascular Endothelial Growth Factor Monoclonal Antibody for the Therapy of Solid Tumors and Other Disorders," *Cancer Res.* 57:4593-4599, The American Association for Cancer Research (1997).

Priano, C., et al., "A Complete Plasmid-based Complementaion System for RNA Coliphage Qβ: Three Proteins of Bacteriophages Qβ (Group III) and SP (Group IV) can be Interchanged," *J. Mol. Biol.* 249:283-297, Academic Press, Ltd. (1995).

Proudfoot, A.E.I., et al., "Preparation and characterization of human interleukin-5 expressed in recombinant *Escherichia coli*," *Biochem. J.* 270:357-361, Portland Press, Ltd. (1990).

Renner, W.A., et al., "Recombinant Cyclin E Expression Activates Proliferation and Obviates Surface Attachment of Chinese Hamster Ovary (CHO) Cells in Protein-Free Medium," *Biotech. Bioeng.* 47:476-482, John Wiley & Sons, Inc. (1995).

Risau, W., "Mechanisms of angiogenesis," *Nature* 386:671-674, Nature Publishing Group (1997).

Ritter, A., et al., "The Pai-associated *leuX* specific tRNA$_5^{Leu}$ affects type 1 fimbriation in pathogenic *Escherichia coli* by control of FimB recombinase expression," *Mol. Microbiol.* 25:871-882, Blackwell Science, Ltd. (1997).

Roesch, P.L., and Blomfield, I.C., "Leucine alters the interaction of the leucine-responsive regulatory protein (Lrp) with the *fim* switch to stimulate site-specific recombination in *Escherichia coli*," *Mol. Microbiol.* 27:751-761, Blackwell Science, Ltd. (1998).

Roher, A.E., et al., "Isolation and Chemical Characterization of Alzheimer's Disease Paired Helical Filament Cytoskeletons: Differentiation from Amyloid Plaque Core Protein," *J. Cell Biol.* 107:2703-2716, The Rockefeller University Press (1988).

Roher, A.E., et al., "Morphological and Biochemical Analyses of Amyloid Plaque Core Proteins Purified from Alzheimer Disease Brain Tissue," *J. Neurochem.* 61:1916-1926, Raven Press, Ltd. (1993).

Romagnani, S., "The Th1/Th2 paradigm," *Immunol. Today* 18:263-266, Elsevier Science, Ltd. (1997).

Rothenberg, M.E., et al., "Targeted Disruption of the Chemokine Eotaxin Partially Reduces Antigen-induced Tissue Eosinophilia," *J. Exp. Med.* 185:785-790, The Rockefeller University Press (1997).

Rusconi, S., et al., "In vitro inhibition of HIV-1 by Met-SDF-1β alone or in combination with antiretroviral drugs," *Antivir. Ther.* 5:199-204, International Medical Press (Sep. 2000).

Russell, P.W., and Orndorff, P.E., "Lesions in Two *Escherichia coli* Type 1 Pilus Genes Alter Pilus Number and Length without Affecting Receptor Binding," *J. Bacteriol.* 174:5923-5935, American Society for Microbiology (1992).

Santos, L., et al., "Role of macrophage migration inhibitory factor (MIF) in murine antigen-induced arthritis: interaction with glucocorticoids," *Clin. Exp. Immunol.* 123:309-314, Blackwell Science (Feb. 2001).

Saulino, E.T., et al., "Ramifications of kinetic partitioning on usher-mediated pilus biogenesis," *EMBO J.* 17:2177-2185, Oxford University Press (1998).

Schenk, D., et al., "Immunization with amyloid-β attenuates Alzheimer-disease-like pathology in the PDAPP mouse," *Nature* 400:173-177, Nature Publishing Group (1999).

Schlesinger, S., "Alphaviruses—vectors for the expression of heterologous genes," *Trends Biotechnol.* 11:18-22, Elsevier Science Publishers, Ltd. (1993).

Selkoe, D.J., "Translating cell biology into therapeutic advances in Alzheimer's disease," *Nature* 399:A23-A31, Nature Publishing Group (1999).

Slonim, L.N., et al., "Interactive surface in the PapD chaperone cleft is conserved in pilus chaperone superfamily and essential in subunit recognition and assembly," *EMBO J.* 11:4747-4756, Oxford University Press (1992).

Smyth, C.J., et al., "Fimbrial adhesins: similarities and variations in structure and biogenesis," *FEMS Immun. Med. Microbiol.* 16:127-139, Elsevier (1996).

Soto, H., et al., "The CC chemokine 6Ckine binds the CXC chemokine receptor CXCR3," *Proc. Natl. Acad. Sci. USA* 95:8205-8210, National Academy Press (1998).

Soto, G.E., et al., "Periplasmic chaperone recognition motif of subunits mediates quaternary interactions in the pilus," *EMBO J.* 17:6155-6167, Oxford University Press (1998).

Soto, G.E., and Hultgren, S.J., "Bacterial Adhesins: Common Themes and Variations in Architecture and Assembly," *J. Bacteriol.* 181:1059-1071, American Society for Microbiology (1999).

Steppan, C.M., et al., "The hormone resistin links obesity to diabetes," *Nature* 409:307-312, Nature Publishing Group (Jan. 2001).

Stollar, V., "Togaviruses in Cultured Arthropod Cells," in *The Togaviruses. Biology, Structure, Replication*, Schlesinger, R.W., ed., Academic Press, Inc. New York, N.Y., pp. 583-621 (1980).

Strauss, J., and Strauss, E.G., "The Alphaviruses: Gene Expression, Replication and Evolution," *Microbiol. Rev.* 58:491-562, American Society for Microbiology (1994).

Striker, R.T., et al., "Stable Fiber-forming and Nonfiber-forming Chaperone-Subunit Complexes in Pilus Biogenesis," *J. Biol. Chem.* 269:12233-12239, The American Society for Biochemistry and Molecular Biology, Inc. (1994).

Sturchler-Pierrat, C., et al., "Two amyloid precursor protein transgenic mouse models with Alzheimer disease-like pathology," *Proc. Natl. Acad. Aci. USA* 94:13287-13292, National Academy Press (1997).

Sun, H.-W., et al., "Crystal structure at the 2.6Å resolution of human macrophage migration inhibitory factor," *Proc. Natl. Acad. Sci. USA* 93:5191-5196, National Academy Press (1996).

Tang, J.-L., et al., "Interleukin-17 antagonism inhibits acute but not chronic vascular rejection," *Transplantation* 72:348-350, Lippincott Williams & Wilkens (Jul. 2001).

Tanimori, H., et al., "Enzyme immunoassay of neocarzinostatin using β-galactosidase as label," *J. Pharm. Dyn.* 4:812-819, Pharmaceutical Society of Japan (1981).

Teixeira, M.M., et al., "Chemokine-induced Eosinophil Recruitment. Evidence of a Role for Endogenous Eotaxin in an In Vivo Allergy Model in Mouse Skin," *J. Clin. Invest.* 100:1657-1666, The American Society for Clinical Investigation, Inc. (1997).

Tewari, R., et al., "Neutrophil Activation by Nascent FimH Subunits of Type I Fimbriae Purified from the Periplasm of *Escherichia coli*," *J. Biol. Chem.* 268:3009-3015, The American Society for Biochemistry and Molecular Biology, Inc. (1993).

Teunissen, M.B.M., et al., "Interleukin-17 and Interferon-γ Synergize in the Enhancement of Proinflammatory Cytokine Production by Human Keratinocytes," *J. Invest. Dermatol.* 111:645-649, The Society for Investigative Dermatology, Inc. (1998).

Thanassi, D.G., et al., "The PapC usher forms an oligomeric channel: Implications for pilus biogenesis across the outer membrane," *Proc. Natl. Acad. Sci. USA.* 95:3146-3151, National Academy Press (1998).

De Togni, P., et al., "Abnormal Development of Peripheral Lymphoid Organs in Mice Deficient in Lymphotoxin," *Science* 264:703-707, American Association for the Advancement of Science (1994).

Topchieva, I., and Karezin, K., "Self-Assembled Supramolecular Micellar Structures Based on Non-ionic Surfactants and Cyclodextrins," *J. Colloid Interface Sci.* 213:29-35, Academic Press (1999).

Twomey, T., et al., "Structure and immunogenicity of experimental foot-and-mouth disease and poliomyelitis vaccines," *Vaccine* 13:1603-1610, Elsevier Science, Ltd. (1995).

Ulrich, R., et al., "Core particles of hepatitis B virus as carrier for foreign epitopes," *Adv. Virus Res.* 50:141-182, Academic Press (1998).

Vicari, A.P., et al., "Antitumor Effects of the Mouse Chemokine 6Ckine/SLC Through Angiostatic and Immunological Mechanisms," *J. Immunol.* 165:1992-2000, The American Association of Immunologists (Aug. 2000).

Visintin, M. et al., "Selection of antibodies for intracellular function using a two-hybrid in vivo system" *Proc. Natl. Acad. Sci. USA* 96:11723-11728, National Academy Press (1999).

Walse, B., et al., "Transferred nuclear Overhauser effect spectroscopy study of a peptide form the PapG pilus subunit bound by the *Escherichia coli* PapD chaperone," *FEBS Lett.* 412:115-120, Elsevier Science B.V. (1997).

Warnes, A., et al., "Expression of the measles virus nucleoprotein gene in *Escherichia coli* and assembly of nucleocapsid-like structures," *Gene* 160:173-178, Elsevier Science B.V. (1995).

Watson, E., et al., "Structure determination of the intact major sialylated oligosaccharide chains of recombinant human erythropoietin expressed in Chinese hamster ovary cells," *Glycobiology* 4:227-237, Oxford University Press (1994).

Wei, Y.Q., et al., "Immunotherapy of tumors with xenogeneic endothelial cells as a vaccine," *Nat. Med.* 6:1160-1166, Nature Publishing Company (Oct. 2000).

Witherell, G.W., and Uhlenbeck, O.C., "Specific RNA binding by Qβ Coat Protein," *Biochemistry* 28:71-76, American Chemical Society (1989).

Wong, C.K., et al., "Elevation of proinflammatory cytosine (IL-18, IL-17, IL-12) and Th2 cytokine (IL-4) concentrations in patients with systemic lupus erythematosus," *Lupus* 9:589-593, Macmillan Publishers Ltd. (2000).

Wu, Q., et al., "Reversal of Spontaneous Autoimmune Insulitis in Nonobese Diabetic Mice by Soluble Lymphotoxin Receptor," *J. Exp. Med.* 193:1327-1332, The Rockefeller University Press (Jun. 2001).

Wuttke, M., et al., "Structural Characterization of Human Recombinant and Bone-derived Bone Sialoprotein," *J. Biol. Chem.* 276:36839-36848, The American Society for Biochemistry and Molecular Biology, Inc. (2001).

Wynne, S.A., et al., "The Crystal Structure of the Human Hepatitis B Virus Capsid," *Mol. Cell* 3:771-780, Cell Press (1999).

Xiong, C., et al., "Sindbis Virus: An Efficient, Broad Host Range Vector for Gene Expression in Animal Cells," *Science* 243:1188-1191, American Association for the Advancement of Science (1989).

Yao, Z., et al., "Human IL-17: A Novel Cytokine Derived from T Cells," *J. Immunol.* 155:5483-5486, The American Association of Immunologists (1995).

Yao, Z., et al., "Molecular characterization of the human interleukin (IL)-17 receptor," *Cytokine* 9:794-800, Academic Press, Ltd. (1997).

Yone, K., et al., "Epitopic Regions for Antibodies against Tumor Necrosis Factor α," *J. Biol. Chem.* 270:19509-19515, The American Society for Biochemistry and Molecular Biology, Inc. (1995).

Yuan, T-T., et al., "Subtype-Independent Immature Secretion and Subtype-Dependent Replication Deficiency of a Highly Frequent, Naturally Occurring Mutation of Human Hepatitis B Virus Core Antigen," *J. Virol.* 73:10122-10128, American Society for Microbiology (1999).

Zang, M., et al., "Production of Recombinant Proteins in Chinese Hamster Ovary Cells Using A Protein-Free Cell Culture Medium," *Bio/Technology* 13:389-392, Nature Publishing Company (1995).

Zhou, S., and Standring, D.N., "Cys Residues of the Hepatitis B Virus Capsid Protein Are Not Essential for the Assembly of Viral Core Particles but Can Influence Their Stability," *J. Virol.* 66:5393-5398, American Society for Microbiology (1992).

Zimmermann, N., et al., "Murine Eotaxin-2: A Constitutive Eosinophil Chemokine Induced by Allergen Challenge and IL-4 Overexpression," *J. Immunol.* 165:5839-5846, The American Association of Immunologists (Nov. 2000).

Ziolkowska, M., et al., "High Levels of IL-17 in Rheumatoid Arthritis Patients: IL-15 Triggers In Vitro IL-17 Production Via Cyclosporin A-Sensitive Mechanism," *J. Immunol.* 164:2832-2838, The American Association of Immunologists (Mar. 2000).

Zuercher, A.W., et al., "Oral anti-IgE immunization with epitope-displaying phage," *Eur. J. Immunol.* 30:128-135, Wiley-Vch Verlag GmbH (Jan. 2000).

Fehr, T., et al., "T cell-independent type I antibody response against B cell epitopes expressed repetitively on recombinant virus particles," *Proc. Natl. Acad. Sci. USA* 95:9477-9481, National Academy Press (1998).

Frenkel, D., et al., "Generation of auto-antibodies towards Alzheimer's disease vaccination," *Vaccine* 19:2615-2619, Elsevier Science, Ltd. (Mar. 2001).

International Search Report for International Application No. PCT/IB02/00166 mailed on Oct. 29, 2002. European Patent Office, Netherlands (2002).

International Search Report for Internatioanl Application No. PCT/IB02/00168 mailed on Nov. 4, 2002. European Patent Office, Netherlands (2002).

Kozlovska, T.M., et al., "RNA Phage Qβ Coat Protein as a Carrier for Foreign Epitopes," *Intervirology* 39:9-15, S. Karger AG (1996).

Kratz, P.A., et al., "Native display of complete foreign protein domains on the surface of hepatitis B virus capsids," *Proc. Natl. Acad. Sci. USA* 96:1915-1920, National Academy of Sciences (1999).

Nieland, J.D., et al., "Chimeric Papillomavirus Virus-like Particles Induce a Murine Self-Antigen-Specific Protective and Therapeutic Antitumor Immune Response," *J. Cell. Biochem.* 73:145-152, Wiley-Liss, Inc. (1999).

Slepushkin, V.A., et al., "Protection of mice against influenza A virus challenge by vaccination with baculovirus-expressed M2 protein," *Vaccine* 13:1399-1402, Elsevier Science Ltd. (1995).

Vasiljeva, I., et al., "Mosaic Qβ coats as a new presentation model," *FEBS Lett.* 431:7-11, Federation of European Biochemical Societies (1998).

International Search Report for International Application No. PCT/IB 02/00166, mailed Jan. 31, 2003. Europaeen Patent Office, Netherlands (2002).

Baba, T.W., et al., "Pathogenicity of Live, Attenuated SIV After Mucosal Infection of Neonatal Macaques," *Science* 267:1820-1825, American Association for the Advancement of Science (1995).

Bachmann, M.F., et al., "Dendritic cells process exogenous viral proteins and virus-like particles for class I presentation to CD8+ cytotoxic T lymphocytes," *Eur. J. Immunol.* 26:2595-2600, VCH Verlagsgesellschaft mbH (1996).

Boorsma, M., et al., "A temperature-regulated replicon-based DNA expression system," *Nat. Biotechnol.* 18:429-432, Nature America, Inc. (Apr. 2000).

Borisova, G., et al., "Hybrid Hepatitis B Virus Nucleocapsid Bearing an Immunodominant Region from Hepatitis B Virus Surface Antigen," *J. Virol.* 67:3696-3701, American Society for Microbiology (1993).

Cesareni, G., "Peptide display on filamentous phage capsids: A new powerful tool to study protein-ligand interaction," *FEBS Lett.* 307:66-70, Elsevier Science Publishers B.V. (1992).

Connor, R.I., et al., "Immunological and Virological Analyses of Persons Infected by Human Immunodeficiency Virus Type 1 while Participating in Trials of Recombinant gp120 Subunit Vaccines," *J. Virol.* 72:1552-1576, American Society for Microbiology (1998).

Crameri, R. and Suter, M., "Display of biologically active proteins on the surface of filamentous phages: a cDNA cloning system for selection of functional gene products linked to the genetic information responsible for their production," *Gene* 137:69-75, Elsevier Science Publishers B.V. (1993).

Daniel, M.D., et al., "Protective Effects of a Live Attenuated SIV Vaccine with a Deletion in the *nef* Gene," *Science* 258:1938-1941, American Association for the Advancement of Science (1992).

de la Cruz, V.F., et al., "Immunogenicity and Epitope Mapping of Foreign Sequences via Genetically Engineered Filamentous Phage," *J. Biol. Chem.* 263:4318-4322, The American Society for Biochemistry and Molecular Biology, Inc. (1988).

Donnelly, J.J., et al., "DNA Vaccines," *Annu. Rev. Immunol.* 15:617-648, Annual Reviews, Inc. (1997).

Ebina, S., et al., "Chemical Modification of Bovine Pancreatic Trypsin Inhibitor for Single Site Coupling of Immunogenic Peptides for NMR Conformational Analysis," *J. Biol. Chem.* 264:7882-7888, The American Society for Biochemistry and Molecular Biology, Inc. (1989).

Esposito, G., et al., "Conformational study of a short *Pertussis* toxin T cell epitope incorporated in a multiple antigen peptide template by CD and two-dimensional NMR: Analysis of the structural effects on the activity of synthetic immunogens," *Eur. J. Biochem.* 217:171-187, Blackwell Science Ltd. on behalf of the Federation of European Biochemical Societies (1993).

Förster, E., et al., "Natural and recombinant enzymatically active or inactive bee venom phospholipase $A_2$ has the same potency to release histamine from basophils in patients with Hymenoptera allergy," *J. Allergy Clin. Immunol.* 95:1229-1235, Mosby-Year Book, Inc. (1995).

Frolov, I., et al., "Alphavirus-based expression vectors: Strategies and applications," *Proc. Natl. Acad. Sci. USA* 93:11371-11377, National Academy Press (1996).

Gilbert, S.C., et al., "A protein particle vaccine containing multiple malaria epitopes," *Nat. Biotechnol.* 15:1280-1284, Nature America Publishing (1997).

Greenstone, H.L., et al., "Chimeric paillomavirus virus-like particles elicit antitumor immunity against the E7 oncoprotein in an HPV16 tumor model," *Proc. Natl. Acad. Sci. USA* 95:1800-1805, National Academy Press (1998).

Hahn, C.S., et al., "Infectious Sindbis virus transient expression vectors for studying antigen processing and presentation," *Proc. Natl. Acad. Sci. USA* 89:2679-2683, National Academy Press (1992).

Harding, C.V., and Song, R., "Phagocytic Processing of Exogenous Particulate Antigens by Macrophages for Presentation by Class I MHC Molecules," *J. Immunol.* 153:4925-4933, The American Association of Immunologists (1994).

Hilleman, M.R., "Six decades of vaccine development—a personal history," *Nat. Med. Vaccine Suppl.* 4:507-514 (May 1998).

Hui, E. K-W. et al., "Hepatitis B viral core proteins with an N-terminal extension can assemble into core-like particles but cannot be enveloped," *J. Gen. Virol.* 80:2647-2659, Society for General Microbiology (1999).

Iannolo, G., et al., "Construction, Exploitation and Evolution of a New Peptide Library Displayed at High Density by Fusion to the Major Coat Protein of Filamentous Phage," *Biol. Chem.* 378:517-521, Walter de Gruyter & Co. (1997).

Iannolo, G., et al., "Modifying Filamentous Phage Capsid: Limits in the Size of the Major Capsid Protein," *J. Mol. Biol.* 248:835-844, Academic Press, Ltd. (1995).

Ikram, H., and Prince, A.M., "A method for coupling the Hepatitis B surface antigen to aldehyde-fixed erythrocytes for use in passive hemagglutination," *J. Virol. Methods* 2:269-275, Elsevier/North-Holland Biomedical Press (1981).

Kovacsovics-Bankowski, M., et al., "Efficient major histocompatibility complex class I presentation of exogenous antigen upon phagocytosis by macrophages," *Proc. Natl. Acad. Sci. USA* 90:4942-4946, National Academy Press (1993).

Lo, K. K-W., et al., "Surface-modified mutants of cytochrome P450cam: enzymatic properties and electrochemistry," *FEBS Lett.* 451:342-346, Elsevier Science B.V. on behalf of the Federation of European Biochemical Societies (1999).

Minenkova, O.O., et al., "Design of specific immunogens using filamentous phage as the carrier," *Gene* 128:85-88, Elsevier Science Publishers B.V. (1993).

Neurath, A.R., et al., "Hepatitis B Virus surface antigen (HBsAg) as carrier for synthetic peptides having an attached hydrophobic tail," *Mol. Immunol.* 26:53-62, Pergamon Press (1989).

Perham, R.N., et al., "Engineering a peptide epitope display system on filamentous bacteriophage," *FEMS Microbiol. Rev.* 17:25-31, Elsevier Science Publishers on behalf of the Federation of European Microbiological Societies (1995).

Petrenko, V.A., et al., "A library of organic landscapes on filamentous phage," *Protein Engin.* 9:797-801, Oxford University Press (1996).

Pumpens, P. and Grens, E., "Hepatitis B core particles as a universal display model: a structure-function basis for development," *FEBS Lett.* 442:1-6, Elsevier Science B.V. on behalf of the Federation of European Biochemical Societies (1999).

Quash, G., et al., "The preparation of latex particles with covalently bound polyamines IgG and measles agglutinins and their use in visual agglutination tests," *J. Immunol. Methods* 22:165-174, Elsevier/North-Holland Biomedical Press (1978).

Raychaudhuri, S., and Rock, K.L., "Fully mobilizing host defense: Building better vaccines," *Nat. Biotechnol.* 16:1025-1031, Nature America, Inc. (1998).

Redfield, R.R., et al., "Disseminated vaccinia in a military recruit with Human Immunodeficiency Virus (HIV) disease," *N. Eng. J. Med.* 316:673-676, Massachusetts Medical Society (1987).

Rudolf, M.P., et al., "Molecular Basis for Nonanaphylactogenicty of a Monoclonal Anti-IgE Antibody," *J. Immunol.* 165:813-819, The American Association of Immunologists (2000).

Sedlik, C., et al., "Recombinant parvovirus-like particles as an antigen carrier: A novel nonreplicative exogenous antigen to elicit protective antiviral cytotoxic T cells," *Proc. Natl. Acad. Sci. USA* 94:7503-7508, National Academy Press (1997).

Shen, L., et al., "Recombinant Virus Vaccine-Induced SIV-Specific CD8+ Cytotoxic T Lymphocytes," *Science* 252:440-443, American Association for the Advancement of Science (1991).

Tanimori, H., et al., "Enzyme Immunoassay of Neocarzinostatin Using β-Galactosidase as Label," *J. Pharm. Dyn.* 4:812-819, Pharmaceutical Society of Japan (1981).

Townsend, A., and Bodmer, H., "Antigen recognition by class I-restricted T lymphocytes," *Ann. Rev. Immunol.* 7:601-624, Annual Reviews, Inc. (1989).

VanCott, T.C., et al., "Antibodies with Specificity to Native gp120 and Neutralization Activity against Primary Human Immunodeficiency Virus Type 1 Isolates Elicited by Immunization with Oligomeric gp160," *J. Virol.* 71:4319-4330, American Society for Microbiology (1997).

Watkins, S.J., et al., "The 'adenobody' approach to viral targeting: specific and enhanced adenoviral gene delivery," *Gene Ther.* 4:1004-1012, Stockton Press (1997).

Willis, A.E., et al., "Immunological properties of foreign peptides in multiple display on a filamentous bacteriophage," *Gene* 128:79-83, Elsevier Science Publishers B.V. (1993).

Dialog File 351, Accession No. 9831660, Derwent WPI English language abstract for WO 94/06472 (Document AP3).

International Preliminary Examination Report for International Application No. PCT/IB99/01925, European Patent Office, Munich (Aug. 2000) (not for publication).

International Search Report for International Application No. PCT/IB99/01925, European Patent Office, Netherlands (Jun. 2000) (not for publication).

NCBI Entrez, GenBank Report, Accession No. P03153, from Seeger, C., et al. (Jan. 1990).

NCBI Entrez, GenBank Report, Accession No. X59397, from Jordan, C.T., et al. (Nov. 1991).

NCBI Entrez, GenBank Report, Accession No. 711678A, from Shipolini, R.A., et al. (Jul. 1992).

NCBI Entrez, GenBank Report, Accession No. M27603, from Orndorff, P.E., and Falkow, S. (Apr. 1993).

NCBI Entrez, GenBank Report, Accession No. M20706, from Nassal M. (Apr. 1993).

NCBI Entrez, GenBank Report, Accession No. AAA37490, from Rouvier E. (Jul. 1993).

NCBI Entrez, GenBank Report, Accession No. M90520, from Kew, M.C., et al. (Aug. 1993).

NCBI Entrez, GenBank Report, Accession No. X00981, from Klemm, P. (Sep. 1993).

NCBI Entrez, GenBank Report, Accession No. VCBPQB, from Maita, T., and Konigsberg, W. (Dec. 1993).

NCBI Entrez, GenBank Report, Accession No. AAA16663, from Kozlovska, T.M., et al. (Mar. 1994).

NCBI Entrez, GenBank Report, Accession No. X02514, from Yanisch-Perron, C., et al. (May 1994).

NCBI Entrez, GenBank Report, Accession No. X85256, from Lai, M.E., et al. (Apr. 1995).

NCBI Entrez, GenBank Report, Accession No. X85259, from Lai, M.E., et al., (Apr. 1995).

NCBI Entrez, GenBank Report, Accession No. X85260, from Lai, M.E., et al. (Apr. 1995).

NCBI Entrez, GenBank Report, Accession No. X85272, from Lai, M.E., et al. (Apr. 1995).

NCBI Entrez, GenBank Report, Accession No. X85275, from Lai, M.E., et al. (Apr. 1995).
NCBI Entrez, GenBank Report, Accession No. X85284, from Lai, M.E., et al. (Apr. 1995).
NCBI Entrez, GenBank Report, Accession No. X85285, from Lai, M.E., et al. (Apr. 1995).
NCBI Entrez, GenBank Report, Accession No. X85286, from Lai, M.E., et al. (Apr. 1995).
NCBI Entrez, GenBank Report, Accession No. X85287, from Lai, M.E., et al. (Apr. 1995).
NCBI Entrez, GenBank Report, Accession No. X85291, from Lai, M.E., et al. (Apr. 1995).
NCBI Entrez, GenBank Report, Accession No. X85293, from Lai, M.E., et al. (Apr. 1995).
NCBI Entrez, GenBank Report, Accession No. X85295, from Lai, M.E., et al. (Apr. 1995).
NCBI Entrez, GenBank Report, Accession No. X85296, from Lai, M.E., et al. (Apr. 1995).
NCBI Entrez, GenBank Report, Accession No. X85297, from Lai, M.E., et al. (Apr. 1995).
NCBI Entrez, GenBank Report, Accession No. X85298, from Lai, M.E., et al. (Apr. 1995).
NCBI Entrez, GenBank Report, Accession No. X85299, from Lai, M.E., et al. (Apr. 1995).
NCBI Entrez, GenBank Report, Accession No. X85301, from Lai, M.E., et al. (Apr. 1995).
NCBI Entrez, GenBank Report, Accession No. X85302, from Lai, M.E., et al. (Apr. 1995).
NCBI Entrez, GenBank Report, Accession No. X85303, from Lai, M.E., et al. (Apr. 1995).
NCBI Entrez, GenBank Report, Accession No. X85305, from Lai, M.E., et al. (Apr. 1995).
NCBI Entrez, GenBank Report, Accession No. X85307, from Lai, M.E., et al. (Apr. 1995).
NCBI Entrez, GenBank Report, Accession No. X85311, from Lai, M.E., et al. (Apr. 1995).
NCBI Entrez, GenBank Report, Accession No. X85314, from Lai, M.E., et al. (Apr. 1995).
NCBI Entrez, GenBank Report, Accession No. X85315, from Lai, M.E., et al. (Apr. 1995).
NCBI Entrez, GenBank Report, Accession No. X85316, from Lai, M.E., et al. (Apr. 1995).
NCBI Entrez, GenBank Report, Accession No. X85317, from Lai, M.E., et al. (Apr. 1995).
NCBI Entrez, GenBank Report, Accession No. X85319, from Lai, M.E., et al. (Apr. 1995).
NCBI Entrez, GenBank Report, Accession No. X80925, from Karayiannis, P. (Dec. 1995).
NCBI Entrez, GenBank Report, Accession No. AAC50341, from Yao, Z., et al. (Jan. 1996).
NCBI Entrez, GenBank Report, Accession No. X72702, from Preisler-Adams, S., et al. (Feb. 1996).
NCBI Entrez, GenBank Report, Accession No. VCBPR7, from Weber, K., et al. (Apr. 1996).
NCBI Entrez, GenBank Report, Accession No. 1604193A, from Gomez, F., et al. (Oct. 1996).
NCBI Entrez, GenBank Report, Accession No. B56338, from Hoffman, D.R. (May 1997).
NCBI Entrez, GenBank Report, Accession No. U95551, from Rao, B.S., et al. (Jun. 1997).
NCBI Entrez, GenBank Report, Accession No. S14764, from Vandermeers, A., et al. (Oct. 1997).
NCBI Entrez, GenBank Report, Accession No. P03611, from Weber, K., et al. (Nov. 1997).
NCBI Entrez, GenBank Report, Accession No. AAC14699, from Beekwilder, M.J., et al. (Apr. 1998).
NCBI Entrez, GenBank Report, Accession No. AAC14704, from Beekwilder, M.J., et al. (Apr. 1998).
NCBI Entrez, GenBank Report, Accession No. AF043593, from Gunther, S., et al. (May 1998).
NCBI Entrez, GenBank Report, Accession No. 1POC, from Scott, D.L., et al. (Sep. 1998).
NCBI Entrez, GenBank Report, Accession No. CAA30374, from Inokuchi, Y., et al. (Feb. 1999).
NCBI Entrez, GenBank Report, Accession No. X02496, from Bichko, V., et al. (Apr. 1999).
NCBI Entrez, GenBank Report, Accession No. MFIV62, from Cox, N.J., et al. (Jul. 1999).
NCBI Entrez, GenBank Report, Accession No. VCBPFR, from Wittmann-Liebold, B., et al. (Jul. 1999).
NCBI Entrez, GenBank Report, Accession No. A59055, from Hoffman, D.R., and Schmidt, J.O. (Aug. 1999).
NCBI Entrez, GenBank Report, Accession No. B59055, from Hoffman, D.R., and Schmidt, J.O. (Aug. 1999).
NCBI Entrez, GenBank Report, Accession No. AF051814, from Boyd, E.F., and Hartl, D.L. (Sep. 1999).
NCBI Entrez, GenBank Report, Accession No. AF051815, from Boyd, E.F., and Hartl, D.L. (Sep. 1999).
NCBI Entrez, GenBank Report, Accession No. AF110999, from Chang, S.F., et al. (Oct. 1999).
NCBI Entrez, GenBank Report, Accession No. AB033559, from Okamoto, H., et al. (Oct. 1999).
NCBI Entrez, GenBank Report, Accession No. AB010289, from Koseki, T., et al. (Dec. 1999).
NCBI Entrez, GenBank Report, Accession No. AJ132364, from Graupner, S., et al. (Apr. 2000).
NCBI Entrez, GenBank Report, Accession No. AF237482, from Johnson, J.R., et al. (May 2000).
NCBI Entrez, GenBank Report, Accession No. M32138, from Tong, S.P., et al. (Jul. 2000).
NCBI Entrez, GenBank Report, Accession No. AF229646, from Skerker, J.M., and Shapiro, L. (Aug. 2000).
NCBI Entrez, GenBank Report, Accession No. M95589, from Shi, H., et al. (Jan. 2001).
NCBI Entrez, GenBank Report, Accession No. VCBPM2, from Min Jou, W., et al. (Jan. 2001).
NCBI Entrez, GenBank Report, Accession No. AF323080, from Steppan, C.M., et al. (Jan. 2001).
NCBI Entrez, GenBank Report, Accession No. AF323081, from Steppan, C.M., et al. (Jan. 2001).
NCBI Entrez, GenBank Report, Accession No. U14003, from Plunkett, G., III, et al. (Jan. 2001).
NCBI Entrez, GenBank Report, Accession No. AF121239, from Hannoun, C., et al. (Feb. 2001).
NCBI Entrez, GenBank Report, Accession No. AF121240, from Hannoun, C., et al. (Feb. 2001).
NCBI Entrez, GenBank Report, Accession No. AF121242, from Hannoun, C., et al. (Feb. 2001).
NCBI Entrez, GenBank Report, Accession No. X59795, from Lai, M.E., et al. (Mar. 2001).
NCBI Entrez, GenBank Report, Accession No. X65257, from Lai, M.E., et al. (Mar. 2001).
NCBI Entrez, GenBank Report, Accession No. X65258, from Lai, M.E., et al. (Mar. 2001).
NCBI Entrez, GenBank Report, Accession No. AF151735, from Gerner, P., et al. (Apr. 2001).
NCBI Entrez, GenBank Report, Accession No. AJ000636, from Gousset, N., et al. (Nov. 2001).
NCBI Entrez, GenBank Report, Accession No. AAB59424, from Kenten, J.H., et al. (Feb. 2002).
NCBI Entrez, GenBank Report, Accession No. AAC06250, from Beekwilder, M.J., et al. (Mar. 2002).
NCBI Entrez, GenBank Report, Accession No. L09137, from Yanisch-Perron, C., et al. (May 2002).
NCBI Entrez, GenBank Report, Accession No. O09006, from Hromas, R., et al. (Jun. 2002).
NCBI Entrez, GenBank Report, Accession No. P40224, from Nagasawa, T., et al. (Jun. 2002).
NCBI Entrez, GenBank Report, Accession No. P34884, from Bernhagen, J., et al. (Jun. 2002).
NCBI Entrez, GenBank Report, Accession No. P06821, from Winter, G., et al. (Jun. 2002).
NCBI Entrez, GenBank Report, Accession No. P30904, from Sakai, M., et al. (Jun. 2002).

NCBI Entrez, GenBank Report, Accession No. NP_040754, from Inokuchi, Y., et al. (Jun. 2003).

NCBI Entrez, GenBank Report, Accession No. NP_061354, from Ishikawa, S., et al. (Sep. 2003).

NCBI Entrez, GenBank Report, Accession No. NP_031804, from Lenda, D.M., et al. (Sep. 2003).

NCBI Entrez, GenBank Report, Accession No. NP_006410, from Luther, S.A., et al. (Sep. 2003).

NCBI Entrez, GenBank Report, Accession No. NP_000748, from Yao, G.Q., et al. (Sep. 2003).

NCBI Entrez, GenBank Report, Accession No. P03069, from Hinnebusch, A.G., et al. (Sep. 2003).

NCBI Entrez, GenBank Report, Accession No. O00585, from Hromas, R., et al. (Sep. 2003).

NCBI Entrez, GenBank Report, Accession No. P14174, from Weiser, W.Y., et al. (Sep. 2003).

NCBI Entrez, GenBank Report, Accession No. P48061, from Spotila, L.D., et al. (Sep. 2003).

NCBI Entrez, GenBank Report, Accession No. P80003, from Vandermeers, A., et al. (Sep. 2003).

Swiss-Prot/TrEMBL, TN11_Mouse, Primary Accession No. O35235, entered in Swiss-Prot in Oct. 2001.

Swiss-Prot/TrEMBL, TN11_Human, Primary Accession No. O14788, entered in Swiss-Prot in Oct. 2001.

Co-pending U.S. Appl. No. 10/264,267, inventors Bachmann, M., filed Oct. 4, 2002 (Not Published).

Co-pending U.S. Appl. No. 10/289,456, inventors Bachmann et al., filed Nov. 7, 2002 (Not Published).

Co-pending U.S. Appl. No. 10/617,876, inventors Bachmann et al., filed Jul. 14, 2003 (Not Published).

Co-pending U.S. Appl. No. 10/346,190, inventors Bachmann et al., filed Jan. 17, 2003 (Not Published).

Co-pending U.S. Appl. No. 10/622,064, inventors Bachmann et al., filed Jul. 18, 2003 (Not Published).

Co-pending U.S. Appl. No. 10/622,124, inventors Bachmann et al., filed Jul. 18, 2003 (Not Published).

Jegerlehner, A., et al., "A molecular assembly system that renders antigens of choice highly repetitive for induction of protective B cell responses," *Vaccine* 20:3104-3112, Elsevier Science, Ltd. (Aug. 2002).

*The Biology of Animal Viruses*, 2nd ed., Fenner, F., et al., eds., Academic Press, New York, NY, pp. 117-119 (1974).

NCBI Entrez, PubMed Abstract, PMID: 2205968, Diallo, A., et al., "Morbillivirus group: genome organization and proteins," *Vet. Microbiol.* 23:155-163 (1990).

* cited by examiner

AMYLOID β1-6 ANTIGEN ARRAYS

CROSS REFERENCE TO RELATED APPLICATIONS

The present application is a nonprovisional of U.S. Provisional Application Nos. 60/396,639, filed Jul. 19, 2002; and 60/470,432, filed May 15, 2003; both of which applications are entirely incorporated by reference herein.

BACKGROUND OF THE INVENTION

1. Field of the Invention

The present invention is related to the fields of molecular biology, virology, immunology and medicine. The invention provides a composition comprising an ordered and repetitive antigen or antigenic determinant array, and in particular an Aβ1-6 peptide-VLP-composition. More specifically, the invention provides a composition comprising a virus-like particle and at least one Aβ1-6 peptide bound thereto. The invention also provides a process for producing the conjugates and the ordered and repetitive arrays, respectively. The compositions of the invention are useful in the production of vaccines for the treatment of Alzheimer's disease and as a pharmaccine to prevent or cure Alzheimer's disease and to efficiently induce immune responses, in particular antibody responses. Furthermore, the compositions of the invention are particularly useful to efficiently induce self-specific immune responses within the indicated context.

2. Related Art

Alzheimer's disease (AD) is the most common cause of dementia among the elderly (age 65 and older) and a serious burden for public health. For example, 4 million people are reported to suffer from the disease in the United Sates of America. The incidence of the disease is expected to increase as the population ages.

The main pathological signs of Alzheimer's disease are age-related changes in behaviour, deposition of β-amyloid into insoluble plaques, called the neuritic plaques or AD plaques, neurofibrillary tangles composed of tau protein within neurons, and loss of neurons throughout the forebrain. In addition to the late onset AD, which occurs in old age (65 years and more), there is an early onset AD, familial AD (FAD) occurring between age 35 and 60. The pathological abnormalities of AD are more widespread, severe and occur earlier in FAD than in late onset or sporadic AD. Mutations in the APP gene, the presenilin 1 and the presenilin 2 genes have been correlated with FAD.

As indicated, one of the key events in Alzheimer's Disease (AD) is the deposition of amyloid as insoluble fibrous masses (amyloidogenesis) resulting in extracellular neuritic plaques and deposits around the walls of cerebral blood vessels (for review see Selkoe, D. J. (1999) Nature. 399, A23-31). The major constituent of the neuritic plaques and congophilic angiopathy is amyloid β (Aβ), although these deposits also contain other proteins such as glycosaminoglycans and apolipoproteins. Aβ is proteolytically cleaved from a much larger glycoprotein known as Amyloid Precursor Protein (APP), which comprises isoforms of 695-770 amino acids with a single hydrophobic transmembrane region. Aβ forms a group of peptides up to 43 amino acids in length showing considerable amino- and carboxy-terminal heterogeneity (truncation) as well as modifications (Roher, A. E., Palmer, K. C., Chau, V., & Ball, M. J. (1988) J. Cell Biol. 107, 2703-2716. Roher, A. E., Palmer, K. C., Yurewicz, E. C., Ball, M. J., & Greenberg, B. D. (1993) J. Neurochem. 61, 1916-1926). Prominent isoforms are Aβ1-40 and 1-42. It has a high propensity to form β-sheets aggregating into fibrils, which ultimately leads to the amyloid.

Aβ peptide has a central role in the neuropathology of Alzheimers disease. Region specific, extracellular accumulation of Aβ peptide is accompanied by microgliosis, cytoskeletal changes, dystrophic neuritis and synaptic loss. These pathological alterations are thought to be linked to the cognitive decline that defines the disease.

Administration of amyloid beta protein or, in particular, Aβ1-28 in amounts of up to $10^{-2}$ mg/dose in the absence of any adjuvants and without any linkage of the amyloid beta protein or Aβ1-28 to a carrier, for the treatment of Alzheimer's disease, is described in EP 526'511.

Others have used administration of Aβ peptides in combination with adjuvants, to induce an immune response, cellular or humoral, against Aβ1-42. In a transgenic mouse model of Alzheimer disease, animals overexpress human amyloid precursor protein containing the mutation APP (717)V-F (PDAPP-mice; Johnson-Wood, K. et al., Proc. Natl. Acad. USA 94: 1550-1555, Games, D. et al., Nature 373: 523-527 (1995a)), leading to overproduction of $A\beta_{1-42}$, develop plaques, dystrophic neuritis, loss of presynaptic terminals, astrocytosis and microgliosis. In a recent study, Schenk, D. et al., (Nature 400:173-77 (1999) and WO 99/27944) report that administration of aggregated $A\beta_{1-42}$ mixed with a strong adjuvant (CFA/IFA), which cannot be used in humans, in the first 4 immunizations, followed by administration of aggregated Aβ1-42 in PBS in the subsequent immunizations, to PDAPP-mice at 6 weeks of age, essentially prevented plaque formation and associated dystrophic neuritis. The same authors reported that immunization of older mice (11 months of age) using the same strategy markedly reduced the extent and progression of Alzheimer's disease (AD)-like neuropathologies. Proliferation of splenocytes from mice immunized using the aforementioned strategy was reported in Example III (Screen for therapeutic Efficacy against established AD) of WO 99/27944, showing that Aβ1-42 specific T-cells were induced by the vaccination procedure. Coupling of Aβ fragments to sheep anti-mouse IgG, and immunization of said coupled fragment in the presence of the adjuvant CFA/IFA is reported in WO 9927944. The use of compositions comprising Aβ fragments linked to polypeptides such as diphtheria toxin for promoting an immune response against Aβ is also disclosed in WO 99/27944. However, no data of immunization are provided.

A monoclonal antibody recognizing an epitope within the N-terminus (1-16) of Aβ (antibody 6C6) has been shown to protect PC12 cells from neurotoxicity of fibrillar β-amyloid, and to disaggregate β-amyloid in vitro (Solomon B. et al., Proc. Natl. Acad. Sci. USA (1997)). A monoclonal antibody raised against Aβ1-28, was also shown to suppress β-amyloid aggregation in vitro (Solomon B. et al., Proc. Natl. Acad. Sci. USA (1996)). Frenkel et al., (J. Neuroimmunol. 88: 85-90 (1998)) have later identified the epitope of two anti-aggregating antibodies, 10D5 and 6C6, as being the epitope "EFRH", i.e. Aβ3-6. In contrast, an antibody specific for Aβ1-7 was unable to prevent β-amyloid aggregation (Frenkel D. et al., J. Neuroimmunol. 95: 136-142 (1999)).

Aβ1-42 is fibrillogenic, and indeed, the vaccine composition described in WO 99/27944 used Aβ1-42 treated in such a way that it can form aggregates. It has been shown that those fibrils are toxic for neuronal cell cultures (Yankner et al., Science 245: 417-420 (1989)), and that a toxic effect is also observed when injected into animal brains (Sigurdson et al., Neurobiol. Aging 17: 893-901 (1996); Sigurdson et al., Neurobiol. Aging 18: 591-608 (1997)). Walsh et al., (Nature 416:535-539 (2002)) report that natural oligomers of Aβ are formed within intracellular vesicles. Those oligomers inhibited long term potentiation in rats in vivo and disrupted synaptic plasticity at concentrations found in human brain and cerebrospinal fluid.

In another study, Bard, F. et al. (*Nature Medicine* 6:916-19 (2000)) reported that peripheral administration of antibodies raised against $A\beta_{1-42}$, was able to reduce amyloid burden, despite relatively modest serum levels. This study utilized either polyclonal antibodies raised against $A\beta_{1-42}$, or monoclonal antibodies raised against synthetic fragments derived from different regions of $A\beta$. Thus induction of antibodies against $A\beta$ peptides bears promises as a potential therapeutic treatment for Alzheimer disease.

Mucosal administration of an antigen associated with $\beta$-amyloid plaques, such as $\beta$-amyloid peptide and $A\beta 1$-40, has been described in WO99/27949. Mucosal administration is said to suppress certain cytokine responses associated with Alzheimer's disease, and to enhance certain other cytokine responses associated with the suppression of inflammatory responses linked to the disease. It is thought that suppression of the inflammatory responses is effected by the "elicitation of T-cells characterized by an anti-inflammatory cytokine profile". Suitable antigens, as described in WO9927949, include antigens specific for AD, and which are recognized by immune T-cells of a human or animal host.

Fusion of epitopes of a monoclonal antibody recognizing $A\beta$ to coat proteins of filamentous phages is described in WO 01/18169. Immunization of mice with the filamentous phages displaying the 15-mer epitope VHEPHEFRHVALNPV (SEQ ID NO: 89) on the coat protein VIII resulted in antibodies recognizing $A\beta 1$-16, and $A\beta 1$-40. This was demonstrated in an inhibition ELISA using $A\beta$ peptides, and an IC50 of 1 µM was found for inhibition of the binding of the sera to $A\beta 1$-16 with $A\beta 1$-40. Solomon (WO 01/18169), however, provides no indication that the sera elicited against the filamentous phages carrying the VHEPHEFRHVALNPV epitope (SEQ ID NO: 89), bind to amyloid plaques or neuritic plaques of AD.

There are a number of drawbacks in using sequences differing from the antigen against which an immune response is to be elicited for immunization. First, antibodies against part of the sequence foreign to the antigen or antigenic determinant may be induced. Second, the conformation of the antigen in the context of the foreign flanking sequence element may be different than in the context of the full-length antigen. Thus, although antibodies cross-reacting to the antigen may be elicited, their binding to the antigen may be suboptimal. The fine specificity of those elicited antibody may also not correspond to the specificity of antibodies elicited against the antigen itself, as additional sid-chains different from the residues present on the full-length $A\beta$ are present in the epitope. Finally, a 15-mer amino-acid sequence may contain T-cell epitopes. Display of the epitope YYEFRH (SEQ ID NO: 90) on the protein III of filamentous phage coat, of which 3-5 copies only are usually present on each phage, is also disclosed in WO 01/18169. Several problems arise when using infectious phages as carrier for immunization. First, production of infectious agents in large scale and in sufficient quantity for large immunization campaigns is problematic. Second, the presence of the DNA of the phage containing antibiotic resistance genes in the vaccine is not unproblematic and is a safety issue. Finally, the feasibility and efficacy of irradiation of large quantities of phages, in the case where non-infectious phages are used as vaccine, is unresolved.

$A\beta$ analogues, wherein $A\beta$ is modified to include T helper epitopes have been described (WO 01/62284). Immunization of TgRND8+ mice, transgenic for human APP, with the $A\beta$ analogue resulted in a 4- to 7.5-fold higher antibody titer over immunization with $A\beta 1$-42 in the absence of adjuvant.

Recent studies demonstrated that a vaccination-induced reduction in brain amyloid deposits has the potential to improve cognitive functions (Schenk, D., et al. *Nature* 400: 173-177 (1999); Janus, C. et al., *Nature* 408: 979-982 (2000); Morgan, D. et al., *Nature* 408: 982-985 (2000)).

The autopsy of a patient immunised with aggregated $A\beta 1$-42 in the Adjuvant QS21 has revealed the presence of a T-lymphocyte meningoencephalitis and infiltration of cerebral white matter by macrophages (Nicoll, J. A. et al., Nature Med. 9: 448-452 (2003)).

Recently, a publication has reported 18 cases of meningoencephalitis in patients immunized by the AN1792, a vaccine composed of aggregated $A\beta 1$-42 and QS-21 as adjuvant (Orgogozo J.-M. et al., Neurology 61: 46-54 (2003)). T-cell activation is reported as a potential mechanism responsible for the disease, while there was no clear relation between disease and anti-$A\beta 1$-42 titers in the serum.

It is well established that the administration of purified proteins alone is usually not sufficient to elicit a strong immune response; isolated antigen generally must be given together with helper substances called adjuvants. Within these adjuvants, the administered antigen is protected against rapid degradation, and the adjuvant provides an extended release of a low level of antigen. In the present invention, $A\beta$ peptides are made immunogenic through binding to a VLP and do not require an adjuvant.

One way to improve the efficiency of vaccination is thus to increase the degree of repetitiveness of the antigen applied. Unlike isolated proteins, viruses induce prompt and efficient immune responses in the absence of any adjuvants both with and without T-cell help (Bachmann and Zinkernagel, *Ann. Rev. Immunol:* 15:235-270 (1991)). Although viruses often consist of few proteins, they are able to trigger much stronger immune responses than their isolated components. For B-cell responses, it is known that one crucial factor for the immunogenicity of viruses is the repetitiveness and order of surface epitopes. Many viruses exhibit a quasi-crystalline surface that displays a regular array of epitopes which efficiently crosslinks epitope-specific immunoglobulins on B cells (Bachmann and Zinkernagel, *Immunol. Today* 17:553-558 (1996)). This crosslinking of surface immunoglobulins on B cells is a strong activation signal that directly induces cell-cycle progression and the production of 1 gM antibodies. Further, such triggered B cells are able to activate T helper cells, which in turn induce a switch from IgM to IgG antibody production in B cells and the generation of long-lived B cell memory—the goal of any vaccination (Bachmann and Zinkernagel, *Ann. Rev. Immunol.* 15:235-270 (1997)). Viral structure is even linked to the generation of anti-antibodies in autoimmune disease and as a part of the natural response to pathogens (see Fehr, T., et al., *J Exp. Med.* 185:1785-1792 (1997)). Thus, antibodies presented by a highly organized viral surface are able to induce strong anti-antibody responses.

As indicated, however, the immune system usually fails to produce antibodies against self-derived structures. For soluble antigens present at low concentrations, this is due to tolerance at the Th cell level. Under these conditions, coupling the self-antigen to a carrier that can deliver T help may break tolerance. For soluble proteins present at high concentrations or membrane proteins at low concentration, B and Th cells may be tolerant. However, B cell tolerance may be reversible (anergy) and can be broken by administration of the antigen in a highly organized fashion coupled to a foreign carrier (Bachmann and Zinkernagel, *Ann. Rev. Immunol.* 15:235-270 (1997)). As shown in pending U.S. application Ser. No. 10/050,902 filed on Jan. 18, 2002, strong immune responses could be induced with compositions comprising Aβ peptides (Aβ1-15, Aβ1-27 and Aβ33-42, which is a self-antigen in mice) bound to a VLP. In particular, the aforementioned human Aβ peptides bound to the VLP of RNA phage Qβ induced high Aβ specific titers in human APP transgenic mice (described in Example) demonstrating that tolerance to the self-antigen Aβ could be overcome by immunizing with Aβ peptides bound to a VLP.

There is thus a need for highly immunogenic safe compositions and vaccines, respectively, to treat Alzheimer diseases, in particular, using immunogens devoid of T-cell epitopes and adjuvants, respectively, which might elicit side-effects, and still being capable of inducing high antibody titers, which antibodies, furthermore, being capable of binding to amyloid plaques.

BRIEF SUMMARY OF THE INVENTION

We have now found that Aβ1-6 peptide, which is bound to a core particle having a structure with an inherent repetitive organization, and hereby in particular to virus-like-particles (VLPs) and subunits of VLPs, respectively, leading to highly ordered and repetitive conjugates represent a potent immunogen for the induction of antibodies specific for Aβ1-6. Therefore, the present invention provides a prophylactic and therapeutic mean for the treatment of Alzheimer's disease, which is based on an ordered and repetitive Aβ1-6-core particle array, and in particular on a VLP-Aβ1-6 peptide conjugate and -array, respectively. This prophylactic and therapeutic is able to induce high titers of anti-Aβ1-6 peptide antibodies, which are cross-reactive to soluble Aβ and are capable of binding to human amyloid plaques of a human APP transgenic mouse model and to AD amyloid plaques. Furthermore, the elicited antibodies do not bind to APP on brain sections.

Moreover, the present invention provides for new compositions, vaccines and methods of treatment of AD. The compositions and vaccines comprising Aβ1-6 peptides are devoid of T-cell epitopes and induce antibodies binding AD plaques and soluble Aβ. The Aβ1-6 peptides are presented to the immune system of the patient in a highly repetitive and ordered fashion through binding of the Aβ peptides or to a core particle, preferably to a VLP, and even more preferably to a VLP of a RNA phage.

In a preferred embodiment, the antigen or antigenic determinant is the human amyloid beta peptide Aβ1-6 (DAEFRH; SEQ ID NO: 75) being a fragment of Aβ (DAEFRHDSGYEVHHQKLVFFAEDVGSNK-GAIIGLMVGGVVIA (SEQ ID NO: 91), wherein the human amyloid beta peptide Aβ1-6 is bound to the core particle and VLP, respectively. The amyloid beta protein is provided in SEQ ID NO: 92. The amyloid beta precursor protein is provided in SEQ ID NO: 93.

The present invention, thus, provides for a composition comprising: (a) a core particle with at least one first attachment site; and (b) at least one antigen or antigenic determinant with at least one second attachment site, wherein said antigen or antigenic determinant is a Aβ1-6 peptide, and wherein said second attachment site being selected from the group consisting of (i) an attachment site not naturally occurring with said antigen or antigenic determinant; and (ii) an attachment site naturally occurring with said antigen or antigenic determinant, wherein said second attachment site is capable of association to said first attachment site; and wherein said antigen or antigenic determinant and said core particle interact through said association to form an ordered and repetitive antigen array. Preferred embodiments of core particles suitable for use in the present invention are a virus, a virus-like particle, a bacteriophage, a virus-like particle of a RNA-phage, a bacterial pilus or flagella or any other core particle having an inherent repetitive structure capable of forming an ordered and repetitive antigen array in accordance with the present invention.

The Aβ fragments of the present invention are soluble and generally do not form aggregates. Moreover, they are bound, and preferably covalently bound to a core particle and VLP, respectively. Therefore, the compositions of the invention do not bear the risk of inducing toxic effects such as seeding of amyloid deposition.

It is an unexpected finding of this invention that a high titer of antibodies cross-reactive with soluble Aβ and AD amyloid plaques could be obtained with a composition comprising the Aβ1-6 peptide bound to a a core particle and VLP, respectively. In particular, VLP have been shown to mediate induction of antibodies against self antigens, thus breaking self-tolerance (WO 02/056905, the disclosure of which is herewith incorporated by reference in its entirety). Furthermore, the small size of this epitope precludes the presence of T-cell epitopes, thus providing new compositions that do not induce Aβ specific T-cell responses. In addition, the elicited antibodies do not bind to APP on brain sections. Thus, the present invention provides for a safe vaccine composition for the prevention and treatment of AD.

More specifically, the invention provides a composition comprising an ordered and repetitive antigen or antigenic determinant array, and hereby in particular Aβ1-6 peptide VLP conjugates. More specifically, the invention provides a composition comprising a virus-like particle and at least one Aβ1-6 peptide bound thereto. The invention also provides a process for producing the conjugates and the ordered and repetitive arrays, respectively. The compositions of the invention are useful in the production of vaccines for the treatment of Alzheimer's disease and as a pharmaccine to prevent or cure Alzheimer's disease and to efficiently induce immune responses, in particular antibody responses. Furthermore, the compositions of the invention are particularly useful to efficiently induce self-specific immune responses within the indicated context.

In the present invention, a Aβ1-6 peptide is bound to a core particle and VLP, respectively, typically in an oriented manner, yielding an ordered and repetitive Aβ1-6 peptide antigen array. Furthermore, the highly repetitive and organized structure of the core particles and VLPs, respectively, mediates the display of the Aβ peptide in a highly ordered and repetitive fashion leading to a highly organized and repetitive antigen array. Furthermore, binding of the Aβ1-6 peptide to the core particle and VLP, respectively, provides T helper cell epitopes, since the core particle and VLP is foreign to the host immunized with the core particle-Aβ1-6 peptide array and VLP-Aβ1-6 peptide array, respectively. Those arrays differ from prior art conjugates, in particular, in their highly organized structure, dimensions, and in the repetitiveness of the antigen on the surface of the array.

In one aspect of the invention, the Aβ1-6 peptide is chemically synthesized, while the core particle and the VLP, repespectively, is expressed and purified from an expression host suitable for the folding and assembly of the core particle and the VLP, repespectively. The Aβ1-6 peptide array is then assembled by binding the Aβ1-6 peptide to the core particle and the VLP, repespectively.

In another aspect, the present invention provides for a composition comprising (a) a virus-like particle, and (b) at least one antigen or antigenic determinant, wherein said antigen or said antigenic determinant is an Aβ1-6 peptide, and wherein said at least one antigen or antigenic determinant is bound to said virus-like particle.

In a further aspect, the present invention provides for a pharmaceutical composition comprising (a) the inventive composition, and (b) an acceptable pharmaceutical carrier.

In still a further aspect, the present invention provides for a vaccine composition comprising a composition, wherein said composition comprising (a) a virus-like particle; and (b) at least one antigen or antigenic determinant, wherein said antigen or said antigenic determinant is a Aβ1-6 peptide; and wherein said at least one antigen or antigenic determinant is bound to said virus-like particle.

In another aspect, the present invention provides for a method of immunization comprising administering the inventive composition, the inventive pharmaceutical composition or the inventive vaccine to an animal.

In still a further aspect, the present invention provides for a process for producing an inventive composition comprising (a) providing a virus-like particle; and (b) providing at least one antigen or antigenic determinant, wherein said antigen or said antigenic determinant is a Aβ1-6 peptide; (c) combining said virus-like particle and said at least one antigen or antigenic determinant so that said at least one antigen or antigenic determinant is bound to said virus-like particle.

Analogously, the present invention provides a process for producing a composition of claim 1 comprising: (a) providing a core particle with at least one first attachment site; (b) providing at least one antigen or antigenic determinant with at least one second attachment site, wherein said antigen or antigenic determinant is a Aβ1-6 peptide, and wherein said second attachment site being selected from the group consisting of (i) an attachment site not naturally occurring with said antigen or antigenic determinant; and (ii) an attachment site naturally occurring with said antigen or antigenic determinant; and wherein said second attachment site is capable of association to said first attachment site; and (c) combining said core particle and said at least one antigen or antigenic determinant, wherein said antigen or antigenic determinant and said core particle interact through said association to form an ordered and repetitive antigen array.

In a further aspect, the present invention provides for a use of a composition of claim 1 for the manufacture of a medicament for treatment of Alzheimer's disease.

In a still further aspect, the present invention provides for a use of a composition of claim 1 for the preparation of a medicament for the therapeutic or prophylactic treatment of Alzheimer's disease. Furthermore, in a still further aspect, the present invention provides for a use of a composition of claim 1, either in isolation or in combination with other agents, or with explicit absence of specific substances such as adjuvants, for the manufacture of a composition, pharmaceutical composition, vaccine, drug or medicament for therapy or prophylaxis of Alzheimer's disease, and/or for stimulating the mammalian immune system.

Therefore, the invention provides, in particular, vaccine compositions which are suitable for preventing and/or attenuating Alzheimer's disease or conditions related thereto. The invention further provides immunization and vaccination methods, respectively, for preventing and/or attenuating Alzheimer's disease or conditions related thereto in humans. The inventive compositions may be used prophylactically or therapeutically.

In specific embodiments, the invention provides methods for preventing and/or attenuating Alzheimer's disease or conditions related thereto which are caused or exacerbated by "self" gene products, i.e. "self antigens" as used herein. In related embodiments, the invention provides methods for inducing immunological responses in animals and individuals, respectively, which lead to the production of antibodies that prevent and/or attenuate Alzheimer's disease or conditions related thereto, which are caused or exacerbated by "self" gene products.

As would be understood by one of ordinary skill in the art, when compositions of the invention are administered to an animal or a human, they may be in a composition which contains salts, buffers, adjuvants, or other substances which are desirable for improving the efficacy of the composition. Examples of materials suitable for use in preparing pharmaceutical compositions are provided in numerous sources including *Remington's Pharmaceutical Sciences* (Osol, A, ed., Mack Publishing Co. (1990)).

Compositions of the invention are said to be "pharmacologically acceptable" if their administration can be tolerated by a recipient individual. Further, the compositions of the invention will be administered in a "therapeutically effective amount" (i.e., an amount that produces a desired physiological effect).

The compositions of the present invention may be administered by various methods known in the art, but will normally be administered by injection, infusion, inhalation, oral administration, or other suitable physical methods. The compositions may alternatively be administered intramuscularly, intravenously, or subcutaneously. Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

Other embodiments of the present invention will be apparent to one of ordinary skill in light of what is known in the art, the following drawings and description of the invention, and the claims.

DETAILED DESCRIPTION OF THE INVENTION

Figure 1:
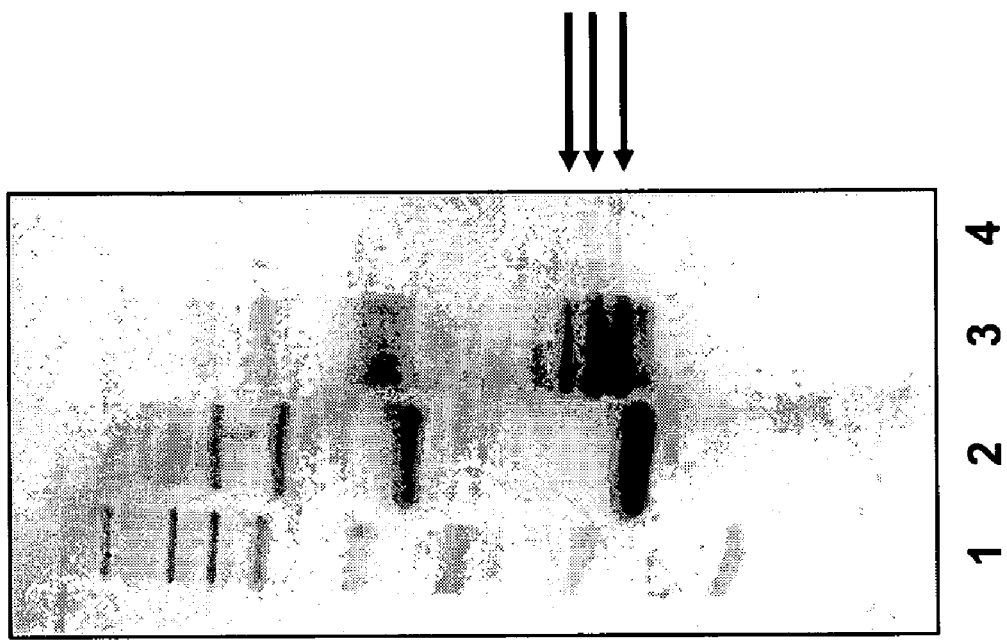
FIG. 1 depicts the SDS-PAGE gel, run under reducing conditions, showing the result of the coupling of the Aβ1-6 peptide (NH2-DAEFRHGGC-CONH2) (SEQ ID NO: 77) to the VLP of Qβ coat protein.
Figure 2:
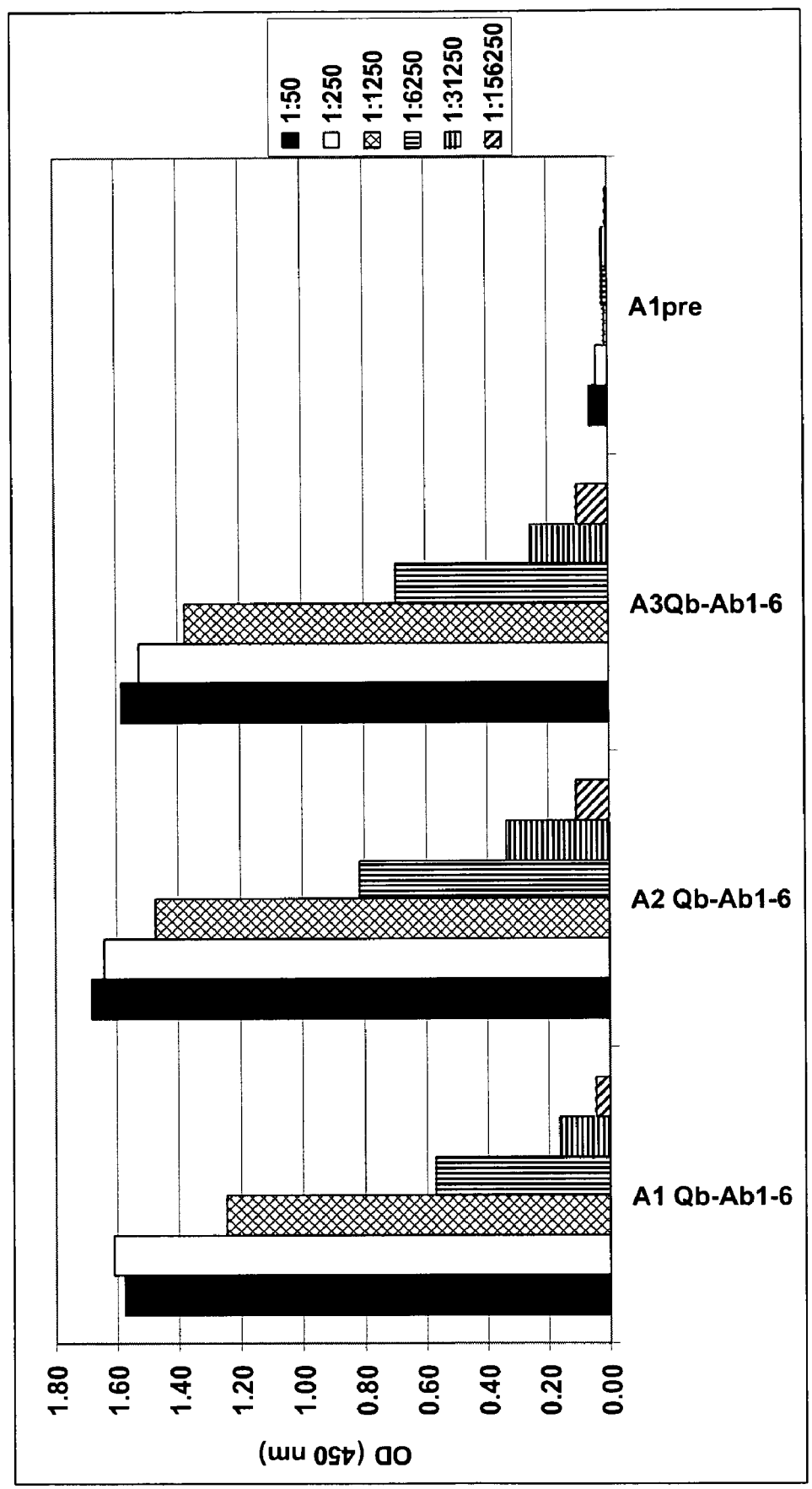
FIG. 2 shows the ELISA analysis of the antibodies specific for Aβ1-6 in sera of mice immunized with Aβ1-6 peptide coupled to the VLP of Qβ coat protein.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are hereinafter described.

1. Definitions:

Aβ1-6 peptide: An Aβ1-6 peptide as used herein refers to peptides having a sequence corresponding to the human Aβ1-6 sequence, or homologous to the human Aβ1-6 sequence. Sequences homologuous to the human Aβ1-6 sequence include, but are not limited to the Aβ1-6 sequences of other species and hereby including, but not limited to, the sequence of primate, rabbit, guinea pig, *Xenopus Laevis*, frog, mouse and rat Aβ1-6. The Aβ1-6 sequences from *Xenopus Laevis* or frog, although differing from human Aβ1-6 at two positions, have conservative mutations (Ala-Ser, Phe-Tyr), and are still considered to be homologuous to Aβ1-6 in accordance with this definition. In accordance with the present invention, however, the Aβ1-6 peptide is typically modified, such that a second attachment site is attached thereto. Preferably, the second attachment site is modified with a linker or an amino acid linker comprising a second attachment site for binding to a core particle and VLP, respectively. While referring herein to Aβ1-6 peptides, a modified Aβ1-6 peptide, as indicated above, i.e. Aβ1-6 peptides with a second attachment site attached thereto, shall be encompassed. Typically, however, the modifications are explicitly indicated in the specification. Further preferred embodiments of an Aβ1-6 peptide being an antigen or antigenic determinant in accordance with the present invention become apparent as this specification proceeds.

Adjuvant: The term "adjuvant" as used herein refers to non-specific stimulators of the immune response or substances that allow generation of a depot in the host which when combined with the vaccine and pharmaceutical composition, respectively, of the present invention may provide for an even more enhanced immune response. A variety of adjuvants can be used. Examples include complete and incomplete Freund's adjuvant, aluminum hydroxide and modified muramyldipeptide. Further adjuvants are mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art. Further adjuvants that can be administered with the compositions of the invention include, but are not limited to, Monophosphoryl lipid immunomodulator, AdjuVax 100a, QS-21, QS-18, CRL1005, Aluminum salts (Alum), MF-59, OM-174, OM-197, OM-294, and Virosomal adjuvant technology. The adjuvants can also comprise a mixture of these substances.

Immunologically active saponin fractions having adjuvant activity derived from the bark of the South American tree Quillaja Saponaria Molina are known in the art. For example QS21, also known as QA21, is an Hplc purified fraction from the Quillaja Saponaria Molina tree and it's method of its production is disclosed (as QA21) in U.S. Pat. No. 5,057,540. Quillaja saponin has also been disclosed as an adjuvant by Scott et al, Int. Archs. Allergy Appl. Immun., 1985, 77, 409. Monosphoryl lipid A and derivatives thereof are known in the art. A preferred derivative is 3 de-o-acylated monophosphoryl lipid A, and is known from British Patent No. 2220211. Further preferred adjuvants are described in WO00/00462, the disclosure of which is herein incorporated by reference.

However, an advantageous feature of the present invention is the high immunogenicty of the inventive compositions. As already outlined herein or will become apparent as this specification proceeds, vaccines and pharmaceutical compositions devoid of adjuvants are provided, in further alternative or preferred embodiments, leading to vaccines and pharmaceutical compositions for treating AD being devoid of adjuvants and, thus, having a superior safety profile since adjuvants may cause side-effects. The term "devoid" as used herein in the context of vaccines and pharmaceutical compositions for treating AD refers to vaccines and pharmaceutical compositions that are used without adjuvants.

Amino acid linker: An "amino acid linker", or also just termed "linker" within this specification, as used herein, either associates the antigen or antigenic determinant with the second attachment site, or more preferably, already comprises or contains the second attachment site, typically—but not necessarily—as one amino acid residue, preferably as a cysteine residue. The term "amino acid linker" as used herein, however, does not intend to imply that such an amino acid linker consists exclusively of amino acid residues, even if an amino acid linker consisting of amino acid residues is a preferred embodiment of the present invention. The amino acid residues of the amino acid linker are, preferably, composed of naturally occurring amino acids or unnatural amino acids known in the art, all-L or all-D or mixtures thereof. However, an amino acid linker comprising a molecule with a sulfhydryl group or cysteine residue is also encompassed within the invention. Such a molecule comprise preferably a C1-C6 alkyl-, cycloalkyl (C5,C6), aryl or heteroaryl moiety. However, in addition to an amino acid linker, a linker comprising preferably a C1-C6 alkyl-, cycloalkyl-(C5,C6), aryl- or heteroaryl-moiety and devoid of any amino acid(s) shall also be encompassed within the scope of the invention. Association between the antigen or antigenic determinant or optionally the second attachment site and the amino acid linker is preferably by way of at least one covalent bond, more preferably by way of at least one peptide bond.

Animal: As used herein, the term "animal" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

Antibody: As used herein, the term "antibody" refers to molecules which are capable of binding an epitope or antigenic determinant. The term is meant to include whole antibodies and antigen-binding fragments thereof, including single-chain antibodies. Most preferably the antibodies are human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies can be from any animal origin including birds and mammals. Preferably, the antibodies are human, murine, rabbit, goat, guinea pig, camel, horse or chicken. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598 by Kucherlapati et al.

Antigen: As used herein, the term "antigen" refers to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

Antigenic determinant: As used herein, the term "antigenic determinant" is meant to refer to that portion of an antigen that is specifically recognized by either B- or T-lymphocytes. B-lymphocytes responding to antigenic determinants produce antibodies, whereas T-lymphocytes respond to antigenic determinants by proliferation and establishment of effector functions critical for the mediation of cellular and/or humoral immunity.

Association: As used herein, the term "association" as it applies to the first and second attachment sites, refers to the binding of the first and second attachment sites that is preferably by way of at least one non-peptide bond. The nature of the association may be covalent, ionic, hydrophobic, polar or any combination thereof, preferably the nature of the association is covalent.

Attachment Site, First: As used herein, the phrase "first attachment site" refers to an element of non-natural or natural origin, to which the second attachment site located on the antigen or antigenic determinant may associate. The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. The first attachment site is located, typically and preferably on the surface, of the core particle such as, preferably the virus-like particle. Multiple first attachment sites are present on the surface of the core and virus-like particle, respectively, typically in a repetitive configuration.

Attachment Site, Second: As used herein, the phrase "second attachment site" refers to an element associated with the antigen or antigenic determinant to which the first attachment site located on the surface of the core particle and virus-like particle, respectively, may associate. The second attachment site of the antigen or antigenic determinant may be a protein, a polypeptide, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. At least one second attachment site is present on the antigen or antigenic determinant. The term "antigen or antigenic determinant with at least one second attachment site" refers, therefore, to an antigen or antigenic construct comprising at least the antigen or antigenic determinant and the second attachment site. However, in particular for a second attachment site, which is of non-natural origin, i.e. not naturally occurring within the antigen or antigenic determinant, these antigen or antigenic constructs comprise an "amino acid linker".

Bound: As used herein, the term "bound" refers to binding or attachment that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term "bound" is broader than and includes terms such as "coupled," "fused" and "attached".

Coat protein(s): As used herein, the term "coat protein(s)" refers to the protein(s) of a bacteriophage or a RNA-phage capable of being incorporated within the capsid assembly of the bacteriophage or the RNA-phage. However, when referring to the specific gene product of the coat protein gene of RNA-phages the term "CP" is used. For example, the specific gene product of the coat protein gene of RNA-phage Qβ is referred to as "Qβ CP", whereas the "coat proteins" of bacteriophage Qβ comprise the "Qβ CP" as well as the A1 protein. The capsid of Bacteriophage Qβ is composed mainly of the Qβ CP, with a minor content of the A1 protein. Likewise, the VLP Qβ coat protein contains mainly Qβ CP, with a minor content of A1 protein.

Core particle: As used herein, the term "core particle" refers to a rigid structure with an inherent repetitive organization. A core particle as used herein may be the product of a synthetic process or the product of a biological process.

Coupled: The term "coupled", as used herein, refers to attachment by covalent bonds or by strong non-covalent interactions, typically and preferably to attachment by covalent bonds. Any method normally used by those skilled in the art for the coupling of biologically active materials can be used in the present invention.

Effective Amount: As used herein, the term "effective amount" refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

Epitope: As used herein, the term "epitope" refers to continuous or discontinuous portions of a polypeptide having antigenic or immunogenic activity in an animal, preferably a mammal, and most preferably in a human. An epitope is recognized by an antibody or a T cell through its T cell receptor in the context of an MHC molecule. An "immunogenic epitope," as used herein, is defined as a portion of a polypeptide that elicits an antibody response or induces a T-cell response in an animal, as determined by any method known in the art. (See, for example, Geysen et al., *Proc. Natl. Acad. Sci. USA* 81:3998-4002 (1983)). The term "antigenic epitope," as used herein, is defined as a portion of a protein to which an antibody can immunospecifically bind its antigen as determined by any method well known in the art. Immunospecific binding excludes non-specific binding but does not necessarily exclude cross-reactivity with other antigens. Antigenic epitopes need not necessarily be immunogenic. Antigenic epitopes can also be T-cell epitopes, in which case they can be bound immunospecifically by a T-cell receptor within the context of an MHC molecule.

An epitope can comprise 3 amino acids in a spatial conformation which is unique to the epitope. Generally, an epitope consists of at least about 5 such amino acids, and more usually, consists of at least about 8-10 such amino acids. If the epitope is an organic molecule, it may be as small as Nitrophenyl.

Fusion: As used herein, the term "fusion" refers to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

Immune response: As used herein, the term "immune response" refers to a humoral immune response and/or cellular immune response leading to the activation or proliferation of B- and/or T-lymphocytes and/or and antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant. Preferably, antigen presenting cell may be activated.

A substance which "enhances" an immune response refers to a substance in which an immune response is observed that is greater or intensified or deviated in any way with the addition of the substance when compared to the same immune response measured without the addition of the substance. For example, the lytic activity of cytotoxic T cells can be measured, e.g. using a $^{51}$Cr release assay, in samples obtained with and without the use of the substance during immunization. The amount of the substance at which the CTL lytic activity is enhanced as compared to the CTL lytic activity without the substance is said to be an amount sufficient to enhance the immune response of the animal to the antigen. In a preferred embodiment, the immune response in enhanced by a factor of at least about 2, more preferably by a factor of about 3 or more. The amount or type of cytokines secreted may also be altered. Alternatively, the amount of antibodies induced or their subclasses may be altered.

Immunization: As used herein, the terms "immunize" or "immunization" or related terms refer to conferring the ability to mount a substantial immune response (comprising antibodies and/or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

Natural origin: As used herein, the term "natural origin" means that the whole or parts thereof are not synthetic and exist or are produced in nature.

Non-natural: As used herein, the term generally means not from nature, more specifically, the term means from the hand of man.

Non-natural origin: As used herein, the term "non-natural origin" generally means synthetic or not from nature; more specifically, the term means from the hand of man.

Ordered and repetitive antigen or antigenic determinant array: As used herein, the term "ordered and repetitive antigen or antigenic determinant array" generally refers to a repeating pattern of antigen or antigenic determinant, characterized by a typically and preferably uniform spacial arrangement of the antigens or antigenic determinants with respect to the core particle and virus-like particle, respectively. In one embodiment of the invention, the repeating pattern may be a geometric pattern. Typical and preferred examples of suitable ordered and repetitive antigen or antigenic determinant arrays are those which possess strictly repetitive paracrystalline orders of antigens or antigenic determinants, preferably with spacings of 0.5 to 30 nanometers, more preferably 5 to 15 nanometers.

Pili: As used herein, the term "pili" (singular being "pilus") refers to extracellular structures of bacterial cells composed of protein monomers (e.g., pilin monomers) which are organized into ordered and repetitive patterns. Further, pili are structures which are involved in processes such as the attachment of bacterial cells to host cell surface receptors, inter-cellular genetic exchanges, and cell-cell recognition. Examples of pili include Type-1 pili, P-pili, F1C pili, S-pili, and 987P-pili. Additional examples of pili are set out below.

Pilus-like structure: As used herein, the phrase "pilus-like structure" refers to structures having characteristics similar to that of pili and composed of protein monomers. One example of a "pilus-like structure" is a structure formed by a bacterial cell which expresses modified pilin proteins that do not form ordered and repetitive arrays that are identical to those of natural pili.

Polypeptide: As used herein, the term "polypeptide" refers to a molecule composed of monomers (amino acids) linearly linked by amide bonds (also known as peptide bonds). It indicates a molecular chain of amino acids and does not refer to a specific length of the product. Thus, peptides, dipeptides, tripeptides, oligopeptides and proteins are included within the definition of polypeptide. This term is also intended to refer to post-expression modifications of the polypeptide, for example, glycosolations, acetylations, phosphorylations, and the like. A recombinant or derived polypeptide is not necessarily translated from a designated nucleic acid sequence. It may also be generated in any manner, including chemical synthesis.

Residue: As used herein, the term "residue" is meant to mean a specific amino acid in a polypeptide backbone or side chain.

Self antigen: As used herein, the tem "self antigen" refers to proteins encoded by the host's DNA and products generated by proteins or RNA encoded by the host's DNA are defined as self. In addition, proteins that result from a combination of two or several self-molecules or that represent a fraction of a self-molecule and proteins that have a high homology two self-molecules as defined above (>95%, preferably >97%, more preferably >99%) may also be considered self.

Treatment: As used herein, the terms "treatment", "treat", "treated" or "treating" refer to prophylaxis and/or therapy. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, e.g., reduce or eliminate the infection or prevent it from becoming worse.

Vaccine: As used herein, the term "vaccine" refers to a formulation which contains the composition of the present invention and which is in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses.

Optionally, the vaccine of the present invention additionally includes an adjuvant which can be present in either a minor or major proportion relative to the compound of the present invention.

Virus-like particle (VLP): As used herein, the term "virus-like particle" refers to a structure resembling a virus particle. Moreover, a virus-like particle in accordance with the invention is non replicative and noninfectious since it lacks all or part of the viral genome, in particular the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, or RNA-phage. The terms "viral capsid" or "capsid", as interchangeably used herein, refer to a macromolecular assembly composed of viral protein subunits. Typically and preferably, the viral protein subunits assemble into a viral capsid and capsid, respectively, having a structure with an inherent repetitive organization, wherein said structure is, typically, spherical or tubular. For example, the capsids of RNA-phages or HBcAg's have a spherical form of icosahedral symmetry. The term "capsid-like structure" as used herein, refers to a macromolecular assembly composed of viral protein subunits ressembling the capsid morphology in the above defined sense but deviating from the typical symmetrical assembly while maintaining a sufficient degree of order and repetitiveness.

Virus-like particle of a bacteriophage: As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also encompass virus-like particles of bacteriophages, in which the aforementioned gene or genes are still present but inactive, and, therefore, also leading to non-replicative and noninfectious virus-like particles of a bacteriophage.

VLP of RNA phage coat protein: The capsid structure formed from the self-assembly of 180 subunits of RNA phage coat protein and optionally containing host RNA is referred to as a "VLP of RNA phage coat protein". A specific example is the VLP of Qβ coat protein. In this particular case, the VLP of Qβ coat protein may either be assembled exclusively from Qβ CP subunits (generated by expression of a Qβ CP gene containing, for example, a TAA stop codon precluding any expression of the longer A1 protein through suppression, see Kozlovska, T. M., et al., *Intervirology* 39: 9-15 (1996)), or additionally contain A1 protein subunits in the capsid assembly.

Virus particle: The term "virus particle" as used herein refers to the morphological form of a virus. In some virus types it comprises a genome surrounded by a protein capsid; others have additional structures (e.g., envelopes, tails, etc.).

One, a, or an: When the terms "one," "a," or "an" are used in this disclosure, they mean "at least one" or "one or more," unless otherwise indicated.

As will be clear to those skilled in the art, certain embodiments of the invention involve the use of recombinant nucleic acid technologies such as cloning, polymerase chain reaction, the purification of DNA and RNA, the expression of recombinant proteins in prokaryotic and eukaryotic cells, etc. Such methodologies are well known to those skilled in the art and can be conveniently found in published laboratory methods manuals (e.g., Sambrook, J. et al., eds., *Molecular Cloning, A Laboratory Manual*, 2nd. edition, Cold Spring Harbor Laboratory Press, Cold Spring Harbor, N.Y. (1989); Ausubel, F. et al., eds., *Current Protocols in Molecular Biology*, John H. Wiley & Sons, Inc. (1997)). Fundamental laboratory techniques for working with tissue culture cell lines (Celis, J., ed., *Cell Biology*, Academic Press, 2$^{nd}$ edition, (1998)) and antibody-based technologies (Harlow, E. and Lane, D., *Antibodies: A Laboratory Manual*, Cold Spring Harbor Laboratory, Cold Spring Harbor, N.Y. (1988); Deutscher, M. P., "Guide to Protein Purification," *Meth. Enzymol.* 128, Academic Press San Diego (1990); Scopes, R. K., *Protein Purification Principles and Practice,* 3rd ed., Springer-Verlag, New York (1994)) are also adequately described in the literature, all of which are incorporated herein by reference.

2. Compositions and Methods for Enhancing an Immune Response

The disclosed invention provides compositions and methods for inducing an immune response against Aβ1-6 peptide in an animal, inducing antibodies capable of binding Aβ amyloid plaques and soluble Aβ. Compositions of the invention comprise, or alternatively consist of (a) a core particle with at least one first attachment site; and (b) at least one antigen or antigenic determinant with at least one second attachment site, wherein said antigen or antigenic determinant is an Aβ1-6 peptide, and wherein said second attachment site being selected from the group consisting of (i) an attachment site not naturally occurring with said antigen or antigenic determinant; and (ii) an attachment site naturally occurring with said antigen or antigenic determinant, wherein said second attachment site is capable of association to said first attachment site; and wherein said antigen or antigenic determinant and said core particle interact through said association to form an ordered and repetitive antigen array. More specifically, compositions of the invention comprise, or alternatively consist of, a virus-like particle and at least one antigen or antigenic determinant, wherein the antigen or antigenic determinant is a Aβ1-6 peptide, and wherein the at least one antigen or antigenic determinant is bound to the virus-like particle so as to form an ordered and repetitive antigen-VLP-array. Furthermore, the invention conveniently enables the practitioner to construct such a composition, inter alia, for treatment and/or prophylactic prevention of Alzheimer's disease. Virus-like particles in the context of the present application refer to structures resembling a virus particle but which are not pathogenic. In general, virus-like particles lack the viral genome and, therefore, are noninfectious. Also, virus-like particles can be produced in large quantities by heterologous expression and can be easily purified.

In one embodiment, the core particle comprises, or is selected from a group consisting of, a virus, a bacterial pilus, a structure formed from bacterial pilin, a bacteriophage, a virus-like particle, a virus-like particle of a RNA phage, a viral capsid particle or a recombinant form thereof Any virus known in the art having an ordered and repetitive coat and/or core protein structure may be selected as a core particle of the invention; examples of suitable viruses include sindbis and other alphaviruses, rhabdoviruses (e.g. vesicular stomatitis virus), picornaviruses (e.g., human rhino virus, Aichi virus), togaviruses (e.g., rubella virus), orthomyxoviruses (e.g., Thogoto virus, Batken virus, fowl plague virus), polyomaviruses (e.g., polyomavirus BK, polyomavirus JC, avian polyomavirus BFDV), parvoviruses, rotaviruses, Norwalk virus, foot and mouth disease virus, a retrovirus, Hepatitis B virus, Tobacco mosaic virus, Flock House Virus, and human Papilomavirus, and preferably a RNA phage, bacteriophage Qβ, bacteriophage R17, bacteriophage M11, bacteriophage MX1, bacteriophage NL95, bacteriophage fr, bacteriophage GA, bacteriophage SP, bacteriophage MS2, bacteriophage f2, bacteriophage PP7 (for example, see Table 1 in Bachmann, M. F. and Zinkernagel, R. M., *Immunol. Today* 17:553-558 (1996)).

In a further embodiment, the invention utilizes genetic engineering of a virus to create a fusion between an ordered and repetitive viral envelope protein and a first attachment site being comprised by, or alternatively or preferably being a heterologous protein, peptide, antigenic determinant or a reactive amino acid residue of choice. Other genetic manipulations known to those in the art may be included in the construction of the inventive compositions; for example, it may be desirable to restrict the replication ability of the recombinant virus through genetic mutation. Furthermore, the virus used for the present invention is replication incompetent due to chemical or physical inactivation or, as indicated, due to lack of a replication competent genome. The viral protein selected for fusion to the first attachment site should have an organized and repetitive structure. Such an organized and repetitive structure includes paracrystalline organizations with a spacing of 5-30 nm, preferably 5-15 nm, on the surface of the virus. The creation of this type of fusion protein will result in multiple, ordered and repetitive first attachment sites on the surface of the virus and reflect the normal organization of the native viral protein. As will be understood by those in the art, the first attachment site may be or be a part of any suitable protein, polypeptide, sugar, polynucleotide, peptide (amino acid), natural or synthetic polymer, a secondary metabolite or combination thereof that may serve to specifically attach the antigen or antigenic determinant leading an ordered and repetitive antigen array.

In another embodiment of the invention, the core particle is a recombinant alphavirus, and more specifically, a recombinant Sinbis virus. Alphaviruses are positive stranded RNA viruses that replicate their genomic RNA entirely in the cytoplasm of the infected cell and without a DNA intermediate (Strauss, J. and Strauss, E., *Microbiol. Rev.* 58:491-562 (1994)). Several members of the alphavirus family, Sindbis (Xiong, C. et al., *Science* 243:1188-1191 (1989); Schlesinger, S., *Trends Biotechnol.* 11:18-22 (1993)), Semliki Forest Virus (SFV) (Liljeström, P. & Garoff, H., *Bio/Technology* 9:1356-1361 (1991)) and others (Davis, N. L. et al., *Virology* 171:189-204 (1989)), have received considerable attention for use as virus-based expression vectors for a variety of different proteins (Lundstrom, K., *Curr. Opin. Biotechnol.* 8:578-582 (1997); Liljeström, P., *Curr. Opin. Biotechnol.* 5:495-500 (1994)) and as candidates for vaccine development. Recently, a number of patents have issued directed to the use of alphaviruses for the expression of heterologous proteins and the development of vaccines (see U.S. Pat. Nos. 5,766,602; 5,792,462; 5,739,026; 5,789,245 and 5,814,482). The construction of the alphaviral core particles of the invention may be done by means generally known in the art of recombinant DNA technology, as described by the aforementioned articles, which are incorporated herein by reference.

A variety of different recombinant host cells can be utilized to produce a viral-based core particle for antigen or antigenic determinant attachment. For example, alphaviruses are known to have a wide host range; Sindbis virus infects cultured mammalian, reptilian, and amphibian cells, as well as some insect cells (Clark, H., *J. Natl. Cancer Inst.* 51:645 (1973); Leake, C., *J. Gen. Virol.* 35:335 (1977); Stollar, V. in THE TOGAVIRUSES, R. W. Schlesinger, Ed., Academic Press, (1980), pp.583-621). Thus, numerous recombinant host cells can be used in the practice of the invention. BHK, COS, Vero, HeLa and CHO cells are particularly suitable for the production of heterologous proteins because they have the potential to glycosylate heterologous proteins in a manner similar to human cells (Watson, E. et al., *Glycobiology* 4:227, (1994)) and can be selected (Zang, M. et al., *Bio/Technology* 13:389 (1995)) or genetically engineered (Renner W. et al., *Biotech. Bioeng.* 4:476 (1995); Lee K. et al. *Biotech. Bioeng.* 50:336 (1996)) to grow in serum-free medium, as well as in suspension.

Introduction of the polynucleotide vectors into host cells can be effected by methods described in standard laboratory manuals (see, e.g., Sambrook, J. et al., eds., MOLECULAR CLONING, A LABORATORY MANUAL, 2nd. edition, Cold Spring Harbor Laboratory Press, Cold Spring Harbor, N.Y. (1989), Chapter 9; Ausubel, F. et al., eds., CURRENT PROTOCOLS IN MOLECULAR BIOLOGY, John H. Wiley & Sons, Inc. (1997), Chapter 16), including methods such as electroporation, DEAE-dextran mediated transfection, transfection, microinjection, cationic lipid-mediated transfection, transduction, scrape loading, ballistic introduction, and infection. Methods for the introduction of exogenous DNA sequences into host cells are discussed in Felgner, P. et al., U.S. Pat. No. 5,580,859.

Packaged RNA sequences can also be used to infect host cells. These packaged RNA sequences can be introduced to host cells by adding them to the culture medium. For example, the preparation of non-infective alpahviral particles is described in a number of sources, including "Sindbis Expression System", Version C (Invitrogen Catalog No. K750-1).

When mammalian cells are used as recombinant host cells for the production of viral-based core particles, these cells will generally be grown in tissue culture. Methods for growing cells in culture are well known in the art (see, e.g., Celis, J., ed., CELL BIOLOGY, Academic Press, $2^{nd}$ edition, (1998); Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997); Freshney, R., CULTURE OF ANIMAL CELLS, Alan R. Liss, Inc. (1983)).

Further examples of RNA viruses suitable for use as core particle in the present invention include, but are not limited to, the following: members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picomaviridae, including the genus Enterovirus (poliovirus, Coxsackie virus A and B, enteric cytopathic human orphan (ECHO) viruses, hepatitis A, C, D, E and G viruses, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); the family Rhabdoviridae, including the genus Vesiculovirus (VSV), Chandipura virus, Flanders-Hart Park virus), the genus Lyssavirus (Rabies virus), fish Rhabdoviruses and, filoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that may be used as core particle include, but are not limited to: the family Poxviridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A, B, C, D and E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc.). Finally, DNA viruses may include viruses such as chronic infectious neuropathic agents (CHINA virus).

In other embodiments, a bacterial pilin, a subportion of a bacterial pilin, or a fusion protein which contains either a bacterial pilin or subportion thereof is used to prepare compositions and vaccine compositions, respectively, of the invention. Examples of pilin proteins include pilins produced by *Escherichia coli, Haemophilus influenzae, Neisseria meningitidis, Neisseria gonorrhoeae, Caulobacter crescentus, Pseudomonas stutzeri*, and *Pseudomonas aeruginosa*. The amino acid sequences of pilin proteins suitable for use with the present invention include those set out in GenBank reports AJ000636, AJ132364, AF229646, AF051814, AF051815, and X00981, the entire disclosures of which are incorporated herein by reference.

Bacterial pilin proteins are generally processed to remove N-terminal leader sequences prior to export of the proteins into the bacterial periplasm. Further, as one skilled in the art would recognize, bacterial pilin proteins used to prepare compositions and vaccine compositions, respectively, of the invention will generally not have the naturally present leader sequence.

One specific example of a pilin protein suitable for use in the present invention is the P-pilin of *E. coli* (GenBank report AF237482 (SEQ ID NO:1)). An example of a Type-1 *E. coli* pilin suitable for use with the invention is a pilin having the amino acid sequence set out in GenBank report P04128 (SEQ ID NO:2), which is encoded by nucleic acid having the nucleotide sequence set out in GenBank report M27603 (SEQ ID NO:3). The entire disclosures of these GenBank reports are incorporated herein by reference. Again, the mature form of the above referenced protein would generally be used to prepare compositions and vaccine compositions, respectively, of the invention.

Bacterial pilins or pilin subportions suitable for use in the practice of the present invention will generally be able to associate to form ordered and repetitive antigen arrays.

Methods for preparing pili and pilus-like structures in vitro are known in the art. Bullitt et al., *Proc. Natl. Acad. Sci. USA* 93:12890-12895 (1996), for example, describe the in vitro reconstitution of *E. coli* P-pili subunits. Furthermore, Eshdat et al., *J. Bacteriol.* 148:308-314 (1981) describe methods suitable for dissociating Type-1 pili of *E. coli* and the reconstitution of pili. In brief, these methods are as follows: pili are dissociated by incubation at 37° C. in saturated guanidine hydrochloride. Pilin proteins are then purified by chromatography, after which pilin dimers are formed by dialysis against 5 mM tris(hydroxymethyl) aminomethane hydrochloride (pH 8.0). Eshdat et al. also found that pilin dimers reassemble to form pili upon dialysis against the 5 mM tris(hydroxymethyl) aminomethane (pH 8.0) containing 5 mM $MgCl_2$.

Further, using, for example, conventional genetic engineering and protein modification methods, pilin proteins may be modified to contain a first attachment site to which an antigen or antigenic determinant is linked through a second attachment site. Alternatively, antigens or antigenic determinants can be directly linked through a second attachment site to amino acid residues which are naturally resident in these proteins. These modified pilin proteins may then be used in vaccine compositions of the invention.

Bacterial pilin proteins used to prepare compositions and vaccine compositions, respectively, of the invention may be modified in a manner similar to that described herein for HBcAg. For example, cysteine and lysine residues may be either deleted or substituted with other amino acid residues and first attachment sites may be added to these proteins. Further, pilin proteins may either be expressed in modified form or may be chemically modified after expression. Similarly, intact pili may be harvested from bacteria and then modified chemically.

In another embodiment, pili or pilus-like structures are harvested from bacteria (e.g., *E. coli*) and used to form compositions and vaccine compositions of the invention. One example of pili suitable for preparing compositions and vaccine compositions is the Type-1 pilus of *E. coli*, which is formed from pilin monomers having the amino acid sequence set out in SEQ ID NO:2.

A number of methods for harvesting bacterial pili are known in the art. Bullitt and Makowski (*Biophys. J.* 74:623-632 (1998)), for example, describe a pilus purification method for harvesting P-pili from *E. coli*. According to this method, pili are sheared from hyperpiliated *E. coli* containing a P-pilus plasmid and purified by cycles of solubilization and $MgCl_2$ (1.0 M) precipitation.

Once harvested, pili or pilus-like structures may be modified in a variety of ways. For example, a first attachment site can be added to the pili to which antigens or antigen determinants may be attached through a second attachment site. In other words, bacterial pili or pilus-like structures can be harvested and modified to lead to ordered and repetitive antigen arrays.

Antigens or antigenic determinants could be linked to naturally occurring cysteine resides or lysine residues present in Pili or pilus-like structures. In such instances, the high order and repetitiveness of a naturally occurring amino acid residue would guide the coupling of the antigens or antigenic determinants to the pili or pilus-like structures. For example, the pili or pilus-like structures could be linked to the second attachment sites of the antigens or antigenic determinants using a heterobifunctional cross-linking agent.

When structures which are naturally synthesized by organisms (e.g., pili) are used to prepare compositions and vaccine compositions of the invention, it will often be advantageous to genetically engineer these organisms so that they produce structures having desirable characteristics. For example, when Type-1 pili of *E. coli* are used, the *E. coli* from which these pili are harvested may be modified so as to produce structures with specific characteristics. Examples of possible modifications of pilin proteins include the insertion of one or more lysine residues, the deletion or substitution of one or more of the naturally resident lysine residues, and the deletion or substitution of one or more naturally resident cysteine residues (e.g., the cysteine residues at positions 44 and 84 in SEQ ID NO:2).

Further, additional modifications can be made to pilin genes which result in the expression products containing a first attachment site other than a lysine residue (e.g., a FOS or JUN domain). Of course, suitable first attachment sites will generally be limited to those which do not prevent pilin proteins from forming pili or pilus-like structures suitable for use in vaccine compositions of the invention.

Pilin genes which naturally reside in bacterial cells can be modified in vivo (e.g., by homologous recombination) or pilin genes with particular characteristics can be inserted into these cells. For examples, pilin genes could be introduced into bacterial cells as a component of either a replicable cloning vector or a vector which inserts into the bacterial chromosome. The inserted pilin genes may also be linked to expression regulatory control sequences (e.g., a lac operator).

In most instances, the pili or pilus-like structures used in compositions and vaccine compositions, respectively, of the invention will be composed of single type of a pilin subunit. Pili or pilus-like structures composed of identical subunits will generally be used because they are expected to form structures which present highly ordered and repetitive antigen arrays.

However, the compositions of the invention also include compositions and vaccines comprising pili or pilus-like structures formed from heterogenous pilin subunits. The pilin subunits which form these pili or pilus-like structures can be expressed from genes naturally resident in the bacterial cell or may be introduced into the cells. When a naturally resident pilin gene and an introduced gene are both expressed in a cell which forms pili or pilus-like structures, the result will generally be structures formed from a mixture of these pilin proteins. Further, when two or more pilin genes are expressed in a bacterial cell, the relative expression of each pilin gene will typically be the factor which determines the ratio of the different pilin subunits in the pili or pilus-like structures.

When pili or pilus-like structures having a particular composition of mixed pilin subunits is desired, the expression of at least one of the pilin genes can be regulated by a heterologous, inducible promoter. Such promoters, as well as other genetic elements, can be used to regulate the relative amounts of different pilin subunits produced in the bacterial cell and, hence, the composition of the pili or pilus-like structures.

In additional, the antigen or antigenic determinant can be linked to bacterial pili or pilus-like structures by a bond which is not a peptide bond, bacterial cells which produce pili or pilus-like structures used in the compositions of the invention can be genetically engineered to generate pilin proteins which are fused to an antigen or antigenic determinant. Such fusion proteins which form pili or pilus-like structures are suitable for use in vaccine compositions of the invention.

In a preferred embodiment, the core particle is a virus-like particle, wherein the virus-like particle is a recombinant virus-like particle. The skilled artisan can produce VLPs using recombinant DNA technology and virus coding sequences which are readily available to the public. For example, the coding sequence of a virus envelope or core protein can be engineered for expression in a baculovirus expression vector using a commercially available baculovirus vector, under the regulatory control of a virus promoter, with appropriate modifications of the sequence to allow functional linkage of the coding sequence to the regulatory sequence. The coding sequence of a virus envelope or core protein can also be engineered for expression in a bacterial expression vector, for example.

Examples of VLPs include, but are not limited to, the capsid proteins of Hepatitis B virus (Ulrich, et al., *Virus Res.* 50:141-182 (1998)), measles virus (Warnes, et al., *Gene* 160:173-178 (1995)), Sindbis virus, rotavirus (U.S. Pat. No. 5,071,651 and U.S. Pat. No. 5,374,426), foot-and-mouth-disease virus (Twomey, et al., *Vaccine* 13:1603-1610, (1995)), Norwalk virus (Jiang, X., et al., *Science* 250:1580-1583 (1990); Matsui, S. M., et al., *J. Clin. Invest.* 87:1456-1461 (1991)), the retroviral GAG protein (WO 96/30523), the retrotransposon Ty protein p1, the surface protein of Hepatitis B virus (WO 92/11291), human papilloma virus (WO 98/15631), RNA phages, Ty, fr-phage, GA-phage, AP205-phage and Qβ-phage.

As will be readily apparent to those skilled in the art, the VLP of the invention is not limited to any specific form. The particle can be synthesized chemically or through a biological process, which can be natural or non-natural. By way of example, this type of embodiment includes a virus-like particle or a recombinant form thereof.

In a more specific embodiment, the VLP can comprise, or alternatively essentially consist of, or alternatively consist of recombinant polypeptides, or fragments thereof, being selected from recombinant polypeptides of Rotavirus, recombinant polypeptides of Norwalk virus, recombinant polypeptides of Alphavirus, recombinant polypeptides of Foot and Mouth Disease virus, recombinant polypeptides of measles virus, recombinant polypeptides of Sindbis virus, recombinant polypeptides of Polyoma virus, recombinant polypeptides of Retrovirus, recombinant polypeptides of Hepatitis B virus (e.g., a HBcAg), recombinant polypeptides of Tobacco mosaic virus, recombinant polypeptides of Flock House Virus, recombinant polypeptides of human Papillomavirus, recombinant polypeptides of bacteriophages, recombinant polypeptides of RNA phages, recombinant polypeptides of Ty, recombinant polypeptides of fr-phage, recombinant polypeptides of GA-phage and recombinant polypeptides of Qβ-phage. The virus-like particle can further comprise, or alternatively essentially consist of, or alternatively consist of, one or more fragments of such polypeptides, as well as variants of such polypeptides. Variants of polypeptides can share, for example, at least 80%, 85%, 90%, 95%, 97%, or 99% identity at the amino acid level with their wild-type counterparts.

In a preferred embodiment, the virus-like particle comprises, consists essentially of, or alternatively consists of recombinant proteins, or fragments thereof, of a RNA-phage. Preferably, the RNA-phage is selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; k) bacteriophage f2; l) bacteriophage PP7, and m) bacteriophage AP205.

In another preferred embodiment of the present invention, the virus-like particle comprises, or alternatively consists essentially of, or alternatively consists of recombinant proteins, or fragments thereof, of the RNA-bacteriophage Qβ or of the RNA-bacteriophage fr, or of the RNA-bacteriophage AP205.

In a further preferred embodiment of the present invention, the recombinant proteins comprise, or alternatively consist essentially of, or alternatively consist of coat proteins of RNA phages.

RNA-phage coat proteins forming capsids or VLPs, or fragments of the bacteriophage coat proteins compatible with self-assembly into a capsid or a VLP, are, therefore, further preferred embodiments of the present invention. Bacteriophage Qβ coat proteins, for example, can be expressed recombinantly in *E. coli*. Further, upon such expression these proteins spontaneously form capsids. Additionally, these capsids form a structure with an inherent repetitive organization.

Specific preferred examples of bacteriophage coat proteins which can be used to prepare compositions of the invention include the coat proteins of RNA bacteriophages such as bacteriophage Qβ (SEQ ID NO:4; PIR Database, Accession No. VCBPQβ referring to Qβ CP and SEQ ID NO: 5; Accession No. AAA16663 referring to Qβ A1 protein), bacteriophage R17 (SEQ ID NO:6; PIR Accession No. VCBPR7), bacteriophage fr (SEQ ID NO:7; PIR Accession No. VCBPFR), bacteriophage GA (SEQ ID NO:8; GenBank Accession No. NP-040754), bacteriophage SP (SEQ ID NO:9; GenBank Accession No. CAA30374 referring to SP CP and SEQ ID NO: 10; Accession No. NP 695026 referring to SP A1 protein), bacteriophage MS2 (SEQ ID NO:11; PIR Accession No. VCBPM2), bacteriophage M11 (SEQ ID NO:12; GenBank Accession No. AAC06250), bacteriophage MX1 (SEQ ID NO:13; GenBank Accession No. AAC14699), bacteriophage NL95 (SEQ ID NO:14; GenBank Accession No. AAC14704), bacteriophage f2 (SEQ ID NO: 15; GenBank Accession No. P03611), bacteriophage PP7 (SEQ ID NO: 16), and bacteriophage AP205 (SEQ ID NO: 28). Furthermore, the A1 protein of bacteriophage Qβ (SEQ ID NO: 5) or C-terminal truncated forms missing as much as 100, 150 or 180 amino acids from its C-terminus may be incorporated in a capsid assembly of Qβ coat proteins. Generally, the percentage of Qβ A1 protein relative to Qβ CP in the capsid assembly will be limited, in order to ensure capsid formation.

Qβ coat protein has also been found to self-assemble into capsids when expressed in *E. coli* (Kozlovska T M. et al., *GENE* 137: 133-137 (1993)). The obtained capsids or virus-like particles showed an icosahedral phage-like capsid structure with a diameter of 25 nm and T=3 quasi symmetry. Further, the crystal structure of phage Qβ has been solved. The capsid contains 180 copies of the coat protein, which are linked in covalent pentamers and hexamers by disulfide bridges (Golmohammadi, R. et al., *Structure* 4: 543-5554 (1996)) leading to a remarkable stability of the capsid of Qβ coat protein. Capsids or VLPs made from recombinant Qβ coat protein may contain, however, subunits not linked via disulfide links to other subunits within the capsid, or incompletely linked. However, typically more than about 80% of the subunits are linked via disulfide bridges to each other within the VLP. Thus, upon loading recombinant Qβ capsid on non-reducing SDS-PAGE, bands corresponding to monomeric Qβ coat protein as well as bands corresponding to the hexamer or pentamer of Qβ coat protein are visible. Incompletely disulfide-linked subunits could appear as dimer, trimer or even tetramer bands in non-reducing SDS-PAGE. Qβ capsid protein also shows unusual resistance to organic solvents and denaturing agents. Surprisingly, we have observed that DMSO and acetonitrile concentrations as high as 30%, and Guanidinium concentrations as high as 1 M do not affect the stability of the capsid. The high stability of the capsid of Qβ coat protein is an advantageous feature, in particular, for its use in immunization and vaccination of mammals and humans in accordance of the present invention.

Upon expression in *E. coli*, the N-terminal methionine of Qβ coat protein is usually removed, as we observed by N-terminal Edman sequencing as described in Stoll, E. et al. J. Biol. Chem. 252:990-993 (1977). VLP composed from Qβ coat proteins where the N-terminal methionine has not been removed, or VLPs comprising a mixture of Qβ coat proteins where the N-terminal methionine is either cleaved or present are also within the scope of the present invention.

Further preferred virus-like particles of RNA-phages, in particular of Qβ, in accordance of this invention are disclosed in WO 02/056905, the disclosure of which is herewith incorporated by reference in its entirety.

Further RNA phage coat proteins have also been shown to self-assemble upon expression in a bacterial host (Kastelein, R A. et al., *Gene* 23: 245-254 (1983), Kozlovskaya, T M. et al., *Dokl. Akad. Nauk SSSR* 287: 452-455 (1986), Adhin, M R. et al., *Virology* 170: 238-242 (1989), Ni, C Z., et al., *Protein Sci.* 5: 2485-2493 (1996), Priano, C. et al., J. Mol. Biol. 249: 283-297 (1995)). The Qβ phage capsid contains, in addition to the coat protein, the so called read-through protein A1 and the maturation protein A2. A1 is generated by suppression at the UGA stop codon and has a length of 329 aa. The capsid of phage Qβ recombinant coat protein used in the invention is devoid of the A2 lysis protein, and contains RNA from the host. The coat protein of RNA phages is an RNA binding protein, and interacts with the stem loop of the ribosomal binding site of the replicase gene acting as a translational repressor during the life cycle of the virus. The sequence and structural elements of the interaction are known (Witherell, G W. & Uhlenbeck, O C. *Biochemistry* 28: 71-76 (1989); Lim F. et al., *J. Biol. Chem.* 271: 31839-31845 (1996)). The stem loop and RNA in general are known to be involved in the virus assembly (Golmohammadi, R. et al., *Structure* 4: 543-5554 (1996)).

In a further preferred embodiment of the present invention, the virus-like particle comprises, or alternatively consists essentially of, or alternatively consists of recombinant proteins, or fragments thereof, of a RNA-phage, wherein the recombinant proteins comprise, alternatively consist essentially of or alternatively consist of mutant coat proteins of a RNA phage, preferably of mutant coat proteins of the RNA phages mentioned above. In another preferred embodiment, the mutant coat proteins of the RNA phage have been modified by removal of at least one, or alternatively at least two, lysine residue by way of substitution, or by addition of at least one lysine residue by way of substitution; alternatively, the mutant coat proteins of the RNA phage have been modified by deletion of at least one, or alternatively at least two, lysine residue, or by addition of at least one lysine residue by way of insertion. The deletion, substitution or addition of at least one lysine residue allows varying the degree of coupling, i.e. the amount of Aβ1-6 peptides per subunits of the VLP of the RNA-phages, in particular, to match and tailor the requirements of the vaccine.

In another preferred embodiment, the virus-like particle comprises, or alternatively consists essentially of, or alternatively consists of recombinant proteins, or fragments thereof, of the RNA-bacteriophage Qβ, wherein the recombinant proteins comprise, or alternatively consist essentially of, or alternatively consist of coat proteins having an amino acid sequence of SEQ ID NO:4, or a mixture of coat proteins having amino acid sequences of SEQ ID NO:4 and of SEQ ID NO: 5 or mutants of SEQ ID NO: 5 and wherein the N-terminal methionine is preferably cleaved.

In a further preferred embodiment of the present invention, the virus-like particle comprises, consists essentially of or alternatively consists of recombinant proteins of Qβ, or fragments thereof, wherein the recombinant proteins comprise, or alternatively consist essentially of, or alternatively consist of mutant Qβ coat proteins. In another preferred embodiment, these mutant coat proteins have been modified by removal of at least one lysine residue by way of substitution, or by addition of at least one lysine residue by way of substitution. Alternatively, these mutant coat proteins have been modified by deletion of at least one lysine residue, or by addition of at least one lysine residue by way of insertion.

Four lysine residues are exposed on the surface of the capsid of Qβ coat protein. Qβ mutants, for which exposed lysine residues are replaced by arginines can also be used for the present invention. The following Qβ coat protein mutants and mutant Qβ VLPs can, thus, be used in the practice of the invention: "Qβ-240" (Lys13-Arg; SEQ ID NO:17), "Qβ-243" (Asn 10-Lys; SEQ ID NO:18), "Qβ-250" (Lys 2-Arg, Lys13-Arg; SEQ ID NO:19), "Qβ-251" (SEQ ID NO:20) and "Qβ-259" (Lys 2-Arg, Lys16-Arg; SEQ ID NO:21). Thus, in further preferred embodiment of the present invention, the virus-like particle comprises, consists essentially of or alternatively consists of recombinant proteins of mutant Qβ coat proteins, which comprise proteins having an amino acid sequence selected from the group of a) the amino acid sequence of SEQ ID NO: 17; b) the amino acid sequence of SEQ ID NO: 18; c) the amino acid sequence of SEQ ID NO: 19; d) the amino acid sequence of SEQ ID NO:20; and e) the amino acid sequence of SEQ ID NO: 21. The construction, expression and purification of the above indicated Qβ coat proteins, mutant Qβ coat protein VLPs and capsids, respectively, are described in WO 02/056905. In particular is hereby referred to Example 18 of above mentioned application.

In a further preferred embodiment of the present invention, the virus-like particle comprises, or alternatively consists essentially of, or alternatively consists of recombinant proteins of Qβ, or fragments thereof, wherein the recombinant proteins comprise, consist essentially of or alternatively consist of a mixture of either one of the foregoing Qβ mutants and the corresponding A1 protein.

In a further preferred embodiment of the present invention, the virus-like particle comprises, or alternatively essentially consists of, or alternatively consists of recombinant proteins, or fragments thereof, of RNA-phage AP205.

The AP205 genome consists of a maturation protein, a coat protein, a replicase and two open reading frames not present in related phages; a lysis gene and an open reading frame playing a role in the translation of the maturation gene (Klovins, J., et al., J. Gen. Virol. 83: 1523-33 (2002)). AP205 coat protein can be expressed from plasmid pAP283-58 (SEQ ID NO: 27), which is a derivative of pQb10 (Kozlovska, T. M. et al., Gene 137:133-37 (1993)), and which contains an AP205 ribosomal binding site. Alternatively, AP205 coat protein may be cloned into pQb185, downstream of the ribosomal binding site present in the vector. Both approaches lead to expression of the protein and formation of capsids as described in the co-pending U.S. provisional patent application with the title "Molecular Antigen Arrays" (Atty. Docket No. 1700.0310000) and having been filed on Jul. 17, 2002, which is incorporated by reference in its entirety. Vectors pQb10 and pQb185 are vectors derived from pGEM vector, and expression of the cloned genes in these vectors is controlled by the trp promoter (Kozlovska, T. M. et al., Gene 137:133-37 (1993)). Plasmid pAP283-58 (SEQ ID NO:27) comprises a putative AP205 ribosomal binding site in the following sequence, which is downstream of the XbaI site, and immediately upstream of the ATG start codon of the AP205 coat protein: tctagaATTTTCTGCGCACCCAT CCCGGGTGGCGC-CCAAAGT<u>GAGGAA</u>AATCACatg (SEQ ID NO:57). The vector pQb185 comprises a Shine Delagarno sequence downstream from the XbaI site and upstream of the start codon (tctagaTTAACCCAACGCGT<u>AGGAG</u> TCAGGC-Catg (SEQ ID NO:58), Shine Delagarno sequence underlined).

In a further preferred embodiment of the present invention, the virus-like particle comprises, or alternatively essentially consists of, or alternatively consists of recombinant coat proteins, or fragments thereof, of the RNA-phage AP205.

This preferred embodiment of the present invention, thus, comprises AP205 coat proteins that form capsids. Such proteins are recombinantly expressed, or prepared from natural sources. AP205 coat proteins produced in bacteria spontaneously form capsids, as evidenced by Electron Microscopy (EM) and immunodiffusion. The structural properties of the capsid formed by the AP205 coat protein (SEQ ID NO: 28) and those formed by the coat protein of the AP205 RNA phage are nearly indistinguishable when seen in EM. AP205 VLPs are highly immunogenic, and can be linked with antigens and/or antigenic determinants to generate vaccine constructs displaying the antigens and/or antigenic determinants oriented in a repetitive manner. High titers are elicited against the so displayed antigens showing that bound antigens and/or antigenic determinants are accessible for interacting with antibody molecules and are immunogenic.

In a further preferred embodiment of the present invention, the virus-like particle comprises, or alternatively essentially consists of, or alternatively consists of recombinant mutant coat proteins, or fragments thereof, of the RNA-phage AP205.

Assembly-competent mutant forms of AP205 VLPs, including AP205 coat protein with the subsitution of proline at amino acid 5 to threonine (SEQ ID NO: 29), may also be used in the practice of the invention and leads to a further preferred embodiment of the invention. These VLPs, AP205 VLPs derived from natural sources, or AP205 viral particles, may be bound to antigens to produce ordered repetitive arrays of the antigens in accordance with the present invention.

AP205 P5-T mutant coat protein can be expressed from plasmid pAP281-32 (SEQ ID No. 30), which is derived directly from pQb185, and which contains the mutant AP205 coat protein gene instead of the Qβ coat protein gene. Vectors for expression of the AP205 coat protein are transfected into E. coli for expression of the AP205 coat protein.

Methods for expression of the coat protein and the mutant coat protein, respectively, leading to the self-assembly into VLPs are described in Example 1. Suitable E. coli strains include, but are not limited to, E. coli K802, JM 109, RR1. Suitable vectors and strains and combinations thereof can be identified by testing expression of the coat protein and mutant coat protein, respectively, by SDS-PAGE and capsid formation and assembly by optionally first purifying the capsids by gel filtration and subsequently testing them in an immunodiffusion assay (Ouchterlony test) or Electron Microscopy (Kozlovska, T. M. et al., *Gene* 137:133-37 (1993)).

AP205 coat proteins expressed from the vectors pAP283-58 and pAP281-32 may be devoid of the initial Methionine amino-acid, due to processing in the cytoplasm of *E. coli*. Cleaved, uncleaved forms of AP205 VLP or mixtures thereof are further preferred embodiments of the invention.

In a further preferred embodiment of the present invention, the virus-like particle comprises, or alternatively essentially consists of, or alternatively consists of a mixture of recombinant coat proteins, or fragments thereof, of the RNA-phage AP205 and of recombinant mutant coat proteins, or fragments thereof, of the RNA-phage AP205.

In a further preferred embodiment of the present invention, the virus-like particle comprises, or alternatively essentially consists of, or alternatively consists of fragments of recombinant coat proteins or recombinant mutant coat proteins of the RNA-phage AP205.

Recombinant AP205 coat protein fragments capable of assembling into a VLP and a capsid, respectively are also useful in the practice of the invention. These fragments may be generated by deletion, either internally or at the termini of the coat protein and mutant coat protein, respectively. Insertions in the coat protein and mutant coat protein sequence or fusions of antigen sequences to the coat protein and mutant coat protein sequence, and compatible with assembly into a VLP, are further embodiments of the invention and lead to chimeric AP205 coat proteins, and particles, respectively. The outcome of insertions, deletions and fusions to the coat protein sequence and whether it is compatible with assembly into a VLP can be determined by electron microscopy.

The particles formed by the AP205 coat protein, coat protein fragments and chimeric coat proteins described above, can be isolated in pure form by a combination of fractionation steps by precipitation and of purification steps by gel filtration using e.g. Sepharose CL-4B, Sepharose CL-2B, Sepharose CL-6B columns and combinations thereof. Other methods of isolating virus-like particles are known in the art, and may be used to isolate the virus-like particles (VLPs) of bacteriophage AP205. For example, the use of ultracentrifugation to isolate VLPs of the yeast retrotransposon Ty is described in U.S. Pat. No. 4,918,166, which is incorporated by reference herein in its entirety.

The crystal structure of several RNA bacteriophages has been determined (Golmohammadi, R. et al., *Structure* 4:543-554 (1996)). Using such information, surface exposed residues can be identified and, thus, RNA-phage coat proteins can be modified such that one or more reactive amino acid residues can be inserted by way of insertion or substitution. As a consequence, those modified forms of bacteriophage coat proteins can also be used for the present invention. Thus, variants of proteins which form capsids or capsid-like structures (e.g., coat proteins of bacteriophage Qβ, bacteriophage R17, bacteriophage fr, bacteriophage GA, bacteriophage SP, bacteriophage AP205, and bacteriophage MS2) can also be used to prepare compositions of the present invention.

Although the sequence of the variants proteins discussed above will differ from their wild-type counterparts, these variant proteins will generally retain the ability to form capsids or capsid-like structures. Thus, the invention further includes compositions and vaccine compositions, respectively, which further includes variants of proteins which form capsids or capsid-like structures, as well as methods for preparing such compositions and vaccine compositions, respectively, individual protein subunits used to prepare such compositions, and nucleic acid molecules which encode these protein subunits. Thus, included within the scope of the invention are variant forms of wild-type proteins which form capsids or capsid-like structures and retain the ability to associate and form capsids or capsid-like structures.

As a result, the invention further includes compositions and vaccine compositions, respectively, comprising proteins, which comprise, or alternatively consist essentially of, or alternatively consist of amino acid sequences which are at least 80%, 85%, 90%, 95%, 97%, or 99% identical to wild-type proteins which form ordered arrays and have an inherent repetitive structure, respectively.

Further included within the scope of the invention are nucleic acid molecules which encode proteins used to prepare compositions of the present invention.

In other embodiments, the invention further includes compositions comprising proteins, which comprise, or alternatively consist essentially of, or alternatively consist of amino acid sequences which are at least 80%, 85%, 90%, 95%, 97%, or 99% identical to any of the amino acid sequences shown in SEQ ID NOs:4-21.

Proteins suitable for use in the present invention also include C-terminal truncation mutants of proteins which form capsids or capsid-like structures, or VLPs. Specific examples of such truncation mutants include proteins having an amino acid sequence shown in any of SEQ ID NOs:4-21 where 1, 2, 5, 7, 9, 10, 12, 14, 15, or 17 amino acids have been removed from the C-terminus. Typically, theses C-terminal truncation mutants will retain the ability to form capsids or capsid-like structures.

Further proteins suitable for use in the present invention also include N-terminal truncation mutants of proteins which form capsids or capsid-like structures. Specific examples of such truncation mutants include proteins having an amino acid sequence shown in any of SEQ ID NOs:4-21 where 1, 2, 5, 7, 9, 10, 12, 14, 15, or 17 amino acids have been removed from the N-terminus. Typically, these N-terminal truncation mutants will retain the ability to form capsids or capsid-like structures.

Additional proteins suitable for use in the present invention include N- and C-terminal truncation mutants which form capsids or capsid-like structures. Suitable truncation mutants include proteins having an amino acid sequence shown in any of SEQ ID NOs:4-21 where 1, 2, 5, 7, 9, 10, 12, 14, 15, or 17 amino acids have been removed from the N-terminus and 1, 2, 5, 7, 9, 10, 12, 14, 15, or 17 amino acids have been removed from the C-terminus. Typically, these N-terminal and C-terminal truncation mutants will retain the ability to form capsids or capsid-like structures.

The invention further includes compositions comprising proteins which comprise, or alternatively consist essentially of, or alternatively consist of, amino acid sequences which are at least 80%, 85%, 90%, 95%, 97%, or 99% identical to the above described truncation mutants.

The invention thus includes compositions and vaccine compositions prepared from proteins which form capsids or VLPs, methods for preparing these compositions from individual protein subunits and VLPs or capsids, methods for preparing these individual protein subunits, nucleic acid molecules which encode these subunits, and methods for vaccinating and/or eliciting immunological responses in individuals using these compositions of the present invention.

As previously stated, the invention includes virus-like particles or recombinant forms thereof In one further preferred embodiment, the particles used in compositions of the invention are composed of a Hepatitis B core protein (HBcAg) or a fragment of a HBcAg. In a further embodiment, the particles used in compositions of the invention are composed of a Hepatitis B core protein (HBcAg) or a fragment of a HBcAg protein, which has been modified to either eliminate or reduce the number of free cysteine residues. Zhou et al. (*J. Virol.* 66:5393-5398 (1992)) demonstrated that HBcAgs which have been modified to remove the naturally resident cysteine residues retain the ability to associate and form capsids. Thus, VLPs suitable for use in compositions of the invention include those comprising modified HBcAgs, or fragments thereof, in which one or more of the naturally resident cysteine residues have been either deleted or substituted with another amino acid residue (e.g., a serine residue).

The HBcAg is a protein generated by the processing of a Hepatitis B core antigen precursor protein. A number of isotypes of the HBcAg have been identified and their amino acids sequences are readily available to those skilled in the art. In most instances, compositions and vaccine compositions, respectively, of the invention will be prepared using the processed form of a HBcAg (i.e., a HBcAg from which the N-terminal leader sequence of the Hepatitis B core antigen precursor protein have been removed).

Further, when HBcAgs are produced under conditions where processing will not occur, the HBcAgs will generally be expressed in "processed" form. For example, when an *E. coli* expression system directing expression of the protein to the cytoplasm is used to produce HBcAgs of the invention, these proteins will generally be expressed such that the N-terminal leader sequence of the Hepatitis B core antigen precursor protein is not present.

The preparation of Hepatitis B virus-like particles, which can be used for the present invention, is disclosed, for example, in WO 00/32227, and hereby in particular in Examples 17 to 19 and 21 to 24, as well as in WO 01/85208, and hereby in particular in Examples 17 to 19, 21 to 24, 31 and 41, and in WO 02/056905. For the latter application, it is in particular referred to Example 23, 24, 31 and 51. All three documents are explicitly incorporated herein by reference.

The present invention also includes HBcAg variants which have been modified to delete or substitute one or more additional cysteine residues. It is known in the art that free cysteine residues can be involved in a number of chemical side reactions. These side reactions include disulfide exchanges, reaction with chemical substances or metabolites that are, for example, injected or formed in a combination therapy with other substances, or direct oxidation and reaction with nucleotides upon exposure to UV light. Toxic adducts could thus be generated, especially considering the fact that HBcAgs have a strong tendency to bind nucleic acids. The toxic adducts would thus be distributed between a multiplicity of species, which individually may each be present at low concentration, but reach toxic levels when together.

In view of the above, one advantage to the use of HBcAgs in vaccine compositions which have been modified to remove naturally resident cysteine residues is that sites to which toxic species can bind when antigens or antigenic determinants are attached would be reduced in number or eliminated altogether.

A number of naturally occurring HBcAg variants suitable for use in the practice of the present invention have been identified. Yuan et al., (*J. Virol.* 73:10122-10128 (1999)), for example, describe variants in which the isoleucine residue at position corresponding to position 97 in SEQ ID NO:22 is replaced with either a leucine residue or a phenylalanine residue. The amino acid sequences of a number of HBcAg variants, as well as several Hepatitis B core antigen precursor variants, are disclosed in GenBank reports AAF121240, AF121239, X85297, X02496, X85305, X85303, AF151735, X85259, X85286, X85260, X85317, X85298, AF043593, M20706, X85295, X80925, X85284, X85275, X72702, X85291, X65258, X85302, M32138, X85293, X85315, U95551, X85256, X85316, X85296, AB033559, X59795, X85299, X85307, X65257, X85311, X85301 (SEQ ID NO:23), X85314, X85287, X85272, X85319, AB010289, X85285, AB010289, AF121242, M90520 (SEQ ID NO:24), P03153, AF110999, and M95589, the disclosures of each of which are incorporated herein by reference. The sequences of the hereinabove mentioned Hepatitis B core antigen precursor variants are further disclosed in WO 01/85208 in SEQ ID NOs: 89-138. These HBcAg variants differ in amino acid sequence at a number of positions, including amino acid residues which corresponds to the amino acid residues located at positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO:25. Further HBcAg variants suitable for use in the compositions of the invention, and which may be further modified according to the disclosure of this specification are described in WO 00/198333, WO 00/177158 and WO 00/214478.

As noted above, generally processed HBcAgs (i.e., those which lack leader sequences) will be used in the compositions and vaccine compositions, respectively, of the invention. The present invention includes vaccine compositions, as well as methods for using these compositions, which employ the above described variant HBcAgs.

Whether the amino acid sequence of a polypeptide has an amino acid sequence that is at least 80%, 85%, 90%, 95%, 97% or 99% identical to one of the above wild-type amino acid sequences, or a subportion thereof, can be determined conventionally using known computer programs such the Bestfit program. When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed.

The amino acid sequences of the hereinabove mentioned HBcAg variants and precursors are relatively similar to each other. Thus, reference to an amino acid residue of a HBcAg variant located at a position which corresponds to a particular position in SEQ ID NO:25, refers to the amino acid residue which is present at that position in the amino acid sequence shown in SEQ ID NO:25. The homology between these HBcAg variants is for the most part high enough among Hepatitis B viruses that infect mammals so that one skilled in the art would have little difficulty reviewing both the amino acid sequence shown in SEQ ID NO:25 and that of a particular HBcAg variant and identifying "corresponding" amino acid residues. Furthermore, the HBcAg amino acid sequence shown in SEQ ID NO:24, which shows the amino acid sequence of a HBcAg derived from a virus which infect woodchucks, has enough homology to the HBcAg having the amino acid sequence shown in SEQ ID NO:25 that it is readily apparent that a three amino acid residue insert is present in SEQ ID NO:25 between amino acid residues 155 and 156 of SEQ ID NO:25.

The invention also includes vaccine compositions which comprise HBcAg variants of Hepatitis B viruses which infect birds, as wells as vaccine compositions which comprise fragments of these HBcAg variants. For these HBcAg variants one, two, three or more of the cysteine residues naturally present in these polypeptides could be either substituted with another amino acid residue or deleted prior to their inclusion in vaccine compositions of the invention.

As discussed above, the elimination of free cysteine residues reduces the number of sites where toxic components can bind to the HBcAg, and also eliminates sites where cross-linking of lysine and cysteine residues of the same or of neighboring HBcAg molecules can occur. Therefore, in another embodiment of the present invention, one or more cysteine residues of the Hepatitis B virus capsid protein have been either deleted or substituted with another amino acid residue.

In other embodiments, compositions and vaccine compositions, respectively, of the invention will contain HBcAgs from which the C-terminal region (e.g., amino acid residues 145-185 or 150-185 of SEQ ID NO: 25) has been removed. Thus, additional modified HBcAgs suitable for use in the practice of the present invention include C-terminal truncation mutants. Suitable truncation mutants include HBcAgs where 1, 5, 10, 15, 20, 25, 30, 34, 35, amino acids have been removed from the C-terminus.

HBcAgs suitable for use in the practice of the present invention also include N-terminal truncation mutants. Suitable truncation mutants include modified HBcAgs where 1, 2, 5, 7, 9, 10, 12, 14, 15, or 17 amino acids have been removed from the N-terminus.

Further HBcAgs suitable for use in the practice of the present invention include N- and C-terminal truncation mutants. Suitable truncation mutants include HBcAgs where 1, 2, 5, 7, 9, 10, 12, 14, 15, and 17 amino acids have been removed from the N-terminus and 1, 5, 10, 15, 20, 25, 30, 34, 35 amino acids have been removed from the C-terminus.

The invention further includes compositions and vaccine compositions, respectively, comprising HBcAg polypeptides comprising, or alternatively essentially consisting of, or alternatively consisting of, amino acid sequences which are at least 80%, 85%, 90%, 95%, 97%, or 99% identical to the above described truncation mutants.

In certain embodiments of the invention, a lysine residue is introduced into a HBcAg polypeptide, to mediate the binding of the Aβ1-6 peptide to the VLP of HBcAg. In preferred embodiments, compositions of the invention are prepared using a HBcAg comprising, or alternatively consisting of, amino acids 1-144, or 1-149, 1-185 of SEQ ID NO:25, which is modified so that the amino acids corresponding to positions 79 and 80 are replaced with a peptide having the amino acid sequence of Gly-Gly-Lys-Gly-Gly (SEQ ID NO:33) resulting in the HBcAg polypeptide having the sequence shown in SEQ ID NO: 26. These compositions are particularly useful in those embodiments where an antigenic determinant is coupled to a VLP of HBcAg. In further preferred embodiments, the cysteine residues at positions 48 and 107 of SEQ ID NO:25 are mutated to serine. The invention further includes compositions comprising the corresponding polypeptides having amino acid sequences shown in any of the hereinabove mentioned Hepatitis B core antigen precursor variants which also have above noted amino acid alterations. Further included within the scope of the invention are additional HBcAg variants which are capable of associating to form a capsid or VLP and have the above noted amino acid alterations. Thus, the invention further includes compositions and vaccine compositions, respectively, comprising HBcAg polypeptides which comprise, or alternatively consist of, amino acid sequences which are at least 80%, 85%, 90%, 95%, 97% or 99% identical to any of the wild-type amino acid sequences, and forms of these proteins which have been processed, where appropriate, to remove the N-terminal leader sequence and modified with above noted alterations.

Compositions or vaccine compositions of the invention may comprise mixtures of different HBcAgs. Thus, these vaccine compositions may be composed of HBcAgs which differ in amino acid sequence. For example, vaccine compositions could be prepared comprising a "wild-type" HBcAg and a modified HBcAg in which one or more amino acid residues have been altered (e.g., deleted, inserted or substituted). Further, preferred vaccine compositions of the invention are those which present highly ordered and repetitive antigen arrays, wherein the antigen is a Aβ1-6 peptide.

In a further preferred embodiment of the present invention, the at least one Aβ1-6 peptide is bound to said virus-like particle and core particle, respectively, by at least one covalent bond. Preferably, the least one Aβ1-6 peptide is bound to the virus-like particle and core particle, respectively, by at least one covalent bond, said covalent bond being a non-peptide bond leading to a Aβ1-6 peptide array and Aβ1-6 peptide-VLP conjugate, respectively. This Aβ1-6 peptide array and conjugate, respectively, has typically and preferably a repetitive and ordered structure since the at least one Aβ1-6 peptide is bound to the VLP and core particle, respectively, in an oriented manner. The formation of a repetitive and ordered Aβ1-6 peptide-VLP array and conjugate, respectively, is ensured by an oriented and directed as well as defined binding and attachment, respectively, of the at least one Aβ1-6 peptide to the VLP and core particle, respectively, as will become apparent in the following. Furthermore, the typical inherent highly repetitive and organized structure of the VLPs and core particles, respectively, advantageously contributes to the display of the Aβ1-6 peptide in a highly ordered and repetitive fashion leading to a highly organized and repetitive Aβ1-6 peptide-VLP array and conjugate, respectively.

Therefore, the preferred inventive conjugates and arrays, respectively, differ from prior art conjugates in their highly organized structure, dimensions, and in the repetitiveness of the antigen on the surface of the array. The preferred embodiment of this invention, furthermore, allows expression of the particle in an expression host guaranteeing proper folding and assembly of the VLP, to which the antigen, i.e the Aβ1-6 peptide, is then further coupled The present invention discloses methods of binding of Aβ1-6 peptide to VLPs. As indicated, in one aspect of the invention, the Aβ1-6 peptide is bound to the VLP by way of chemical cross-linking, typically and preferably by using a heterobifunctional cross-linker. Several hetero-bifunctional cross-linkers are known to the art. In preferred embodiments, the hetero-bifunctional cross-linker contains a functional group which can react with preferred first attachment sites, i.e. with the side-chain amino group of lysine residues of the VLP or at least one VLP subunit, and a further functional group which can react with a preferred second attachment site, i.e. a cysteine residue fused to the Aβ1-6 peptide and optionally also made available for reaction by reduction. The first step of the procedure, typically called the derivatization, is the reaction of the VLP with the cross-linker. The product of this reaction is an activated VLP, also called activated carrier. In the second step, unreacted cross-linker is removed using usual methods such as gel filtration or dialysis. In the third step, the Aβ1-6 peptide is reacted with the activated VLP, and this step is typically called the coupling step. Unreacted Aβ1-6 peptide may be optionally removed in a fourth step, for example by dialysis. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., USA), and having one functional group reactive towards amino groups and one functional group reactive towards cysteine residues. The above mentioned cross-linkers all lead to formation of a thioether linkage. Another class of cross-linkers suitable in the practice of the invention is characterized by the introduction of a disulfide linkage between the Aβ1-6 peptide and the VLP upon coupling. Preferred cross-linkers belonging to this class include for example SPDP and Sulfo-LC-SPDP (Pierce). The extent of derivatization of the VLP with cross-linker can be influenced by varying experimental conditions such as the concentration of each of the reaction partners, the excess of one reagent over the other, the pH, the temperature and the ionic strength. The degree of coupling, i.e. the amount of Aβ1-6 peptides per subunits of the VLP can be adjusted by varying the experimental conditions described above to match the requirements of the vaccine.

A particularly favored method of binding of Aβ1-6 peptides to the VLP, is the linking of a lysine residue on the surface of the VLP with a cysteine residue on the Aβ1-6 peptide. In some embodiments, fusion of an amino acid linker containing a cysteine residue, as a second attachment site or as a part thereof, to Aβ1-6 for coupling to the VLP may be required.

In general, flexible amino acid linkers are favored. Examples of the amino acid linker are selected from the group consisting of (a) CGG; (b) N-terminal gamma 1-linker; (c) N-terminal gamma 3-linker; (d) Ig hinge regions; (e) N-terminal glycine linkers; (f) $(G)_kC(G)_n$ with n=0-12 and k=0-5 (SEQ ID NO: 34); (g) N-terminal glycine-serine linkers; (h) $(G)_kC(G)_m(S)_l(GGGGS)_n$ with n=0-3, k=0-5, m=0-10, l=0-2 (SEQ ID NO: 35); (i) GGC; (k) GGC-NH2; (l) C-terminal gamma 1-linker; (m) C-terminal gamma 3-linker; (n) C-terminal glycine linkers; (o) $(G)_nC(G)_k$ with n=0-12 and k=0-5 (SEQ ID NO: 36); (p) C-terminal glycine-serine linkers; (q) $(G)_n(S)_l(GGGGS)_n(G)_oC(G)_k$ with n=0-3, k=0-5, m=0-10, l=0-2, and o=0-8 (SEQ ID NO: 37).

Further examples of amino acid linkers are the hinge region of Immunoglobulins, glycine serine linkers $(GGGGS)_n$ (SEQ ID NO: 38), and glycine linkers $(G)_n$ all further containing a cysteine residue as second attachment site and optionally further glycine residues. Typically preferred examples of said amino acid linkers are N-terminal gamma 1: CGDKTHTSPP (SEQ ID NO: 39); C-terminal gamma 1: DKTHTSPPCG (SEQ ID NO: 40); N-terminal gamma 3: CGGPKPSTPPGSSGGAP (SEQ ID NO: 41); C-terminal gamma 3: PKPSTPPGSSGGAPGGCG (SEQ ID NO: 42); N-terminal glycine linker: GCGGGG (SEQ ID NO: 43) and C-terminal glycine linker: GGGGCG (SEQ ID NO: 44).

Other amino acid linkers particularly suitable in the practice of the invention, when a hydrophobic Aβ pepide is bound to a VLP, are CGKKGG (SEQ ID NO: 46), or CGDEGG (SEQ ID NO: 31) for N-terminal linkers, or GGKKGC (SEQ ID NO: 45) and GGEDGC (SEQ ID NO: 32), for the C-terminal linkers. For the C-terminal linkers, the terminal cysteine is optionally C-terminally amidated.

In preferred embodiments of the present invention, GGCG (SEQ ID NO: 47), GGC or GGC-NH2 ("NH2" stands for amidation) linkers at the C-terminus of the peptide or CGG at its N-terminus are preferred as amino acid linkers. In general, glycine residues will be inserted between bulky amino acids and the cysteine to be used as second attachment site, to avoid potential steric hindrance of the bulkier amino acid in the coupling reaction. In the most preferred embodiment of the invention, the amino acid linker GGC-NH2 is fused to the C-terminus of Aβ1-6.

The cysteine residue present on the Aβ1-6 peptide has to be in its reduced state to react with the hetero-bifunctional cross-linker on the activated VLP, that is a free cysteine or a cysteine residue with a free sulfhydryl group has to be available. In the instance where the cysteine residue to function as binding site is in an oxidized form, for example if it is forming a disulfide bridge, reduction of this disulfide bridge with e.g. DTT, TCEP or β-mercaptoethanol is required. Low concentrations of reducing agent are compatible with coupling as described in WO 02/056905, higher concentrations inhibit the coupling reaction, as a skilled artisan would know, in which case the reductand has to be removed or its concentration decreased prior to coupling, e.g. by dialysis, gel filtration or reverse phase HPLC.

Binding of the Aβ1-6 peptide to the VLP by using a hetero-bifunctional cross-linker according to the preferred methods described above, allows coupling of Aβ1-6 peptide to the VLP in an oriented fashion. Other methods of binding the Aβ1-6 peptide to the VLP include methods wherein the Aβ1-6 peptide is cross-linked to the VLP using the carbodiimide EDC, and NHS. In further methods, the Aβ1-6 peptide is attached to the VLP using a homo-bifunctional cross-linker such as glutaraldehyde, DSG, BM[PEO]$_4$, BS$^3$, (Pierce Chemical Company, Rockford, Ill., USA) or other known homo-bifunctional cross-linkers whith functional groups reactive towards amine groups or carboxyl groups of the VLP.

Other methods of binding the VLP to a Aβ1-6 peptide include methods where the VLP is biotinylated, and the Aβ1-6 peptide expressed as a streptavidin-fusion protein, or methods wherein both the Aβ1-6 peptide and the VLP are biotinylated, for example as described in WO 00/23955. In this case, the Aβ1-6 peptide may be first bound to streptavidin or avidin by adjusting the ratio of Aβ1-6 peptide to streptavidin such that free binding sites are still available for binding of the VLP, which is added in the next step. Alternatively, all components may be mixed in a "one pot" reaction. Other ligand-receptor pairs, where a soluble form of the receptor and of the ligand is available, and are capable of being cross-linked to the VLP or the Aβ1-6 peptide, may be used as binding agents for binding Aβ1-6 peptide to the VLP. Alternatively, either the ligand or the receptor may be fused to the Aβ1-6 peptide, and so mediate binding to the VLP chemically bound or fused either to the receptor, or the ligand respectively. Fusion may also be effected by insertion or substitution.

As already indicated, in a favored embodiment of the present invention, the VLP is the VLP of a RNA phage, and in a more preferred embodiment, the VLP is the VLP of RNA phage Qβ coat protein.

One or several antigen molecules, i.e. a Aβ1-6 peptide, can be attached to one subunit of the capsid or VLP of RNA phages coat proteins, preferably through the exposed lysine residues of the VLP of RNA phages, if sterically allowable. A specific feature of the VLP of the coat protein of RNA phages and in particular of the Qβ coat protein VLP is thus the possibility to couple several antigens per subunit. This allows for the generation of a dense antigen array.

In a preferred embodiment of the invention, the binding and attachment, respectively, of the at least one Aβ1-6 peptide to the virus-like particle is by way of interaction and association, respectively, between at least one first attachment site of the virus-like particle and at least one second attachment of the antigen or antigenic determinant.

VLPs or capsids of Qβ coat protein display a defined number of lysine residues on their surface, with a defined topology with three lysine residues pointing towards the interior of the capsid and interacting with the RNA, and four other lysine residues exposed to the exterior of the capsid. These defined properties favor the attachment of antigens to the exterior of the particle, rather than to the interior of the particle where the lysine residues interact with RNA. VLPs of other RNA phage coat proteins also have a defined number of lysine residues on their surface and a defined topology of these lysine residues.

In further preferred embodiments of the present invention, the first attachment site is a lysine residue and/or the second attachment comprises sulfhydryl group or a cysteine residue. In a very preferred embodiment of the present invention, the first attachment site is a lysine residue and the second attachment is a cysteine residue.

In very preferred embodiments of the invention, the Aβ1-6 peptide is bound via a cysteine residue, to lysine residues of the VLP of RNA phage coat protein, and in particular to the VLP of Qβ coat protein.

Another advantage of the VLPs derived from RNA phages is their high expression yield in bacteria that allows production of large quantities of material at affordable cost.

As indicated, the inventive conjugates and arrays, respectively, differ from prior art conjugates in their highly organized structure, dimensions, and in the repetitiveness of the antigen on the surface of the array. Moreover, the use of the VLPs as carriers allow the formation of robust antigen arrays and conjugates, respectively, with variable antigen density. In particular, the use of VLPs of RNA phages, and hereby in particular the use of the VLP of RNA phage Qβ coat protein allows achieving very high epitope density. In particular, a density of more than 1.5 epitopes per subunit could be reached by coupling the human Aβ1-6 peptide to the VLP of Qβ coat protein. The preparation of compositions of VLPs of RNA phage coat proteins with a high epitope density can be effected using the teaching of this application. In prefered embodiment of the invention, when a Aβ1-6 peptide is coupled to the VLP of Qβ coat protein, an average number of Aβ1-6 peptide per subunit of 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4 2.5, 2.6, 2.7, 2.8, 2.9, or higher is preferred.

The second attachment site, as defined herein, may be either naturally or non-naturally present with the antigen or the antigenic determinant. In the case of the absence of a suitable natural occurring second attachment site on the antigen or antigenic determinant, such a, then non-natural second attachment has to be engineered to the antigen.

As described above, four lysine residues are exposed on the surface of the VLP of Qβ coat protein. Typically these residues are derivatized upon reaction with a cross-linker molecule. In the instance where not all of the exposed lysine residues can be coupled to an antigen, the lysine residues which have reacted with the cross-linker are left with a cross-linker molecule attached to the ε-amino group after the derivatization step. This leads to disappearance of one or several positive charges, which may be detrimental to the solubility and stability of the VLP. By replacing some of the lysine residues with arginines, as in the disclosed Qβ coat protein mutants described below, we prevent the excessive disappearance of positive charges since the arginine residues do not react with the cross-linker. Moreover, replacement of lysine residues by arginines may lead to more defined antigen arrays, as fewer sites are available for reaction to the antigen.

Accordingly, exposed lysine residues were replaced by arginines in the following Qβ coat protein mutants and mutant Qβ VLPs disclosed in this application: Qβ-240 (Lys13-Arg; SEQ ID NO: 17), Qβ-250 (Lys 2-Arg, Lys13-Arg; SEQ ID NO: 19) and Qβ-259 (Lys 2-Arg, Lys16-Arg; SEQ ID NO:21). The constructs were cloned, the proteins expressed, the VLPs purified and used for coupling to peptide and protein antigens. Qβ-251; (SEQ ID NO: 20 was also constructed, and guidance on how to express, purify and couple the VLP of Qβ-251 coat protein can be found throughout the application.

In a further embodiment, we disclose a Qβ mutant coat protein with one additional lysine residue, suitable for obtaining even higher density arrays of antigens. This mutant Qβ coat protein, Qβ-243 (Asn 10-Lys; SEQ ID NO: 18), was cloned, the protein expressed, and the capsid or VLP isolated and purified, showing that introduction of the additional lysine residue is compatible with self-assembly of the subunits to a capsid or VLP. Thus, Aβ1-6 peptide arrays and conjugates, respectively, may be prepared using VLP of Qβ coat protein mutants. A particularly favored method of attachment of antigens to VLPs, and in particular to VLPs of RNA phage coat proteins is the linking of a lysine residue present on the surface of the VLP of RNA phage coat proteins with a cysteine residue added to the antigen, i.e. the Aβ1-6 peptide. In order for a cysteine residue to be effective as second attachment site, a sulfhydryl group must be available for coupling. Thus, a cysteine residue has to be in its reduced state, that is, a free cysteine or a cysteine residue with a free sulfhydryl group has to be available. In the instant where the cysteine residue to function as second attachment site is in an oxidized form, for example if it is forming a disulfide bridge, reduction of this disulfide bridge with e.g. DTT, TCEP or β-mercaptoethanol is required. The concentration of reductant, and the molar excess of reductand over antigen has to be adjusted for each antigen. A titration range, starting from concentrations as low as 10 μM or lower, up to 10 to 20 mM or higher reductand if required is tested, and coupling of the antigen to the carrier assessed. Although low concentrations of reductant are compatible with the coupling reaction as described in WO 02/056905, higher concentrations inhibit the coupling reaction, as a skilled artisan would know, in which case the reductand has to be removed or its concentration decreased, e.g. by dialysis, gel filtration or reverse phase HPLC. Advantageously, the pH of the dialysis or equilibration buffer is lower than 7, preferably 6. The compatibility of the low pH buffer with antigen activity or stability has to be tested.

Epitope density on the VLP of RNA phage coat proteins can be modulated by the choice of cross-linker and other reaction conditions. For example, the cross-linkers Sulfo-GMBS and SMPH typically allow reaching high epitope density. Derivatization is positively influenced by high concentration of reactants, and manipulation of the reaction conditions can be used to control the number of antigens coupled to VLPs of RNA phage coat proteins, and in particular to VLPs of Qβ coat protein.

Prior to the design of a non-natural second attachment site the position at which it should be fused, inserted or generally engineered has to be chosen. The selection of the position of the second attachment site may, by way of example, be based on a crystal structure of the antigen. Such a crystal structure of the antigen may provide information on the availability of the C- or N-termini of the molecule (determined for example from their accessibility to solvent), or on the exposure to solvent of residues suitable for use as second attachment sites, such as cysteine residues. Exposed disulfide bridges, as is the case for Fab fragments, may also be a source of a second attachment site, since they can be generally converted to single cysteine residues through mild reduction, with e.g. 2-mercaptoethylamine, TCEP, β-mercaptoethanol or DTT. Mild reduction conditions not affecting the immunogenicity of the antigen will be chosen. In general, in the case where immunization with a self-antigen is aiming at inhibiting the interaction of this self-antigen with its natural ligands, the second attachment site will be added such that it allows generation of antibodies against the site of interaction with the natural ligands. Thus, the location of the second attachment site will be selected such that steric hindrance from the second attachment site or any amino acid linker containing the same is avoided. In further embodiments, an antibody response directed at a site distinct from the interaction site of the self-antigen with its natural ligand is desired. In such embodiments, the second attachment site may be selected such that it prevents generation of antibodies against the interaction site of the self-antigen with its natural ligands.

Other criteria in selecting the position of the second attachment site include the oligomerization state of the antigen, the site of oligomerization, the presence of a cofactor, and the availability of experimental evidence disclosing sites in the antigen structure and sequence where modification of the antigen is compatible with the function of the self-antigen, or with the generation of antibodies recognizing the self-antigen.

In the most preferred embodiments, the Aβ1-6 peptide comprises a single second attachment site or a single reactive attachment site capable of association with the first attachment sites on the core particle and the VLPs or VLP subunits, respectively. This ensures a defined and uniform binding and association, respectively, of the at least one, but typically more than one, preferably more than 10, 20, 40, 80, 120, 150, 180, 210, 240, 270, 300, 360, 400, 450 antigens to the core particle and VLP, respectively. The provision of a single second attachment site or a single reactive attachment site on the antigen, thus, ensures a single and uniform type of binding and association, respectively leading to a very highly ordered and repetitive array. For example, if the binding and association, respectively, is effected by way of a lysine-(as the first attachment site) and cysteine-(as a second attachment site) interaction, it is ensured, in accordance with this preferred embodiment of the invention, that only one cysteine residue per antigen, independent whether this cysteine residue is naturally or non-naturally present on the antigen, is capable of binding and associating, respectively, with the VLP and the first attachment site of the core particle, respectively.

In some embodiments, engineering of a second attachment site onto the antigen require the fusion of an amino acid linker containing an amino acid suitable as second attachment site according to the disclosures of this invention. Therefore, in a preferred embodiment of the present invention, an amino acid linker is bound to the antigen or the antigenic determinant by way of at least one covalent bond.

Preferably, the amino acid linker comprises, or alternatively consists of, the second attachment site. In a further preferred embodiment, the amino acid linker comprises a sulfhydryl group or a cysteine residue. In another preferred embodiment, the amino acid linker is cysteine. Some criteria of selection of the amino acid linker as well as further preferred embodiments of the amino acid linker according to the invention have already been mentioned above.

In a further preferred embodiment of the invention, the at least one antigen or antigenic determinant, i.e. the Aβ1-6 peptide is fused to the virus-like particle. As outlined above, a VLP is typically composed of at least one subunit assembling into a VLP. Thus, in again a further preferred embodiment of the invention, the antigen or antigenic determinant, preferably the at least one Aβ1-6 peptide is fused to at least one subunit of the virus-like particle or of a protein capable of being incorporated into a VLP generating a chimeric VLP-subunit-Aβ1-6 peptide protein fusion.

Fusion of the Aβ1-6 peptides can be effected by insertion into the VLP subunit sequence, or by fusion to either the N- or C-terminus of the VLP-subunit or protein capable of being incorporated into a VLP. Hereinafter, when referring to fusion proteins of a peptide to a VLP subunit, the fusion to either ends of the subunit sequence or internal insertion of the peptide within the subunit sequence are encompassed.

Fusion may also be effected by inserting the Aβ1-6 peptide sequences into a variant of a VLP subunit where part of the subunit sequence has been deleted, that are further referred to as truncation mutants. Truncation mutants may have N- or C-terminal, or internal deletions of part of the sequence of the VLP subunit. For example, the specific VLP HBcAg with, for example, deletion of amino acid residues 79 to 81 is a truncation mutant with an internal deletion. Fusion of Aβ1-6 peptides to either the N- or C-terminus of the truncation mutants VLP-subunits also lead to embodiments of the invention. Likewise, fusion of an epitope into the sequence of the VLP subunit may also be effected by substitution, where for example for the specific VLP HBcAg, amino acids 79-81 are replaced with a foreign epitope. Thus, fusion, as referred to hereinafter, may be effected by insertion of the Aβ1-6 peptide sequence in the sequence of a VLP subunit, by substitution of part of the sequence of the VLP subunit with the Aβ1-6 peptide, or by a combination of deletion, substitution or insertions.

The chimeric Aβ1-6 peptide-VLP subunit will be in general capable of self-assembly into a VLP. VLP displaying epitopes fused to their subunits are also herein referred to as chimeric VLPs. As indicated, the virus-like particle comprises or alternatively is composed of at least one VLP subunit. In a further embodiment of the invention, the virus-like particle comprises or alternatively is composed of a mixture of chimeric VLP subunits and non-chimeric VLP subunits, i.e. VLP subunits not having an antigen fused thereto, leading to so called mosaic particles. This may be advantageous to ensure formation of, and assembly to a VLP. In those embodiments, the proportion of chimeric VLP-subunits may be 1, 2, 5, 10, 20, 30, 40, 50, 60, 70, 80, 90, 95% or higher.

Flanking amino acid residues may be added to either end of the sequence of the peptide or epitope to be fused to either end of the sequence of the subunit of a VLP, or for internal insertion of such peptidic sequence into the sequence of the subunit of a VLP. Glycine and serine residues are particularly favored amino acids to be used in the flanking sequences added to the peptide to be fused. Glycine residues confer additional flexibility, which may diminish the potentially destabilizing effect of fusing a foreign sequence into the sequence of a VLP subunit.

In a specific embodiment of the invention, the VLP is a Hepatitis B core antigen VLP. Fusion proteins of the Aβ1-6 peptide to either the N-terminus of a HBcAg (Neyrinck, S. et al., *Nature Med.* 5:1157-1163 (1999)) or insertions in the so called major immunodominant region (MIR) have been described (Pumpens, P. and Grens, E., *Intervirology* 44:98-114 (2001)), WO 01/98333), and are preferred embodiments of the invention. Naturally occurring variants of HBcAg with deletions in the MIR have also been described (Pumpens, P. and Grens, E., *Intervirology* 44:98-114 (2001), which is expressly incorporated by reference in its entirety), and fusions to the N- or C-terminus, as well as insertions at the position of the MIR corresponding to the site of deletion as compared to a wt HBcAg are further embodiments of the invention. Fusions to the C-terminus have also been described (Pumpens, P. and Grens, E., *Intervirology* 44:98-114 (2001)). One skilled in the art will easily find guidance on how to construct fusion proteins using classical molecular biology techniques (Sambrook, J. et al., eds., *Molecular Cloning, A Laboratory Manual*, 2nd. edition, Cold Spring Habor Laboratory Press, Cold Spring Harbor, N.Y. (1989), Ho et al., *Gene* 77:51 (1989)). Vectors and plasmids encoding HBcAg and HBcAg fusion proteins and useful for the expression of a HBcAg and HBcAg fusion proteins have been described (Pumpens, P. & Grens, E. Intervirology 44: 98-114 (2001), Neyrinck, S. et al., *Nature Med.* 5:1157-1163 (1999)) and can be used in the practice of the invention. We also describe by way of example (Example 6) the insertion of an epitope into the MIR of HBcAg, resulting in a chimeric self-assembling HBcAg. An important factor for the optimization of the efficiency of self-assembly and of the display of the epitope to be inserted in the MIR of HBcAg is the choice of the insertion site, as well as the number of amino acids to be deleted from the HBcAg sequence within the MIR (Pumpens, P. and Grens, E., *Intervirology* 44:98-114 (2001); EP 0 421 635; U.S. Pat. No. 6,231,864) upon insertion, or in other words, which amino acids form HBcAg are to be substituted with the new epitope. For example, substitution of HBcAg amino acids 76-80, 79-81, 79-80, 75-85 or 80-81 with foreign epitopes has been described (Pumpens, P. and Grens, E., *Intervirology* 44:98-114 (2001); EP0421635; U.S. Pat. No. 6,231,864). HBcAg contains a long arginine tail (Pumpens, P. and Grens, E., *Intervirology* 44:98-114 (2001))which is dispensable for capsid assembly and capable of binding nucleic acids (Pumpens, P. and Grens, E., *Intervirology* 44:98-114 (2001)). HBcAg either comprising or lacking this arginine tail are both embodiments of the invention.

In a further preferred embodiment of the invention, the VLP is a VLP of a RNA phage. The major coat proteins of RNA phages spontaneously assemble into VLPs upon expression in bacteria, and in particular in *E. coli*. Specific examples of bacteriophage coat proteins which can be used to prepare compositions of the invention include the coat proteins of RNA bacteriophages such as bacteriophage Qβ (SEQ ID NO:4; PIR Database, Accession No. VCBPQβ referring to Qβ CP and SEQ ID NO: 5; Accession No. AAA16663 referring to Qβ A1 protein) and bacteriophage fr (SEQ ID NO: 7; PIR Accession No. VCBPFR).

In a more preferred embodiment, the at least one Aβ1-6 peptide is fused to a Qβ coat protein. Fusion protein constructs wherein foreign epitopes have been fused to the C-terminus of a truncated form of the A1 protein of Qβ, or inserted within the A1 protein have been described (Kozlovska, T. M., et al., *Intervirology*, 39:9-15 (1996)). The Al protein is generated by suppression at the UGA stop codon and has a length of 329 aa, or 328 aa, if the cleavage of the N-terminal methionine is taken into account. Cleavage of the N-terminal methionine before an alanine (the second amino acid encoded by the Qβ CP gene) usually takes place in *E. coli*, and such is the case for N-termini of the Qβ coat proteins. The part of the A1 gene, 3' of the UGA amber codon encodes the CP extension, which has a length of 195 amino acids. Insertion of the at least one Aβ1-6 peptide between position 72 and 73 of the CP extension leads to further embodiments of the invention (Kozlovska, T. M., et al., *Intervirology* 39:9-15 (1996)). Fusion of a Aβ1-6 peptide at the C-terminus of a C-terminally truncated Qβ A1 protein leads to further preferred embodiments of the invention. For example, Kozlovska et al., (*Intervirology*, 39: 9-15 (1996)) describe Qβ A1 protein fusions where the epitope is fused at the C-terminus of the Qβ CP extension truncated at position 19.

As described by Kozlovska et al. (*Intervirology*, 39: 9-15 (1996)), assembly of the particles displaying the fused epitopes typically requires the presence of both the A1 protein-Aβ1-6 peptide fusion and the wt CP to form a mosaic particle. However, embodiments comprising virus-like particles, and hereby in particular the VLPs of the RNA phage Qβ coat protein, which are exclusively composed of VLP subunits having at least one Aβ1-6 peptide fused thereto, are also within the scope of the present invention.

The production of mosaic particles may be effected in a number of ways. Kozlovska et al., *Intervirology*, 39:9-15 (1996), describe three methods, which all can be used in the practice of the invention. In the first approach, efficient display of the fused epitope on the VLPs is mediated by the expression of the plasmid encoding the Qβ A1 protein fusion having a UGA stop codong between CP and CP extension in a *E. coli* strain harboring a plasmid encoding a cloned UGA suppressor tRNA which leads to translation of the UGA codon into Trp (pISM3001 plasmid (Smiley B. K., et al, *Gene* 134:33-40 (1993))). In another approach, the CP gene stop codon is modified into UAA, and a second plasmid expressing the A1 protein-Aβ1-6 peptide fusion is cotransformed. The second plasmid encodes a different antibiotic resistance and the origin of replication is compatible with the first plasmid (Kozlovska, T. M., et al., *Intervirology* 39:9-15 (1996)). In a third approach, CP and the A1 protein-Aβ1-6 peptide fusion are encoded in a bicistronic manner, operatively linked to a promoter such as the Trp promoter, as described in FIG. 1 of Kozlovska et al., *Intervirology*, 39:9-15 (1996).

In a further embodiment, the Aβ1-6 peptide is inserted between amino acid 2 and 3 (numbering of the cleaved CP, that is wherein the N-terminal methionine is cleaved) of the fr CP, thus leading to a Aβ1-6 peptide-fr CP fusion protein. Vectors and expression systems for construction and expression of fr CP fusion proteins self-assembling to VLP and useful in the practice of the invention have been described (Pushko P. et al., *Prot. Eng.* 6:883-891 (1993)). In a specific embodiment, the Aβ1-6 peptide sequence is inserted into a deletion variant of the fr CP after amino acid 2, wherein residues 3 and 4 of the fr CP have been deleted (Pushko P. et al., *Prot. Eng.* 6:883-891 (1993)).

Fusion of epitopes in the N-terminal protuberant β-hairpin of the coat protein of RNA phage MS-2 and subsequent presentation of the fused epitope on the self-assembled VLP of RNA phage MS-2 has also been described (WO 92/13081), and fusion of Aβ1-6 peptide by insertion or substitution into the coat protein of MS-2 RNA phage is also falling under the scope of the invention.

In another embodiment of the invention, the Aβ1-6 peptide is fused to a capsid protein of papillomavirus. In a more specific embodiment, the Aβ1-6 peptide is fused to the major capsid protein L1 of bovine papillomavirus type 1 (BPV-1). Vectors and expression systems for construction and expression of BPV-1 fusion proteins in a baculovirus/insect cells systems have been described (Chackerian, B. et al., *Proc. Natl. Acad. Sci. USA* 96:2373-2378 (1999), WO 00/23955). Substitution of amino acids 130-136 of BPV-1 L1 with a Aβ1-6 peptide leads to a BPV-1 L1-Aβ1-6 peptide fusion protein, which is a preferred embodiment of the invention. Cloning in a baculovirus vector and expression in baculovirus infected Sf9 cells has been described, and can be used in the practice of the invention (Chackerian, B. et al., *Proc. Natl. Acad. Sci. USA* 96:2373-2378 (1999), WO 00/23955). Purification of the assembled particles displaying the fused Aβ1-6 peptide can be performed in a number of ways, such as for example gel filtration or sucrose gradient ultracentrifugation (Chackerian, B. et al., *Proc. Natl. Acad. Sci. USA* 96:2373-2378 (1999), WO 00/23955).

In a further embodiment of the invention, the Aβ1-6 peptide is fused to a Ty protein capable of being incorporated into a Ty VLP. In a more specific embodiment, the Aβ1-6 peptide is fused to the p1 or capsid protein encoded by the TYA gene (Roth, J. P., *Yeast* 16:785-795 (2000)). The yeast retrotransposons Ty1, 2, 3 and 4 have been isolated from *Saccharomyces Serevisiae*, while the retrotransposon Tf1 has been isolated from *Schizosaccharomyces Pombae* (Boeke, J. D. and Sandmeyer, S. B., "Yeast Transposable elements," in *The molecular and Cellular Biology of the Yeast Saccharomyces: Genome dynamics, Protein Synthesis, and Energetics*, p. 193, Cold Spring Harbor Laboratory Press (1991)). The retrotransposons Ty1 and 2 are related to the copia class of plant and animal elements, while Ty3 belongs to the gypsy family of retrotransposons, which is related to plants and animal retroviruses. In the Ty1 retrotransposon, the p1 protein, also referred to as Gag or capsid protein, has a length of 440 amino acids. P1 is cleaved during maturation of the VLP at position 408, leading to the p2 protein, the essential component of the VLP.

Fusion proteins to p1 and vectors for the expression of said fusion proteins in Yeast have been described (Adams, S. E., et al., *Nature* 329:68-70 (1987)). So, for example, a Aβ1-6 peptide may be fused to p1 by inserting a sequence coding for the Aβ1-6 peptide into the BamHI site of the pMA5620 plasmid (Adams, S. E., et al., *Nature* 329:68-70 (1987)). The cloning of sequences coding for foreign epitopes into the pMA5620 vector leads to expression of fusion proteins comprising amino acids 1-381 of p1 of Ty1-15, fused C-terminally to the N-terminus of the foreign epitope. Likewise, N-terminal fusion of a Aβ1-6 peptide, or internal insertion into the p1 sequence, or substitution of part of the p1 sequence are also meant to fall within the scope of the invention. In particular, insertion of a Aβ1-6 peptide into the Ty sequence between amino acids 30-31, 67-68, 113-114 and 132-133 of the Ty protein p1 (EP0677111) leads to preferred embodiments of the invention.

Further VLPs suitable for fusion of Aβ1-6 peptides are, for example, Retrovirus-like-particles (WO9630523), HIV2 Gag (Kang, Y. C., et al, *Biol. Chem.* 380:353-364 (1999)), Cowpea Mosaic Virus (Taylor, K. M. et al., *Biol. Chem.* 380:387-392 (1999)), parvovirus VP2 VLP (Rueda, P. et al., *Virology* 263:89-99 (1999)), HBsAg (U.S. Pat. No. 4,722,840, EP0020416B1).

Examples of chimeric VLPs suitable for the practice of the invention are also those described in *Intervirology* 39:1 (1996). Further examples of VLPs contemplated for use in the invention are: HPV-1, HPV-6, HPV-11, HPV-16, HPV-18, HPV-33, HPV-45, CRPV, COPV, HIV GAG, Tobacco Mosaic Virus. Virus-like particles of SV-40, Polyomavirus, Adenovirus, Herpes Simplex Virus, Rotavirus and Norwalk virus have also been made, and chimeric VLPs of those VLPs comprising a Aβ1-6 peptide are also within the scope of the present invention.

In preferred embodiments of the invention, Aβ1-6 peptides suitable for generating vaccines of the invention are modified with an amino acid linker for binding to a VLP. Those Aβ1-6 peptides include, but are not limited to: Aβ1-6 fused C-terminally to the linker GGC. Amino acid linkers suitable for fusion to the N-terminus of Aβ1-6 fragments include but are not limited to the sequence CGG and CGHGNKS. Linkers suitable for fusion to the C-terminus of Aβ1-6 include but are not limited to the sequence GGC. In a preferred embodiment, when a linker is fused to the C-terminus of Aβ or Aβ fragments, the C-terminal Cysteine is amidated. In a preferred embodiment, Aβ1-6 is fused to an amino acid linker and has the sequence: "NH2-DAEFRHGGC-CONH2, wherein the C-terminal Cysteine is amidated, which is indicated by the C-terminal "—CONH2", and the N-terminus of the peptide is free, which is further indicated by "NH2-". Amino acid linkers are preferably short, to avoid induction of immune responses against amino acids of said linker, but should allow the induction of antibodies cross-reactive with soluble Aβ and AD plaques and may facilitate the interaction of antibodies with the Aβ1-6 peptide. Other suitable properties of the amino acid linker are flexibility, and preferably lack of bulky amino acids which might interfere with coupling, and/or generate an immune response against the linker itself. In more preferred embodiments, the amino acid linker containing a cysteine residue as second attachment site is fused to the C-terminus of the Aβ1-6 peptide.

Additional Aβ fragments suitable in the practice of the invention include Aβ fragments corresponding to the aforementioned fragments, also modified as described above, from other animal species and eliciting Antibodies cross-reactive with human amyloid plaques and soluble human Aβ. Examples of such fragments are Aβ1-6 from primates (DAEFRH; SEQ ID NO: 84), rabbit (DAEFRH; SEQ ID NO: 85), guinea pig (DAEFRH: SEQ ID NO: 88), mouse (DAEFGH; SEQ ID NO: 76), rat (DAEFGH SEQ ID NO: 87), and *xaenopus laevis* (DSEYRH; 86).

A number of animal models of AD based on transgenic mice overexpressing mutated forms of human APP have been reported (Games, D. et al., *Nature* 373: 523-527 (1995a); Sturchler-Pierrat et al., *Proc. Natl. Acad. Sci. USA* 94: 13287-13292 (1997); Hsiao, K., et al., *Science* 274: 99-102 (1996); Chen, G. et al., *Nature* 408: 975-979 (2000); Janus, C. et al., *Nature* 408: 979-982 (2000); Morgan, D. et al., *Nature* 408: 982-985 (2000)). Those mice models differ from each other in the level of overexpression of the transgene, the AD mutations present on the transgene and the promoter under which overexpression of the transgene is directed. These animal models fail to display all of the pathological signs of AD, which are in particular age-related changes in behaviour, deposition of β-amyloid into insoluble plaques, neurofibrillary tangles within neurons, and loss of neurons throughout the forebrain (Chapman, P. F. *Nature* 408: 915-916 (2000)). Memory deficits and methods to identify them could however be identified in those models, and may be used in testing the effect of the compositions of the invention in animal models (Chen, G. et al., *Nature* 408: 975-979 (2000); Janus, C. et al., *Nature* 408: 979-982

(2000); Morgan, D. et al., *Nature* 408: 982-985 (2000)). Furthermore, age related deposition of Aβ into amyloid plaques can be studied in those models, which also develop astrocytosis and microgliosis.

It will be understood by one of ordinary skill in the relevant arts that other suitable modifications and adaptations to the methods and applications described herein are readily apparent and may be made without departing from the scope of the invention or any embodiment thereof Having now described the present invention in detail, the same will be more clearly understood by reference to the following examples, which are included herewith for purposes of illustration only and are not intended to be limiting of the invention.

EXAMPLES

Example 1

Cloning and Construction, Respectively, Expression and Purification of Preferred Core Particles and VLP of RNA Phages, Respectively A. Construction and expression of mutant Qβ coat proteins, and purification of mutant Qβ coat protein VLPs or Capsids.

Plasmid Construction and Cloning of Mutant Coat Proteins

Construction of pQβ-240:

The plasmid pQβ10 (Kozlovska, T M, et al., *Gene* 137: 133-137) was used as an initial plasmid for the construction of pQβ-240. The mutation Lys13→Arg was created by inverse PCR. The inverse primers were designed in inverted tail-to-tail directions:

(SEQ ID NO: 48)
5'-GGTAACATCGGTCGAGATGGAAAACAAACTCTGGTCC-3' and (SEQ ID NO: 49)
5'-GGACCAGAGTTTGTTTTCCATCTCGACCGATGTTACC-3'.

The products of the first PCR were used as templates for the second PCR reaction, in which an upstream primer (SEQ ID NO: 50)
5'-AGCTCGCCCGGGGATCCTCTAG-3' and a downstream primer (SEQ ID NO: 51)
5'-CGATGCATTTCATCCTTAGTTATCAATACGCTGGGTTCAG-3' were used. The product of the second PCR was digested with XbaI and Mph1103I and cloned into the pQβ10 expression vector, which was cleaved by the same restriction enzymes. The PCR reactions were performed with PCR kit reagents and according to producer protocol (MBI Fermentas, Vilnius, Lithuania).

Sequencing using the direct label incorporation method verified the desired mutations. *E. coli* cells harbouring pQβ-240 supported efficient synthesis of 14-kD protein co migrating upon SDS-PAGE with control Qβ coat protein isolated from Qβ phage particles.

Resulting amino acid sequence: (SEQ ID NO: 17)

AKLETVTLGNIGRDGKQTLVLNPRGVNPTNGVASLSQAGAVP

ALEKRVTVSVSQPSRNRKNYKVQVKIQNPTACTANGSCDPSVTRQ

KYADVTFSFTQYSTDEERAFVRTELAALLASPLLIDAIDQLNPAY

Construction of pQβ-243:

The plasmid pQβ10 was used as an initial plasmid for the construction of pQβ-243. The mutation Asn10→Lys was created by inverse PCR. The inverse primers were designed in inverted tail-to-tail directions:

(SEQ ID NO: 52)
5'-GGCAAAATTAGAGACTGTTACTTTAGGTAAGATCGG-3' and (SEQ ID NO: 53)
5'-CCGATCTTACCTAAAGTAACAGTCTCTAATTTTGCC-3'.

The products of the first PCR were used as templates for the second PCR reaction, in which an upstream primer
    5'-AGCTCGCCCGGGGATCCTCTAG-3' (SEQ ID NO: 50) and a downstream primer
    5'-CGATGCATTTCATCCTTAGTTAT-CAATACGCTGGGTTCAG-3' (SEQ ID NO: 51)
were used. The product of the second PCR was digested with XbaI and Mph1103I and cloned into the pQβ10 expression vector, which was cleaved by the same restriction enzymes. The PCR reactions were performed with PCR kit reagents and according to producer protocol (MBI Fermentas, Vilnius, Lithuania).

Sequencing using the direct label incorporation method verified the desired mutations. *E. coli* cells harbouring pQβ-243 supported efficient synthesis of 14-kD protein co migrating upon SDSD-PAGE with control Qβ coat protein isolated from Qβ phage particles.

Resulting Amino Acid Sequence: (SEQ ID NO: 18)

AKLETVTLGKIGKDGKQTLVLNPRGVNPTNGVASLSQAGAVP

ALEKRVTVSVSQPSRNRKNYKVQVKIQNPTACTANGSCDPSVTRQ

KYADVTFSFTQYSTDEERAFVRTELAALLASPLLIDAIDQLNPAY

Construction of pQβ-250:

The plasmid pQβ-240 was used as an initial plasmid for the construction of pQβ-250. The mutation Lys2→Arg was created by site-directed mutagenesis. An upstream primer
    5'-GGCCATGGCACGACTCGAGACTGT-TACTTTAGG-3' (SEQ ID NO: 54)

and a downstream primer
    5'-GATTTAGGTGACACTATAG-3' (SEQ ID NO: 55)

were used for the synthesis of the mutant PCR-fragment, which was introduced into the pQβ-185 expression vector at the unique restriction sites NcoI and HindIII. The PCR reactions were performed with PCR kit reagents and according to producer protocol (MBI Fermentas, Vilnius, Lithuania).

Sequencing using the direct label incorporation method verified the desired mutations. *E. coli* cells harbouring pQβ-250 supported efficient synthesis of 14-kD protein co migrating upon PAGE with control Qβ coat protein isolated from Qβ phage particles.

Resulting Amino Acid Sequence: (SEQ ID NO: 19)

```
ARLETVTLGNIGRDGKQTLVLNPRGVNPTNGVASLSQAGAVP

ALEKRVTVSVSQPSRNRKNYKVQVKIQNPTACTANGSCDPSVTRQ

KYADVTFSFTQYSTDEERAFVRTELAALLASPLLIDAIDQLNPAY
```

Construction of pQβ-251:

The plasmid pQβ10 was used as an initial plasmid for the construction of pQβ-251. The mutation Lys16→Arg was created by inverse PCR. The inverse primers were designed in inverted tail-to-tail directions:

5'-

(SEQ ID NO: 56)
5'-GATGGACGTCAAACTCTGGTCCTCAATCCGCGTGGGG-3' and (SEQ ID NO: 57)
5'-CCCCACGCGGATTGAGGACCAGAGTTTGACGTCCATC-3'.

The products of the first PCR were used as templates for the second PCR reaction, in which an upstream primer 5'-AGCTCGCCCGGGGATCCTCTAG-3' (SEQ ID NO: 50) and a downstream primer

5'-CGATGCATTTCATCCTTAGTTAT-CAATACGCTGGGTTCAG-3' (SEQ ID NO: 51)

were used. The product of the second PCR was digested with XbaI and Mph1103I and cloned into the pQβ10 expression vector, which was cleaved by the same restriction enzymes. The PCR reactions were performed with PCR kit reagents and according to producer protocol (MBI Fermentas, Vilnius, Lithuania).

Sequencing using the direct label incorporation method verified the desired mutations. *E. coli* cells harbouring pQβ-251 supported efficient synthesis of 14-kD protein co migrating upon SDS-PAGE with control Qβ coat protein isolated from Qβ phage particles. The resulting amino acid sequence encoded by this construct is shown in (SEQ. ID NO: 20).

Construction of pQβ-259:

The plasmid pQβ-251 was used as an initial plasmid for the construction of pQβ-259. The mutation Lys2→Arg was created by site-directed mutagenesis. An upstream primer

5'-GGCCATGGCACGACTCGAGACTGT-TACTTTAGG-3' (SEQ ID NO: 54)

and a downstream primer

5'-GATTTAGGTGACACTATAG-3' (SEQ ID NO: 55)

were used for the synthesis of the mutant PCR-fragment, which was introduced into the pQβ-185 expression vector at the unique restriction sites NcoI and HindIII. The PCR reactions were performed with PCR kit reagents and according to producer protocol (MBI Fermentas, Vilnius, Lithuania).

Sequencing using the direct label incorporation method verified the desired mutations. *E. coli* cells harbouring pQβ-259 supported efficient synthesis of 14-kD protein co migrating upon SDS-PAGE with control Qβ coat protein isolated from Qβ phage particles.

Resulting Amino Acid Sequence: (SEQ ID NO: 21)

```
AKLETVTLGNIGKDGKQTLVLNPRGVNPTNGVASLSQAGAVP

ALEKRVTVSVSQPSRNRKNYKVQVKIQNPTACTANGSCDPSVTRQ

KYADVTFSFTQYSTDEERAFVRTELAALLASPLLIDAIDQLNPAY
```

General procedures for Expression and purification of Qβ and Qβ mutants

Expression

*E. coli* JM109 was transformed with Qβ coat protein expression plasmids. 5 ml of LB liquid medium containing 20 µg/ml ampicillin were inoculated with clones transformed with with Qβ coat protein expression plasmids. The inoculated culture was incubated at 37° C. for 16-24 h without shaking. The prepared inoculum was subsequently diluted 1:100 in 100-300 ml of fresh LB medium, containing 20 µg/ml ampicillin. and incubated at 37° C. overnight without shaking. The resulting second inoculum was diluted 1:50 in M9 medium containing 1% Casamino acids and 0.2% glucose in flasks, and incubated at 37° C. overnight under shaking.

Purification

Solutions and buffers for the purification procedure:
1. Lysis buffer LB
   50 mM Tris-HCl pH8,0 with 5 mM EDTA, 0,1% tritonX100 and freshly prepared PMSF at a concentration of 5 micrograms per ml. Without lysozyme and DNAse.
2. SAS
   Saturated ammonium sulphate in water
3. Buffer NET.
   20 mM Tris-HCl, pH 7.8 with 5 mM EDTA and 150 mM NaCl.
4. PEG
   40% (w/v) polyethylenglycol 6000 in NET Disruption and Lysis Frozen cells were resuspended in LB at 2 ml/g cells. The mixture was sonicated with 22 kH five times for 15 seconds, with intervals of 1 min to cool the solution on ice. The lysate was then centrifuged at 14 000 rpm, for 1 h using a Janecki K 60 rotor. The centrifugation steps described below were all performed using the same rotor, except otherwise stated. The supernatant was stored at 4° C., while cell debris were washed twice with LB. After centrifugation, the supernatants of the lysate and wash fractions were pooled.

Fractionation

A saturated ammonium sulphate solution was added drop-wise under stirring to the above pooled lysate. The volume of the SAS was adjusted to be one fifth of total volume, to obtain 20% of saturation. The solution was left standing overnight, and was centrifuged the next day at 14 000 rpm, for 20 min. The pellet was washed with a small amount of 20% ammonium sulphate, and centrifuged again. The obtained supernatants were pooled, and SAS was added dropwise to obtain 40% of saturation. The solution was left standing overnight, and was centrifuged the next day at 14 000 rpm, for 20 min. The obtained pellet was solubilised in NET buffer.

Chromatography

The capsid or VLP protein resolubilized in NET buffer was loaded on a Sepharose CL-4B column. Three peaks eluted during chromatography. The first one mainly contained membranes and membrane fragments, and was not collected. Capsids were contained in the second peak, while the third one contained other *E. coli* proteins.

The peak fractions were pooled, and the NaCl concentration was adjusted to a final concentration of 0.65 M. A volume of PEG solution corresponding to one half of the pooled peak fraction was added dropwise under stirring. The solution was left to stand overnight without stirring. The capsid protein was sedimented by centrifugation at 14 000 rpm for 20 min. It was then solubilized in a minimal volume of NET and loaded again on the Sepharose CL-4B column. The peak fractions were pooled, and precipitated with ammonium sulphate at 60% of saturation (w/v). After centrifugation and resolubilization in NET buffer, capsid protein was loaded on a Sepharose CL-6B column for rechromatography.

Dialysis and Drying

The peak fractions obtained above were pooled and extensively dialysed against sterile water, and lyophilized for storage.

Expression and Purification Qβ-240

Cells (*E. coli* JM 109, transformed with the plasmid pQβ-240) were resuspended in LB, sonicated five times for 15 seconds (water ice jacket) and centrifuged at 13000 rpm for one hour. The supernatant was stored at 4° C. until further processing, while the debris were washed 2 times with 9 ml of LB, and finally with 9 ml of 0.7 M urea in LB. All supernatants were pooled, and loaded on the Sepharose CL-4B column. The pooled peak fractions were precipitated with ammonium sulphate and centrifuged. The resolubilized protein was then purified further on a Sepharose 2B column and finally on a Sepharose 6B column. The capsid peak was finally extensively dialyzed against water and lyophilized as described above. The assembly of the coat protein into a capsid was confirmed by electron microscopy.

Expression and Purification Qβ-243

Cells (*E. coli* RR1) were resuspended in LB and processed as described in the general procedure. The protein was purified by two successive gel filtration steps on the sepharose CL-4B column and finally on a sepharose CL-2B column. Peak fractions were pooled and lyophilized as described above. The assembly of the coat protein into a capsid was confirmed by electron microscopy.

Expression and Purification of Qβ-250

Cells (*E. coli* JM 109, transformed with pQβ-250) were resuspended in LB and processed as described above. The protein was purified by gel filtration on a Sepharose CL-4B and finally on a Sepharose CL-2B column, and lyophilized as described above. The assembly of the coat protein into a capsid was confirmed by electron microscopy.

Expression and Purification of Qβ-259

Cells (*E. coli* JM 109, transformed with pQβ-259 ) were resuspended in LB and sonicated. The debris were washed once with 10 ml of LB and a second time with 10 ml of 0,7 M urea in LB. The protein was purified by two gel-filtration chromatogaphy steps, on a Sepharose CL-4 B column. The protein was dialyzed and lyophilized, as described above. The assembly of the coat protein into a capsid was confirmed by electron microscopy.

B. Cloning, Expression and Purification of Recombinant AP205 VLP

Cloning of the AP205 Coat Protein gene

The cDNA of AP205 coat protein (CP) (SEQ ID NO: 28) was assembled from two cDNA fragments generated from phage AP205 RNA by using a reverse transcription-PCR technique and cloning in the commercial plasmid pCR 4-TOPO for sequencing. Reverse transcription techniques are well known to those of ordinary skill in the relevant art. The first fragment, contained in plasmid p205-246, contained 269 nucleotides upstream of the CP sequence and 74 nucleotides coding for the first 24 N-terminal amino acids of the CP. The second fragment, contained in plasmid p205-262, contained 364 nucleotides coding for amino acids 12-131 of CP and an additional 162 nucleotides downstream of the CP sequence. Both p205-246 and p205-262 were a generous gift from J. Klovins.

The plasmid 283-58 was designed by two-step PCR, in order to fuse both CP fragments from plasmids p205-246 and p205-262 in one full-length CP sequence.

An upstream primer p1.44 containing the NcoI site for cloning into plasmid pQb185, or p1.45 containing the XbaI site for cloning into plasmid pQb10, and a downstream primer p1.46 containing the HindIII restriction site were used (recognition sequence of the restriction enzyme underlined):

```
p1.44  5'-AACC ATG GCA AAT AAG CCA ATG CAA CCG-3'      (SEQ ID NO: 79)

p1.45  5'-AATCTAGAATTTTCTGCGCACCCATCCCGG-3'            (SEQ ID NO: 80)

p1.46  5'-AAAAGC TTA AGC AGT AGT ATC AGA CGA TAC G-3'  (SEQ ID NO: 81)
```

Two additional primers, p1.47, annealing at the 5' end of the fragment contained in p205-262, and p1.48, annealing at the 3' end of the fragment contained in plasmid p205-246 were used to amplify the fragments in the first PCR. Primers p1.47 and p1.48 are complementary to each other.

```
p1.47: 5'-GAGTGATCCAACTCGTTTATCAACTACATTTTCAGCAAGTCTG-3'   (SEQ ID NO: 82)

p1.48: 5'-CAGACTTGCTGAAAATGTAGTTGATAAACGAGTTGGATCACTC-3'   (SEQ ID NO: 83)
```

In the first two PCR reactions, two fragments were generated. The first fragment was generated with primers p1.45 and p1.48 and template p205-246. The second fragment was generated with primers p1.47 and p1.46, and template p205-262. Both fragments were used as templates for the second PCR reaction, a splice-overlap extension, with the primer combination p1.45 and p1.46 or p1.44 and p1.46. The product of the two second-step PCR reactions were digested with XbaI or NcoI respectively, and HindIII, and cloned with the same restriction sites into pQb10 or pQb185 respectively, two pGEM-derived expression vectors under the control of *E. coli* tryptophan operon promoter.

Two plasmids were obtained, pAP283-58 (SEQ ID NO: 27), containing the gene coding for wt AP205 CP (SEQ ID NO: 28) in pQb10, and pAP281-32 (SEQ ID NO: 30) with mutation Pro5→Thr (SEQ ID NO: 29), in pQb185 The coat protein sequences were verified by DNA sequencing. PAP283-58 contains 49 nucleotides upstream of the ATG codon of the CP, downstream of the XbaI site, and contains the putative original ribosomal binding site of the coat protein mRNA.

Expression and Purification of Recombinant AP205 VLP

A. Expression of Recombinant AP205 VLP

E. coli JM109 was transformed with plasmid pAP283-58. 5 ml of LB liquid medium with 20 µg/ml ampicillin were inoculated with a single colony, and incubated at 37° C. for 16-24 h without shaking.

The prepared inoculum was diluted 1:100 in 100-300 ml of LB medium, containing 20 µg/ml ampicillin and incubated at 37° C. overnight without shaking. The resulting second inoculum was diluted 1:50 in 2TY medium, containing 0.2% glucose and phosphate for buffering, and incubated at 37° C. overnight on a shaker. Cells were harvested by centrifugation and frozen at −80° C.

B. Purification of Recombinant AP205 VLP

Solutions and buffers:
1. Lysis buffer
   50 mM Tris-HCl pH 8.0 with 5mM EDTA, 0.1% tritonX100 and PMSF at 5 micrograms per ml.
2. SAS
   Saturated ammonium sulphate in water
3. Buffer NET.
   20 mM Tris-HCl, pH 7.8 with 5 mM EDTA and 150 mM NaCl.
4. PEG
   40% (w/v) polyethylenglycol 6000 in NET Lysis:

Frozen cells were resuspended in lysis buffer at 2 ml/g cells. The mixture was sonicated with 22 kH five times for 15 seconds, with intervals of 1 min to cool the solution on ice. The lysate was then centrifuged for 20 minutes at 12 000 rpm, using a F34-6-38 rotor (Ependorf). The centrifugation steps described below were all performed using the same rotor, except otherwise stated. The supernatant was stored at 4° C., while cell debris were washed twice with lysis buffer. After centrifugation, the supernatants of the lysate and wash fractions were pooled.

Ammonium-sulphate precipitation can be further used to purify AP205 VLP. In a first step, a concentration of ammonium-sulphate at which AP205 VLP does not precipitate is chosen. The resulting pellet is discarded. In the next step, an ammonium sulphate concentration at which AP205 VLP quantitatively precipitates is selected, and AP205 VLP is isolated from the pellet of this precipitation step by centrifugation (14 000 rpm, for 20 min). The obtained pellet is solubilised in NET buffer.

Chromatography:

The capsid protein from the pooled supernatants was loaded on a Sepharose 4B column (2.8×70 cm), and eluted with NET buffer, at 4 ml/hour/fraction. Fractions 28-40 were collected, and precipitated with ammonium sulphate at 60% saturation. The fractions were analyzed by SDS-PAGE and Western Blot with an antiserum specific for AP205 prior to precipitation. The pellet isolated by centrifugation was resolubilized in NET buffer, and loaded on a Sepharose 2B column (2.3×65 cm), eluted at 3 ml/h/fraction. Fractions were analysed by SDS-PAGE, and fractions 44-50 were collected, pooled and precipitated with ammonium sulphate at 60% saturation. The pellet isolated by centrifugation was resolubilized in NET buffer, and purified on a Sepharose 6B column (2.5×47 cm), eluted at 3 ml/hour/fraction. The fractions were analysed by SDS-PAGE. Fractions 23-27 were collected, the salt concentration adjusted to 0.5 M, and precipitated with PEG 6000, added from a 40% stock in water and to a final concentration of 13.3%. The pellet isolated by centrifugation was resolubilized in NET buffer, and loaded on the same Sepharose 2B column as above, eluted in the same manner. Fractions 43-53 were collected, and precipitated with ammonium sulphate at a saturation of 60%. The pellet isolated by centrifugation was resolubilized in water, and the obtained protein solution was extensively dialyzed against water. About 10 mg of purified protein per gram of cells could be isolated.

Examination of the virus-like particles in Electron microscopy showed that they were identical to the phage particles.

Example 2

Insertion of a Peptide Containing a Lysine Residue Into the c/e1 Epitope of HBcAg(1-149)

The c/e1 epitope (residues 72 to 88) of HBcAg is located in the tip region on the surface of the Hepatitis B virus capsid (HBcAg). A part of this region (Proline 79 and Alanine 80) was genetically replaced by the peptide Gly-Gly-Lys-Gly-Gly (SEQ ID NO: 33), resulting in the HBcAg-Lys construct (SEQ ID NO: 26). The introduced Lysine residue contains a reactive amino group in its side chain that can be used for intermolecular chemical crosslinking of HBcAg particles with any antigen containing a free cysteine group.

HBcAg-Lys DNA, having the amino acid sequence shown in SEQ ID NO:78, was generated by PCRs: The two fragments encoding HBcAg fragments (amino acid residues 1 to 78 and 81 to 149) were amplified separately by PCR. The primers used for these PCRs also introduced a DNA sequence encoding the Gly-Gly-Lys-Gly-Gly peptide (SEQ ID NO: 33). The HBcAg (1 to 78) fragment was amplified from pEco63 using primers EcoRIHBcAg(s) and Lys-HBcAg(as). The HBcAg (81 to 149) fragment was amplified from pEco63 using primers Lys-HBcAg(s) and HBcAg(1-149)Hind(as). Primers Lys-HBcAg(as) and Lys-HBcAg(s) introduced complementary DNA sequences at the ends of the two PCR products allowing fusion of the two PCR products in a subsequent assembly PCR. The assembled fragments were amplified by PCR using primers EcoRIHBcAg(s) and HbcAg(1-149)Hind(as).

For the PCRs, 100 pmol of each oligo and 50 ng of the template DNAs were used in the 50 ml reaction mixtures with 2 units of Pwo polymerase, 0.1 mM dNTPs and 2 mM MgSO4. For both reactions, temperature cycling was carried out as follows: 94° C. for 2 minutes; 30 cycles of 94° C. (1 minute), 50° C. (1 minute), 72° C. (2 minutes).

Primer Sequences:

```
EcoRIHBcAg(s):
(5'-CCGGAATTCATGGACATTGACCCTTATAAAG-3');                            (SEQ ID NO: 58)

Lys-HBcAg(as):
(5'-CCTAGAGCCACCTTTGCCACCATCTTCTAAATTAGTACCCACCCAGGTAGC-3');         (SEQ ID NO: 59)
```

```
Lys-HBcAg(s):
(5'-GAAGATGGTGGCAAAGGTGGCTCTAGGGACCTAGTAGTCAGTTATGTC-3');    (SEQ ID NO: 60)

HBcAg(1-149)Hind(as):
(5'-CGCGTCCCAAGCTTCTAAACAACAGTAGTCTCCGGAAG-3').             (SEQ ID NO: 61)
```

For fusion of the two PCR fragments by PCR 100 pmol of primers EcoRIHBcAg(s) and HBcAg(1-149)Hind(as) were used with 100 ng of the two purified PCR fragments in a 50 ml reaction mixture containing 2 units of Pwo polymerase, 0.1 mM dNTPs and 2 mM MgSO$_4$. PCR cycling conditions were: 94° C. for 2 minutes; 30 cycles of 94° C. (1 minute), 50° C. (1 minute), 72° C. (2 minutes). The assembled PCR product was analyzed by agarose gel electrophoresis, purified and digested for 19 hours in an appropriate buffer with EcoRI and HindIII restriction enzymes. The digested DNA fragment was ligated into EcoRI/HindIII-digested pKK vector to generate pKK-HBcAg-Lys expression vector. Insertion of the PCR product into the vector was analyzed by EcoRI/HindIII restriction analysis and DNA sequencing of the insert.

Example 3

Expression and Purification of HBcAg-Lys

*E. coli* strains K802 or JM109 were transformed with pKK-HBcAg-Lys. 1 ml of an overnight culture of bacteria was used to innoculate 100 ml of LB medium containing 100 μg/ml ampicillin. This culture was grown for 4 hours at 37° C. until an OD at 600 nm of approximately 0.8 was reached. Induction of the synthesis of HBcAg-Lys was performed by addition of IPTG to a final concentration of 1 mM. After induction, bacteria were further shaken at 37° C. for 4 hours. Bacteria were harvested by centrifugation at 5000×g for 15 minutes. The pellet was frozen at −80° C. The pellet was thawed and resuspended in bacteria lysis buffer (10 mM Na$_2$HPO$_4$, pH 7.0, 30 mM NaCl, 0.25% Tween-20, 10 mM EDTA) supplemented with 200 μg/ml lysozyme and 10 μl of Benzonase (Merck). Cells were incubated for 30 minutes at room temperature and disrupted by sonication. *E. coli* cells harboring pKK-HBcAg-Lys expression plasmid or a control plasmid were used for induction of HBcAg-Lys expression with IPTG. Prior to the addition of IPTG, a sample was removed from the bacteria culture carrying the pKK-HBcAg-Lys plasmid and from a culture carrying the control plasmid. Four hours after addition of IPTG, samples were again removed from the culture containing pKK-HBcAg-Lys and from the control culture. Protein expression was monitored by SDS-PAGE followed by Coomassie staining.

The lysate was then centrifuged for 30 minutes at 12,000×g in order to remove insoluble cell debris. The supernatant and the pellet were analyzed by Western blotting using a monoclonal antibody against HBcAg (YVS1841, purchased from Accurate Chemical and Scientific Corp., Westbury, N.Y., USA), indicating that a significant amount of HBcAg-Lys protein was soluble. Briefly, lysates from *E. coli* cells expressing HBcAg-Lys and from control cells were centrifuged at 14,000×g for 30 minutes. Supernatant (=soluble fraction) and pellet (=insoluble fraction) were separated and diluted with SDS sample buffer to equal volumes. Samples were analyzed by SDS-PAGE followed by Western blotting with anti-HBcAg monoclonal antibody YVS 1841.

The cleared cell lysate was used for step-gradient centrifugation using a sucrose step gradient consisting of a 4 ml 65% sucrose solution overlaid with 3 ml 15% sucrose solution followed by 4 ml of bacterial lysate. The sample was centrifuged for 3 hrs with 100,000×g at 4° C. After centrifugation, 1 ml fractions from the top of the gradient were collected and analyzed by SDS-PAGE followed by Coomassie staining. The HBcAg-Lys protein was detected by Coomassie staining.

The HBcAg-Lys protein was enriched at the interface between 15 and 65% sucrose indicating that it had formed a capsid particle. Most of the bacterial proteins remained in the sucrose-free upper layer of the gradient, therefore step-gradient centrifugation of the HBcAg-Lys particles led both to enrichment and to a partial purification of the particles.

Expression and purification of HBcAg-Lys in large scale was performed as follows. An overnight culture was prepared by inoculating a single colony in 100 ml LB, 100 μg/ml Ampicillin and growing the culture overnight at 37° C. 25 ml of the preculture were diluted in 800 ml LB Ampicillin medium the next day, and the culture grown to an optical density OD$^{600}$ of 0.6-0.8. The culture was then induced with 1 mM IPTG, and left to grow for another 4 hours. The cells were harvested and lysed essentially as described above.

HBcAg-Lys was then purified by first precipitating the protein with ammonium sulphate (30% saturation) from the cleared cell lysate, then loading the resolubilized pellet on a gel filtration column (Sephacryl S-400, Pharmacia). The pooled fractions were precipitated again with ammonium sulphate, the pellet resolubilized and loaded a second time on the same gel filtration column. The fractions were finally pooled and concentrated, and the concentration assessed using a Bradford test (BioRad).

Example 4

Construction of a HBcAg Devoid of Free Cysteine Residues and Containing an Inserted Lysine Residue A Hepatitis core Antigen (HBcAg), referred to herein as HBcAg-lys-2cys-Mut, devoid of cysteine residues at positions corresponding to 48 and 107 in SEQ ID NO:25 and containing an inserted lysine residue was constructed using the following methods.

The two mutations were introduced by first separately amplifying three fragments of the HBcAg-Lys gene prepared as described above in Example 2 with the following PCR primer combinations. PCR methods and conventional cloning techniques were used to prepare the HBcAg-lys-2cys-Mut gene.

In brief, the following primers were used to prepare fragment 1:

```
Primer 1: EcoRIHBcAg(s)
                                    (SEQ ID NO: 58)
CCGGAATTCATGGACATTGACCCTTATAAAG Primer 2: 48as
                                    (SEQ ID NO: 62)
GTGCAGTATGGTGAGGTGAGGAATGCTCAGGAGACTC
```

The following primers were used to prepare fragment 2:

```
Primer 3: 48s
                                    (SEQ ID NO: 63)
GSGTCTCCTGAGCATTCCTCACCTCACCATACTGCAC Primer 4: 107as
                                    (SEQ ID NO: 64)
CTTCCAAAAGTGAGGGAAGAAATGTGAAACCAC
```

The following primers were used to prepare fragment 3:

```
Primer 5: HBcAg149hind-as
CGCGTCCCAAGCTTCTAAACAACAGTAGTCTCCGGAAGCGTTGATAG    (SEQ ID NO: 65)

Primer 6: 107s
GTGGTTTCACATTTCTTCCCTCACTTTTGGAAG                  (SEQ ID NO: 66)
```

Fragments 1 and 2 were then combined with PCR primers EcoRIHBcAg(s) and 107as to give fragment 4. Fragment 4 and fragment 3 were then combined with primers EcoRIHBcAg(s) and HBcAg149hind-as to produce the full length gene. The full length gene was then digested with the EcoRI (GAATTC) and HindIII (AAGCTT) enzymes and cloned into the pKK vector (Pharmacia) cut at the same restriction sites. Expression and purification of HBcAg-lys-2cys-Mut were performed as set out in Example 3.

Example 5

Construction of HBcAg1-185-Lys

Hepatitis core Antigen (HBcAg) 1-185 was modified as described in Example 2. A part of the c/e1 epitope (residues 72 to 88) region (Proline 79 and Alanine 80) was genetically replaced by the peptide Gly-Gly-Lys-Gly-Gly (SEQ ID NO: 33), resulting in the HBcAg-Lys construct (SEQ ID NO: 26). The introduced Lysine residue contains a reactive amino group in its side chain that can be used for intermolecular chemical crosslinking of HBcAg particles with any antigen containing a free cysteine group. PCR methods and conventional cloning techniques were used to prepare the HBcAg1-185-Lys gene.

The Gly-Gly-Lys-Gly-Gly sequence (SEQ ID NO: 33) was inserted by amplifying two separate fragments of the HBcAg gene from pEco63, as described above in Example 2 and subsequently fusing the two fragments by PCR to assemble the full length gene. The following PCR primer combinations were used:

```
fragment 1:
Primer 1: EcoRIHBcAg(s)              (SEQ ID NO: 58) (see Example 2)

Primer 2: Lys-HBcAg(as)              (SEQ ID NO: 59) (see Example 2)

fragment 2:
Primer 3: Lys-HBcAg(s)               (SEQ ID NO: 60) (see Example 2)

Primer 4: HBcAgwtHindIIII

CGCGTCCCAAGCTTCTAACATTGAGATTCCCGAGATTG   (SEQ ID NO: 67)

Assembly:
Primer 1: EcoRIHBcAg(s)              (SEQ ID NO: 58) (see example 2)

Primer 2: HBcAgwtHindIIII            (SEQ ID NO: 67)
```

The assembled full length gene was then digested with the EcoRI (GAATTC) and HindIII (AAGCTT) enzymes and cloned into the pKK vector (Pharmacia) cut at the same restriction sites.

Example 6

Fusion of a Peptide Epitope in the MIR Region of HbcAg

The residues 79 and 80 of HBcAg1-185 were substituted with the epitope CεH3 of sequence VNLTWSRASG (SEQ ID NO: 68). The CεH3 sequence stems from the sequence of the third constant domain of the heavy chain of human IgE. The epitope was inserted in the HBcAg1-185 sequence using an assembly PCR method. In the first PCR step, the HBcAg1-185 gene originating from ATCC clone pEco63 and amplified with primers HBcAg-wt EcoRI fwd and HBcAg-wt Hind III rev was used as template in two separate reactions to amplify two fragments containing sequence elements coding for the CεH3 sequence. These two fragments were then assembled in a second PCR step, in an assembly PCR reaction.

Primer combinations in the first PCR step: CεH3fwd with HBcAg-wt Hind III rev, and HBcAg-wt EcoRI fwd with CεH3rev. In the assembly PCR reaction, the two fragments isolated in the first PCR step were first assembled during 3 PCR cycles without outer primers, which were added afterwards to the reaction mixture for the next 25 cycles. Outer primers: HBcAg-wt EcoRI fwd and HBcAg-wt Hind III rev.

The PCR product was cloned in the pKK223.3 using the EcoRI and HindIII sites, for expression in *E. coli* (see Example 2). The chimeric VLP was expressed in *E. coli* and purified as described in Example 2. The elution volume at which the HBcAg1-185-CεH3 eluted from the gel filtration showed assembly of the fusion proteins to a chimeric VLP.

Primer Sequences:

```
CεH3fwd:
5' GTT AAC TTG ACC TGG TCT CGT GCT TCT GGT GCA TCC AGG GAT CTA GTA GTC 3'   (SEQ ID NO: 69)

V   N   L   T   W   S   R   A   S   G   A80 S   R   D   L   V   V86     (SEQ ID NO: 70)

CεH3rev:
5' ACC AGA AGC ACG AGA CCA GGT CAA GTT AAC ATC TTC CAA ATT ATT ACC CAC 3'   (SEQ ID NO: 71)

D78 E   L   N   N   G   V72         (SEQ ID NO: 72)

HBcAg-wt EcoRI fwd:
5' CCGgaattcATGGACATTGACCCTTATAAAG                                          (SEQ ID NO: 73)

HBcAg-wt Hind III rev:
5' CGCGTCCCaagcttCTAACATTGAGATTCCCGAGATTG                                   (SEQ ID NO: 74)
```

Example 7

Fusion of Aβ1-6 Peptide in the MIR Region of HbcAg

The residues 79 and 80 of HBcAg1-185 are substituted with the Aβ1-6 peptide of sequence: DAEFRH (SEQ ID NO: 75) or DAEFGH (SEQ ID NO: 76). Two overlapping primers are designed using the same strategy described in Example 6, and the fusion protein constructed by assembly PCR. The PCR product is cloned in the pKK223.3 vector, and expressed in *E. coli* K802. The chimeric VLPs are expressed and purified as described in Example 3.

Example 8

Fusion of a Aβ1-6 Peptide to the C-Terminus of the Qβ A1 Protein Truncated at Position 19 of the CP Extension A primer annealing to the 5' end of the Qβ A1 gene and a primer annealing to the 3' end of the A1 gene and comprising additionally a sequence element coding for the Aβ1-6 peptide, of sequence DAEFRH (SEQ ID NO: 75) or DAEFGH (SEQ ID NO: 76), are used in a PCR reaction with pQβ10 as template. The PCR product is cloned in pQβ10 (Kozlovska T. M. et al., *Gene* 137: 133-37 (1993)), and the chimeric VLP expressed and purified as described in Example 1.

Example 9

Insertion of a Aβ1-6 Peptide Between Positions 2 and 3 of fr Coat Protein

Complementary primers coding for the sequence of the Aβ1-6 peptide of sequence DAEFRH (SEQ ID NO: 75) or DAEFGH (SEQ ID NO: 76), and containing Bsp119I compatible ends and additional nucleotides enabling in frame insertion, are inserted in the Bsp119I site of the pFrd8 vector (Pushko, P. et al., *Prot. Eng.* 6: 883-91 (1993)) by standard molecular biology techniques. Alternatively, the overhangs of the pFrd8 vector are filled in with Klenow after digestion with Bsp119I, and oligonucleotides coding for the sequence of the Aβ1-6 peptide and additional nucleotides for in frame cloning are ligated in pFrd8 after the Klenow treatment. Clones with the insert in the right orientation are analysed by sequencing. Expression and purification of the chimeric fusion protein in *E. coli* JM109 or *E. coli* K802 is performed as described in Pushko, P. et al, *Prot. Eng.* 6:883-91 (1993), but for the chromatography steps which are performed using a Sepharose CL-4B or Sephacryl S-400 (Pharmacia) column. The cell lysate is precipitated with ammonium sulphate, and purified by two successive gel filtration purification steps, similarly to the procedure described for Qβ in Example 1.

Example 10

Insertion of a Aβ1-6 Peptide Between Positions 67 and 68 of Ty1 Protein p1 in the Vector pOGS8111

Two complementary oligonucleotides coding for the Aβ1-6 peptide, of sequence DAEFRH (SEQ ID NO: 75) or DAEFGH (SEQ ID NO: 76), with ends compatible with the NheI site of pOGS8111 are synthesized. Additional nucleotides are added to allow for in frame insertion of a sequence coding for the Aβ1-6 peptide according to the description of EP 677'111. The amino acids AS and SS flanking the inserted epitope are encoded by the altered NheI sites resulting from the insertion of the oligonucleotide in the TyA(d) gene of pOGS811.

POGS8111 is transformed into S. cervisiae strain MC2, for expression of the chimeric Ty VLP as described in EP0677111 and references therein. The chimeric Ty VLP is purified by sucrose gradient ultracentrifugation as described in EP 677'111.

Example 11

Insertion of a Aβ1-6 Peptide Into the Major Capsid Protein L1 of Papillomavirus Type 1 (BPV-1)

A sequence coding for the Aβ1-6 peptide having the sequence DAEFRH (SEQ ID NO: 75) or DAEFGH (SEQ ID NO: 76) is substituted to the sequence coding for amino acids 130-136 of the BPV-1 L1 gene cloned in the pFastBac1 (GIBCO/BRL) vector as described (Chackerian, B. et al., *Proc. Natl. Acad. USA* 96: 2373-2378 (1999)). The sequence of the construct is verified by nucleotide sequence analysis. Recombinant baculovirus is generated using the GIBCO/BRL baculovirus system as described by the manufacturer. The chimeric VLPs are purified from baculovirus infected Sf9 cells as described by Kirnbauer, R. et al., Proc. Natl. Acad. Sci. 89:12180-84 (1992) and Greenstone, H. L., et al., Proc. Natl. Acad. Sci. 95:1800-05 (1998).

Example 12

Immunization of Mice with Aβ1-6 Peptide Fused to VLPs

Chimeric VLPs displaying the Aβ1-6 peptide of sequence DAEFRH (SEQ ID NO: 75) or DAEFGH (SEQ ID NO: 76) generated in Examples 7-11 are used for immunization of human transgenic APP mice or C57/BL6 mice as described in Example 13 and 14. The sera obtained from the immunized mice are analysed in a Aβ1-6 peptide or Aβ1-40 or Aβ1-42 specific ELISA as described in Example 13.

The protective effect of the vaccine is examined by immunizing a large group of human APP transgenic mice as described in Example 14.

Example 13

Coupling of Aβ1-6 Peptide to Qβ VLP (QβAβ1-6), and Immunization of Mice with QβAβ1-6

A. Coupling of Aβ1-6 Peptide Qβ VLP

The Aβ1-6 peptide (sequence: NH2-DAEFRHGGC-CONH2) (SEQ ID NO: 77) was chemically synthesized; the initial NH2 group indicates that the peptide has a free N-terminus, and the terminal NH2 group indicates that the peptide has an amidated carboxy-terminus. Qβ VLP was expressed and purified as described in example 1. Qβ VLP, in 20 mM Hepes, 150 mM NaCl, pH 8.2 (HBS, pH 8.2) was reacted at a concentration of 2 mg/ml (determined in a Bradford assay), with 1.43 mM SMPH (Pierce, Rockford Ill.), diluted from a stock in DMSO, for 30 minutes at room temperature (RT). The reaction mixture was then dialyzed against HBS, pH 8.2 buffer at 4° C., and reacted with 0.36 mM of Aβ1-6 peptide, diluted in the reaction mixture from a 50 mM stock in DMSO. The coupling reaction was left to proceed for 2 hours at 15° C., and the reaction mixture dialyzed 2×2 hours against a 1000-fold volume HBS, pH 8.2, and flash frozen in liquid nitrogen in aliquots for storage at −80° C. until further use.

An aliquot was thawed, and coupling of the Aβ1-6 peptide to the Qβ VLP subunits assessed by SDS-PAGE and the protein concentration measured in a Bradford assay. The result of the coupling reactions are shown in FIG. 1.

FIG. 1 shows the SDS-PAGE analysis of the coupling reaction of Aβ1-6 peptide and Qβ VLP. The samples were run under reducing conditions on a 16% Tris-glycine gel, stained with coomassie brilliant blue. Lane 1 is the protein marker, with corresponding molecular weights indicated on the left border of the gel; lane 2, derivatized Qβ VLP protein; lane 3, the supernatant of the coupling reaction of Qβ VLP protein to the Aβ1-6 peptide; lane 4, the pellet of the coupling reaction of Qβ VLP protein to the Aβ1-6 peptide; Coupling products corresponding to the coupling of 1, 2 and 3 peptides per monomer are indicated by arrows in the Figure. More than 1.5 peptides per subunit were coupled on average; nearly no subunits were left uncoupled.

B. Immunisation of Mice with Aβ1-6 Peptide Coupled to Qβ VLP and Analysis of Immune Response Qβ VLP coupled to Aβ1-6 peptide (denominated here Qb-Ab-1-6) was injected s.c. in mice (3 mice) at day 0 and 14. Aβ1-6 peptide was coupled to Qβ VLP protein as described above. Each mice (C57BL/6) was immunized with 10 μg of vaccine diluted in PBS to 200 μl. Mice were retroorbitally bled on day 21, and the titer of the antibodies specific for the Aβ1-6 peptide were measured in an ELISA against Aβ1-6. The Aβ1-6 peptide was coupled to bovine RNAse A using the chemical cross-linker sulfo-SPDP. ELISA plates were coated with coupled RNAse preparations at a concentration of 10 μg/ml. The plates were blocked and then incubated with serially diluted mouse sera. Bound antibodies were detected with enzymatically labeled anti-mouse IgG antibodies. As a control, preimmune sera of the same mice were also tested. The results are shown in FIG. 2.

FIG. 2 shows an ELISA analysis of the IgG antibodies specific for Aβ1-6 peptide in sera of mice immunized against the Aβ1-6 peptide coupled to Qβ VLP. The results are shown for the three mice immunized (A1-A3), the pre-immune serum is indicated as "pre" in the figure; the result for one pre-immune serum is shown. Comparison of the pre-immune sera with the sera of mice immunized with "Qb-Ab-1-6" shows that a strong specific antibody response against peptide Aβ1-6 could be obtained in the absence of adjuvant.

C. ELISA Against Aβ1-40 Peptide

Human Aβ1-40 or Aβ1-42 peptide stock was made in DMSO and diluted in coating buffer before use. ELISA plates were coated with 0.1 μg/well Aβ1-40 peptide. The plates were blocked and then incubated with serially diluted mouse serum obtained above. Bound antibodies were detected with enzymatically labeled anti-mouse IgG antibody. As a control, sera obtained before vaccination were also included. The serum dilution showing a mean three standard deviations above baseline was calculated and defined as "ELISA titer". No specific antibodies were detected in preimmune sera. The titer obtained for the three mice was of 1:100000, showing a strong specific immune response against Aβ1-40. Thus, immunization with Aβ1-6 coupled to Qβ VLP elicits strong antibody titers cross-reactive with Aβ1-40.

Figure 3:
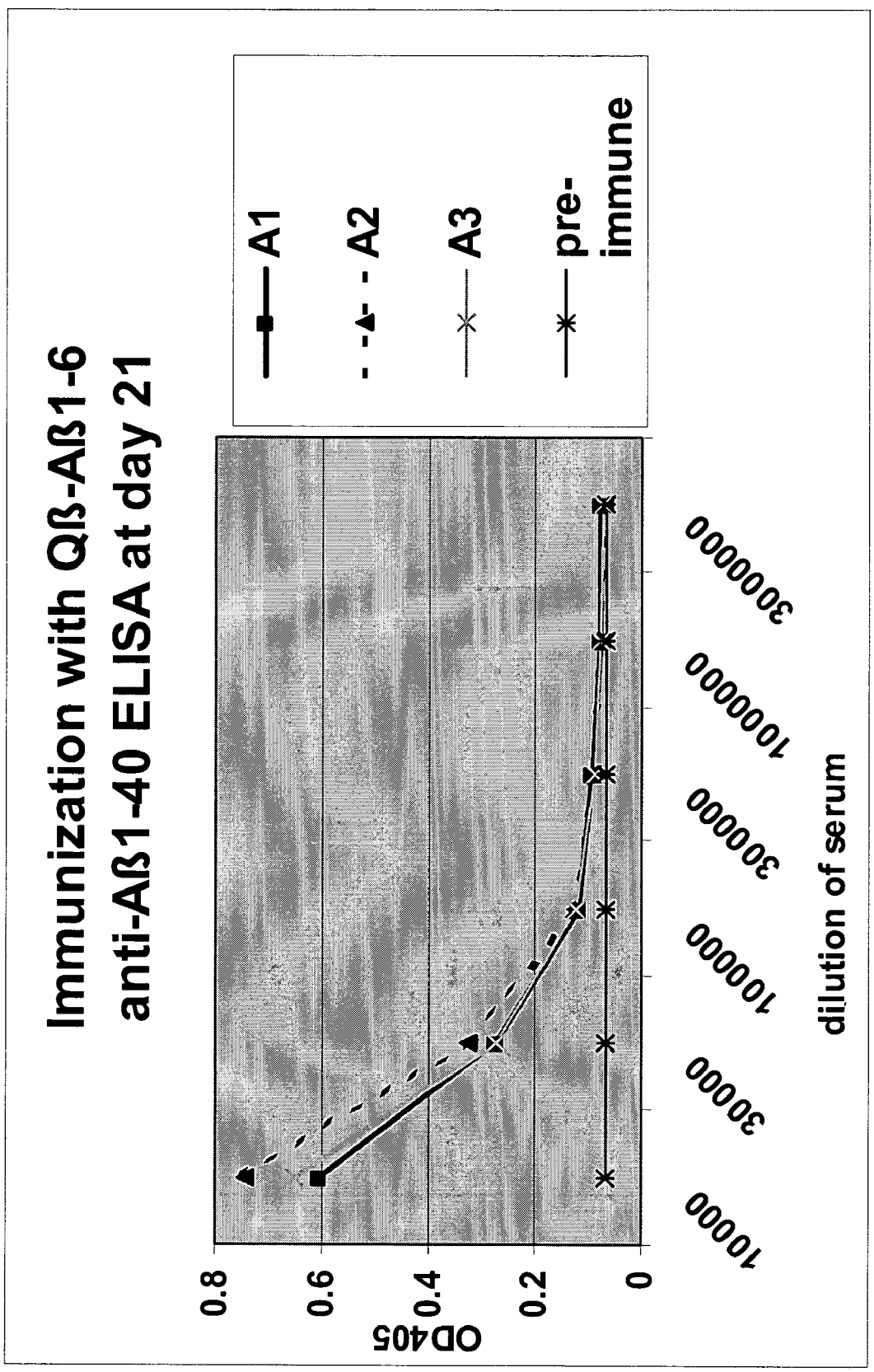
FIG. 3 shows the ELISA analysis of the antibodies specific for Aβ1-40 in sera of mice immunized with Aβ1-6 peptide coupled to the VLP of Qβ coat protein.

FIG. 3 shows the result of the ELISA. The ELISA signal as the optical density at 405 nm, obtained for the sera of three mice (A1-A3) immunized with Aβ1-6 peptide coupled to Qβ VLP as described above, is plotted for each of the dilutions, indicated on the x-axis. The result for the three mice bled at day 21 is shown. Also included is a pre-immune serum. The titer of the antibodies in the sera was determined as described above, and was of 1:100000 for all three mice.

Example 14

Immunization of Human APP Transgenic Mice 8 months old female APP23 mice which carry a human APP transgene (Sturchler-Pierrat et al., *Proc. Natl. Acad. Sci. USA* 94: 13287-13292 (1997)) are used for vaccination. The mice are injected subcutaneously with 25 μg vaccine diluted in sterile PBS and 14 days later boosted with the same amount of vaccine. Mice are bled from the tail vein before the start of immunization and 7 days after the booster injection. The sera are analyzed for the presence of antibodies specific to a Aβ1-6, to Aβ1-40 and Aβ1-42 by ELISA as described in Example 13.

Example 15

Coupling of Murine Aβ1-6 to Qβ VLP, Injection of the Vaccine in Mice, and Analysis of the Immune Response Murine Aβ1-6 peptide (sequence: NH2-DAEFGHGGC-CONH2) (SEQ ID NO: 78) is chemically synthesized, and used for coupling to Qβ VLP as described in Example 13. The vaccine is injected in C57BL/6 mice, and the titer of the elicited antibodies against murine Aβ1-6, murine Aβ1-40 and murine Aβ1-42 determined. The immunization and the ELISA determination are performed as described in Example 13.

Example 16

Binding of sera Elicited Against Aβ1-6 to Human APP Transgenic Mice Plaques and AD Plaques Immunohistochemistry in Brain Slices Consecutive paraffin brain sections of a 18 months, old heterozygous APP23 mouse and entorhinal cortex sections from an AD patient Braak Stage III (Institute of Pathology, University Basel) were used for staining. Antigenicity was enhanced by treating human brain sections with concentrated formic acid for five minutes and mouse brain sections by microwave heating at 90° C. for 3 minutes. Mice sera elicited against human Aβ1-6 (obtained as described in Example 13) were diluted 1:1000 in PBS with 3% goat serum and incubated over night. Following rinsing, sections were incubated for 1 hour with biotinylated anti mouse secondary antibody diluted 1:200 in PBS. After rinsing, sections were further processed with the avidin-biotin-peroxidase technique (ABC-Elite Kit PK6100; Vector Laboratories). Finally, sections were reacted with Diaminobenzidine (DAB) metal enhanced substrate (Boehringer, Code 1718096), counterstaind with Hemalum, dehydrated, cleared in Xylene and coversliped.

Figure 4A:
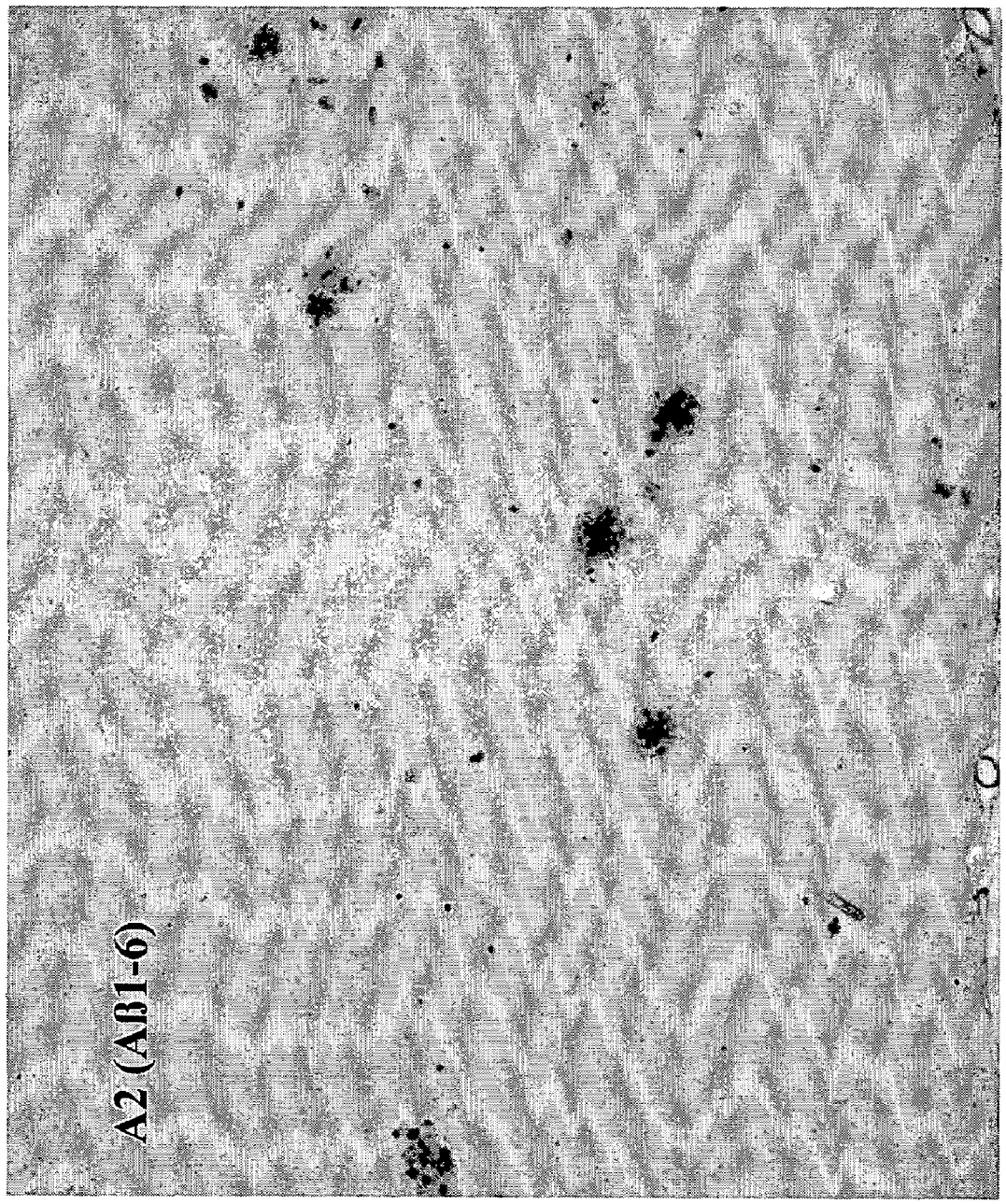
FIG. 4A-B show a brain section of an APP23 mouse (A) and an entorhinal cortex section from an AD patient (B) stained with sera of mice immunized with Aβ1-6 peptide coupled to the VLP of Qβ coat protein.
Figure 4B:
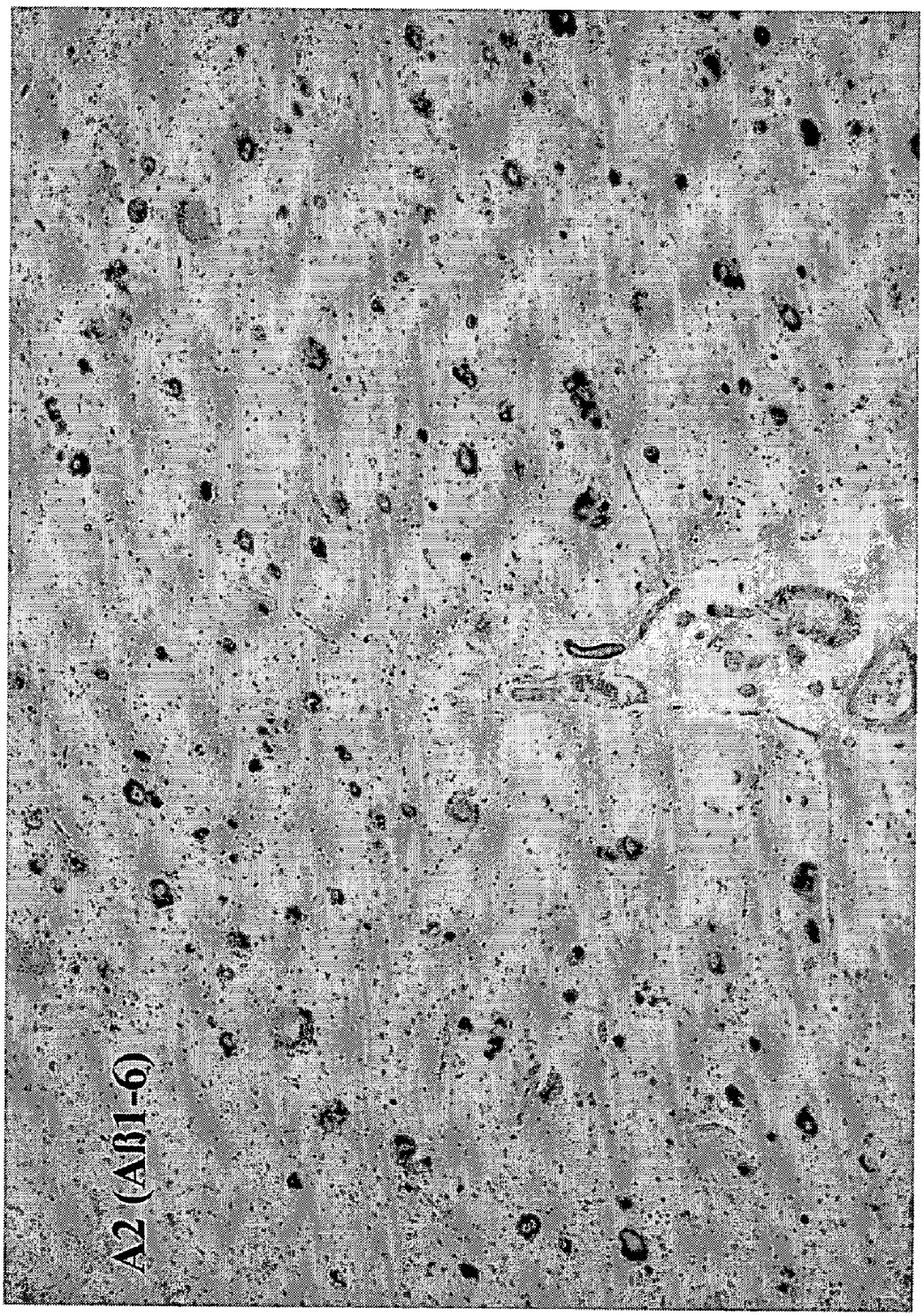

The result of the histologic stains are shown in FIG. 4A and B. Sections were stained with the sera of the three mice immunized against human Aβ1-6 coupled to Qβ VLP. Each serum stained positively the amyloid plaques from transgenic mice and AD. Results for one of the three sera are shown. Sera elicited against human Aβ1-6 clearly stain amyloid plaques of the transgenic human APP23 mouse, as well as amyloid plaques from AD patients. Pre-immune sera were negative. Extracellular amyloid plaques and isolated blood vessels are stained by the antibodies.

Example 17

Specificity of Sera Elicited Against Human Aβ1-6, Assessed by Histology of Mice Plaques Immunohistochemistry in Brain Slices Consecutive paraffin brain sections of a 3 months and an 18 months old heterozygous APP23 mouse overexpressing human APP were stained as described in Example 16 with a representative mouse serum elicited against human Aβ1-6 as described in Example 13, or with a rabbit polyclonal antibody specific for the last 20 amino acids of murine or human APP and which therefore does not recognizes Aβ. The sections incubated with the rabbit polyclonal antibody were treated as described in Example 16, except for the use of a biotinylated anti rabbit secondary antibody (BA1000, Vector Laboratories).

Figure 5:
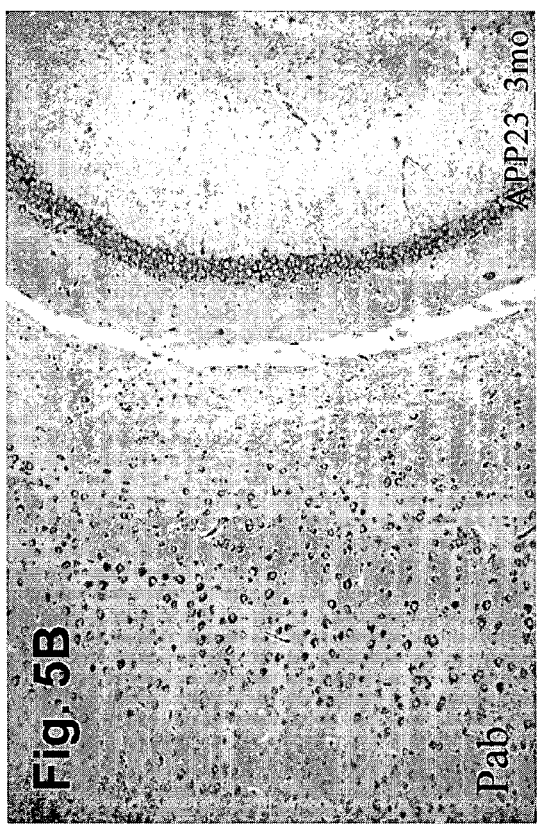
FIGS. 5A-E show brain sections of an APP23 mouse stained with sera of mice immunized with Aβ1-6 peptide coupled to the VLP of Qβ coat protein, or with a polyclonal rabbit antiserum specific for the C-terminus of human or mouse APP.
Figure 5:
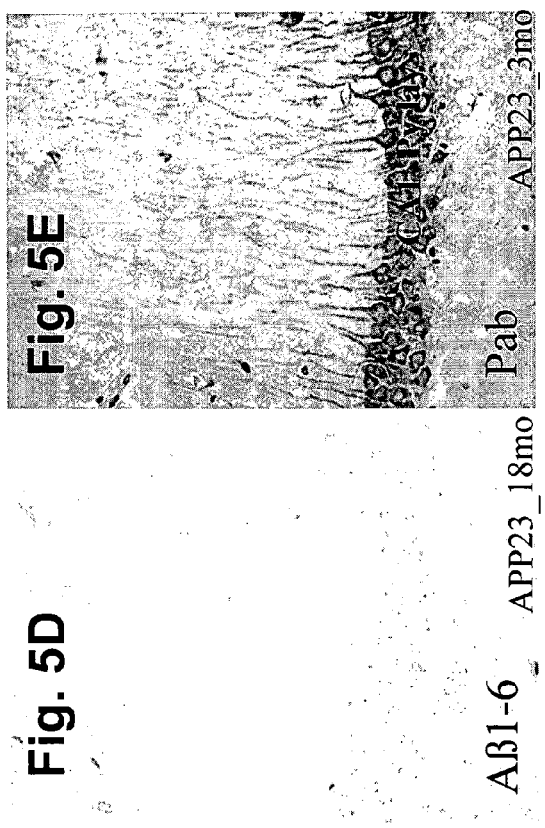
Figure 5:
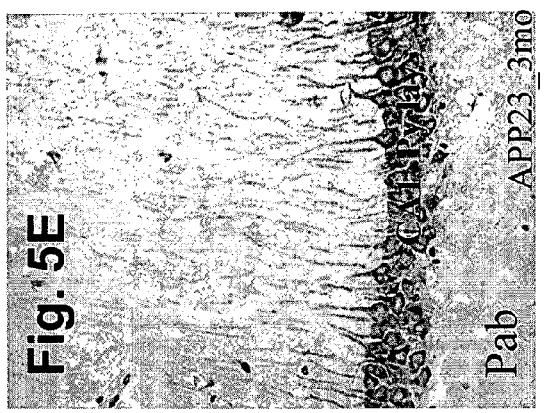
Figure 5:
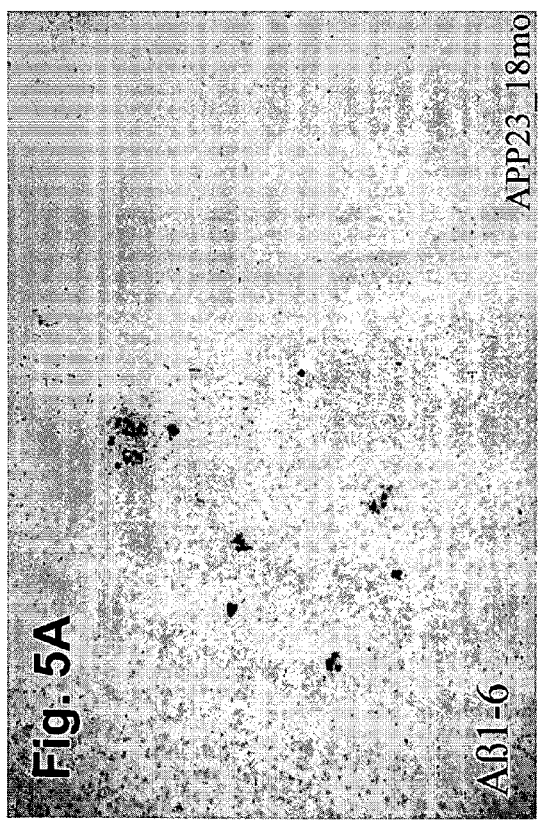
Figure 5:
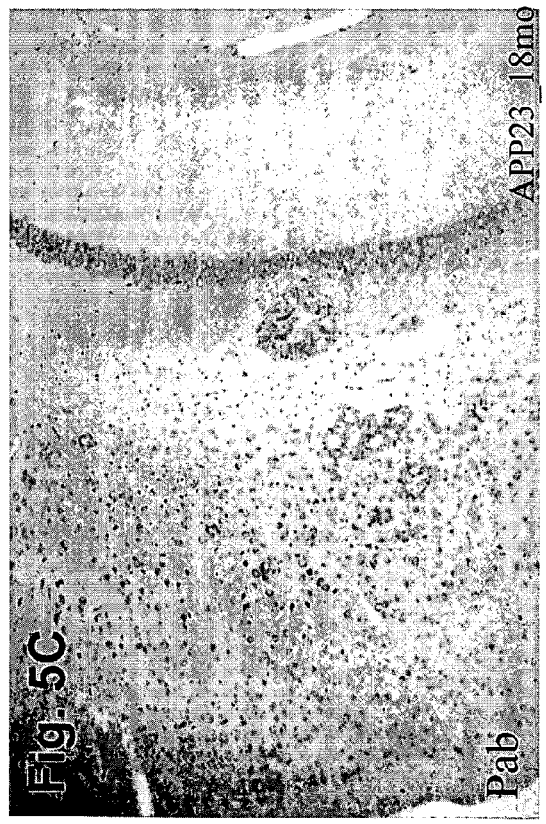

The result of the histologic stains are shown on FIG. 5A, B, C, D and E. Aβ1-6, marked on the bottom left of the sections indicate that sera elicited against Aβ1-6 have been used for the staining, while "Pab" indicates that the sections have been stained with the polyclonal antibody specific for the last 20 amino acids of murine or human APP, corresponding to positions 676-695 in $APP_{695}$.

Comparison of the staining of sections from 18 months old mice (FIG. 5A and C) shows that the sera elicited against Aβ1-6 do not cross-react with APP expressed in the brain, which is however stained by the control polyclonal antibody. FIG. 5B shows a brain section from a 3 months old mouse, a timepoint where amyloid deposits are not yet visible, stained with the polyclonal antibody specific for APP. FIG. 5D and 5E show a magnification of the CA1 pyramidal layer of the hippocampus from FIG. 5A. and FIG. 5B, respectively.

Example 18

A. Coupling of Aβ1-6 Peptide to fr Capsid Protein

A solution of 120 μM fr capsid protein in 20 mM Hepes, 150 mM NaCl pH 7.2 is reacted for 30 minutes with a 10 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed fr reaction mixture is then reacted with a a five-fold molar excess of Aβ1-6 peptide (sequence: NH2-DAEFRHGGC-CONH2) (SEQ ID NO: 77) for 2 hours at 16° C. on a rocking shaker. Coupling products are analysed by SDS-PAGE.

B. Coupling of Aβ1-6 Peptide to HBcAg-Lys-2cys-Mut

A solution of 1 ml of 120 μM HBcAg-Lys-2cys-Mut in 20 mM Hepes, 150 mM NaCl pH 7.2 is reacted for 30 minutes with a 10 fold molar excess of SMPH (Pierce), diluted from a stock solution in DMSO, at 25° C. on a rocking shaker. The reaction solution is subsequently dialyzed twice for 2 hours against 1 L of 20 mM Hepes, 150 mM NaCl, pH 7.2 at 4° C. The dialyzed HBcAg-Lys-2cys-Mut reaction mixture is then reacted with a five-fold molar excess of Aβ1-6 peptide (sequence: NH2-DAEFRHGGC-CONH2) (SEQ ID NO: 77) for 2 hours at 16° C. on a rocking shaker. Coupling products are analysed by SDS-PAGE.

C. Coupling of Aβ1-6 Peptide to Pili

A solution of 125 μM Type-1 pili of E. coli in 20 mM Hepes, pH 7.4, is reacted for 60 minutes with a 50-fold molar excess of cross-linker SMPH (Pierce), diluted from a stock solution in DMSO, at RT on a rocking shaker. The reaction mixture is desalted on a PD-10 column (Amersham-Pharmacia Biotech). The protein-containing fractions eluating from the column are pooled, and the desalted derivatized pili protein is reacted with a five-fold molar excess of Aβ1-6 peptide (sequence: NH2-DAEFRHGGC-CONH2) (SEQ ID NO: 77) for 2 hours at 16° C. on a rocking shaker. Coupling products are analysed by SDS-PAGE.

D. Immunization of Mice with Aβ1-6 Peptide Coupled to fr-Capsid Protein, HBcAg-Lys-2cys-Mut or Pili Aβ1-6 peptide coupled to fr-capsid protein, HBcAg-Lys-2cys-Mut or pili as described above is injected s.c. in mice (3 mice) at day 0 and 14. Each mice (C57BL/6) is immunized with 10 μg of vaccine diluted in PBS to 200 μl. Mice are retroorbitally bled on day 21, and the titer of the antibodies specific for the Aβ1-6 peptide or Aβ1-40 or Aβ1-42 are measured by ELISA as described in Example 13.

Example 19

Immunisation of Rhesus Monkeys with QβhAβ1-6

In order to test induction of antibodies against human Aβ using a human Aβ1-6 peptide based vaccine in the case where Aβ1-6 is a self antigen, rhesus monkeys were immunized with QβhAβ1-6, as the Aβ sequence is identical between humans and Rhesus monkeys. QβhAβ1-6 vaccine was made as described in Example 13. Four Rhesus monkeys, between 10 and 15 years of age, were immunized at day 0 with 50 μg of vaccine, and boosted twice at day 28 and 56 with 25 μg of vaccine. The monkeys were immunized subcutaneously in the back. The animals were bled at day 0 (prebleed), 42 and 70. 4 ml of blood were collected from the V. cephalica antebrachii. The titer of antibodies specific for Aβ1-40 were measured by ELISA essentially as described in Example 13, using a secondary antibody specific for Monkey IgG.

As humans and rhesus monkeys share the same Aβ sequence, the generation of high titer antibodies in rhesus monkeys specific for Aβ1-40 shows that immunization with hAβ1-6 coupled to Qβ breaks tolerance against the self-antigen Aβ. Furthermore, antibodies recognizing full length Aβ are generated with the coupled Aβ1-6 fragment in primates.

Figure 6:
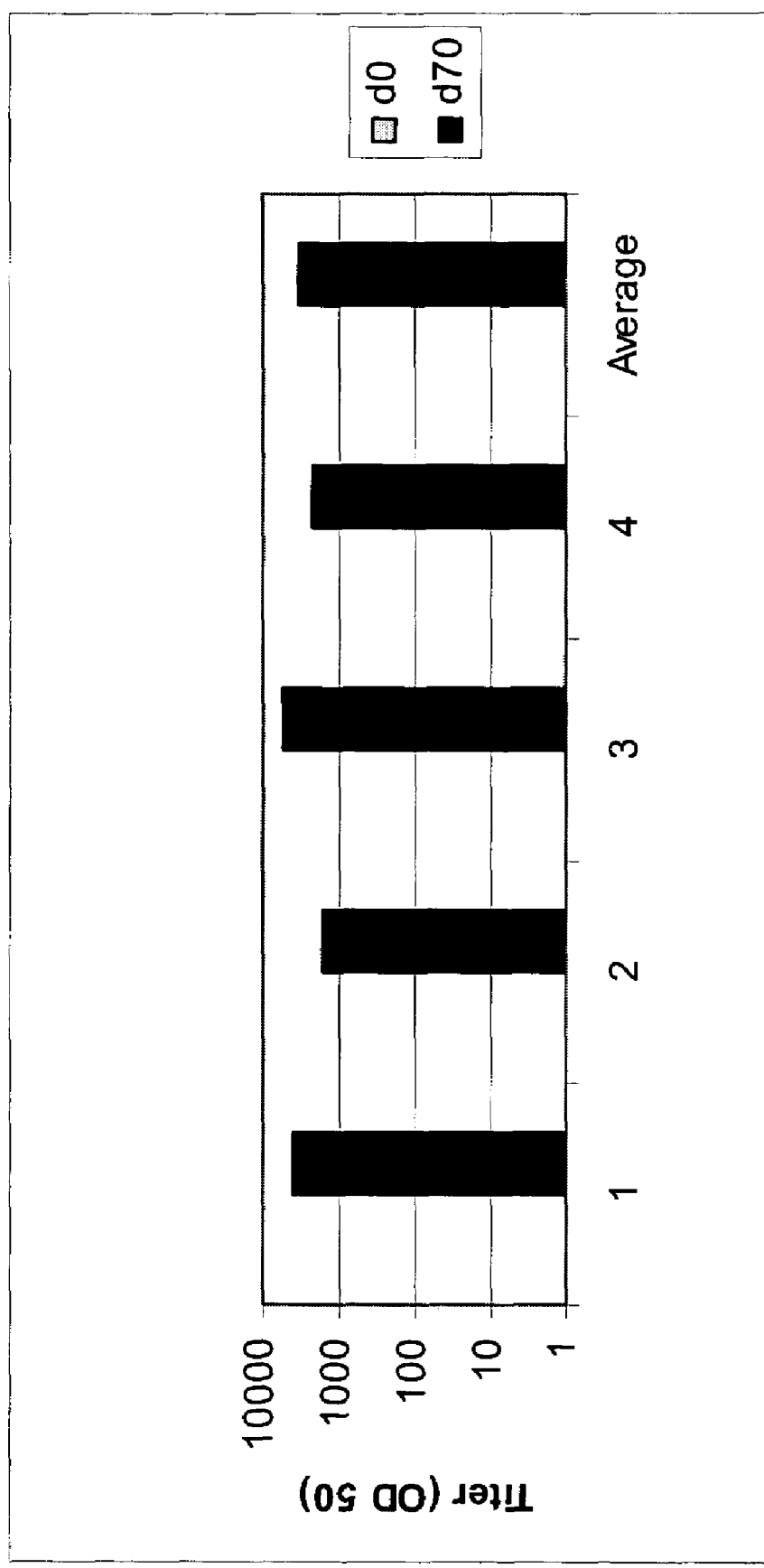
FIG. 6 shows the result of the immunization of rhesus monkeys with human Aβ1-6 coupled to Qβ VLP as measured in an ELISA assay.

The results of the ELISA are shown in FIG. 6. Plotted in the diagram are the titers of Aβ1-40 specific antibodies measured in the sera of the 4 monkeys (1-4) immunized with QβhAβ1-6 and the average of the titers of the 4 monkeys. The titers are represented as OD50 titers. OD50 is the dilution of the antibodies at which the signal reaches half of its maximal value. The maximal value (OD max) was obtained from a reference serum originating from a monkey immunised with QβhAβ1-27 and recognizing Aβ1-40 as well, and measured on the same ELISA plate.

Two monkeys (described above) were bled at day 97, 110, 117, 124, 138, 143, 152, 159, 166, and received a third boost with 25 μg of vaccine at day 110. Sera were pooled (99 ml) and used for affinity purification of Aβ1-6-specific antibodies. These antibodies were used for immunohistochemical staining at a concentration of 1.5 μg/ml and a biotinylated secondary anti-monkey antibody was used for detection. Paraffine brain sections of 18 months old heterozygous APP23 mouse and an AD patient—Braak Stage III—were used for staining. Plaque-specific staining was observed both in APP23 mouse brain sections and in the AD patient brain sections (FIG. 7).

Figure 7B:
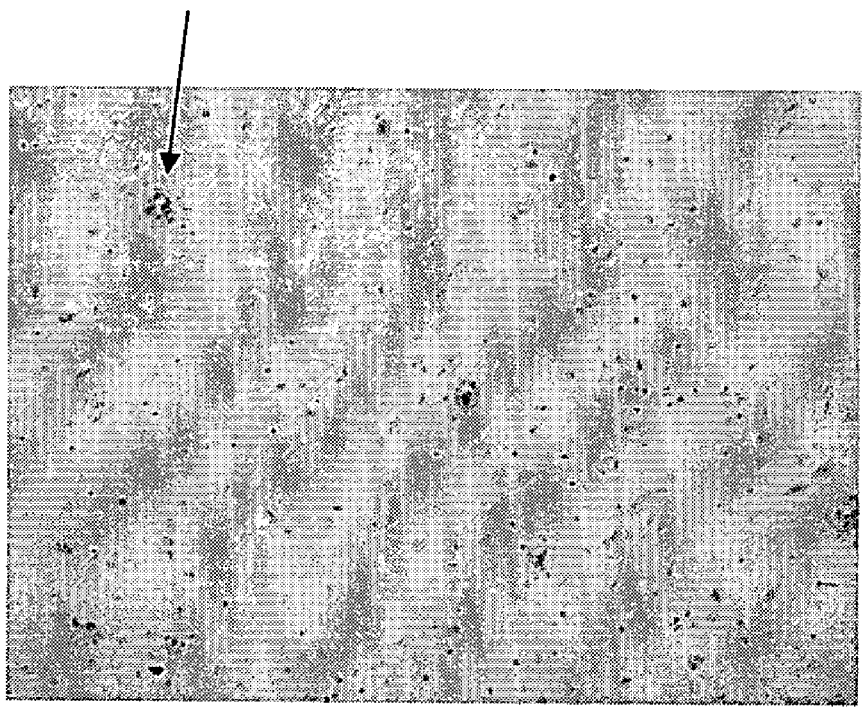
FIG. 7 shows the result of the binding to plaques of sera from monkeys immunized with human Aβ1-6 coupled to Qβ VLP, as measured by histology on human AD and transgenic mouse plaques.
Figure 7A:
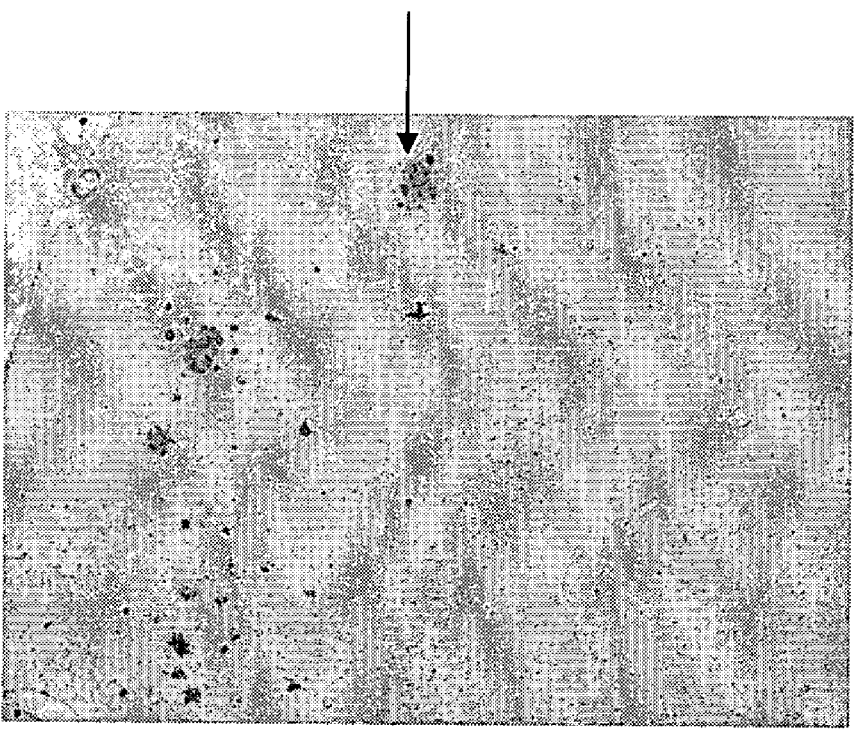

The result of the histological analysis is shown in FIG. 7A and B. Depicted in FIG. 7A is the staining of human APP transgenic mouse plaques (APP23 strain) with the above described affinity purified antiserum specific for Aβ1-6. FIG. 7B shows the staining of human AD plaques with the same purified antiserum. The purified antiserum was used at a concentration of 1.5 μg/ml in both cases. Typical plaques are indicated by an arrow on both figures.

Example 20

Coupling of Murine Aβ1-6 to AP205 VLP, Immunisation of Mice and Analysis of Immune Response A. Coupling of Murine Aβ1-6 Peptide to AP205 VLP The peptide murine Aβ1-6 (mAβ1-6, sequence: NH2-DAEFGHGGC-CONH2 (SEQ ID NO: 78) was chemically synthesized; the initial NH2 group indicates that the peptide has a free N-terminus, and the terminal NH2 group indicates that the peptide has an amidated carboxy-terminus). AP205 VLP (expressed and purified as described in Example 1), in 20 mM Hepes, 150 mM NaCl, pH 8.0 (HBS, pH 8.0) was reacted at a concentration of 2 mg/ml (determined in a Bradford assay), with 2.86 mM SMPH (Pierce, Rockford Ill.), diluted from a 100 mM stock in DMSO, for 30 minutes at room temperature (RT). The reaction mixture was then dialyzed twice against a 1000-fold volume of HBS, pH 7.4. at 4° C. for two hours; the resulting dialyzed and derivatized AP205 VLP was flash frozen in liquid nitrogen and stored at −20° C. overnight. Derivatized AP205 VLP was diluted with one volume of 20 mM HBS, pH 7.4, and reacted 2 hours at 15° C. under shaking with 719 μM mAβ1-6 peptide diluted in the reaction mixture from a 50 mM stock in DMSO. The coupling reaction was dialyzed twice against a 1000-fold volume HBS, pH 7.4, for 2 hours and overnight. The dialyzed reaction mixture was flash frozen in liquid nitrogen in aliquots for storage at −80° C. until further use.

An aliquot was thawed, and coupling of the mAβ1-6 peptide to the AP205 VLP subunits assessed by SDS-PAGE and the protein concentration measured in a Bradford assay. The result of the coupling reaction is shown in FIG. 8.

Figure 8:
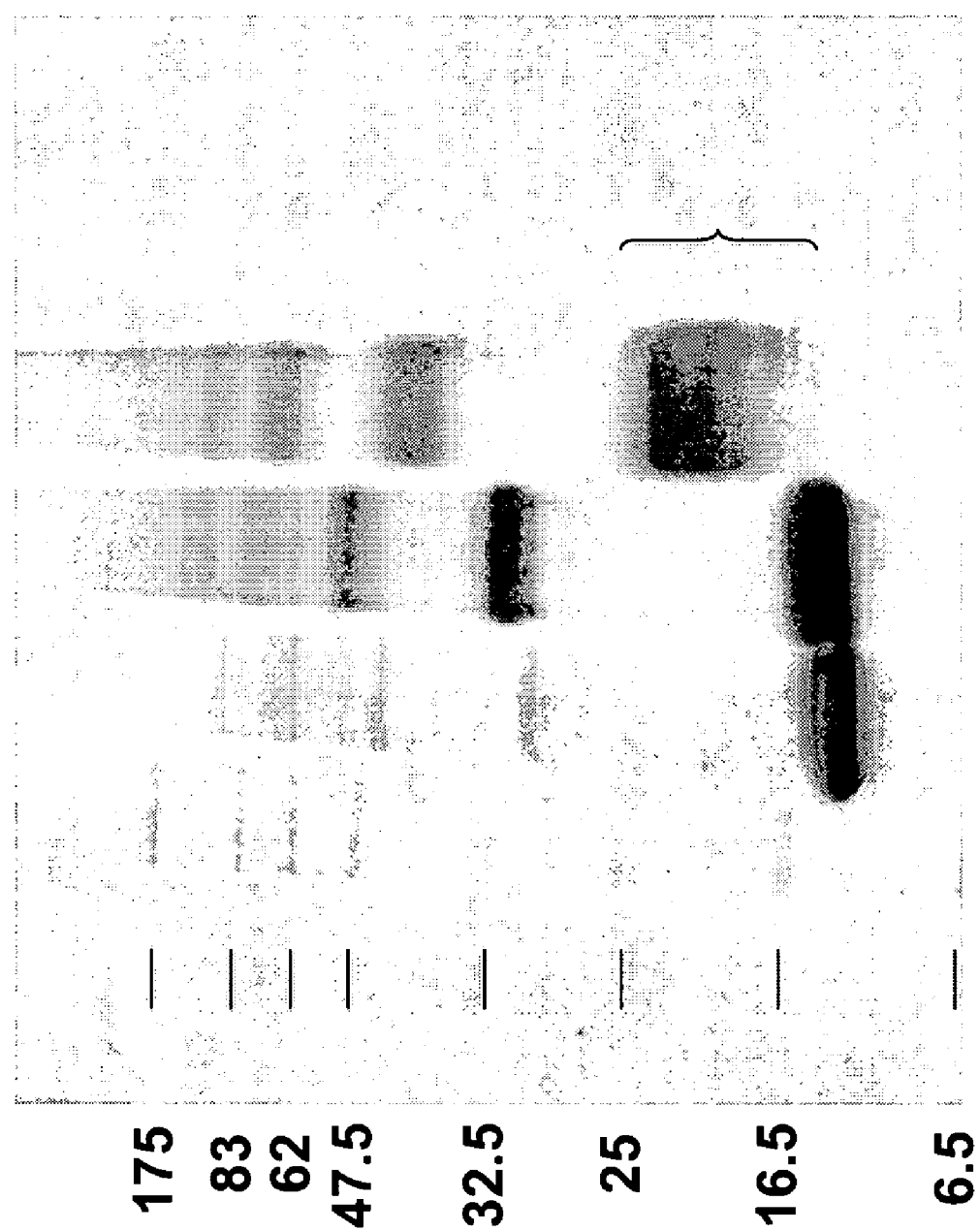
FIG. 8 depicts the SDS-PAGE analysis of the coupling of murine Aβ1-6 to AP205 VLP.

FIG. 8 shows the SDS-PAGE analysis of the coupling reaction of mAβ1-6 peptide to AP205 VLP. The samples were run under reducing conditions on a 16% Tris-glycine gel and stained with coomassie brilliant blue. Lane 1 is the protein marker, with corresponding molecular weights indicated on the left border of the gel; lane 2, AP205 VLP protein; lane 3, derivatized AP205 VLP; lane 4, the supernatant of the coupling reaction of AP205 VLP to mAβ1-6 peptide; lane 5, the pellet of the coupling reaction of AP205 VLP to mAβ1-6 peptide. No AP205 VLP subunits left uncoupled could be detected on the gel, while bands corresponding to several peptides per subunits were visible, demonstrating a very high coupling efficiency. In particular, there is much more than one Aβ1-6 peptide per AP205 VLP subunit.

B. Immunisation of Mice with mAβ1-6 Peptide Coupled to AP205 VLP and Analysis of Immune Response AP205 VLP coupled to mAβ1-6 peptide was injected s.c. in mice (3 mice) at day 0 and 14. mAβ1-6 peptide was coupled to AP205 VLP as described above. Each mice (C57BL/6) was immunized with 25 µg of vaccine diluted in PBS to 200 µl. Mice were retroorbitally bled on day 21, and the titer of the antibodies specific for the mAβ1-6 peptide were measured in an ELISA against mAβ1-6. The mAβ1-6 peptide was coupled to bovine RNAse A using the chemical cross-linker sulfo-SPDP. ELISA plates were coated with preparations of RNAse-mAβ1-6 at a concentration of 10 µg/ml. The plates were blocked and then incubated with serially diluted mouse sera. Bound antibodies were detected with enzymatically labeled anti-mouse IgG antibodies. As a control, preimmune sera of the same mice were also tested. The results are shown in FIG. 9.

Figure 9:
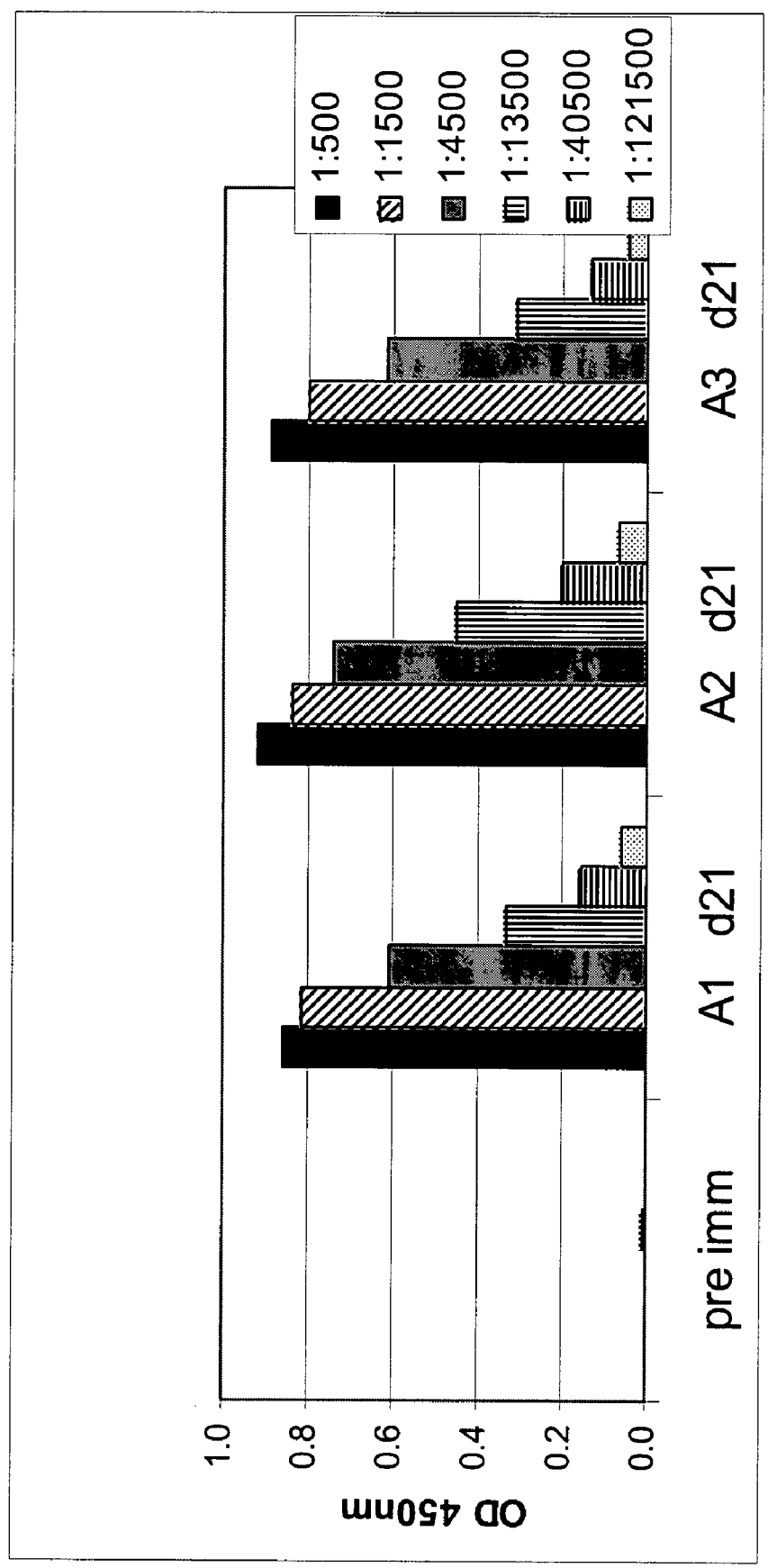
FIG. 9 shows the result of the immunisation of mice with murine Aβ1-6 coupled to AP205 as measured in an ELISA assay.

FIG. 9 shows an ELISA analysis of the IgG antibodies specific for mAβ1-6 peptide in sera of mice immunized with the mAβ1-6 peptide coupled to AP205 VLP. The results are shown for the sera of the three immunized mice collected at day 21 (A1 d21-A3 d21), the pre-immune serum is indicated as "pre imm" in the figure; the result for one pre-immune serum is shown. Comparison of the pre-immune serum with the sera of the mice immunized with mAβ1-6 coupled to AP205 VLP shows that a strong specific antibody response against peptide mAβ1-6, which is a self-antigen, could be obtained in the absence of adjuvant. Furthermore, coupling of a self-peptide to AP205 VLP leads to break of tolerance against this peptide, and to a very high specific immune response. Thus, AP205 VLP is suitable for generating high antibody titers against AP peptides in the absence of adjuvant.

Example 21

Immunisation with QβhAβ1-6 Reduces Amyloid Plaques in Transgenic Mice Over-expressing the "Swedish/London" Mutant Amyloid Precursor Protein This example demonstrates that immunization with QβhAβ1-6 in a mouse model developing Alzheimer's disease-like diffuse (Congo-Red negative) amyloid plaques, resulted in a massive reduction of plaque density in neocortical and subcortical brain areas. Histological occurrence of diffuse amyloid plaques is a prominent feature of AD brain pathology (Selkoe, 1994, Annu. Rev. Neurosci. 17:489-517) and, therefore, the example demonstrates that immunization with QβhAβ1-6 provides an effective approach for the treatment of Alzheimer's disease.

To evaluate the therapeutic efficacy of immunization with QβP-Aβ1-6 transgenic mice over-expressing the "Swedish/London" mutant amyloid precursor protein under the control of the mouse Thy-1 promoter (APP24; K670N/M671L; V717I, patent No. WO980-36-4423) were used. This mouse strain is characterized by a large number amyloid plaques in the neocortex, hippocampus, caudate putamen, and thalamus at an age of 18 months. Plaques can be first observed at an age of 9 months. Histologically, the amyloid plaques in APP24 mice are predominantly of a diffuse type, i.e. they are negative in Congo-Red staining. To a lesser degree, also compact amyloid plaques (Congo-Red positive) can be found.

Human Aβ1-6 peptide coupled to Qβ VLP (QβhAβ1-6) was made as described in Example 13. In terms of the experimental procedure followed, which is not necessary for describing or enabling the invention, APP24 transgenic mice 9.5 months of age were injected subcutaneously at day 0 with 25 µg of QβhAβ1-6 in phosphate-buffered saline (PBS) (administered as 2×100 µl per mouse) (n=16) or as negative controls with PBS (administered as 2×100 µl per mouse) (n=9) or with Qβ virus-like particle devoid of coupled antigen (n=11). Mice were subsequently injected 25 µg of QβhAβ1-6-vaccine, Qβ, or PBS on day 15, 49, 76, 106, 140, 169, 200, 230, 259, and 291. Animals were bled 1-2 days before the first immunization (day 0) and on day 56, 90, 118, 188, 214, 246, and 272 via the tail vein. Blood serum was also collected on day 305, at which time also brains were collected for histopathology (age of the mice at this time point: 19.5 months).

Figure 10:
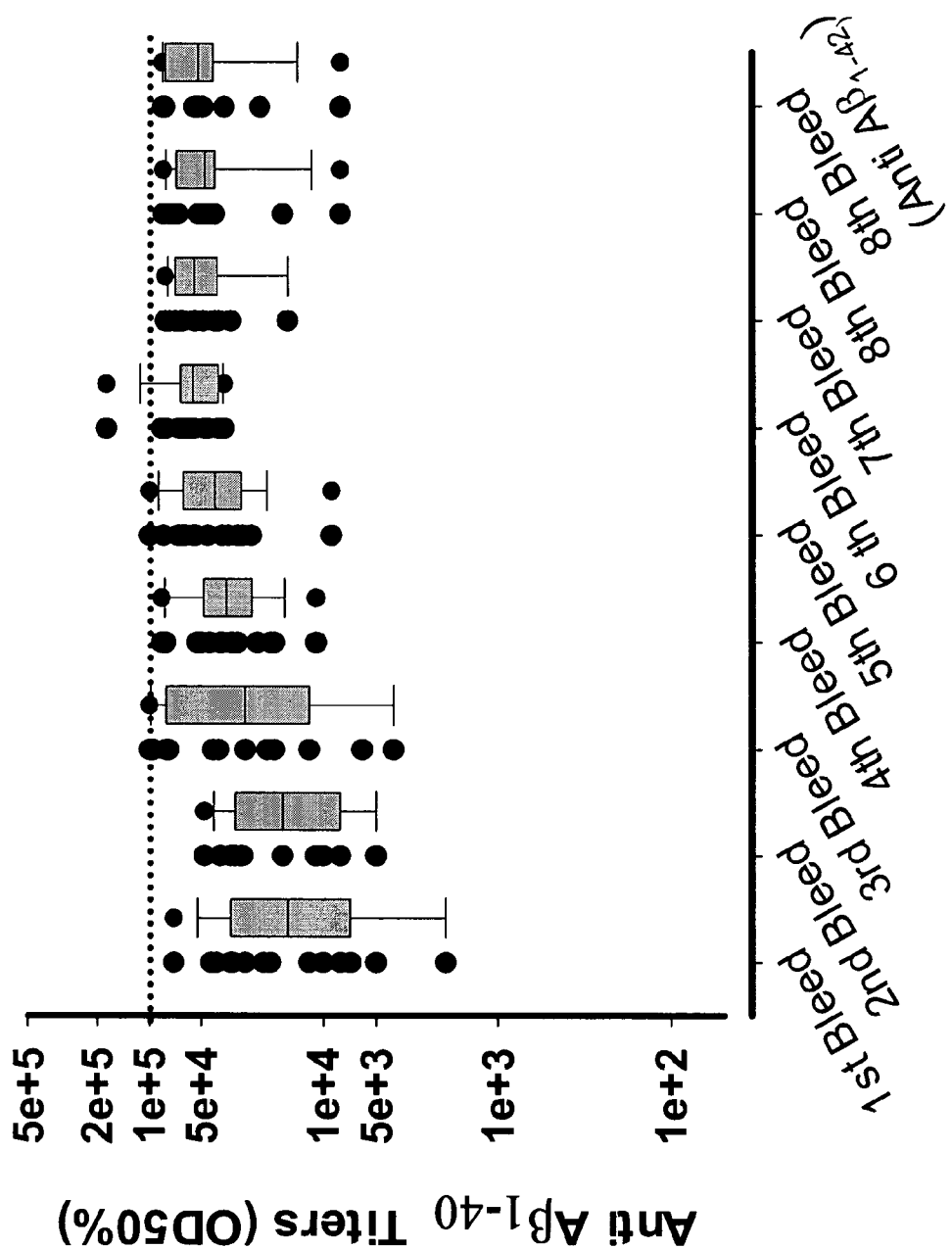
FIG. 10 shows the analysis by ELISA of the anti-Aβ40 and anti-Aβ42 titers in the sera of "Swedish/London" transgenic mice immunized with QβhAβ1-6 between 9.5 and 19 months of age.

The titer of antibodies specific for Aβ1-40 were measured by ELISA essentially as described in Example 13. The results of the ELISA are shown in FIG. 10. Plotted in the diagram are the titers of Aβ1-40 or Aβ1-42 specific antibodies measured in the sera of mice immunized with QβhAβ1-6. The titers are represented as OD50% titers. OD50% is the dilution of the antibodies at which the signal reaches half of its maximal value. The maximal value (OD max) was obtained from a reference antibody recognizing Aβ1-40 and Ab42, and measured on the same ELISA plate. All QβhAβ1-6 immunized mice developed OD50% titers above 1:8000 (pre-immune serum titers were below 1:100) demonstrating a consistent antibody response to QβhAβ1-6 even in old APP24 mice (FIG. 10). Median OD50% titers in the immunized group were in the range of 1:20'000 to 1:50'000 throughout the immunization period.

For quantification of amyloid plaques, brains were fixed by immersion in 4% formaldehyde in 0.1 M PBS at 4° C. After dehydration with ethanol, brains were embedded in paraffin and cut sagitally with a microtome at 4 µm thickness. Sections were mounted onto super frost slides and dried at 37° C. Sections were washed in PBS and antigenicity enhanced by microwave heating at 90° C. for 3 minutes in 0.1 M citric acid buffer. NT11 antisera (anti Aβ1-40, Sturchler-Pierrat et al., 1997, Proc. Natl. Acad. Sci. 94: 13287-13292) were diluted 1:1000 in PBS with 3% goat serum and incubated over night at 4° C. Following rinsing, sections were incubated for 1 hour with biotinylated anti rabbit IgG secondary antibody (BA1000, Vector Laboratories) diluted 1:200 in PBS. After rinsing, sections were further processed with the avidin-biotin-peroxidase technique (ABC-Elite Kit PK6100; Vector Laboratories). Finally, sections were reacted with Diaminobenzidine (DAB) metal enhanced substrate (Boehringer, Code 1718096), counterstained with Hemalum, dehydrated, cleared in Xylene and cover slipped. Systematic-random series of brain sections at three different anatomical planes per animal were used for the analysis. Amyloid plaques were quantified using an MCID image analyzer (Imaging Research, Brock University, Ontario-Canada, Program Version M5 elite). The microscopic image was digitized by use of a Xillix black and white CCD TV camera and stored with 640×480 pixel resolution at 256 gray levels. The pixel size was calibrated using an object micrometer at 5× magnification (Leica Neoplan Objective). Using a motor driven microscope stage for exact positioning of adjacent object fields the entire neocortex and olfactory nucleus of each section was analysed. For each object field the anatomical area was defined by manual outline. For each individual section the sample area was defined by manual threshold setting (grey level) between immunopositive amyloid plaques and tissue background. Isolated tissue artifacts were excluded by manual outline. Raw data are measured as individual counts (amyloid deposits) and proportional area values (immunopositive amyloid/cortex or olfactory nucleus).

Figure 11B:
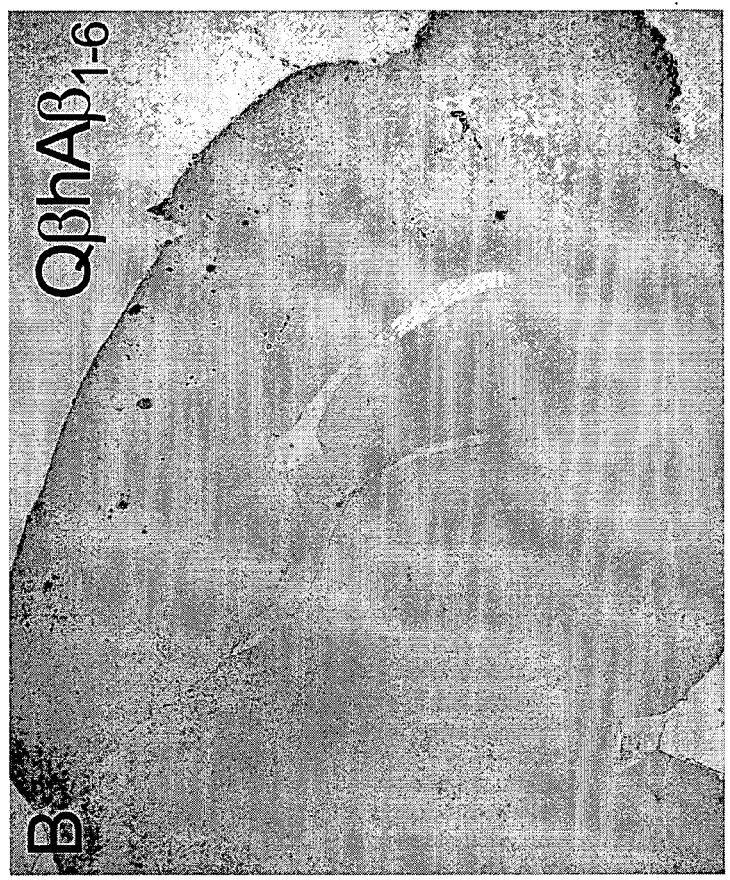
FIG. 11 shows the immunohistochemical staining of brain sections of "Swedish/London" transgenic mice immunized with QβhAβ1-6 or PBS.
Figure 11A:
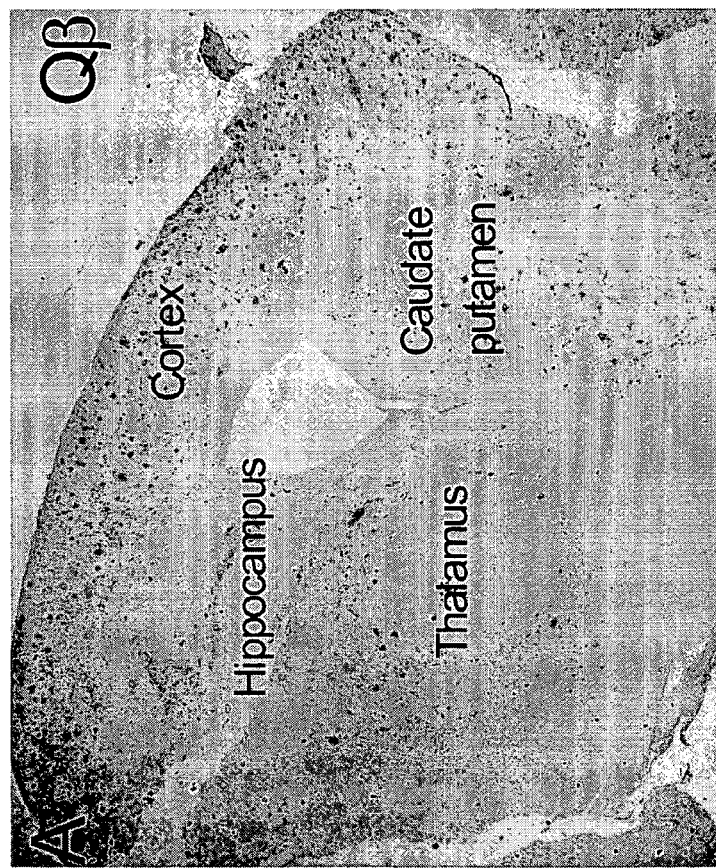
Figures 12A, 12B:
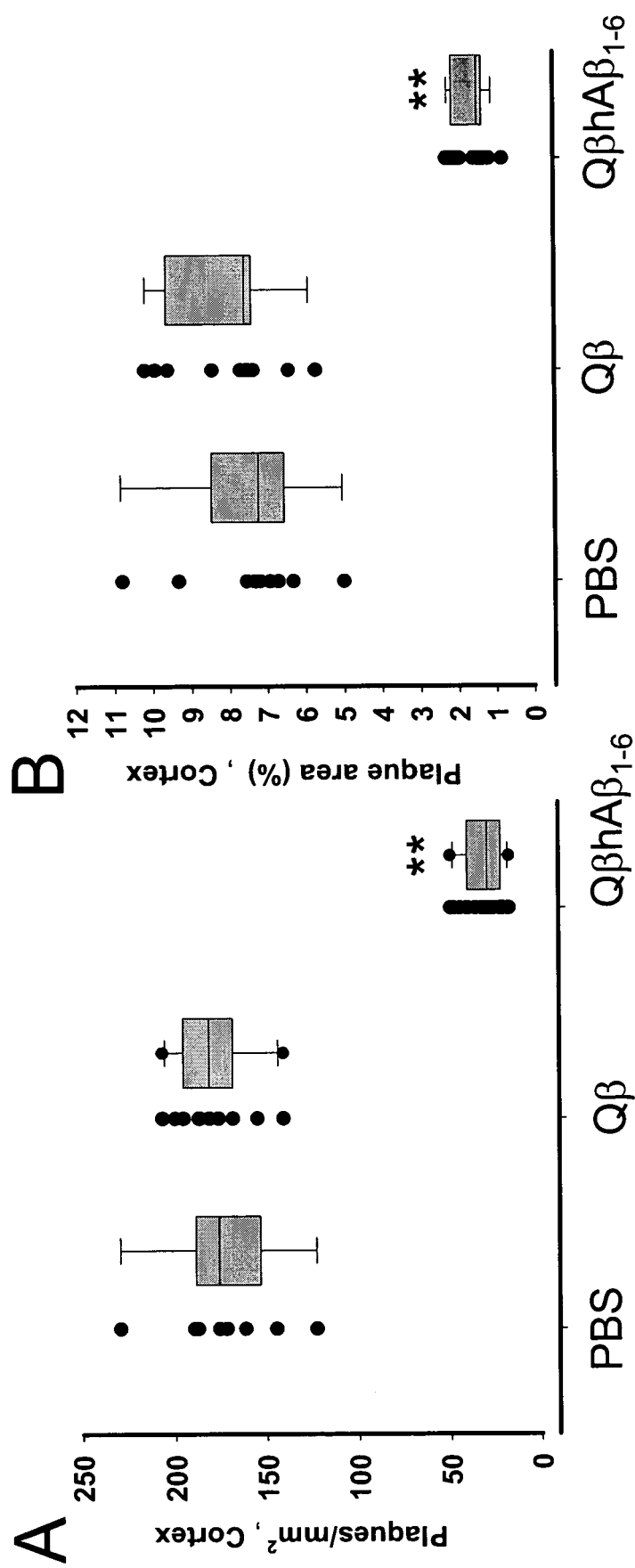
FIG. 12 shows the quantification of plaque deposition in "Swedish/London" transgenic mice immunized with QβhAβ1-6, Qβ or PBS between 9.5 and 19 months of age.
Figures 12C, 12D:
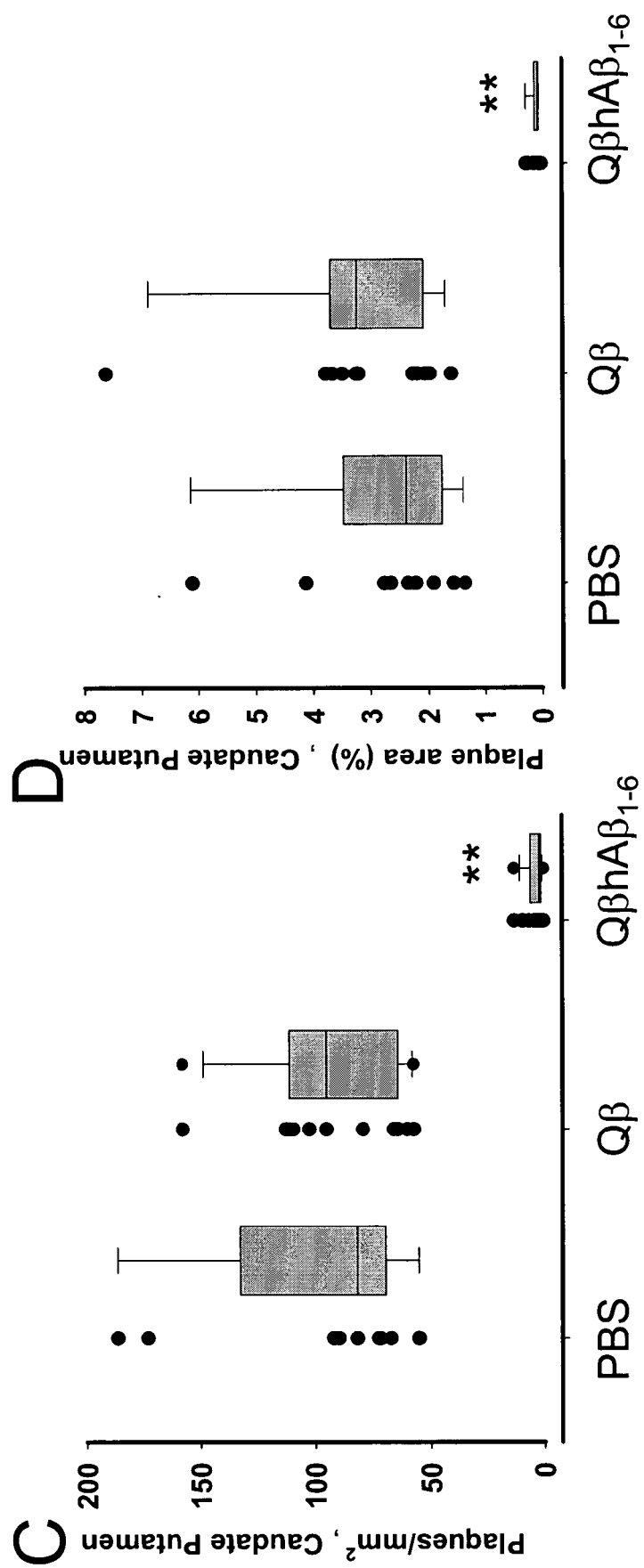
Figures 12E, 12F:
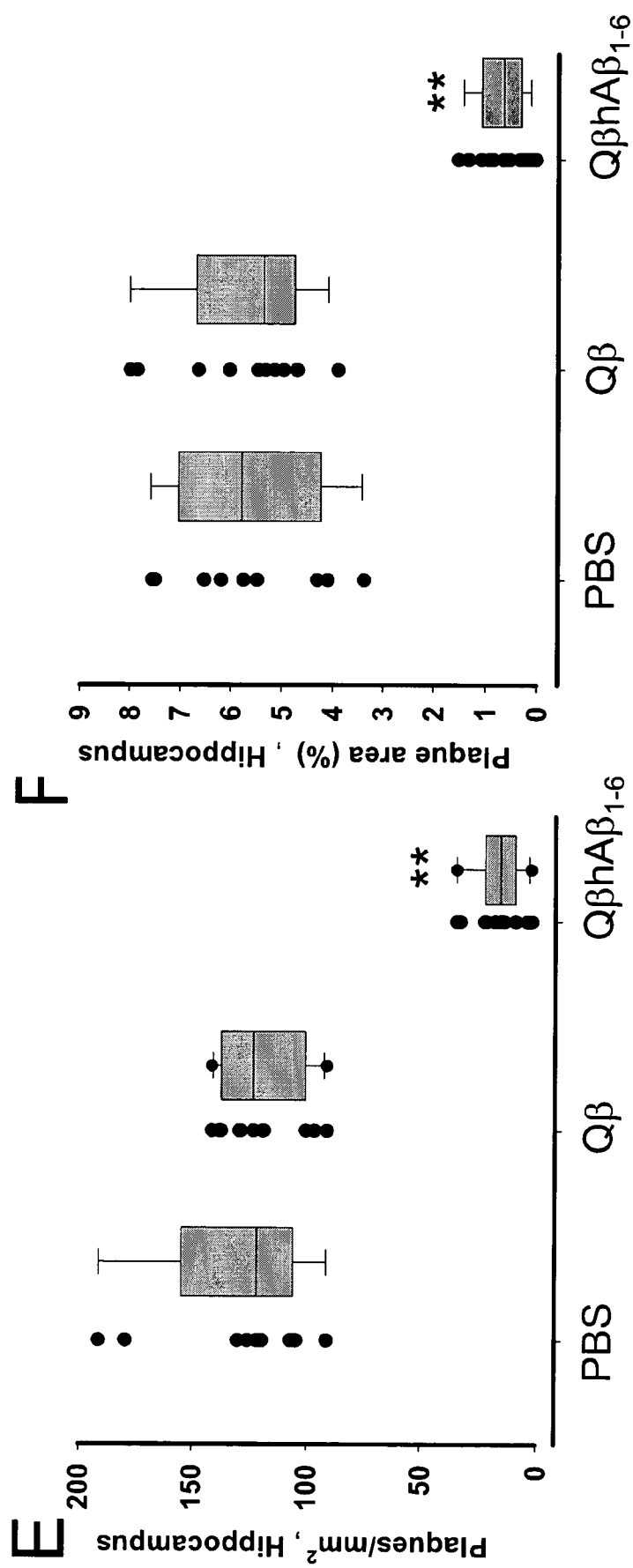
Figures 12G, 12H:
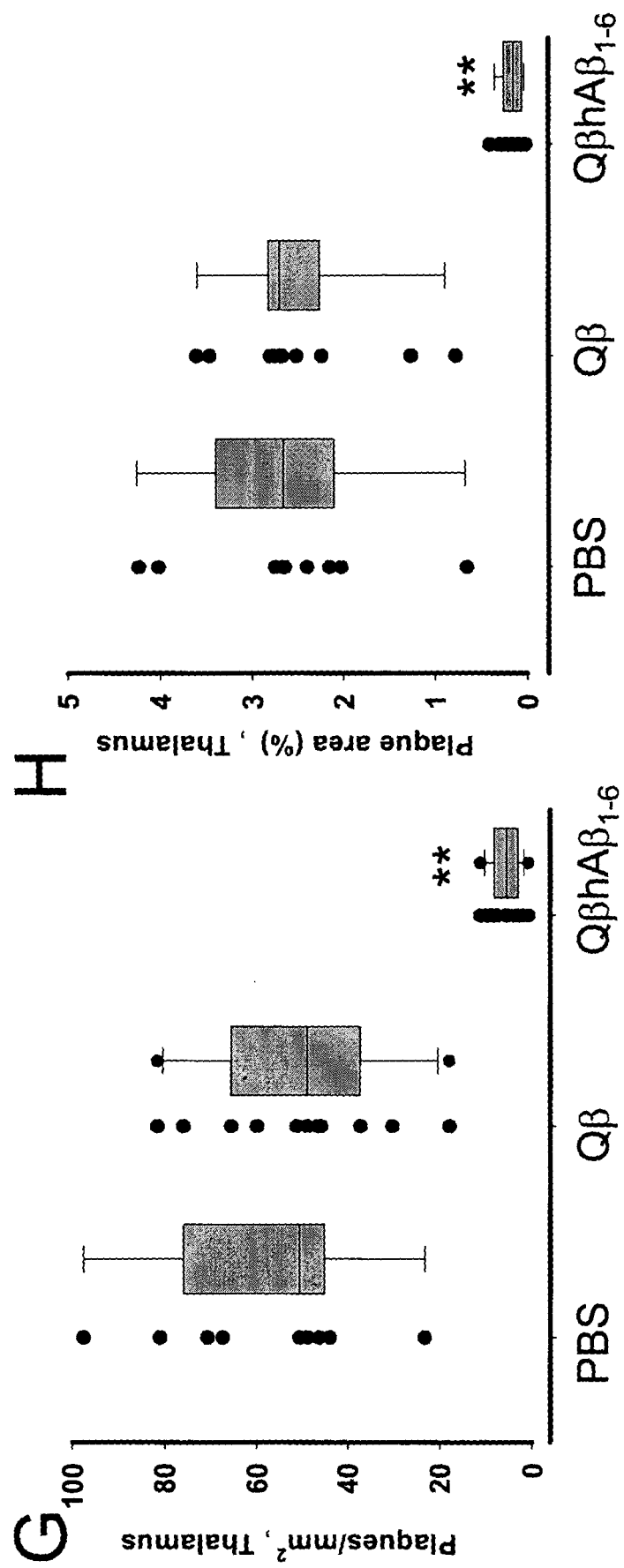
Figures 13A, 13B:
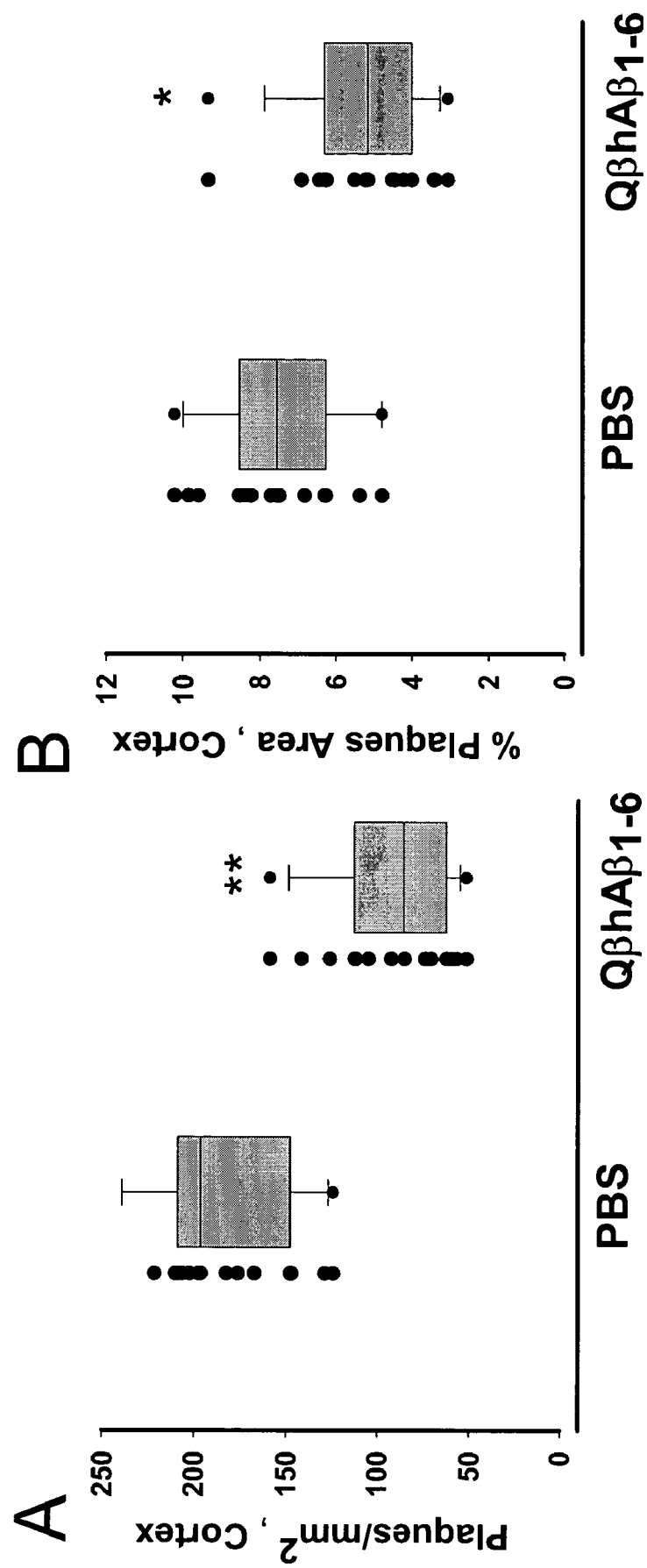
FIG. 13 shows the quantification of plaque deposition in "Swedish/London" transgenic mice immunized with QβhAβ1-6 or PBS between 13.5 and 19 months of age.
Figures 13C, 13D:
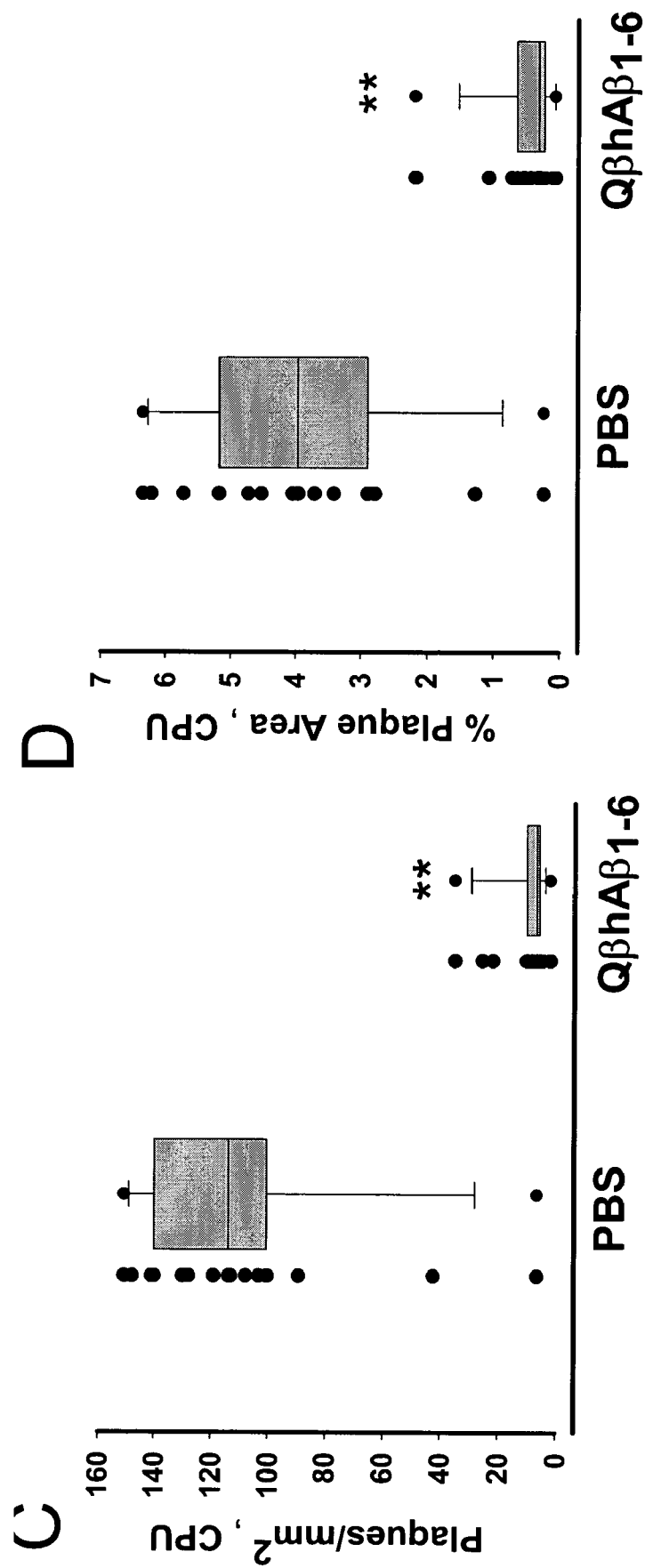
Figures 13E, 13F:
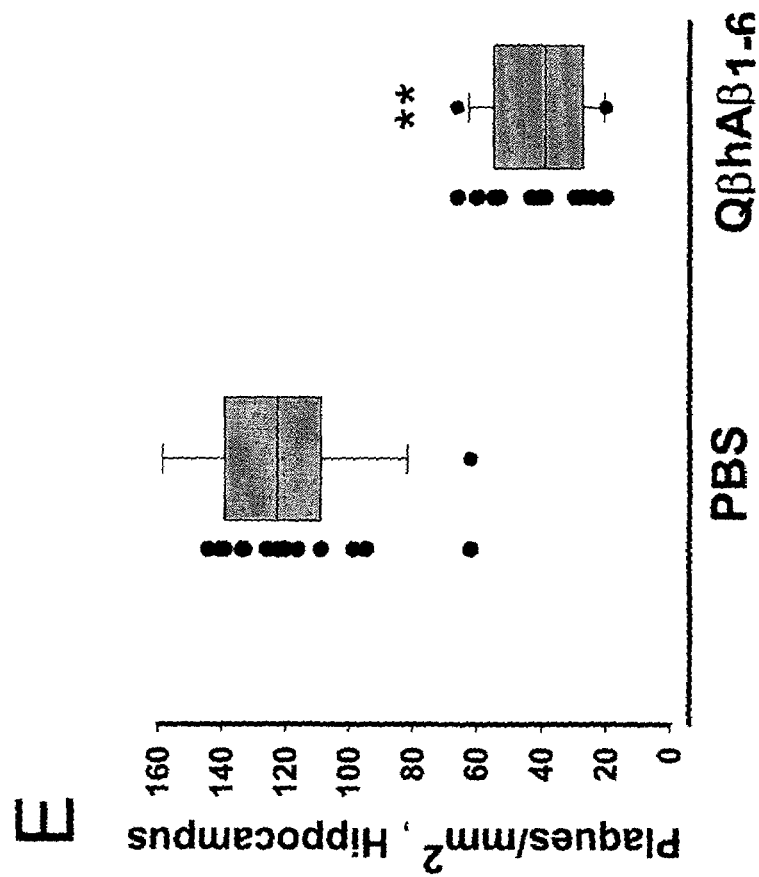
Figures 13G, 13H:
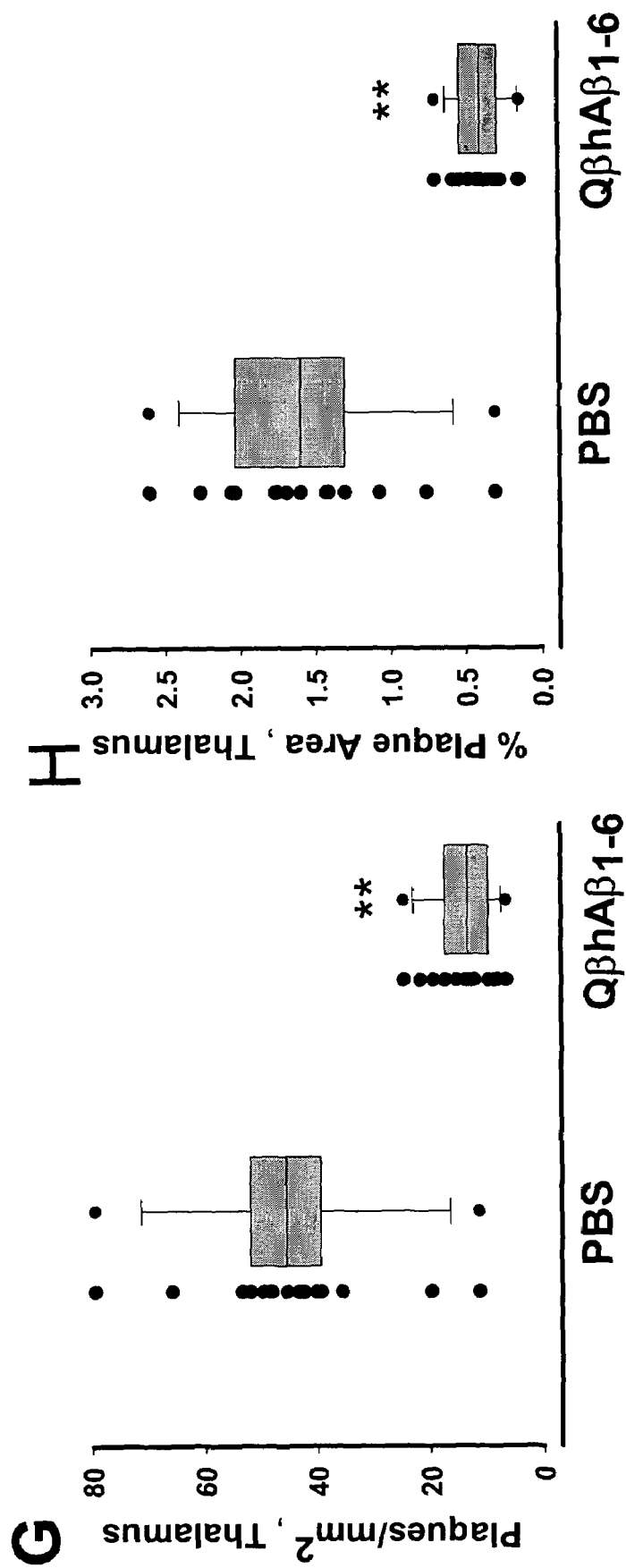

Data of each mouse were normalized to number of deposits (plaques) per mm$^2$ and total plaque area in % of the entire neocortex. QβhAβ1-6 immunized mice revealed a dramatic reduction of amyloid deposits in the cortex and subcortical areas as compared to either PBS or Qβ injected control groups (FIG. 11). Both the median number of deposits and the total plaque area were highly significantly reduced between 80-98% compared to the PBS group in the cortex, caudate putamen, hippocampus, and thalamus (p<0.001 vs. PBS-group, Mann-Whitney test; FIG. 12).

In a second study, APP24 transgenic mice 13.5 months of age were injected subcutaneously at day 0 with 25 μg of QβhAβ1-6 in phosphate-buffered saline (PBS) (administered as 2×100 μl per mouse) (n=15) or as negative controls with PBS (administered as 2×100 μl per mouse) (n=15). Mice were subsequently injected 25 μg of QβhAβ1-6-vaccine, or PBS on day 16, 46, 76, 109, 140, and 170. Animals were bled 1-2 days before the first immunization (day 0) and on day 31, 59, 128, and 154 via the tail vein. Blood serum was also collected on day 184, at which time also brains were collected for histopathology (age of the mice at this time point: 19.5 months). The titer of antibodies specific for Aβ1-40 were determined and expressed as described above and again all immunized mice were found to respond to QβhAβ1-6 immunization with serum OD50% titers at least above 1:2000 (not shown). Median OD50% titers were in the range of 1:10'000 to 1:50'000 throughout the immunization period. Quantification of amyloid deposits was done as described above. Compared to the experiment where immunization was initiated earlier (i.e. at an age of 9.5 months) the reduction of plaque deposit number (−55%) and area (−32%) was less dramatic in the neocortex, but still very pronounced (FIG. 13) and highly significant (p>0.001 vs. PBS, Mann-Whitney test). In subcortical areas plaque deposit number and area were reduced by 60-90% in the to QβhAβ1-6 immunized group. The more pronounced effect in these areas as compared to the cortex is probably related to the more protracted time course of plaque formation in these areas.

Taken together, both experiments demonstrate that QβhAβ1-6 immunization in transgenic mice over-expressing the "Swedish/London" mutant amyloid precursor protein dramatically reduces the occurrence of amyloid deposits in these mice.

FIG. 10: Serum anti Aβ40/42 antibody titers (OD50%) in transgenic mice over-expressing the "Swedish/London" mutant amyloid precursor protein. Mice were immunized with QβhAβ1-6 between 9.5 and 19 months of age. Shown are individual values (black dots) and box plots, where the ends of the boxes define the 25$^{th}$ and 75$^{th}$ percentiles, with a line at the median and error bars defining the 10$^{th}$ and 90$^{th}$ percentiles (outlyers are shown as dots).

FIG. 11: Immunhistochemical staining of amyloid plaques in sagittal brain sections. The sagittal brain section of a transgenic mouse over-expressing the "Swedish/London" mutant amyloid precursor protein immunized with Qβ (A) or QβhAβ1-6 (B) vaccine is shown in the Figure.

FIG. 12: Quantification of plaque deposition in transgenic mice over-expressing the "Swedish/London" mutant amyloid precursor protein after immunization between 9.5 and 19 months of age. (A) Cortical plaque density. (B) Cortical plaque area. (C) Plaque density in the caudate putamen. (D) Plaque area in the caudate putamen. (E) Plaque density in the hippocampus. (F) Plaque area in the hippocampus. (G) Plaque density in the thalamus. (H) Plaque area in the thalamus. Plaque density is expressed in plaques/mm, plaque area in percent of tissue area covered by amyloid beta. Data are shown as individual values (black dots) and box plot. The ends of the boxes define the 25$^{th}$ and 75$^{th}$ percentiles, with a line at the median and error bars defining the 10$^{th}$ and 90$^{th}$ percentiles. ** p<0.001 (Mann Whitney Rank Sum Test). PBS, n=9, Qβ, n=11, QβhAβ1-6, n=16.

Example 22

Immunisation with QβhAβ1-6 Reduces Amyloid Plaques in Transgenic Mice Over-expressing the "Swedish" Mutant Amyloid Precursor Protein This example demonstrates that immunization with QβhAβ1-6 provides an effective approach for the treatment of Alzheimer's disease even when the immunization is initiated in a very advanced stage of amyloid plaque pathology. The amyloid plaque deposition process in the AD mouse model used in this example starts already at an age about 6 months (Sturchler-Pierrat et al., 1997, Proc. Natl. Acad. Sci. 94: 13287-13292). In the study described herein, immunization with QβhAβ1-6 was initiated at an age of 18 months, where already a high number of compact plaques had been formed in the cortex. The example also demonstrates the ability of QβhAβ1-6 to induce Aβ40/42 antibodies in very aged animals (no non-responders in 19 immunized mice).

To evaluate the therapeutic effects of immunization with QβhAβ1-6 transgenic mice over-expressing the "Swedish" mutant amyloid precursor protein (APP23; K670N/M671L, Sturchler-Pierrat et al., 1997, Proc. Natl. Acad. Sci. 94: 13287-13292) were used. The Alzheimer's-like pathology in these mice has been extensively characterized (Calhoun et al., 1998, Nature 395: 755-756; Phinney et al., 1999, J. Neurosci. 19: 8552-8559; Bondolfi et al., 2002, J. Neurosci. 22: 515-522).

Human Aβ1-6 peptide coupled to Qβ VLP (QβhAβ1-6) was made as described in Example 13. In terms of the experimental procedure followed, which is not necessary for describing or enabling the invention, APP23 transgenic mice 18 months of age were injected subcutaneously at day 0 with 25 μg of QβhAβ1-6 dissolved in phosphate-buffered saline (administered as 2×100 μl per mouse) (n=19) or phosphate-buffered saline as a negative control (n=17) and boosted on day 13, 27-34, 61-63, 90-96, and 123-130 with 25 μg of vaccine. Animals were bled 1-2 days before the first immunization (day 0) and on day 41-45, and day 68 via the tail vein. Blood serum was also collected on day 152-154, at which time also brains were collected for histopathology (age of the mice at this time point: 23 months).

Figure 14:
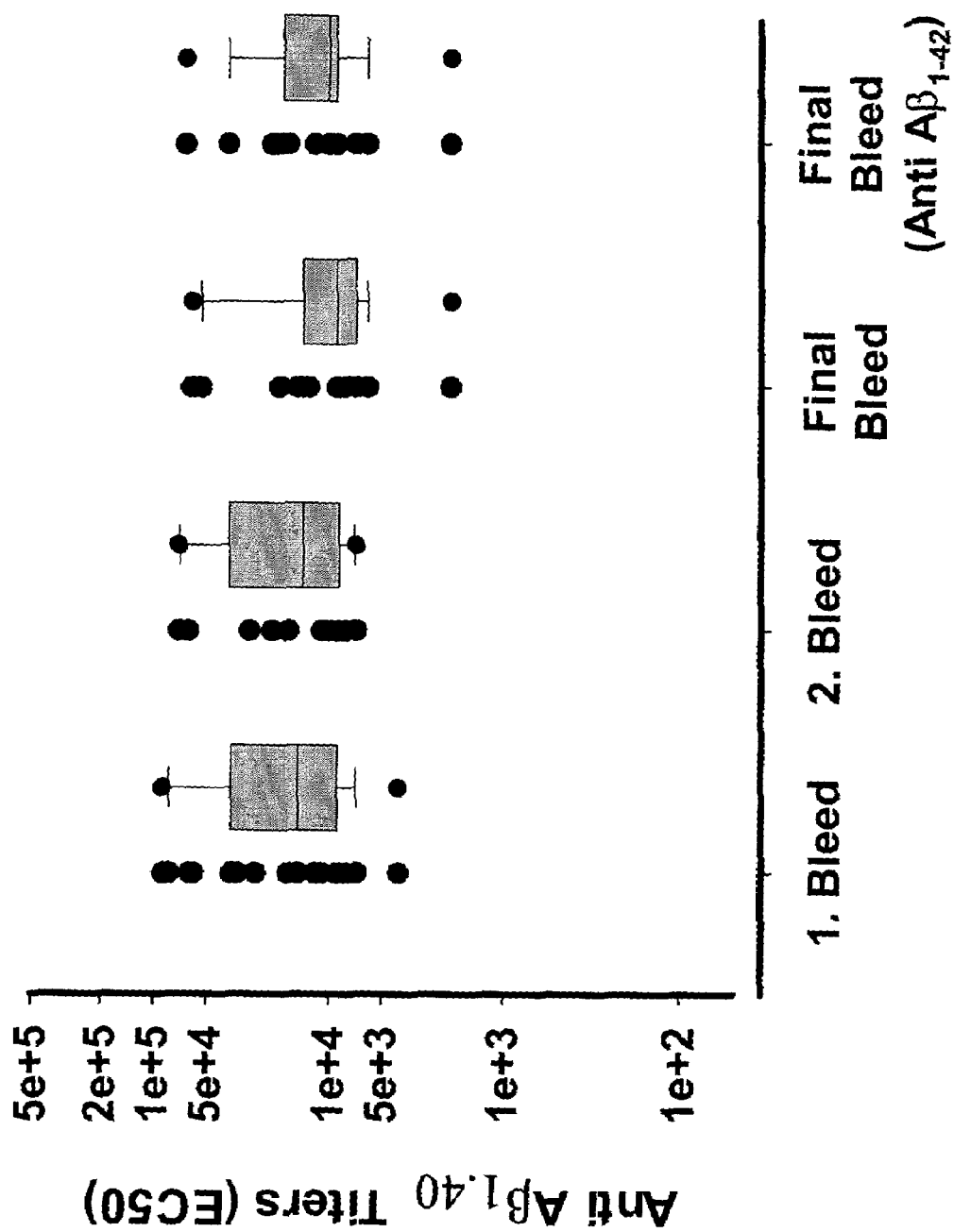
FIG. 14 shows the analysis by ELISA of the anti-Aβ40 and anti-Aβ42 titers in the sera of "Swedish" transgenic mice immunized with QβhAβ1-6.

The titer of antibodies specific for Aβ1-40 were measured by ELISA essentially as described in Example 13 and the results expressed as described in Example 21. The results of the ELISA are shown in FIG. 14. All QβhAβ1-6 immunized mice developed OD50% titers above 1:2000 (pre-immune serum titers were below 1:100) demonstrating a consistent antibody response to Qβ-Aβ1-6 even in very old mice (FIG. 14). Median OD50% titers were in the range of 1:9'000 to 1:20'000 throughout the immunization period.

Quantification of amyloid plaques was done as described in Example 21. Data of each mouse were normalized to number of deposits (plaques) per mm$^2$ and total plaque area in % of the entire neocortex. QβhAβ1-6 immunized mice revealed a smaller number of deposits in the cortex (FIG. 15, FIG. 16), mostly due to a reduction of small sized plaques. Compared to the non-immunized group the median plaque number was reduced by 33% in the QβhAβ1-6 immunized group (p<0.001 vs PBS-group, Mann-Whitney test). Since mostly small-sized plaques were affected the reduction of the total plaque area was moderate and amounted to 10% (p<0.01 vs. PBS group, Mann-Whitney test).

FIG. 14: Serum anti Aβ40/42 antibody titers (OD50%) in transgenic mice over-expressing the "Swedish" mutant amyloid precursor protein. Mice were immunized with QβhAβ1-6 between 18 and 23 months of age. Shown are individual values (black dots) and box plots, where the ends of the boxes define the 25$^{th}$ and 75$^{th}$ percentiles, with a line at the median and error bars defining the 10$^{th}$ and 90$^{th}$ percentiles (outlyers are shown as dots).

Figure 15B:
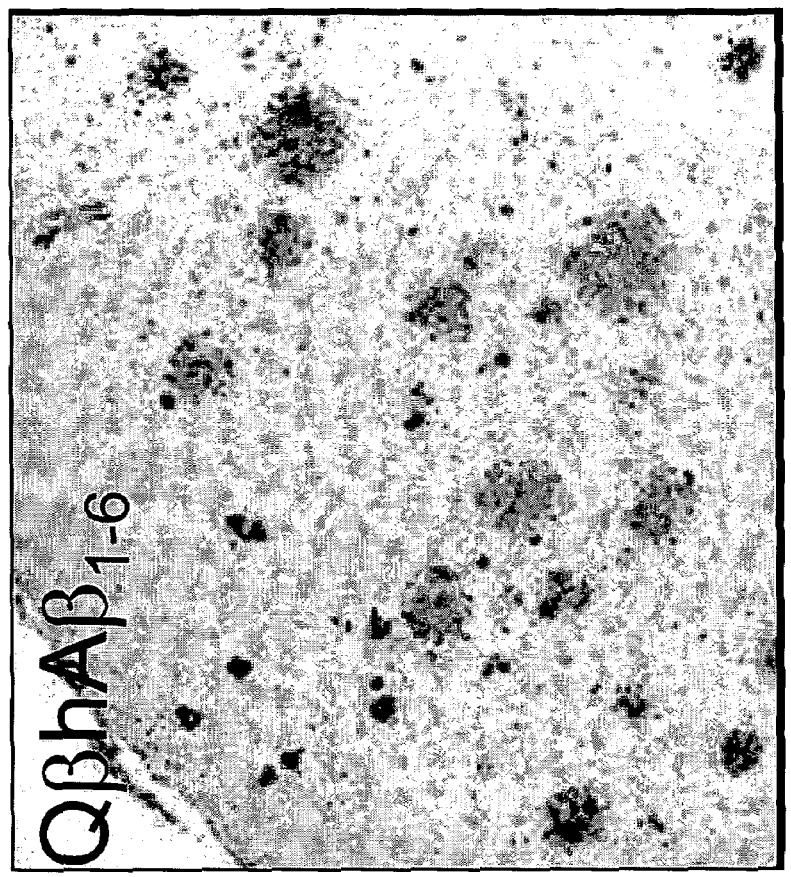
FIG. 15 shows the immunohistochemical staining of brain sections from "Swedish" transgenic mice immunized with QβhAβ1-6 or PBS.
Figure 15A:
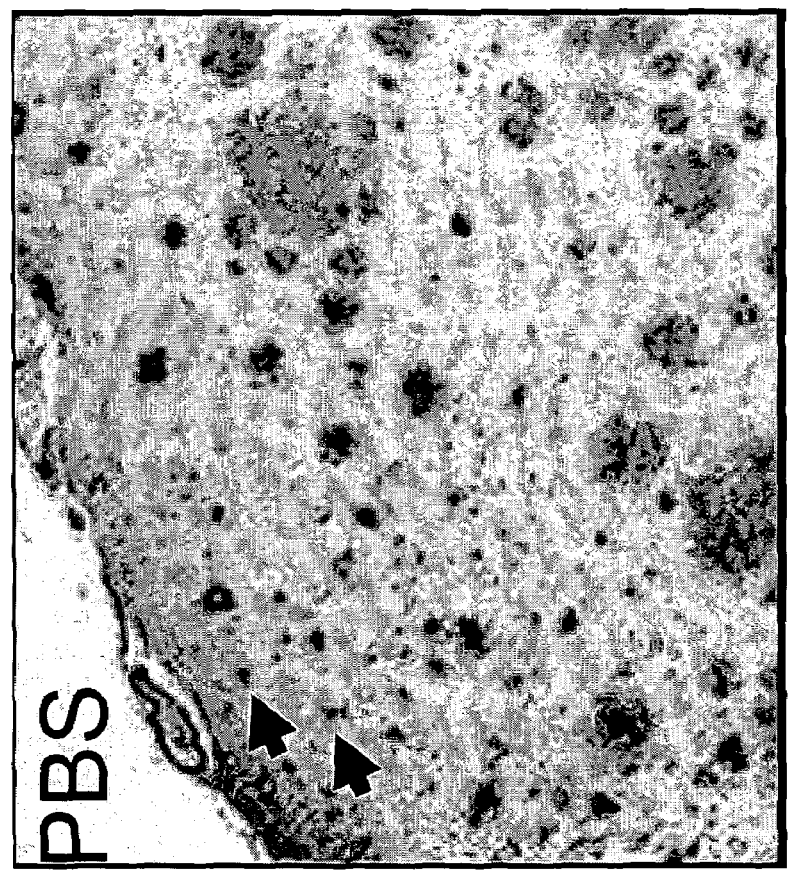

FIG. 15: Immunhistochemical staining of amyloid plaques in sagittal brain sections. Arrows point to small sized deposits. Shown in the Figure is a sagittal brain section from a transgenic mouse over-expressing the "Swedish" mutant amyloid precursor protein immunized with PBS (A) or Qβ-Aβ1-6 (B).

Figures 16A, 16B:
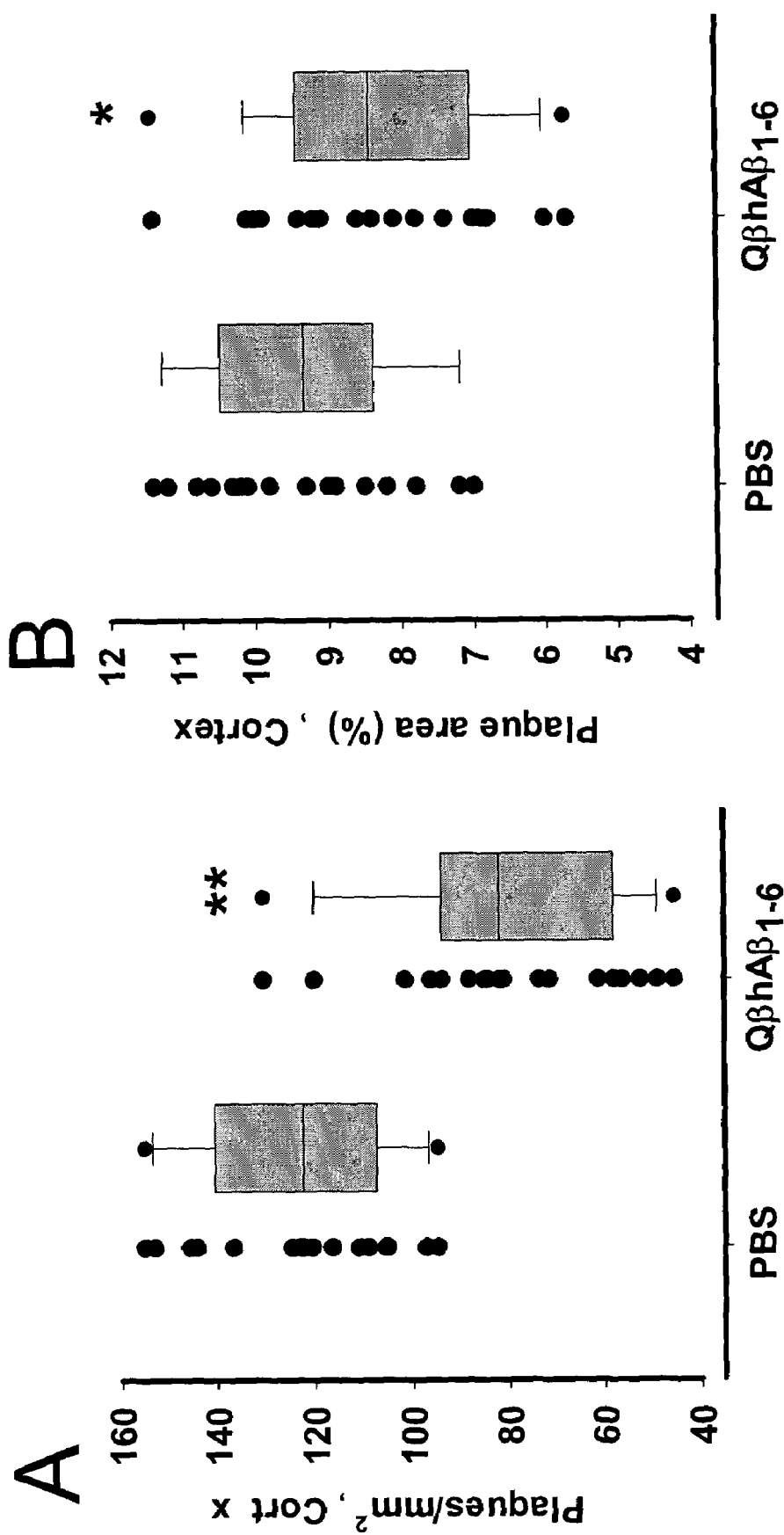
FIG. 16 shows the quantification of plaque deposition in "Swedish" transgenic mice immunized with QβhAβ1-6 or PBS.

FIG. 16: Quantification of plaque deposition in transgenic mice over-expressing the "Swedish" mutant amyloid precursor protein after immunization between 18 and 23 months of age. (A) Cortical plaque density. (B) Cortical plaque area. Plaque density is expressed in plaques/mm$^2$, plaque area in percent of tissue area covered by amyloid beta. Data are shown as individual values (black dots) and box plot. The ends of the boxes define the 25$^{th}$ and 75$^{th}$ percentiles, with a line at the median and error bars defining the 10$^{th}$ and 90$^{th}$ percentiles. ** p<0.001 (Mann Whitney Rank Sum Test). PBS, n=17, QβhAβ1-6, n=19.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A composition comprising:
   (a) a core particle with at least one first attachment site, wherein said core particle is a virus-like particle of an RNA-bacteriophage; and
   (b) at least one antigen or antigenic determinant with at least one second attachment site,
   wherein said antigen or antigenic determinant is a Aβ1-6 peptide, and wherein said second attachment site being selected from the group consisting of:
      (i) an attachment site not naturally occurring with said antigen or antigenic determinant; and
      (ii) an attachment site naturally occurring with said antigen or antigenic determinant,
   wherein said second attachment site associates with said first attachment site through at least one non-peptide bond, and wherein said Aβ1-6 peptide and said core particle interact through said association to form an ordered and repetitive antigen array.

2. The composition of claim 1, wherein said virus-like particle of an RNA-bacteriophage comprises, or alternatively consists of, recombinant proteins, or fragments thereof of an RNA-bacteriophage.

3. The composition of claim 2, wherein said RNA-bacteriophage is selected from the group consisting of:
   (a) bacteriophage Qβ;
   (b) bacteriophage R17;
   (c) bacteriophage fr;
   (d) bacteriophage GA;
   (e) bacteriophage SP;
   (f) bacteriophage MS2;
   (g) bacteriophage M11;
   (h) bacteriophage MX1;
   (i) bacteriophage NL95;
   (k) bacteriophage f2;
   (l) bacteriophage PP7; and
   (m) bacteriophage AP205.

4. The composition of claim 2, wherein the recombinant proteins comprise, or alternatively consist essentially of, or alternatively consist of coat proteins of RNA-bacteriophages.

5. The composition of claim 4, wherein said coat proteins of RNA-bacteriophages having an amino acid are selected from the group consisting of:
   (a) SEQ ID NO:4;
   (b) a mixture of SEQ ID NO:4 and SEQ ID NO:5;
   (c) SEQ ID NO:6;
   (d) SEQ ID NO:7;
   (e) SEQ ID NO:8;
   (f) SEQ ID NO:9;
   (g) a mixture of SEQ ID NO:9 and SEQ ID NO:10;
   (h) SEQ ID NO:11;
   (i) SEQ ID NO:12;
   (k) SEQ ID NO:13;
   (l) SEQ ID NO:14;
   (m) SEQ ID NO:15;
   (n) SEQ ID NO:16; and
   (o) SEQ IDNO:28.

6. The composition of claim 2, wherein the recombinant proteins comprise, or alternatively consist essentially of, or alternatively consist of mutant coat proteins of RNA-bacteriophages.

7. The composition of claim 6, wherein said RNA-bacteriophage is selected from the group consisting of:
   (a) bacteriophage Qβ;
   (b) bacteriophage R17;
   (c) bacteriophage fr;
   (d) bacteriophage GA;
   (e) bacteriophage SP;
   (f) bacteriophage MS2;
   (g) bacteriophage M11;
   (h) bacteriophage MX1;
   (i) bacteriophage NL95;
   (k) bacteriophage f2;
   (l) bacteriophage PP7; and
   (m) bacteriophage AP205.

8. The composition of claim 7, wherein said mutant coat proteins of said RNA-bacteriophage have been modified by removal of at least one lysine residue by way of substitution.

9. The composition of claim 7, wherein said mutant coat proteins of said RNA-bacteriophage have been modified by addition of at least one lysine residue by way of substitution.

10. The composition of claim 7, wherein said mutant coat proteins of said RNA-bacteriophage have been modified by deletion of at least one lysine residue.

11. The composition of claim 7, wherein said mutant coat proteins of said RNA-bacteriophage have been modified by addition of at least one lysine residue by way of insertion.

12. The composition of claim 1, wherein said virus-like particle of an RNA-bacteriophage comprises, or alternatively consists of, recombinant proteins, or fragments thereof, of RNA-bacteriophage Qβ.

13. The composition of claim 1, wherein said virus-like particle of an RNA-bacteriophage comprises, or alternatively consists of, recombinant proteins, or fragments thereof, of RNA-bacteriophage fr.

14. The composition of claim 1, wherein said virus-like particle of an RNA-bacteriophage comprises, or alternatively consists of, recombinant proteins, or fragments thereof of RNA-bacteriophage AP205.

15. The composition of claim 1, wherein said second attachment site is capable of association to said first attachment site through at least one covalent bond.

16. The composition of claim 1, wherein said Aβ1-6 peptide is selected from the group consisting of:
   (a) human Aβ1-6 peptide having an amino acid sequence of SEQ ID NO:75;
   (b) murine Aβ1-6 peptide having an amino acid sequence of SEQ ID NO:76;
   (c) primate Aβ1-6 peptide having an amino acid sequence of SEQ ID NO:84;
   (d) rabbit Aβ1-6 peptide having an amino acid sequence of SEQ ID NO: 85;
   (e) rat Aβ1-6 peptide having an amino acid sequence of SEQ ID NO:87; and
   (f) guinea pig Aβ1-6 peptide having an amino acid sequence of SEQ ID NO:88.

17. The composition of claim 1, wherein said Aβ1-6 peptide has an amino acid sequence of SEQ ID NO:75.

18. The composition of claim 1 further comprising an amino acid linker, wherein said amino acid linker comprises, or alternatively consists of, said second attachment site.

19. The composition of claim 1 or claim 18, wherein said second attachment or said amino acid linker with said second attachment site is bound to said Aβ1-6 peptide at its C-terminus.

20. The composition of claim 1 or claim 18, wherein said second attachment site or said amino acid linker with said second attachment site is selected from the group consisting of:
   (a) GGC;
   (b) GGC-CONH2;
   (c) GC;
   (d) GC-CONH2;
   (e) C; and
   (f) C-CONH2.

21. The composition of claim 1 or claim 18, wherein said second attachment site or said amino acid linker with said second attachment site is GGC or GGC-CONH2.

22. The composition of claim 1, wherein said Aβ1-6 peptide with said at least second attachment site is NH2-DAEFRHGGC-CONH2 (SEQ ID NO: 77).

23. The composition of claim 22, wherein said virus-like particle is a virus-like particle of RNA-bacteriophage Qβ coat protein.

24. A composition comprising the composition of claim 1 and a pharmaceutically acceptable carrier or excipient.

25. A method of treating Alzheimer and related diseases comprising administering the composition of claim 1 to an animal or human.

26. A method of inducing the production of anti-amyloid antibodies in an animal or human, comprising administering the composition of claim 1 to an animal or human, wherein the administration of said composition results in an immune response in said animal or human whereby anti-amyloid antibodies are produced.

27. The composition of claim 1, wherein said second attachment site comprises a sulfhydryl group.

28. The composition of claim 1, wherein said second attachment site comprises a cysteine residue.

29. The composition of claim 1, wherein said first attachment site is a lysine residue and said second attachment site is a cysteine residue.

30. A method of reducing amyloid plaques in the brain of an animal or human, comprising administering the composition of claim 1 to an animal or human having one or more amyloid plaques in its brain, wherein the administration of said composition results in a reduction in amyloid plaques in the brain of said animal or human.

* * * * *

UNITED STATES PATENT AND TRADEMARK OFFICE
CERTIFICATE OF CORRECTION

PATENT NO. : 7,279,165 B2 Page 1 of 1
APPLICATION NO. : 10/622087
DATED : October 9, 2007
INVENTOR(S) : Bachmann et al.

It is certified that error appears in the above-identified patent and that said Letters Patent is hereby corrected as shown below:

On the Title page, first column, section (73), please delete "Cytos Biotechnology AG, Zurich-Schlieren (CH)", and insert therein -- Cytos Biotechnology AG, Zurich-Schlieren (CH); Novartis Pharma AG, Basel, Switzerland (CH) --.

Signed and Sealed this

Twenty-eighth Day of October, 2008

JON W. DUDAS
*Director of the United States Patent and Trademark Office*

```
                      SEQUENCE LISTING

<160> NUMBER OF SEQ ID NOS: 93

<210> SEQ ID NO 1
<211> LENGTH: 172
<212> TYPE: PRT
<213> ORGANISM: Escherichia coli

<400> SEQUENCE: 1

Met Ala Val Val Ser Phe Gly Val Asn Ala Ala Pro Thr Thr Pro Gln
1               5                   10                  15

Gly Gln Gly Arg Val Thr Phe Asn Gly Thr Val Val Asp Ala Pro Cys
            20                  25                  30

Ser Ile Ser Gln Lys Ser Ala Asp Gln Ser Ile Asp Phe Gly Gln Leu
        35                  40                  45

Ser Lys Ser Phe Leu Ala Asn Asp Gly Gln Ser Lys Pro Met Asn Leu
    50                  55                  60

Asp Ile Glu Leu Val Asn Cys Asp Ile Thr Ala Phe Lys Asn Gly Asn
65                  70                  75                  80

Ala Lys Thr Gly Ser Val Lys Leu Ala Phe Thr Gly Pro Thr Val Ser
                85                  90                  95

Gly His Pro Ser Glu Leu Ala Thr Asn Gly Gly Pro Gly Thr Ala Ile
            100                 105                 110

Met Ile Gln Ala Ala Gly Lys Asn Val Pro Phe Asp Gly Thr Glu Gly
        115                 120                 125

Asp Pro Asn Leu Leu Lys Asp Gly Asp Asn Val Leu His Tyr Thr Thr
    130                 135                 140

Val Gly Lys Lys Ser Ser Asp Gly Asn Ala Gln Ile Thr Glu Gly Ala
145                 150                 155                 160

Phe Ser Gly Val Ala Thr Phe Asn Leu Ser Tyr Gln
                165                 170
```

-continued

<210> SEQ ID NO 2
<211> LENGTH: 182
<212> TYPE: PRT
<213> ORGANISM: Escherichia coli

<400> SEQUENCE: 2

Met Lys Ile Lys Thr Leu Ala Ile Val Val Leu Ser Ala Leu Ser Leu
1               5                   10                  15

Ser Ser Thr Ala Ala Leu Ala Ala Ala Thr Thr Val Asn Gly Gly Thr
            20                  25                  30

Val His Phe Lys Gly Glu Val Val Asn Ala Ala Cys Ala Val Asp Ala
        35                  40                  45

Gly Ser Val Asp Gln Thr Val Gln Leu Gly Gln Val Arg Thr Ala Ser
    50                  55                  60

Leu Ala Gln Glu Gly Ala Thr Ser Ser Ala Val Gly Phe Asn Ile Gln
65                  70                  75                  80

Leu Asn Asp Cys Asp Thr Asn Val Ala Ser Lys Ala Ala Val Ala Phe
                85                  90                  95

Leu Gly Thr Ala Ile Asp Ala Gly His Thr Asn Val Leu Ala Leu Gln
            100                 105                 110

Ser Ser Ala Ala Gly Ser Ala Thr Asn Val Gly Val Gln Ile Leu Asp
        115                 120                 125

Arg Thr Gly Ala Ala Leu Thr Leu Asp Gly Ala Thr Phe Ser Ser Glu
    130                 135                 140

Thr Thr Leu Asn Asn Gly Thr Asn Thr Ile Pro Phe Gln Ala Arg Tyr
145                 150                 155                 160

Phe Ala Thr Gly Ala Ala Thr Pro Gly Ala Ala Asn Ala Asp Ala Thr
                165                 170                 175

Phe Lys Val Gln Tyr Gln
            180

<210> SEQ ID NO 3
<211> LENGTH: 853
<212> TYPE: DNA
<213> ORGANISM: Escherichia coli

<400> SEQUENCE: 3
acgtttctgt ggctcgacgc atcttcctca ttcttctctc caaaaaccac ctcatgcaat    60
ataaacatct ataaataaag ataacaaata gaatattaag ccaacaaata aactgaaaaa   120
gtttgtccgc gatgctttac ctctatgagt caaaatggcc ccaatgtttc atcttttggg   180
ggaaactgtg cagtgttggc agtcaaactc gttgacaaac aaagtgtaca gaacgactgc   240
ccatgtcgat ttagaaatag ttttttgaaa ggaaagcagc atgaaaatta aaactctggc   300
aatcgttgtt ctgtcggctc tgtccctcag ttctacgacg gctctggccg ctgccacgac   360
ggttaatggt gggaccgttc actttaaagg ggaagttgtt aacgccgctt gcgcagttga   420
tgcaggctct gttgatcaaa ccgttcagtt aggacaggtt cgtaccgcat cgctggcaca   480
ggaaggagca accagttctg ctgtcggttt taacattcag ctgaatgatt gcgataccaa   540
tgttgcatct aaagccgctg ttgccttttt aggtacggcg attgatgcgg gtcataccaa   600
cgttctggct ctgcagagtt cagctgcggg tagcgcaaca aacgttggtg tgcagatcct   660
ggacagaacg ggtgctgcgc tgacgctgga tggtgcgaca tttagttcag aaacaaccct   720
gaataacgga accaatacca ttccgttcca ggcgcgttat tttgcaaccg ggccgcaaac   780
cccgggtgct gctaatgcgg atgcgacctt caaggttcag tatcaataac ctacctaggt   840

-continued

```
tcagggacgt tca                                                853
```

<210> SEQ ID NO 4
<211> LENGTH: 132
<212> TYPE: PRT
<213> ORGANISM: Bacteriophage Q-beta

<400> SEQUENCE: 4

Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
        130

<210> SEQ ID NO 5
<211> LENGTH: 329
<212> TYPE: PRT
<213> ORGANISM: Bacteriophage Q-beta

<400> SEQUENCE: 5

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr Trp Thr Leu Leu Ile Ala Gly Gly Ser Gly
    130                 135                 140

Ser Lys Pro Asp Pro Val Ile Pro Asp Pro Ile Asp Pro Pro
145                 150                 155                 160

Gly Thr Gly Lys Tyr Thr Cys Pro Phe Ala Ile Trp Ser Leu Glu Glu
                165                 170                 175

```
Val Tyr Glu Pro Pro Thr Lys Asn Arg Pro Trp Pro Ile Tyr Asn Ala
            180                 185                 190

Val Glu Leu Gln Pro Arg Glu Phe Asp Val Ala Leu Lys Asp Leu Leu
            195                 200                 205

Gly Asn Thr Lys Trp Arg Asp Trp Asp Ser Arg Leu Ser Tyr Thr Thr
            210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
            245                 250                 255

Gly Lys Lys Pro Gly Ala Phe Gly Asn Ile Glu Arg Phe Ile Tyr Leu
            260                 265                 270

Lys Ser Ile Asn Ala Tyr Cys Ser Leu Ser Asp Ile Ala Ala Tyr His
            275                 280                 285

Ala Asp Gly Val Ile Val Gly Phe Trp Arg Asp Pro Ser Ser Gly Gly
            290                 295                 300

Ala Ile Pro Phe Asp Phe Thr Lys Phe Asp Lys Thr Lys Cys Pro Ile
305                 310                 315                 320

Gln Ala Val Ile Val Val Pro Arg Ala
            325

<210> SEQ ID NO 6
<211> LENGTH: 129
<212> TYPE: PRT
<213> ORGANISM: Bacteriophage R17

<400> SEQUENCE: 6

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
            35                  40                  45

Arg Gln Ser Ser Ala Gln Asn Arg Lys Tyr Thr Ile Lys Val Glu Val
50                  55                  60

Pro Lys Val Ala Thr Gln Thr Val Gly Gly Val Glu Leu Pro Val Ala
65                  70                  75                  80

Ala Trp Arg Ser Tyr Leu Asn Met Glu Leu Thr Ile Pro Ile Phe Ala
            85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
            115                 120                 125

Tyr

<210> SEQ ID NO 7
<211> LENGTH: 130
<212> TYPE: PRT
<213> ORGANISM: Bacteriophage fr

<400> SEQUENCE: 7

Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
```

```
                35                  40                  45
Val Arg Gln Ser Ser Ala Asn Asn Arg Lys Tyr Thr Val Lys Val Glu
    50                  55                  60
Val Pro Lys Val Ala Thr Gln Val Gln Gly Gly Val Glu Leu Pro Val
65                  70                  75                  80
Ala Ala Trp Arg Ser Tyr Met Asn Met Glu Leu Thr Ile Pro Val Phe
                85                  90                  95
Ala Thr Asn Asp Asp Cys Ala Leu Ile Val Lys Ala Leu Gln Gly Thr
            100                 105                 110
Phe Lys Thr Gly Asn Pro Ile Ala Thr Ala Ile Ala Ala Asn Ser Gly
        115                 120                 125
Ile Tyr
    130

<210> SEQ ID NO 8
<211> LENGTH: 130
<212> TYPE: PRT
<213> ORGANISM: Bacteriophage GA

<400> SEQUENCE: 8

Met Ala Thr Leu Arg Ser Phe Val Leu Val Asp Asn Gly Gly Thr Gly
1               5                   10                  15
Asn Val Thr Val Val Pro Val Ser Asn Ala Asn Gly Val Ala Glu Trp
            20                  25                  30
Leu Ser Asn Asn Ser Arg Ser Gln Ala Tyr Arg Val Thr Ala Ser Tyr
        35                  40                  45
Arg Ala Ser Gly Ala Asp Lys Arg Lys Tyr Ala Ile Lys Leu Glu Val
    50                  55                  60
Pro Lys Ile Val Thr Gln Val Val Asn Gly Val Glu Leu Pro Gly Ser
65                  70                  75                  80
Ala Trp Lys Ala Tyr Ala Ser Ile Asp Leu Thr Ile Pro Ile Phe Ala
                85                  90                  95
Ala Thr Asp Asp Val Thr Val Ile Ser Lys Ser Leu Ala Gly Leu Phe
            100                 105                 110
Lys Val Gly Asn Pro Ile Ala Glu Ala Ile Ser Ser Gln Ser Gly Phe
        115                 120                 125
Tyr Ala
    130

<210> SEQ ID NO 9
<211> LENGTH: 132
<212> TYPE: PRT
<213> ORGANISM: Bacteriophage SP

<400> SEQUENCE: 9

Met Ala Lys Leu Asn Gln Val Thr Leu Ser Lys Ile Gly Lys Asn Gly
1               5                   10                  15
Asp Gln Thr Leu Thr Leu Thr Pro Arg Gly Val Asn Pro Thr Asn Gly
            20                  25                  30
Val Ala Ser Leu Ser Glu Ala Gly Ala Val Pro Ala Leu Glu Lys Arg
        35                  40                  45
Val Thr Val Ser Val Ala Gln Pro Ser Arg Asn Arg Lys Asn Phe Lys
    50                  55                  60
Val Gln Ile Lys Leu Gln Asn Pro Thr Ala Cys Thr Arg Asp Ala Cys
65                  70                  75                  80
Asp Pro Ser Val Thr Arg Ser Ala Phe Ala Asp Val Thr Leu Ser Phe
```

```
            85                  90                  95
Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
            115                 120                 125

Asn Pro Ala Tyr
    130

<210> SEQ ID NO 10
<211> LENGTH: 329
<212> TYPE: PRT
<213> ORGANISM: Bacteriophage SP

<400> SEQUENCE: 10

Ala Lys Leu Asn Gln Val Thr Leu Ser Lys Ile Gly Lys Asn Gly Asp
1               5                   10                  15

Gln Thr Leu Thr Leu Thr Pro Arg Gly Val Asn Pro Thr Asn Gly Val
            20                  25                  30

Ala Ser Leu Ser Glu Ala Gly Ala Val Pro Ala Leu Glu Lys Arg Val
            35                  40                  45

Thr Val Ser Val Ala Gln Pro Ser Arg Asn Arg Lys Asn Phe Lys Val
    50                  55                  60

Gln Ile Lys Leu Gln Asn Pro Thr Ala Cys Thr Arg Asp Ala Cys Asp
65              70                  75                  80

Pro Ser Val Thr Arg Ser Ala Phe Ala Asp Val Thr Leu Ser Phe Thr
            85                  90                  95

Ser Tyr Ser Thr Asp Glu Glu Arg Ala Leu Ile Arg Thr Glu Leu Ala
            100                 105                 110

Ala Leu Leu Ala Asp Pro Leu Ile Val Asp Ala Ile Asp Asn Leu Asn
            115                 120                 125

Pro Ala Tyr Trp Ala Ala Leu Leu Val Ala Ser Ser Gly Gly Gly Asp
    130                 135                 140

Asn Pro Ser Asp Pro Asp Val Pro Val Val Pro Asp Val Lys Pro Pro
145                 150                 155                 160

Asp Gly Thr Gly Arg Tyr Lys Cys Pro Phe Ala Cys Tyr Arg Leu Gly
            165                 170                 175

Ser Ile Tyr Glu Val Gly Lys Glu Gly Ser Pro Asp Ile Tyr Glu Arg
            180                 185                 190

Gly Asp Glu Val Ser Val Thr Phe Asp Tyr Ala Leu Glu Asp Phe Leu
            195                 200                 205

Gly Asn Thr Asn Trp Arg Asn Trp Asp Gln Arg Leu Ser Asp Tyr Asp
            210                 215                 220

Ile Ala Asn Arg Arg Arg Cys Arg Gly Asn Gly Tyr Ile Asp Leu Asp
225                 230                 235                 240

Ala Thr Ala Met Gln Ser Asp Asp Phe Val Leu Ser Gly Arg Tyr Gly
            245                 250                 255

Val Arg Lys Val Lys Phe Pro Gly Ala Phe Gly Ser Ile Lys Tyr Leu
            260                 265                 270

Leu Asn Ile Gln Gly Asp Ala Trp Leu Asp Leu Ser Glu Val Thr Ala
            275                 280                 285

Tyr Arg Ser Tyr Gly Met Val Ile Gly Phe Trp Thr Asp Ser Lys Ser
            290                 295                 300

Pro Gln Leu Pro Thr Asp Phe Thr Gln Phe Asn Ser Ala Asn Cys Pro
305                 310                 315                 320
```

-continued

Val Gln Thr Val Ile Ile Ile Pro Ser
              325

<210> SEQ ID NO 11
<211> LENGTH: 130
<212> TYPE: PRT
<213> ORGANISM: Bacteriophage MS2

<400> SEQUENCE: 11

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 12
<211> LENGTH: 133
<212> TYPE: PRT
<213> ORGANISM: Bacteriophage M11

<400> SEQUENCE: 12

Met Ala Lys Leu Gln Ala Ile Thr Leu Ser Gly Ile Gly Lys Lys Gly
1               5                   10                  15

Asp Val Thr Leu Asp Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ser Asp Val Thr Phe Ser
                85                  90                  95

Phe Thr Gln Tyr Ser Thr Val Glu Glu Arg Ala Leu Val Arg Thr Glu
            100                 105                 110

Leu Gln Ala Leu Leu Ala Asp Pro Met Leu Val Asn Ala Ile Asp Asn
        115                 120                 125

Leu Asn Pro Ala Tyr
    130

<210> SEQ ID NO 13
<211> LENGTH: 133
<212> TYPE: PRT
<213> ORGANISM: Bacteriophage MX1

<400> SEQUENCE: 13

```
Met Ala Lys Leu Gln Ala Ile Thr Leu Ser Gly Ile Gly Lys Asn Gly
1               5                   10                  15

Asp Val Thr Leu Asn Leu Asn Pro Arg Gly Val Asn Pro Thr Asn Gly
            20                  25                  30

Val Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ala Asp Val Thr Phe Ser
                85                  90                  95

Phe Thr Gln Tyr Ser Thr Asp Glu Glu Arg Ala Leu Val Arg Thr Glu
                100                 105                 110

Leu Lys Ala Leu Leu Ala Asp Pro Met Leu Ile Asp Ala Ile Asp Asn
            115                 120                 125

Leu Asn Pro Ala Tyr
        130
```

<210> SEQ ID NO 14
<211> LENGTH: 330
<212> TYPE: PRT
<213> ORGANISM: Bacteriophage NL95

<400> SEQUENCE: 14

```
Met Ala Lys Leu Asn Lys Val Thr Leu Thr Gly Ile Gly Lys Ala Gly
1               5                   10                  15

Asn Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Tyr Lys
    50                  55                  60

Val Gln Ile Lys Leu Gln Asn Pro Thr Ala Cys Thr Lys Asp Ala Cys
65                  70                  75                  80

Asp Pro Ser Val Thr Arg Ser Gly Ser Arg Asp Val Thr Leu Ser Phe
                85                  90                  95

Thr Ser Tyr Ser Thr Glu Arg Glu Arg Ala Leu Ile Arg Thr Glu Leu
                100                 105                 110

Ala Ala Leu Leu Lys Asp Asp Leu Ile Val Asp Ala Ile Asp Asn Leu
            115                 120                 125

Asn Pro Ala Tyr Trp Ala Ala Leu Leu Ala Ala Ser Pro Gly Gly Gly
        130                 135                 140

Asn Asn Pro Tyr Pro Gly Val Pro Asp Ser Pro Asn Val Lys Pro Pro
145                 150                 155                 160

Gly Gly Thr Gly Thr Tyr Arg Cys Pro Phe Ala Cys Tyr Arg Arg Gly
                165                 170                 175

Glu Leu Ile Thr Glu Ala Lys Asp Gly Ala Cys Ala Leu Tyr Ala Cys
            180                 185                 190

Gly Ser Glu Ala Leu Val Glu Phe Glu Tyr Ala Leu Glu Asp Phe Leu
        195                 200                 205

Gly Asn Glu Phe Trp Arg Asn Trp Asp Gly Arg Leu Ser Lys Tyr Asp
    210                 215                 220
```

```
Ile Glu Thr His Arg Arg Cys Arg Gly Asn Gly Tyr Val Asp Leu Asp
225                 230                 235                 240

Ala Ser Val Met Gln Ser Asp Glu Tyr Val Leu Ser Gly Ala Tyr Asp
                245                 250                 255

Val Val Lys Met Gln Pro Pro Gly Thr Phe Asp Ser Pro Arg Tyr Tyr
            260                 265                 270

Leu His Leu Met Asp Gly Ile Tyr Val Asp Leu Ala Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Arg Phe Asn Arg His Asn Cys Pro
305                 310                 315                 320

Val Gln Thr Val Ile Val Ile Pro Ser Leu
                325                 330

<210> SEQ ID NO 15
<211> LENGTH: 129
<212> TYPE: PRT
<213> ORGANISM: Bacteriophage f2

<400> SEQUENCE: 15

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Leu Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr

<210> SEQ ID NO 16
<211> LENGTH: 128
<212> TYPE: PRT
<213> ORGANISM: Bacteriophage PP7

<400> SEQUENCE: 16

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
```

-continued

```
                85                  90                  95
Glu Ala Ser Arg Lys Ser Leu Tyr Asp Leu Thr Lys Ser Leu Val Ala
            100                 105                 110

Thr Ser Gln Val Glu Asp Leu Val Val Asn Leu Val Pro Leu Gly Arg
        115                 120                 125

<210> SEQ ID NO 17
<211> LENGTH: 132
<212> TYPE: PRT
<213> ORGANISM: Artificial Sequence
<220> FEATURE:
<223> OTHER INFORMATION: Bacteriophage Qbeta 240 mutant

<400> SEQUENCE: 17

Ala Lys Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 18
<211> LENGTH: 132
<212> TYPE: PRT
<213> ORGANISM: Artificial Sequence
<220> FEATURE:
<223> OTHER INFORMATION: Bacteriophage Q-beta 243 mutant

<400> SEQUENCE: 18

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125
```

Asn Pro Ala Tyr
    130

<210> SEQ ID NO 19
<211> LENGTH: 132
<212> TYPE: PRT
<213> ORGANISM: Artificial Sequence
<220> FEATURE:
<223> OTHER INFORMATION: Bacteriophage Q-beta 250 mutant

<400> SEQUENCE: 19

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 20
<211> LENGTH: 132
<212> TYPE: PRT
<213> ORGANISM: Artificial Sequence
<220> FEATURE:
<223> OTHER INFORMATION: Bacteriophage Q-beta 251 mutant

<400> SEQUENCE: 20

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 21

```
<211> LENGTH: 132
<212> TYPE: PRT
<213> ORGANISM: Artificial Sequence
<220> FEATURE:
<223> OTHER INFORMATION: Bacteriophage Q-beta 259 mutant

<400> SEQUENCE: 21

Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 22
<211> LENGTH: 185
<212> TYPE: PRT
<213> ORGANISM: Hepatitis B virus

<400> SEQUENCE: 22

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185
```

```
<210> SEQ ID NO 23
<211> LENGTH: 212
<212> TYPE: PRT
<213> ORGANISM: Hepatitis B virus

<400> SEQUENCE: 23

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Asn
                85                  90                  95

Leu Ala Thr Trp Val Gly Gly Asn Leu Glu Asp Pro Val Ser Arg Asp
            100                 105                 110

Leu Val Val Gly Tyr Val Asn Thr Thr Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 24
<211> LENGTH: 188
<212> TYPE: PRT
<213> ORGANISM: Hepatitis B virus

<400> SEQUENCE: 24

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110
```

His Thr Val Gln Glu Phe Leu Val Ser Phe Gly Val Trp Ile Arg Thr
            115                 120                 125

Pro Ala Pro Tyr Arg Pro Pro Asn Ala Pro Ile Leu Ser Thr Leu Pro
    130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Thr Asn Cys
            180                 185

<210> SEQ ID NO 25
<211> LENGTH: 185
<212> TYPE: PRT
<213> ORGANISM: Hepatitis B virus

<400> SEQUENCE: 25

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185

<210> SEQ ID NO 26
<211> LENGTH: 152
<212> TYPE: PRT
<213> ORGANISM: Hepatitis B virus

<400> SEQUENCE: 26

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

```
Leu Met Thr Leu Ala Thr Trp Val Gly Thr Asn Leu Glu Asp Gly Gly
65                  70                  75                  80

Lys Gly Gly Ser Arg Asp Leu Val Val Ser Tyr Val Asn Thr Asn Val
                85                  90                  95

Gly Leu Lys Phe Arg Gln Leu Leu Trp Phe His Ile Ser Cys Leu Thr
            100                 105                 110

Phe Gly Arg Glu Thr Val Leu Glu Tyr Leu Val Ser Phe Gly Val Trp
        115                 120                 125

Ile Arg Thr Pro Pro Ala Tyr Arg Pro Pro Asn Ala Pro Ile Leu Ser
    130                 135                 140

Thr Leu Pro Glu Thr Thr Val Val
145                 150
```

<210> SEQ ID NO 27
<211> LENGTH: 3635
<212> TYPE: DNA
<213> ORGANISM: Artificial Sequence
<220> FEATURE:
<223> OTHER INFORMATION: plasmid pAP283-58

<400> SEQUENCE: 27

```
cgagctcgcc cctggcttat cgaaattaat acgactcact atagggagac cggaattcga      60
gctcgcccgg ggatcctcta gaattttctg cgcacccatc ccgggtggcg cccaaagtga     120
ggaaaatcac atggcaaata agccaatgca accgatcaca tctacagcaa ataaaattgt     180
gtggtcggat ccaactcgtt tatcaactac attttcagca agtctgttac gccaacgtgt     240
taaagttggt atagccgaac tgaataatgt ttcaggtcaa tatgtatctg tttataagcg     300
tcctgcacct aaaccggaag ttgtgcaga tgcctgtgtc attatgccga tgaaaaccaa     360
atccattcgc acagtgattt cagggtcagc cgaaaacttg gctaccttaa aagcagaatg     420
ggaaactcac aaacgtaacg ttgacacact cttcgcgagc ggcaacgccg gtttgggttt     480
ccttgaccct actgcggcta tcgtatcgtc tgatactact gcttaagctt gtattctata     540
gtgtcaccta atcgtatgt gtatgataca taaggttatg tattaattgt agccgcgttc     600
taacgacaat atgtacaagc ctaattgtgt agcatctggc ttactgaagc agaccctatc     660
atctctctcg taaactgccg tcagagtcgg tttggttgga cgaaccttct gagtttctgg     720
taacgccgtt ccgcaccccg gaaatggtca ccgaaccaat cagcagggtc atcgctagcc     780
agatcctcta cgccggacgc atcgtggccg gcatcaccgg cgcacacagt gcggttgctg     840
gcgcctatat cgccgacatc accgatgggg aagatcgggc tcgccacttc gggctcatga     900
gcgcttgttt cggcgtgggt atggtggcag gccccgtggc cggggggactg ttgggcgcca     960
tctccttgca tgcaccattc cttgcggcgg cggtgcttca acggcctcaa cctactactg    1020
ggctgcttcc taatgcagga gtcgcataag ggagagcgtc gatatggtgc actctcagta    1080
caatctgctc tgatgccgca tagttaagcc aactccgcta tcgctacgtg actgggtcat    1140
ggctgcgccc cgacacccgc caacacccgc tgacgcgccc tgacgggctt gtctgctccc    1200
ggcatccgct tacagacaag ctgtgaccgt ctccgggagc tgcatgtgtc agaggttttc    1260
accgtcatca ccgaaacgcg cgaggcagct tgaagacgaa agggcctcgt gatacgccta    1320
tttttatagg ttaatgtcat gataataatg gtttcttaga cgtcaggtgg cacttttcgg    1380
ggaaatgtgc gcggaacccc tatttgttta ttttctaaa tacattcaaa tatgtatccg    1440
ctcatgagac aataaccctg ataaatgctt caataatatt gaaaaggaa gagtatgagt    1500
attcaacatt tccgtgtcgc ccttattccc ttttttgcgg cattttgcct tcctgttttt    1560
```

-continued

```
gctcacccag aaacgctggt gaaagtaaaa gatgctgaag atcagttggg tgcacgagtg    1620
ggttacatcg aactggatct caacagcggt aagatccttg agagttttcg ccccgaagaa    1680
cgttttccaa tgatgagcac ttttaaagtt ctgctatgtg cgcggtatt atcccgtatt    1740 gacgccgggc aagagcaact cggtcgccgc atacactatt ctcagaatga cttggttgag    1800
tactcaccag tcacagaaaa gcatcttacg gatggcatga cagtaagaga attatgcagt    1860
gctgccataa ccatgagtga taacactgcg gccaacttac ttctgacaac gatcggagga    1920
ccgaaggagc taaccgcttt tttgcacaac atgggggatc atgtaactcg ccttgatcgt    1980
tgggaaccgg agctgaatga agccatacca acgacgagc gtgacaccac gatgcctgta    2040
gcaatggcaa caacgttgcg caaactatta actggcgaac tacttactct agcttcccgg    2100
caacaattaa tagactggat ggaggcggat aaagttgcag gaccacttct gcgctcggcc    2160
cttccggctg gctggtttat tgctgataaa tctggagccg gtgagcgtgg gtctcgcggt    2220
atcattgcag cactggggcc agatggtaag ccctcccgta tcgtagttat ctacacgacg    2280
gggagtcagg caactatgga tgaacgaaat agacagatcg ctgagatagg tgcctcactg    2340
attaagcatt ggtaactgtc agaccaagtt tactcatata tactttagat tgatttaaaa    2400
cttcattttt aatttaaaag gatctaggtg aagatccttt ttgataatct catgaccaaa    2460
atcccttaac gtgagttttc gttccactga gcgtcagacc ccgtagaaaa gatcaaagga    2520
tcttcttgag atcctttttt tctgcgcgta atctgctgct tgcaaacaaa aaaaccaccg    2580
ctaccagcgg tggtttgttt gccggatcaa gagctaccaa ctcttttcc gaaggtaact    2640 ggcttcagca gagcgcagat accaaatact gtccttctag tgtagccgta gttaggccac    2700
cacttcaaga actctgtagc accgcctaca tacctcgctc tgctaatcct gttaccagtg    2760
gctgctgcca gtggcgataa gtcgtgtctt accgggttgg actcaagacg atagttaccg    2820
gataaggcgc agcggtcggg ctgaacgggg gttcgtgca cacagcccag cttggagcga    2880
acgacctaca ccgaactgag atacctacag cgcgagcatt gagaaagcgc cacgcttccc    2940
gaagggagaa aggcggacag gtatccggta agcggcaggg tcggaacagg agagcgcacg    3000
agggagcttc cagggggaaa cgcctggtat ctttatagtc ctgtcgggtt tcgccacctc    3060
tgacttgagc gtcgattttt gtgatgctcg tcagggggc ggagcctatg gaaaaacgcc    3120
agcaacgcgg ccttttacg gttcctggcc ttttgctggc cttttgctca catgttcttt    3180
cctgcgttat cccctgattc tgtggataac cgtattaccg cctttgagtg agctgatacc    3240
gctcgccgca gccgaacgac gagcgcagcg agtcagtgag cgaggaagcg gaagagcgcc    3300
caatacgcaa accgcctctc cccgcgcgtt ggccgattca ttaatgcagc tgtggtgtca    3360
tggtcggtga tcgccagggt gccgacgcgc atctcgactg catggtgcac caatgcttct    3420
ggcgtcaggc agccatcgga agctgtggta tggccgtgca ggtcgtaaat cactgcataa    3480
ttcgtgtcgc tcaaggcgca ctcccgttct ggataatgtt ttttgcgccg acatcataac    3540
ggttctggca aatattctga aatgagctgt tgacaattaa tcatcgaact agttaactag    3600
tacgcaagtt cacgtaaaaa gggtatcgcg gaatt                              3635
```

<210> SEQ ID NO 28
<211> LENGTH: 131
<212> TYPE: PRT
<213> ORGANISM: Bacteriophage AP205

<400> SEQUENCE: 28

```
Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65              70                  75                  80

Thr Val Ile Ser Gly Ser Ala Glu Asn Leu Ala Thr Leu Lys Ala Glu
            85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 29
<211> LENGTH: 131
<212> TYPE: PRT
<213> ORGANISM: Artificial Sequence
<220> FEATURE:
<223> OTHER INFORMATION: AP205 coat protein

<400> SEQUENCE: 29

Met Ala Asn Lys Thr Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65              70                  75                  80

Thr Val Ile Ser Gly Ser Ala Glu Asn Leu Ala Thr Leu Lys Ala Glu
            85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 30
<211> LENGTH: 3607
<212> TYPE: DNA
<213> ORGANISM: Artificial Sequence
<220> FEATURE:
<223> OTHER INFORMATION: plasmid pAP281-32

<400> SEQUENCE: 30
cgagctcgcc cctggcttat cgaaattaat acgactcact ataggggagac cggaattcga     60 gctcgcccgg ggatcctcta gattaaccca acgcgtagga gtcaggccat ggcaaataag    120
acaatgcaac cgatcacatc tacagcaaat aaaattgtgt ggtcggatcc aactcgttta    180
```

-continued

| | | |
|---|---|---|
| tcaactacat tttcagcaag tctgttacgc caacgtgtta agttggtat agccgaactg | 240 |
| aataatgttt caggtcaata tgtatctgtt tataagcgtc ctgcacctaa accgaaggtc | 300 |
| agatgcctgt gtcattatgc cgaatgaaaa ccaatccatt cgcacagtga tttcagggtc | 360 |
| agccgaaaac ttggctacct taaaagcaga atgggaaact cacaaacgta acgttgacac | 420 |
| actcttcgcg agcggcaacg ccggtttggg tttccttgac cctactgcgg ctatcgtatc | 480 |
| gtctgatact actgcttaag cttgtattct atagtgtcac ctaaatcgta tgtgtatgat | 540 |
| acataaggtt atgtattaat ggtagccgcg ttctaacgac aatatgtaca agcctaattg | 600 |
| tgtagcatct ggcttactga agcagaccct atcatctctc tcgtaaactg ccgtcagagt | 660 |
| cggttgggtt ggacagacct ctgagtttct ggtaacgccg ttccgcaccc cggaaatggt | 720 |
| caccgaacca ttcagcaggg tcatcgctag ccagatcctc tacgccggac gcatcgtggc | 780 |
| ccgcatcacc ggcgccacag gtgcggtgct ggcgcctata tcgccgacat caccgatggg | 840 |
| gaagatcggg ctcgccactt cgggctcatg atcgctggtt tccgcctggg tatggtggca | 900 |
| ggccccgtgg cccgggggac tgttgggcgc catctccttg catgcaccat tccttgcggc | 960 |
| ggcggtgctc aacggcctca acctactact gggctgcttc ctaatgcagg agtcgcataa | 1020 |
| gggagagcgt cgatatggtg cactctcagt acaatctgct ctgatgccgc atagttaagc | 1080 |
| caactccgct atcgctacgt gactgggtca tggctgcgcc ccgacacccg ccaacacccg | 1140 |
| ctgacgcgcc ctgacgggct tgtctgcttc cggcatccgc ttacagacaa gctgtgaccg | 1200 |
| tctccgggag ctgcatgtgt cagaggtttt caccgtcatc accgaaacgc gcgaggcagc | 1260 |
| ttgaagacga aagggcctcg tgatacgcct atttttatag gttaatgtca tgataataat | 1320 |
| ggtttcttag acgtcaggtg gcacttttcg gggaaatgtg cgcggacccc ctattggttt | 1380 |
| atttttctaa atacattcaa atatgtatcc gctcatgaga caataaccct gataaatgct | 1440 |
| tcaataatat tgaaaaagga agagtatgag tattcaacat ttccgtgtcg cccttattcc | 1500 |
| cttttttgcg gcattttgcc ttcctgtttt tgctcaccca gaaacgctgg tgaaagtaaa | 1560 |
| agatgctgaa gatcagttgg gtgcacgagt gggttacatc gaactggatc tcaacagcgg | 1620 |
| taagatcctt gagagttttc gccccgaaga acgttttca atgatgagca cttttaaagt | 1680 |
| tctgctatgt gtcgcggtat tatcccgtat tgacgccggg caagagcaac tcggtcgccg | 1740 |
| catacactat tctcagaatg acttggtggt acctaccagt cacagaaaag catcttacgg | 1800 |
| atggcatgac agtaagagaa ttatgcagtg ctgccataac catgagtgat aacactgcgg | 1860 |
| ccaacttact tctgacaacg atcggaggac cgaaggagct aaccgctttt ttgcacaaca | 1920 |
| tgggggatca tgtaactcgc cttgatcgtt gggaaccgga gctgaatgaa gccataccaa | 1980 |
| acgacgagcg tgacaccacg atgcctgtac gaacggcaac aacgttgcgc aaactattaa | 2040 |
| ctggcgaact acttactcta gcttcccggc aacaattaat agactggatg gaggcggata | 2100 |
| aagttgcagg accacttctg cgctcggccc ttccggctgg ctggtttatt gctgataaat | 2160 |
| ctggagccgg tgagcgtggg tctcgcggta tcattgcagc actggggcca gatggtaagc | 2220 |
| cctcccgtat cgtagttatc tacacgacgg ggagtcaggc aactatggat gaacgaaata | 2280 |
| gacagatcgc tgagataggt gcctcactga ttaagcattg gtaactgtca gaccaagttt | 2340 |
| actcatatat actttagatt gatttaaaac ttcattttta atttaaaagg atctaggtga | 2400 |
| agatccttt tgataatctc atgaccaaaa tcccttaacg tgagttttcg ttccactgag | 2460 |
| cggtcagacc ccgtagaaag atcaaaggat cttcttgaga tccttttttt ctgcgcgtaa | 2520 |

```
tctgctgctt gcaaacaaaa aaaccaccgc taccagcggt ggtttgtttg ccggatcaag    2580
agctaccaac tcttttttccg aaggtaactg gcttcagcag agcgcagata ccaaatactg    2640
tccttctagt gtagccgtag ttaggccacc acttcaagaa ctctgtagca ccgcctacat    2700
acctcgctct gctaatcctg ttaccagtgg ctgctgccag tggcgataag tcgtgtctta    2760
ccgggttgga ctcaagacga taggtaccgg ataaggcgca gcggtcgggc tgaacggggg    2820
gttcgtgcac acagcccagc ttggagcgaa cgacctacac cgaactgaga tacctacagc    2880
gcgagcattg agaaagcgcc acgcttcccg aagggagaaa ggcggacagg tatccggtaa    2940
gcggcagggt cggaacaaga gagcgcacga gggagcttcc aggggggaaac gcctggtatc    3000 tttatagtcc tgtcgggttt cgccacctct gacttgagcg tcgatttttg tgatgctcgt    3060
caggggggcg gagcctatgg aaaaacgcca gcaacgcggc cttttttacgg ttcctggcct    3120 ttggctggcc ttttgctcac atgttctttc ctgcgttatc ccctgattct gtggataacc    3180
gtattaccgc ctttgagtga gctgataccg ctcgccgcag ccgaacgacc gacgcgcag    3240 cgagtcagtg agcgaggaag cggaagagcg cccaatacgc aaaccgcctc tccccgcgcg    3300
ttggccgatt cattaatgca gctgtggtgt catggtcggt gatcgccagg gtgccgacgc    3360
gcatctcgac tgcatggtgc accaatgctt ctggcgtcag gcagccatcg gaagctgtgg    3420 tatgccgtg caggtcgtaa atcactgcat aattcgtgtc gctcaaggcg cactcccgtt    3480
ctggataatg ttttttgcgg cgacatcata acggttctgg caaatattct gaaatgagct    3540
ggtgacaatt aatcatcgaa ctagttaact agtacgcaag ttcacgtaaa aagggtatcg    3600
cggaatt                                                              3607

<210> SEQ ID NO 31
<211> LENGTH: 6
<212> TYPE: PRT
<213> ORGANISM: Artificial Sequence
<220> FEATURE:
<223> OTHER INFORMATION: N-terminal linker

<400> SEQUENCE: 31

Cys Gly Asp Glu Gly Gly
1               5

<210> SEQ ID NO 32
<211> LENGTH: 6
<212> TYPE: PRT
<213> ORGANISM: Artificial Sequence
<220> FEATURE:
<223> OTHER INFORMATION: C-terminal linker

<400> SEQUENCE: 32

Gly Gly Glu Asp Gly Cys
1               5

<210> SEQ ID NO 33
<211> LENGTH: 5
<212> TYPE: PRT
<213> ORGANISM: Artificial Sequence
<220> FEATURE:
<223> OTHER INFORMATION: Linker

<400> SEQUENCE: 33

Gly Gly Lys Gly Gly
1               5

<210> SEQ ID NO 34
```

```
<211> LENGTH: 3
<212> TYPE: PRT
<213> ORGANISM: Artificial Sequence
<220> FEATURE:
<223> OTHER INFORMATION: N-terminal glycine linker
<220> FEATURE:
<221> NAME/KEY: REPEAT
<222> LOCATION: (1)..(1)
<223> OTHER INFORMATION: Glycine can be repeated from zero to five times
<220> FEATURE:
<221> NAME/KEY: REPEAT
<222> LOCATION: (3)..(3)
<223> OTHER INFORMATION: Glycine can be repeated from zero to twelve
      times

<400> SEQUENCE: 34

Gly Cys Gly
1

<210> SEQ ID NO 35
<211> LENGTH: 9
<212> TYPE: PRT
<213> ORGANISM: Artificial Sequence
<220> FEATURE:
<223> OTHER INFORMATION: N terminal glycine serine linkers
<220> FEATURE:
<221> NAME/KEY: REPEAT
<222> LOCATION: (1)..(1)
<223> OTHER INFORMATION: Glycine can be repeated from zero to five times
<220> FEATURE:
<221> NAME/KEY: REPEAT
<222> LOCATION: (3)..(3)
<223> OTHER INFORMATION: Glycine can be repeated from zero to ten times
<220> FEATURE:
<221> NAME/KEY: REPEAT
<222> LOCATION: (4)..(4)
<223> OTHER INFORMATION: Serine can be repeated from zero to two times
<220> FEATURE:
<221> NAME/KEY: REPEAT
<222> LOCATION: (5)..(9)
<223> OTHER INFORMATION: These residues can be repeated from zero to
      three times as a group

<400> SEQUENCE: 35

Gly Cys Gly Ser Gly Gly Gly Gly Ser
1               5

<210> SEQ ID NO 36
<211> LENGTH: 3
<212> TYPE: PRT
<213> ORGANISM: Artificial Sequence
<220> FEATURE:
<223> OTHER INFORMATION: C-terminal glycine linker
<220> FEATURE:
<221> NAME/KEY: REPEAT
<222> LOCATION: (1)..(1)
<223> OTHER INFORMATION: Glycine can be repeated from zero to twelve
      times
<220> FEATURE:
<221> NAME/KEY: REPEAT
<222> LOCATION: (3)..(3)
<223> OTHER INFORMATION: Glycine can be repeated from zero to five times

<400> SEQUENCE: 36

Gly Cys Gly
1

<210> SEQ ID NO 37
<211> LENGTH: 10
<212> TYPE: PRT
<213> ORGANISM: Artificial Sequence
<220> FEATURE:
<223> OTHER INFORMATION: C terminal glycine serine linkers
```

```
<220> FEATURE:
<221> NAME/KEY: REPEAT
<222> LOCATION: (1)..(1)
<223> OTHER INFORMATION: Glycine can be repeated from zero to ten times
<220> FEATURE:
<221> NAME/KEY: REPEAT
<222> LOCATION: (2)..(2)
<223> OTHER INFORMATION: Serine can be repeated from zero to two times
<220> FEATURE:
<221> NAME/KEY: REPEAT
<222> LOCATION: (3)..(7)
<223> OTHER INFORMATION: These residues can be repeated from zero to
      three times as a group
<220> FEATURE:
<221> NAME/KEY: REPEAT
<222> LOCATION: (8)..(8)
<223> OTHER INFORMATION: Glycine can be repeated from zero to eight
      times
<220> FEATURE:
<221> NAME/KEY: REPEAT
<222> LOCATION: (10)..(10)
<223> OTHER INFORMATION: Glycine can be repeated from zero to five times

<400> SEQUENCE: 37

Gly Ser Gly Gly Gly Gly Ser Gly Cys Gly
1               5                   10

<210> SEQ ID NO 38
<211> LENGTH: 5
<212> TYPE: PRT
<213> ORGANISM: Artificial Sequence
<220> FEATURE:
<223> OTHER INFORMATION: Glycine serine linker
<220> FEATURE:
<221> NAME/KEY: REPEAT
<222> LOCATION: (1)..(5)
<223> OTHER INFORMATION: These residues can be repeated any times as a
      group

<400> SEQUENCE: 38

Gly Gly Gly Gly Ser
1               5

<210> SEQ ID NO 39
<211> LENGTH: 10
<212> TYPE: PRT
<213> ORGANISM: Artificial Sequence
<220> FEATURE:
<223> OTHER INFORMATION: N-terminal gamma1

<400> SEQUENCE: 39

Cys Gly Asp Lys Thr His Thr Ser Pro Pro
1               5                   10

<210> SEQ ID NO 40
<211> LENGTH: 10
<212> TYPE: PRT
<213> ORGANISM: Artificial Sequence
<220> FEATURE:
<223> OTHER INFORMATION: C-terminal gamma 1

<400> SEQUENCE: 40

Asp Lys Thr His Thr Ser Pro Pro Cys Gly
1               5                   10

<210> SEQ ID NO 41
<211> LENGTH: 17
<212> TYPE: PRT
<213> ORGANISM: Artificial Sequence
<220> FEATURE:
<223> OTHER INFORMATION: N-terminal gamma 3
```

```
<400> SEQUENCE: 41

Cys Gly Gly Pro Lys Pro Ser Thr Pro Pro Gly Ser Ser Gly Gly Ala
1               5                   10                  15
Pro

<210> SEQ ID NO 42
<211> LENGTH: 18
<212> TYPE: PRT
<213> ORGANISM: Artificial Sequence
<220> FEATURE:
<223> OTHER INFORMATION: C-terminal gamma 3

<400> SEQUENCE: 42

Pro Lys Pro Ser Thr Pro Pro Gly Ser Ser Gly Gly Ala Pro Gly Gly
1               5                   10                  15
Cys Gly

<210> SEQ ID NO 43
<211> LENGTH: 6
<212> TYPE: PRT
<213> ORGANISM: Artificial Sequence
<220> FEATURE:
<223> OTHER INFORMATION: N-terminal glycine linker

<400> SEQUENCE: 43

Gly Cys Gly Gly Gly Gly
1               5

<210> SEQ ID NO 44
<211> LENGTH: 6
<212> TYPE: PRT
<213> ORGANISM: Artificial Sequence
<220> FEATURE:
<223> OTHER INFORMATION: C-terminal glycine linker

<400> SEQUENCE: 44

Gly Gly Gly Gly Cys Gly
1               5

<210> SEQ ID NO 45
<211> LENGTH: 6
<212> TYPE: PRT
<213> ORGANISM: Artificial Sequence
<220> FEATURE:
<223> OTHER INFORMATION: C-terminal glycine-lysine linker

<400> SEQUENCE: 45

Gly Gly Lys Lys Gly Cys
1               5

<210> SEQ ID NO 46
<211> LENGTH: 6
<212> TYPE: PRT
<213> ORGANISM: Artificial Sequence
<220> FEATURE:
<223> OTHER INFORMATION: N-terminal glycine-lysine linker

<400> SEQUENCE: 46

Cys Gly Lys Lys Gly Gly
1               5

<210> SEQ ID NO 47
<211> LENGTH: 4
<212> TYPE: PRT
```

<213> ORGANISM: Artificial Sequence
<220> FEATURE:
<223> OTHER INFORMATION: C.terminal linker

<400> SEQUENCE: 47

Gly Gly Cys Gly
1

<210> SEQ ID NO 48
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 48
ggtaacatcg gtcgagatgg aaaacaaact ctggtcc                37

<210> SEQ ID NO 49
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 49
ggaccagagt ttgttttcca tctcgaccga tgttacc                37

<210> SEQ ID NO 50
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 50
agctcgcccg gggatcctct ag                                22

<210> SEQ ID NO 51
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 51
cgatgcattt catccttagt tatcaatacg ctgggttcag             40

<210> SEQ ID NO 52
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 52
ggcaaaatta gagactgtta ctttaggtaa gatcgg                 36

<210> SEQ ID NO 53
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 53

```
ccgatcttac ctaaagtaac agtctctaat tttgcc                                36
```

<210> SEQ ID NO 54
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 54

```
ggccatggca cgactcgaga ctgttacttt agg                                   33
```

<210> SEQ ID NO 55
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 55

```
gatttaggtg acactatag                                                   19
```

<210> SEQ ID NO 56
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 56

```
gatggacgtc aaactctggt cctcaatccg cgtgggg                               37
```

<210> SEQ ID NO 57
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 57

```
ccccacgcgg attgaggacc agagtttgac gtccatc                               37
```

<210> SEQ ID NO 58
<211> LENGTH: 31
<212> TYPE: DNA
<213> ORGANISM: Artificial Sequence
<220> FEATURE:
<223> OTHER INFORMATION: EcoRIHBcAg(s) primer

<400> SEQUENCE: 58

```
ccggaattca tggacattga cccttataaa g                                     31
```

<210> SEQ ID NO 59
<211> LENGTH: 51
<212> TYPE: DNA
<213> ORGANISM: Artificial Sequence
<220> FEATURE:
<223> OTHER INFORMATION: Lys-HBcAg(as) primer

<400> SEQUENCE: 59

```
cctagagcca cctttgccac catcttctaa attagtaccc acccaggtag c               51
```

<210> SEQ ID NO 60
<211> LENGTH: 48
<212> TYPE: DNA
<213> ORGANISM: Artificial Sequence

```
<220> FEATURE:
<223> OTHER INFORMATION: Lys-HBcAg(s) primer

<400> SEQUENCE: 60
gaagatggtg gcaaaggtgg ctctagggac ctagtagtca gttatgtc         48

<210> SEQ ID NO 61
<211> LENGTH: 38
<212> TYPE: DNA
<213> ORGANISM: Artificial Sequence
<220> FEATURE:
<223> OTHER INFORMATION: HBcAg(1-149)Hind(as) primer

<400> SEQUENCE: 61
cgcgtcccaa gcttctaaac aacagtagtc tccggaag                    38

<210> SEQ ID NO 62
<211> LENGTH: 37
<212> TYPE: DNA
<213> ORGANISM: Artificial Sequence
<220> FEATURE:
<223> OTHER INFORMATION: 48as primer

<400> SEQUENCE: 62
gtgcagtatg gtgaggtgag gaatgctcag gagactc                     37

<210> SEQ ID NO 63
<211> LENGTH: 37
<212> TYPE: DNA
<213> ORGANISM: Artificial Sequence
<220> FEATURE:
<223> OTHER INFORMATION: 48s primer

<400> SEQUENCE: 63
gagtctcctg agcattcctc acctcaccat actgcac                     37

<210> SEQ ID NO 64
<211> LENGTH: 33
<212> TYPE: DNA
<213> ORGANISM: Artificial Sequence
<220> FEATURE:
<223> OTHER INFORMATION: 107as primer

<400> SEQUENCE: 64
cttccaaaag tgagggaaga aatgtgaaac cac                         33

<210> SEQ ID NO 65
<211> LENGTH: 47
<212> TYPE: DNA
<213> ORGANISM: Artificial Sequence
<220> FEATURE:
<223> OTHER INFORMATION: HBcAg149hind-as

<400> SEQUENCE: 65
cgcgtcccaa gcttctaaac aacagtagtc tccggaagcg ttgatag          47

<210> SEQ ID NO 66
<211> LENGTH: 33
<212> TYPE: DNA
<213> ORGANISM: Artificial Sequence
<220> FEATURE:
<223> OTHER INFORMATION: 107s primer

<400> SEQUENCE: 66
gtggtttcac atttcttccc tcacttttgg aag                         33
```

```
<210> SEQ ID NO 67
<211> LENGTH: 38
<212> TYPE: DNA
<213> ORGANISM: Artificial Sequence
<220> FEATURE:
<223> OTHER INFORMATION: HBcAgwtHindIIII primer

<400> SEQUENCE: 67
cgcgtcccaa gcttctaaca ttgagattcc cgagattg                              38

<210> SEQ ID NO 68
<211> LENGTH: 10
<212> TYPE: PRT
<213> ORGANISM: Artificial Sequence
<220> FEATURE:
<223> OTHER INFORMATION: epitope CeH3

<400> SEQUENCE: 68

Val Asn Leu Thr Trp Ser Arg Ala Ser Gly
1               5                   10

<210> SEQ ID NO 69
<211> LENGTH: 51
<212> TYPE: DNA
<213> ORGANISM: Artificial Sequence
<220> FEATURE:
<223> OTHER INFORMATION: CeH3fwd primer
<220> FEATURE:
<221> NAME/KEY: CDS
<222> LOCATION: (1)..(51)

<400> SEQUENCE: 69 gtt aac ttg acc tgg tct cgt gct tct ggt gca tcc agg gat cta gta      48
Val Asn Leu Thr Trp Ser Arg Ala Ser Gly Ala Ser Arg Asp Leu Val
1               5                   10                  15 gtc                                                                    51
Val

<210> SEQ ID NO 70
<211> LENGTH: 17
<212> TYPE: PRT
<213> ORGANISM: Artificial Sequence
<220> FEATURE:
<223> OTHER INFORMATION: CeH3fwd primer

<400> SEQUENCE: 70

Val Asn Leu Thr Trp Ser Arg Ala Ser Gly Ala Ser Arg Asp Leu Val
1               5                   10                  15

Val

<210> SEQ ID NO 71
<211> LENGTH: 51
<212> TYPE: DNA
<213> ORGANISM: Artificial Sequence
<220> FEATURE:
<223> OTHER INFORMATION: CeH3rev primer

<400> SEQUENCE: 71
accagaagca cgagaccagg tcaagttaac atcttccaaa ttattaccca c              51

<210> SEQ ID NO 72
<211> LENGTH: 7
<212> TYPE: PRT
<213> ORGANISM: Artificial Sequence
<220> FEATURE:
<223> OTHER INFORMATION: CeH3rev primer peptide
```

```
<400> SEQUENCE: 72

Asp Glu Leu Asn Asn Gly Val
1               5

<210> SEQ ID NO 73
<211> LENGTH: 31
<212> TYPE: DNA
<213> ORGANISM: Artificial Sequence
<220> FEATURE:
<223> OTHER INFORMATION: HBcAg-wt EcoRI fwd primer

<400> SEQUENCE: 73
ccggaattca tggacattga cccttataaa g                              31

<210> SEQ ID NO 74
<211> LENGTH: 38
<212> TYPE: DNA
<213> ORGANISM: Artificial Sequence
<220> FEATURE:
<223> OTHER INFORMATION: HBcAg-wt Hind III rev primer

<400> SEQUENCE: 74
cgcgtcccaa gcttctaaca ttgagattcc cgagattg                       38

<210> SEQ ID NO 75
<211> LENGTH: 6
<212> TYPE: PRT
<213> ORGANISM: Homo sapiens

<400> SEQUENCE: 75

Asp Ala Glu Phe Arg His
1               5

<210> SEQ ID NO 76
<211> LENGTH: 6
<212> TYPE: PRT
<213> ORGANISM: Mus musculus

<400> SEQUENCE: 76

Asp Ala Glu Phe Gly His
1               5

<210> SEQ ID NO 77
<211> LENGTH: 9
<212> TYPE: PRT
<213> ORGANISM: Artificial Sequence
<220> FEATURE:
<223> OTHER INFORMATION: Abeta 1-6 GGC

<400> SEQUENCE: 77

Asp Ala Glu Phe Arg His Gly Gly Cys
1               5

<210> SEQ ID NO 78
<211> LENGTH: 9
<212> TYPE: PRT
<213> ORGANISM: Artificial Sequence
<220> FEATURE:
<223> OTHER INFORMATION: murine Abeta 1-6 GGC

<400> SEQUENCE: 78

Asp Ala Glu Phe Gly His Gly Gly Cys
1               5
```

```
<210> SEQ ID NO 79
<211> LENGTH: 28
<212> TYPE: DNA
<213> ORGANISM: Artificial Sequence
<220> FEATURE:
<223> OTHER INFORMATION: primer p1.44

<400> SEQUENCE: 79
aaccatggca aataagccaa tgcaaccg                                        28

<210> SEQ ID NO 80
<211> LENGTH: 30
<212> TYPE: DNA
<213> ORGANISM: Artificial Sequence
<220> FEATURE:
<223> OTHER INFORMATION: primer p1.45

<400> SEQUENCE: 80
aatctagaat tttctgcgca cccatcccgg                                      30

<210> SEQ ID NO 81
<211> LENGTH: 30
<212> TYPE: DNA
<213> ORGANISM: Artificial Sequence
<220> FEATURE:
<223> OTHER INFORMATION: primer p1.46

<400> SEQUENCE: 81
aaaagcttaa gcagtagtat cagacgatac                                      30

<210> SEQ ID NO 82
<211> LENGTH: 43
<212> TYPE: DNA
<213> ORGANISM: Artificial Sequence
<220> FEATURE:
<223> OTHER INFORMATION: primer p1.47

<400> SEQUENCE: 82
gagtgatcca actcgtttat caactacatt ttcagcaagt ctg                       43

<210> SEQ ID NO 83
<211> LENGTH: 43
<212> TYPE: DNA
<213> ORGANISM: Artificial Sequence
<220> FEATURE:
<223> OTHER INFORMATION: primer p1.48

<400> SEQUENCE: 83
cagacttgct gaaaatgtag ttgataaacg agttggatca ctc                       43

<210> SEQ ID NO 84
<211> LENGTH: 6
<212> TYPE: PRT
<213> ORGANISM: homo sapiens

<400> SEQUENCE: 84

Asp Ala Glu Phe Arg His
1               5

<210> SEQ ID NO 85
<211> LENGTH: 6
<212> TYPE: PRT
<213> ORGANISM: Oryctolagus cuniculus

<400> SEQUENCE: 85

Asp Ala Glu Phe Arg His
```

-continued

```
1               5

<210> SEQ ID NO 86
<211> LENGTH: 6
<212> TYPE: PRT
<213> ORGANISM: Xenopus laevis

<400> SEQUENCE: 86

Asp Ser Glu Tyr Arg His
1               5

<210> SEQ ID NO 87
<211> LENGTH: 6
<212> TYPE: PRT
<213> ORGANISM: Rattus norvegicus

<400> SEQUENCE: 87

Asp Ala Glu Phe Gly His
1               5

<210> SEQ ID NO 88
<211> LENGTH: 6
<212> TYPE: PRT
<213> ORGANISM: Cavia porcellus

<400> SEQUENCE: 88

Asp Ala Glu Phe Arg His
1               5

<210> SEQ ID NO 89
<211> LENGTH: 15
<212> TYPE: PRT
<213> ORGANISM: Mus musculus

<400> SEQUENCE: 89

Val His Glu Pro His Glu Phe Arg His Val Ala Leu Asn Pro Val
1               5                   10                  15

<210> SEQ ID NO 90
<211> LENGTH: 6
<212> TYPE: PRT
<213> ORGANISM: Mus musculus

<400> SEQUENCE: 90

Tyr Tyr Glu Phe Arg His
1               5

<210> SEQ ID NO 91
<211> LENGTH: 42
<212> TYPE: PRT
<213> ORGANISM: Homo sapiens

<400> SEQUENCE: 91

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 92
<211> LENGTH: 770
<212> TYPE: PRT
<213> ORGANISM: Homo sapiens
```

<400> SEQUENCE: 92

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
```

```
                    405                 410                 415
Glu Arg Gln Ala Lys Asn Leu Pro Lys Ala Asp Lys Lys Ala Val Ile
                420                 425                 430
Gln His Phe Gln Glu Lys Val Glu Ser Leu Glu Gln Glu Ala Ala Asn
            435                 440                 445
Glu Arg Gln Gln Leu Val Glu Thr His Met Ala Arg Val Glu Ala Met
        450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
                485                 490                 495
Tyr Val Arg Ala Glu Gln Lys Asp Arg Gln His Thr Leu Lys His Phe
                500                 505                 510
Glu His Val Arg Met Val Asp Pro Lys Lys Ala Ala Gln Ile Arg Ser
            515                 520                 525
Gln Val Met Thr His Leu Arg Val Ile Tyr Glu Arg Met Asn Gln Ser
        530                 535                 540
Leu Ser Leu Leu Tyr Asn Val Pro Ala Val Ala Glu Glu Ile Gln Asp
545                 550                 555                 560
Glu Val Asp Glu Leu Leu Gln Lys Glu Gln Asn Tyr Ser Asp Asp Val
                565                 570                 575
Leu Ala Asn Met Ile Ser Glu Pro Arg Ile Ser Tyr Gly Asn Asp Ala
                580                 585                 590
Leu Met Pro Ser Leu Thr Glu Thr Lys Thr Thr Val Glu Leu Leu Pro
            595                 600                 605
Val Asn Gly Glu Phe Ser Leu Asp Asp Leu Gln Pro Trp His Ser Phe
        610                 615                 620
Gly Ala Asp Ser Val Pro Ala Asn Thr Glu Asn Glu Val Glu Pro Val
625                 630                 635                 640
Asp Ala Arg Pro Ala Ala Asp Arg Gly Leu Thr Thr Arg Pro Gly Ser
                645                 650                 655
Gly Leu Thr Asn Ile Lys Thr Glu Glu Ile Ser Glu Val Lys Met Asp
                660                 665                 670
Ala Glu Phe Arg His Asp Ser Gly Tyr Glu Val His His Gln Lys Leu
            675                 680                 685
Val Phe Phe Ala Glu Asp Val Gly Ser Asn Lys Gly Ala Ile Ile Gly
        690                 695                 700
Leu Met Val Gly Gly Val Val Ile Ala Thr Val Ile Val Ile Thr Leu
705                 710                 715                 720
Val Met Leu Lys Lys Lys Gln Tyr Thr Ser Ile His His Gly Val Val
                725                 730                 735
Glu Val Asp Ala Ala Val Thr Pro Glu Glu Arg His Leu Ser Lys Met
                740                 745                 750
Gln Gln Asn Gly Tyr Glu Asn Pro Thr Tyr Lys Phe Phe Glu Gln Met
            755                 760                 765
Gln Asn
770

<210> SEQ ID NO 93
<211> LENGTH: 82
<212> TYPE: PRT
<213> ORGANISM: Homo sapiens

<400> SEQUENCE: 93
```

-continued

```
Gly Ser Gly Leu Thr Asn Ile Lys Thr Glu Glu Ile Ser Glu Val Lys
1               5                   10                  15

Met Asp Ala Glu Phe Arg His Asp Ser Gly Tyr Glu Val His His Gln
                20                  25                  30

Lys Leu Val Phe Phe Ala Glu Asp Val Gly Ser Asn Lys Gly Ala Ile
                35                  40                  45

Ile Gly Leu Met Val Gly Gly Val Val Ile Ala Thr Val Ile Ile Ile
        50                  55                  60

Thr Leu Val Met Leu Lys Lys Gln Tyr Thr Ser Asn His His Gly Val
65                  70                  75                  80

Val Glu
```